US011091779B2

(12) United States Patent
Frueh et al.

(10) Patent No.: US 11,091,779 B2
(45) Date of Patent: Aug. 17, 2021

(54) METHODS AND COMPOSITIONS USEFUL IN GENERATING NON CANONICAL CD8+ T CELL RESPONSES

(71) Applicant: Oregon Health & Science University, Portland, OR (US)

(72) Inventors: Klaus Frueh, Portland, OR (US); Louis Picker, Portland, OR (US); Scott Hansen, Portland, OR (US); Jonah Sacha, Beaverton, OR (US); Daniel Malouli, Hillsboro, OR (US)

(73) Assignee: OREGON HEALTH & SCIENCE UNIVERSITY, Portland, OR (US)

(*) Notice: Subject to any disclaimer, the term of this patent is extended or adjusted under 35 U.S.C. 154(b) by 0 days.

(21) Appl. No.: 16/738,178

(22) Filed: Jan. 9, 2020

(65) Prior Publication Data

US 2020/0392534 A1 Dec. 17, 2020

Related U.S. Application Data

(63) Continuation of application No. 15/549,814, filed as application No. PCT/US2016/017373 on Feb. 10, 2016, now abandoned.

(60) Provisional application No. 62/114,203, filed on Feb. 10, 2015, provisional application No. 62/196,520, (Continued)

(51) Int. Cl.
| C12N 15/86 | (2006.01) |
| C12N 9/02 | (2006.01) |
| C12Q 1/68 | (2018.01) |
| C12N 15/00 | (2006.01) |
| A61K 39/12 | (2006.01) |
| A61K 35/17 | (2015.01) |
| A61K 39/21 | (2006.01) |
| A61K 39/245 | (2006.01) |

(Continued)

(52) U.S. Cl.
CPC .............. *C12N 15/86* (2013.01); *A61K 35/17* (2013.01); *A61K 39/12* (2013.01); *A61K 39/21* (2013.01); *A61K 39/245* (2013.01); *C12N 7/00* (2013.01); *C12N 9/0093* (2013.01); *C12N 15/00* (2013.01); *C12Q 1/68* (2013.01); *C12Y 117/04001* (2013.01); *A61K 2039/5158* (2013.01); *A61K 2039/5252* (2013.01); *A61K 2039/5256* (2013.01); *A61K 2039/53* (2013.01); *A61K 2039/57* (2013.01); *A61K 2039/575* (2013.01); *C12N 2710/16134* (2013.01); *C12N 2710/16143* (2013.01); *C12N 2740/15034* (2013.01); *C12N 2740/15043* (2013.01); *Y02A 50/30* (2018.01)

(58) Field of Classification Search
CPC .......... C12N 15/86; C12N 2710/16134; C12N 2740/15043; C12N 2710/16143; C12N 2740/15034; C12N 5/0636; C12N 15/00; C12N 7/00; C12N 9/0093; C12N 2710/16111; C12N 2710/16162; C12N 15/64; C12N 15/67; C12N 2710/16011; C12N 2710/16034; C12N 2710/16041; C12N 2710/16061; C12N 2710/16141; C12Q 1/68; C12Y 117/04001; Y02A 50/30; A61K 2039/5252; A61K 2039/5256; A61K 2039/53; A61K 39/12; A61K 35/17; A61K 39/21; A61K 39/245; A61K 2039/57; A61K 2039/5158; A61K 2039/575; A61P 37/06; A61P 37/04; A61P 37/02; A61P 35/02; A61P 35/00; A61P 33/00; A61P 31/22; A61P 31/20; A61P 31/18; A61P 31/14; A61P 31/12; A61P 31/06; A61P 31/00; C07K 14/005

See application file for complete search history.

(56) References Cited

U.S. PATENT DOCUMENTS

| 5,168,062 A | 12/1992 | Stinski |
| 5,273,876 A | 12/1993 | Hock et al. |
| 5,385,839 A | 1/1995 | Stinski |

(Continued)

FOREIGN PATENT DOCUMENTS

| EP | 0521427 A1 | 1/1993 |
| WO | WO-8810311 A1 | 12/1988 |

(Continued)

OTHER PUBLICATIONS

Basta, S., et al., "Inhibitory Effects of Cytomegalovirus Proteins Us2 and Us11 Point to Contributions From Direct Priming and Cross-priming in Induction of Vaccinia Virus-specific Cd8(+) T Cells," Journal of Immunology 168(11):5403-5408, American Association of Immunologists, United States (Jun. 2002).

(Continued)

*Primary Examiner* — Rachel B Gill
(74) *Attorney, Agent, or Firm* — Sterne, Kessler, Goldstein & Fox P.L.L.C.

(57) ABSTRACT

Methods of inducing a CD8+ T cell response to a heterologons antigen in which at least 10% of the CD8+ T cells are MHC-E restricted are disclosed. The method involves immunizing with a CMV vector that does not express UL128 and UL130 proteins. Also disclosed are recombinant CMV vectors comprising nucleic acids encoding a heterologous protein antigen, a UL40 protein, and a US28 protein but that do not express an active UL128 and UL130 protein. Also, disclosed are recombinant CMV vectors comprising nucleic acids encoding a heterologous protein antigen, but that do not express an active UL40 protein, UL128 protein, UL130 protein, and optionally a US28 protein. Also disclosed are recombinant CMV vectors comprising nucleic acids encoding a heterologous protein antigen, but that do not express an active US28 protein, UL128 protein, UL130 protein, and optionally a UL40 protein.

20 Claims, 51 Drawing Sheets

Specification includes a Sequence Listing.

Related U.S. Application Data filed on Jul. 24, 2015, provisional application No. 62/220,703, filed on Sep. 18, 2015.

(51) Int. Cl.
*C12N 7/00* (2006.01)
*A61K 39/00* (2006.01)

(56) References Cited

U.S. PATENT DOCUMENTS

| | | | |
|---|---|---|---|
| 5,720,957 | A | 2/1998 | Jones et al. |
| 5,830,745 | A | 11/1998 | Hock et al. |
| 5,833,993 | A | 11/1998 | Wardley et al. |
| 6,033,671 | A | 3/2000 | Frueh et al. |
| 7,537,770 | B2 | 5/2009 | Kemble et al. |
| 7,892,822 | B1 | 2/2011 | Koszinowski et al. |
| 9,249,427 | B2 | 2/2016 | Picker et al. |
| 9,541,553 | B2 | 1/2017 | Picker et al. |
| 9,783,823 | B2 | 10/2017 | Picker et al. |
| 9,862,972 | B2 | 1/2018 | Picker et al. |
| 9,982,241 | B2 | 5/2018 | Picker et al. |
| 10,101,329 | B2 | 10/2018 | Picker et al. |
| 10,167,321 | B2 | 1/2019 | Carfi et al. |
| 2002/0176870 | A1 | 11/2002 | Schall et al. |
| 2003/0118568 | A1 | 6/2003 | Crew |
| 2003/0138454 | A1 | 7/2003 | Adrian et al. |
| 2004/0086489 | A1 | 5/2004 | Schall et al. |
| 2004/0110188 | A1 | 6/2004 | Hahn et al. |
| 2004/0248300 | A1 | 12/2004 | Preston |
| 2005/0064394 | A1 | 3/2005 | Liu et al. |
| 2005/0118192 | A1 | 6/2005 | Boursnell et al. |
| 2006/0019369 | A1 | 1/2006 | Hahn |
| 2008/0071037 | A1 | 3/2008 | Carr et al. |
| 2008/0199493 | A1 | 8/2008 | Picker et al. |
| 2009/0148477 | A1 | 6/2009 | Bruder et al. |
| 2009/0203144 | A1 | 8/2009 | Beaton et al. |
| 2009/0297555 | A1 | 12/2009 | Kemble et al. |
| 2010/0142823 | A1 | 6/2010 | Wang et al. |
| 2013/0089559 | A1 | 4/2013 | Grawunder et al. |
| 2013/0136768 | A1 | 5/2013 | Picker et al. |
| 2013/0142823 | A1 | 6/2013 | Picker et al. |
| 2013/0202638 | A1 | 8/2013 | Thirion et al. |
| 2014/0141038 | A1 | 5/2014 | Picker et al. |
| 2016/0010112 | A1 | 1/2016 | Picker et al. |
| 2016/0114027 | A1 | 4/2016 | Hahn et al. |
| 2016/0354461 | A1 | 12/2016 | Picker et al. |
| 2017/0143809 | A1 | 5/2017 | Nelson et al. |
| 2017/0350887 | A1 | 12/2017 | Picker et al. |
| 2018/0016599 | A1 | 1/2018 | Evans et al. |
| 2018/0087069 | A1 | 3/2018 | Picker et al. |
| 2018/0133321 | A1 | 5/2018 | Picker et al. |
| 2018/0282378 | A1 | 10/2018 | Frueh et al. |
| 2018/0298404 | A1 | 10/2018 | Freuh et al. |

FOREIGN PATENT DOCUMENTS

| | | |
|---|---|---|
| WO | WO-9503399 A2 | 2/1995 |
| WO | WO-9604383 A1 | 2/1996 |
| WO | WO-9631241 A1 | 10/1996 |
| WO | WO-9906582 A1 | 2/1999 |
| WO | WO-9907869 A1 | 2/1999 |
| WO | WO-02062296 A2 | 8/2002 |
| WO | WO-2003093455 A2 | 11/2003 |
| WO | WO-2006031264 A2 | 3/2006 |
| WO | WO-2006125983 A1 | 11/2006 |
| WO | WO-2010101663 A2 | 9/2010 |
| WO | WO-2011093858 A1 | 8/2011 |
| WO | WO-2011119920 A2 | 9/2011 |
| WO | WO-2011138040 A2 | 11/2011 |
| WO | WO-2011143650 A2 | 11/2011 |
| WO | WO-2011143653 A2 | 11/2011 |
| WO | WO-2012170765 A2 | 12/2012 |
| WO | WO-2014138209 A1 | 9/2014 |
| WO | WO-2016011293 A1 | 1/2016 |
| WO | WO-2016130693 A1 | 8/2016 |
| WO | WO-2017087921 A1 | 5/2017 |
| WO | WO-2018005559 A1 | 1/2018 |

OTHER PUBLICATIONS

Besold, K., et al., "Immune Evasion Proteins GpUS2 and GpUS11 of Human Cytomegalovirus Incompletely Protect Infected Cells From CD8 T Cell Recognition," Virology 391(1):5-19, Academic Press, United States (Aug. 2009).

Borst, E and Messerle, M, "Development of a Cytomegalovirus Vector for Somatic Gene Therapy," Bone Marrow Transplant 25 Suppl 2:S80-S82, Nature Publishing Group (May 2000).

Borst, E.M and Messerle, M, "Construction of a Cytomegalovirus-based Amplicon: a Vector With a Unique Transfer Capacity," Human Gene Therapy 14(10):959-970, M.A. Liebert, United States (Jul. 2003).

Bresnahan, W.A and Shenk, T.E, "UL82 Virion Protein Activates Expression of Immediate Early Viral Genes in Human Cytomegalovirus-infected Cells," Proceedings of the National Academy of Sciences of the United States of America 97(26):14506-14511, National Academy of Sciences, United States (Dec. 2000).

Bresnahan, W.A., et al., "Replication of Wild-type and Mutant Human Cytomegalovirus in Life-extended Human Diploid Fibroblasts," Journal of Virology 74(22):10816-10818, American Society for Microbiology, United States (Nov. 2000).

Brondke, H. "Human Herpesvirus 5, Towne Strain," US3 (NCBI GenBank Acc. No. AAS49002), Dep. Apr. 8, 2004.

Brondke, H. "Human Herpesvirus 5, Towne Strain," US6 (NCBI GenBank Acc. No. AAS49004), Dep. Apr. 8, 2004.

Brown, B.D and Naldini.L, "Exploiting and Antagonizing MicroRNA Regulation for Therapeutic and Experimental Applications," Nature reviews Genetics 10(8):578-585, Nature Publishing Group, England (Aug. 2009).

Campadelli-Flume, et al., Editors, "Chapter 15: Betaherpes Viral Genes and Their Functions" Human Herpesviruses: Biology, Therapy, and Immunoprophylaxis. Cambridge: Cambridge University Press, 2007.

Cantrell, S.R and Bresnahan, W.A, "Human Cytomegalovirus (Hcmv) UL82 Gene Product (pp71) Relieves hDaxx-mediated Repression of Hcmv Replication," Journal of Virology 80(12):6188-6191, American Society for Microbiology, United States (Jun. 2006).

Cantrell, S.R and Bresnahan, W.A, "Interaction Between the Human Cytomegalovirus UL82 Gene Product (pp71) and HDaxx Regulates Immediate-early Gene Expression and Viral Replication," Journal of Virology 79(12):7792-7802, American Society for Microbiology, United States (Jun. 2005).

Chang, W.L and Barry, P.A, "Cloning of the Full-length Rhesus Cytomegalovirus Genome as an Infectious and Self-Excisable Bacterial Artificial Chromosome for Analysis of Viral Pathogenesis," Journal of Virology 77(9):5073-5083, American Society for Microbiology, United States (May 2003).

Chau, N.H., et al., "Transcriptional Regulation of the Human Cytomegalovirus Us11 Early Gene," Journal of Virology 73(2):863-870, American Society for Microbiology, United States (Feb. 1999).

Davison, A.J and Stow, N.D, "New Genes From Old: Redeployment of DUTPase by Herpesviruses," Journal of Virology 79(20):12880-12892, American Society for Microbiology, United States (Oct. 2005).

Dudek, T and Knipe, D.M, "Replication-defective Viruses as Vaccines and Vaccine Vectors," Virology 344(1):230-239, Academic Press, United States (Jan. 2006).

Dunn, W., et al., "Functional Profiling of a Human Cytomegalovirus Genome," Proceedings of the National Academy of Sciences of the United States of America 100(24):14223-14228, National Academy of Sciences, United States (Nov. 2003).

European Search Report for EP Application No. EP16200334, The Hague, dated May 18, 2017.

European Search Report for EP Application No. EP17197412, Munich, Germany, dated Apr. 23, 2018.

Prod'Homme, V., et al., "Human Cytomegalovirus UL40 Signal peptide Regulates Cell Surface Expression of the NK Cell Ligands

(56) References Cited

OTHER PUBLICATIONS

HLA-E and gpUL18," J. Immunology 188(6):2794-2804, American Society of Immunologist, United States (2012).
Goodrum, F., et al., "Human Cytomegalovirus Persistence," Cellular Microbiology 14(5):644-655, Wiley-Blackwell, England (May 2012).
Gorman, S., et al., "Prior Infection with Murine Cytomegalovirus (Mcmv) Limits the Immunocontraceptive Effects of an MCMV Vector Expressing the Mouse Zona-Pellucida-3 Protein," Vaccine 26(31):3860-3869, Elsevier Science, Netherlands (Jul. 2008).
Grimwood, J., et al. "NCBI GenBank Direct Submission," Acc. No. AC146906, Sub. Nov. 5, 2003.
Hagemier, S.C., "Functional Analysis of the Human Cytomegalovirus UL82 gene product PP71 protein during Virus Replication," Doctoral Dissertation, The University of Texas Southwestern Medical Center at Dallas, May 2007, pp. 1-181.
Hahn, G., et al., "Human Cytomegalovirus UL131-128 Genes are Indispensable for Virus Growth in Endothelial Cells and Virus Transfer to Leukocytes," Journal of Virology 78(18):10023-10033, American Society for Microbiology, United States (Sep. 2004).
Halary, F., et al., "Human Cytomegalovirus Binding to DC-SIGN is Required for Dendritic Cell Infection and Target Cell Trans-Infection," Immunity 17(5):653-664, Cell Press, United States (Nov. 2002).
Hansen, S.G., et al., "Complete Sequence and Genomic Analysis of Rhesus Cytomegalovirus," Journal of Virology 77(12):6620-6636, American Society for Microbiology, United States (Jun. 2003).
Hansen, S.G., et al., "Effector Memory T Cell Responses are Associated With Protection of Rhesus Monkeys From Mucosal Simian Immunodeficiency Virus Challenge," Nature Medicine 15(3):293-299, Nature Publishing Company, United States (Mar. 2009).
Hansen, S.G., et al., "Evasion of Cd8+ T Cells Is Critical for Superinfection by Cytomegalovirus," Science 328(5974):102-106, American Association for the Advancement of Science, United States (Apr. 2010).
Hansen, S.G., et al., "Profound Early Control of Highly Pathogenic SIV by an Effector Memory T-cell Vaccine," Nature 473(7348):523-527, Nature Publishing Group, England (May 2011).
International Search Report and Written opinion for International Application No. PCT/US2011/036657, Korean Intellectual Property Office, Republic of Korea, dated Mar. 28, 2012, 12 pages.
Jones, T.R., et al., "Multiple Independent Loci Within the Human Cytomegalovirus Unique Short Region Down-regulate Expression of Major Histocompatibility Complex Class I Heavy Chains," Journal of Virology 69(8):4830-4841, American Society for Microbiology, United States (Aug. 1995).
Jones, T.R., et al., "Replacement Mutagenesis of the Human Cytomegalovirus Genome: US10 and US11 Gene Products are Nonessential," Journal of Virology 65(11):5860-5872, American Society for Microbiology, United States (Nov. 1991).
Kaech, S.M., et al., "Effector and Memory T-cell Differentiation: Implications for Vaccine Development," Nature Reviews. Immunology 2(4):251-262, Nature Pub. Group, England (Apr. 2002).
Kalejta, R.F, "Human Cytomegalovirus PP71: a New Viral Tool to Probe the Mechanisms of Cell Cycle Progression and Oncogenesis Controlled by the Retinoblastoma Family of Tumor Suppressors," Journal of Cellular Biochemistry 93(1):37-45, Wiley-Liss, United States (Sep. 2004).
Karrer, U., et al., "Expansion of Protective CD8+ T-Cell Responses Driven by Recombinant Cytomegaloviruses," Journal of Virology 78(5):2255-2264, American Society for Microbiology, United States (Mar. 2004).
Kropff, B and Mach, M, "Identification of the Gene Coding for Rhesus Cytomegalovirus Glycoprotein B and Immunological Analysis of the Protein," 78(Pt 8):1999-2007, Microbiology Society, England (Aug. 1997).
Lilja, A.E., et al., "Functional Genetic Analysis of Rhesus Cytomegalovirus: Rh01 Is an Epithelial Cell Tropism Factor," Journal of Virology 82(5):2170-2181, American Society for Microbiology, United States (Mar. 2008).
Mahmood, K., et al., "Human Cytomegalovirus Plasmid-based Amplicon Vector System for Gene Therapy," Genetic vaccines and therapy 3(1):1, BioMed Central, England (Jan. 2005).
Marshall, K.R., et al., "Activity and Intracellular Localization of the Human Cytomegalovirus Protein PP71," The Journal of general virology 83(Pt 7):1601-1612, Microbiology Society, England (Jul. 2002).
Maussang, D., et al., "Human Cytomegalovirus-encoded Chemokine Receptor US28 Promotes Tumorigenesis," Proceedings of the National Academy of Sciences of the United States of America 103(35):13068-13073, National Academy of Sciences, United States (Aug. 2006).
McGregor, A., et al., "Molecular, Biological, and in Vivo Characterization of the Guinea Pig Cytomegalovirus (CMV) Homologs of the Human Cmv Matrix Proteins pp71 (UL82) and pp65 (UL83)," Journal of virology 78(18):9872-9889, American Society for Microbiology, United States (Sep. 2004).
Mohr, C.A., et al., "A Spread-deficient Cytomegalovirus for Assessment of First-target Cells in Vaccination," Journal of virology 84(15):7730-7742, American Society for Microbiology, United States (Aug. 2010).
Mohr, C.A., et al., "Engineering of Cytomegalovirus Genomes for Recombinant Live Herpesvirus Vaccines," International Journal of Medical Microbiology 298(1-2):115-125, Urban & Fischer Verlag, Germany (Jan. 2008).
Moutaftsi, M., et al., "Human Cytomegalovirus Inhibits Maturation and Impairs Function of Monocyte-derived Dendritic Cells," Blood 99(8):2913-2921, American Society of Hematology, United States (Apr. 2002).
Murphy, C.G., et al., "Vaccine Protection Against Simian Immunodeficiency Virus by Recombinant Strains of Herpes Simplex Virus," Journal of virology 74(17):7745-7754, American Society for Microbiology, United States (Sep. 2000).
Murphy, E., et al., "Coding Potential of Laboratory and Clinical Strains of Human Cytomegalovirus," Proceedings of the National Academy of Sciences of the United States of America 100(25):14976-14981, National Academy of Sciences, United States (Dec. 2003).
Wu., H.L., et al., "Cytomegalovirus vaccine vector 68-1 elicits universal, MHC-E-restricted CD8 T-cell responses against SIV," Journal of Medical Primatology 44(5):313, Wiley Online Library, United States (2014).
Olaleye, O.D., et al., "Cytomegalovirus Infection Among Tuberculosis Patients in a Chest Hospital in Nigeria," Comparative Immunology, Microbiology and Infectious Diseases 13(2):101-106, Elsevier Science Ltd, England (1990).
Onuffer, J.J and Horuk, R, "Chemokines, Chemokine Receptors and Small-molecule Antagonists: Recent Developments," Trends in Pharmacological Sciences 23(10):459-467, Published by Elsevier in Association with the International Union of Pharmacology, England (Oct. 2002).
Oxford, K.L., et al., "Protein Coding Content of the ULb' Region of Wild-Type Rhesus Cytomegalovirus," Virology 373(1):181-188, Academic Press, United States (Mar. 2008).
Plotkin, S.A., et al., "Vaccines for the Prevention of Human Cytomegalovirus Infection," Reviews of Infectious Diseases 12 Suppl 7:S827-S838, University of Chicago Press, United States (Sep.-Oct. 1990).
Powers, C and Fruh, K, "Rhesus CMV: an Emerging Animal Model for Human CMV," Medical Microbiology and Immunology 197(2):109-115, Springer-Verlag, Germany (Jun. 2008).
Redwood, A.J., et al., "Use of a Murine Cytomegalovirus K181-derived Bacterial Artificial Chromosome as a Vaccine Vector for Immunocontraception," Journal of virology 79(5):2998-3008, American Society for Microbiology, United States (Mar. 2005).
Rizvanov, A.A., et al., "Generation of a Recombinant Cytomegalovirus for Expression of a Hantavirus Glycoprotein," Journal of virology 77(22):12203-12210, American Society for Microbiology, United States (Nov. 2003).
Ryckman, B.J., et al., "Characterization of the Human Cytomegalovirus Gh/gl/ul128-131 Complex That Mediates Entry Into Epithelial and Endothelial Cells," Journal of virology 82(1):60-70, American Society for Microbiology, United States (Jan. 2008).

(56) References Cited

OTHER PUBLICATIONS

Schleiss, M.R., et al., "Genetically Engineered Live-attenuated Cytomegalovirus (CMV) Vaccines Improve Pregnancy Outcome in the Guinea-pig Model of Congenital CMV Infection," Retrovirology 5(1):1-3, (Apr. 2008).
European Search Report for EP Application No. EP11008462, Munich, Germany, dated Jul. 26, 2012.
GenBank Report, Accession No. NP_057850, (published Aug. 1, 2000).
Fruh, K., et al., "CD8+ T cell programming by cytomegalovirus vectors: applications in prophylactic and therapeutic vaccination," Current Opinion in Immunology 47:52-56, Elsevier, Netherlands(2017).
Oxxon Terapeutics Licenses Rights to Xenova's DISC-HSV and DISC-GM-CSF Vector Technolgies, BusinessWire, Jan. 13, 2005.
Tessmer, M.S., et al., "Salivary Gland NK Cells Are Phenotypically and Functionally Unique," PLoS Pathogens 7(1):e1001254, Public Library of Science, United States (Jan. 2011).
Ulmer, J.B, "Tuberculosis DNA Vaccines," Scandinavian Journal of Infectious Diseases 33(4):246-248, Informs Healthcare, England (2001).
Wang, X., et al., "Murine Cytomegalovirus Abortively Infects Human Dendritic Cells, Leading to Expression and Presentation of Virally Vectored Genes," Journal of virology 77(13):7182-7192, American Society for Microbiology, United States (Jul. 2003).
Wiertz, E.J., et al., "The Human Cytomegalovirus US11 Gene Product Dislocates Mhc Class I Heavy Chains From the Endoplasmic Reticulum to the Cytosol," Cell 84(5):769-779, Cell Press, United States (Mar. 1996).
Altschul, S.F. and Gish W., "Local Alignment Statistics," Methods in Enzymology 266:460-480, Academic Press, United States (1996).
Altschul, S.F., et al., "Basic Local Alignment Search Tool," Journal of Molecular Biology 215(3):403-410, Elsevier, England (Oct. 1990).
Andre, S., et al., "Increased Immune Response Elicited by DNA Vaccination With a Synthetic gp120 Sequence With Optimized Codon Usage," Journal of Virology 72(2):1497-1503, American Society for Microbiology, United States (Feb. 1998).
Barsov, E.V., et al., "Transduction of Siv-specific Tcr Genes Into Rhesus Macaque Cd8+ T Cells Conveys the Ability to Suppress Siv Replication," PLoS One 6(8):e23703, Public Library of Science, United States ( Aug. 2011).
Do, J.S., et al., "Unexpected Role for MHC II-Peptide Complexes in Shaping CD8 T-Cell Expansion and Differentiation in Vivo," Proceedings of the National Academy of Sciences 109(31):12698-12703, National Academy of Sciences, United States (Jul. 2012).
Felgner, J.H., et al., "Enhanced Gene Delivery and Mechanism Studies With a Novel Series of Cationic Lipid Formulations," Journal of Biological Chemistry 269(4):2550-2561, American Society for Biochemistry and Molecular Biology, United States (Jan. 1994).
Gilicze, A.B., et al., "Myeloid-Derived microRNAs, miR-223, miR27a, and miR-652, Are Dominant Players in Myeloid Regulation," BioMed Research International 2014:870267, Hindawi Publishing Corporation, United States (Aug. 2014).
Gill, R.B., et al., "Coding Potential of Ul/b' From the Initial Source of Rhesus Cytomegalovirus Strain 68-1," Virology 447(1-2):208-212, Academic Press, United States (Dec. 2013).
Gish, W and States, D.J, "Identification of Protein Coding Regions by Database Similarity Search," Nature Genetics 3(3):266-272, Nature Publishing Group, United States (Mar. 1993).
Goodman-Snitkoff, G., et al., "Role of Intrastructural/intermolecular Help in Immunization With Peptide-phospholipid Complexes," Journal of Immunology 147(2):410-415, American Association of Immunologists, United States (Jul. 1991).
Wang, D and Shenk,T ., "Human cytomegalovirus UL131 Open Reading Frame is Required for Epithelial Cell Tropism," Journal of Virology, 79(16):10330-10338, American Society for Microbiology, United States (Aug. 2005).

Hancock, M.H., et al., "Rhesus Cytomegalovirus Encodes Seventeen Micrornas that are Differentially Expressed In Vitro and In Vivo," Virology 425(2):133-142, Academic Press, United States (Apr. 2012).
Hansen, S.G., et al., "Broadly Targeted Cd8+ T Cell Responses Restricted by Major Histocompatibility Complex E," Science 351(6274):714-720, American Association for the Advancement of Science, United States (Feb. 2016).
Hansen, S.G., et al., "Cytomegalovirus Vectors Violate CD8+ T Cell Epitope Recognition Paradigms," Science 340(6135):1237874, American Association for the Advancement of Science, United States (May 2013).
Hansen, S.G., et al., "Immune Clearance of Highly Pathogenic SIV Infection," Nature 502(7469):100-104, Nature Publishing Group, United Kingdom (Oct. 2013).
Higgins, D.G and Sharp, P.M, "Clustal: A Package for Performing Multiple Sequence Alignment on a Microcomputer," Gene 73(1):237-244, Elsevier/North-Holland, Netherlands (Dec. 1988).
Higgins, D.G., and Sharp, P.M., "Fast and Sensitive Multiple Sequence Alignments on a Microcomputer," Computer Applications in the Biosciences 5(2):151-153, Oxford University Press, United Kingdom (Apr. 1989).
Huang, X., et al., "Parallelization of a Local Similarity Algorithm," Computer Applications in the Biosciences 8(2):155-165, Oxford University Press, England (Apr. 1992).
International Preliminary Report on Patentability for International Application No. PCT/US2016/017373, The International Bureau of WIPO, Geneva, Switzerland, dated Aug. 15, 2017, 8 pages.
International Search Report and Written Opinion for International Application No. PCT/US2015/040807, European Patent Office, HV Rijswijk, dated Oct. 28, 2015, 6 pages.
International Search Report and Written opinion for International Application No. PCT/US2016/017373, Korean Intellectual Property Office, Republic of Korea, dated May 23, 2016.
International Search Report for International Application No. PCT/US2012/041475, Korean Intellectual Property Office, Republic of Korea, dated Dec. 14, 2012.
James, SH and Prichard, M.N., "The Genetic Basis of Human Cytomegalovirus Resistance and Current Trends in Antiviral Resistance Analysis," Infectious Disorders Drug Targets, 11(5):504-513, Bentham Science Publishers, United Arab Emirates (Oct. 2011).
Karlin, S. and Altschul, S.E., "Methods for Assessing the Statistical Significance of Molecular Sequence Features by using General Scoring Schemes," Proceedings of the National Academy of Sciences USA 87(6):2264-2268, National Academy of Sciences, United States (Mar. 1990).
Karlin, S, and Altschul, S.F., "Applications and Statistics for Multiple High-scoring Segments in Molecular Sequences," Proceedings of the National Academy of Sciences USA 90(12):5873-5877, National Academy of Sciences, United States (Jun. 1993).
Malouli, D., et al., "Reevaluation of the Coding Potential and Proteomic Analysis of the Bac-derived Rhesus Cytomegalovirus Strain 68-1," Journal of Virology 86(17):8959-8973, American Society for Microbiology, United States (Sep. 2012).
McGregor, A., et al., "Expression of the Human Cytomegalovirus UL97 Gene in a Chimeric Guinea Pig Cytomegalovirus (GPCMV) Results in Viable Virus with Increased Susceptibility to Ganciclovir and Maribavir," Antiviral Research 78(3):250-259, Elsevier, Netherlands (Jun. 2008).
Miller, M.D., et al., "Vaccination of Rhesus Monkeys With Synthetic Peptide in a Fusogenic Proteoliposome Elicits Simian Immunodeficiency Virus-specific Cd8+ Cytotoxic T Lymphocytes," Journal of Experimental Medicine 176(6):1739-1744, Rockefeller University Press, United States (Dec. 1992).
Murrell, L., et al., "Impact of Sequence Variation in the UL128 Locus on Production of Human Cytomegalovirus in Fibroblast and Epithelial Cells," Journal of Virology 87(19):10489-10500, American Society for Microbiology, United States (Oct. 2013).
Myers, E.W., and Miller, W., "Optimal Alignment in Linear Space," Computer Applications in the Biosciences 4(1):1-13, Oxford University Press, England (Mar. 1988).

(56) References Cited

OTHER PUBLICATIONS

Kim, S., et al., "Human Cytomegalovirus MicroRNA miR-US4-1 Inhibits CD8(+) T cell Responses by Targeting the Aminopeptidase ERAP1," Nature Immunology 12(10):984-991, Nature America Inc, United States (Sep. 2011).

Needleman, S.B. and Wunsch, C.D., "A General Method Applicable to the Search for Similarities in the Amino Acid Sequence of Two Proteins," Journal of Molecular Biology 48(3):443-453, Academic Press, England (Mar. 1970).

Oxford, K.L., et al., "Protein Coding Content of the UL)b' Region of Wild-type Rhesus Cytomegalovirus," Virology, 373(1):181-183, Academic Press, United States (Mar. 2008).

Pearce, E.L., et al., "Functional Characterization of MHC Class II-Restricted CD8+CD4- and CD8-CD4-T cell Responses to Infection in CD4−/− Mice," Journal of Immunology 173(4):2494-2499, American Association of Immunologists, United States (Aug. 2004).

Pearson, W.R. and Lipman, D.J., "Improved Tools for Biological Sequence Comparison," Proceedings of the National Academy of Sciences of the United States of America 85(8):2444-2448, National Academy of Sciences, United States (Apr. 1988).

Pearson, W.R., "Using the FASTA Program to Search Protein and DNA Sequence Databases," Methods in Molecular Biology 24:307-331, Humana Press, United States (Feb. 1994).

Hanley, P.J., et al., "Controlling cytomegalovirus: helping the immune system take the lead," Viruses, 6(6):2242-2258, MDPI, Switzerland (May 2014).

Heineman, T.C., "Chapter 71: Human cytomegalovirus vaccines." In: Arvin, A, Campadelli-Fiume, G, Mocarski, E, et al., eds. Human Herpesviruses: Biology, Therapy, and Immunoprophylaxis, Cambridge: Cambridge University Press, 2007.

Picker, L.J., et al., "New paradigms for HIV/AIDS vaccine development," Annual Review of Medicine 63:95-111, Annual Reviews, United States (Feb. 2012).

Pietra, G., et al., "HLA-E-Restricted Recognition of Cytomegalovirus-derived Peptides by Human CD8+ Cytolytic T Lymphocytes," Proceedings of the National Academy of Sciences of the United States of America 100(19):10896-10901, National Academy of Sciences, United States (Sep. 2003).

International Preliminary Report on Patentability for International Application No. PCT/US2015/040807, The International Bureau of WIPO, Geneva, Switzerland, dated Jan. 17, 2017, 8 pages.

Pietra, G., et al., "The Emerging Role of HLA-E-restricted CD8+ T Lymphocytes in the Adaptive Immune Response to Pathogens and Tumors," Journal of Biomedicine and Biotechnology 2010(9070921):1-8, Hindawi, India (2010).

Lauron, E.J., et al., "Human Cytomegalovirus Infection of Langerhans-Type Dendritic Cells Does Not Require the Presence of the gH/gL/UL128-131A Complex and Is Blocked after Nuclear Deposition of Viral Genomes in Immature Cells," Journal of Virology, 88(1): 403-416, American Society for Microbiology, United States (Jan. 2014).

Smith, I.L., et al., "High-level resistance of cytomegalovirus to ganciclovir is associated with alterations in both the UL97 and DNA polymerase genes," Journal of Infectious Diseases, 176(1): 69-77, Oxford University Press, United States (Jul. 1997). Erratum in: Journal of Infectious Diseases, 177(4):1140-1141 (Apr. 1998).

Wu, F., et al., "Role of Specific MicroRNAs for Endothelial Function and Angiogenesis," Biochemical and Biophysical Research Communications 386(4):549-553, Elsevier, United States (Sep. 2009).

Sambrook, J., et al., "Molecular Cloning: A Laboratory Manual," Second Edition, Cold Spring Harbor Laboratory Press, United States (1989).

Schuessler, A., et al., "Charge Cluster-to-Alanine Scanning of UL 12B for Fine Tuning of the Endothelial Cell Tropism of Human Cytomegalovirus," Journal of Virology, 82(22):11239-11246, American Society for Microbiology, United States (Nov. 2008).

Schuessler, A., et al., "Mutational Mapping of UL130 of Human Cytomegalovirus Defines Peptide Motifs within the C-Terminal Third as Essential for Endothelial Cell Infection," Journal of Virology, 84(18): 9019-9026, American Society for Microbiology, United States (Sep. 2010).

Smith, T.F. and Waterman, M.S., "Comparison of Biosequences," Advances in Applied Mathematics 2(4):482-489, Academic Press, Inc., United States (Dec. 1981).

Michaelson, J.S and Leder, P., "RNAi Reveals Anti-Apoptotic and Transcriptionally Repressive Activities of DAXX," Journal of Cell Science 116(Pt 2):345-352, Company of Biologists, London (Jan. 2003).

Nicholson J.P., et al., "Properties of Virion Transactivator Proteins encoded by Primate Cytomegaloviruses," Journal of Virology, 6:65, BioMed Central, England (May 2009).

Ulmer, J.B., et al., "Heterologous Protection against Influenza by injection of DNA Encoding a Viral Protein," Science 259(5102):1745-1749, American Association for the Advancement of Science, United States (Mar. 1993).

Cranage, M., et al., "Carriers for the delivery of a vaccine against respiratory syncytial virus," Expert Opinion on Biological therapy 5(7):939-952, Taylor & Francis, United States (2005).

Antonis, A.F., "Vaccination with recombinant modified vaccinia virus Ankara expressing bovine respiratory syncytial virus (bRSV) proteins protects calves against RSV challenge." Vaccine 15(25):4818-4827, Elsevier, Netherlands (2007).

Kovarik, J., et al., "Induction of adult-like antibody, Th1, and CTL responses to measles hemagglutinin by early life murine immunization with an attenuated vaccinia-derived NYVAC (K1L) viral vector," Virology 285(1):12-20, Elsevier, Netherlands (2001).

Welter, J., et al., "Mucosal vaccination with recombinant poxvirus vaccines protects ferrets against symptomatic CDV infection," Vaccine 17(4):308-318, Elsevier, Netherlands (1999).

Guillaume, V., et al., "Nipah Virus: Vaccination and passive protection studies in a hamster model," Journal of Virology 78(2):834-840, American Society for Microbiology, United States (2004).

Wyatt, L.S., et al., "Development of a replication-deficient recombinant vaccinia virus vaccine effective against parainfluenza virus 3 infection in an animal model," Vaccine 14(15):1451-1458, Elsevier, Netherlands (1996).

Kenjiro, I., et al., "Long-term protective immunity to rinderpest in cattle following a single vaccination with recombinant vaccinia virus expressing the virus haemagglutinin protein," Journal of General Virology 81(6):1439-1446.

Grey, F., et al., "A human cytomegalovirus-encoded microRNA regulates expression of multiple viral genes involved in replication," PLOS pathogens 3(11):1593-1602, Public Library of Science, United States (2007.).

Ojha, M., et al., "Spatial and cellular localization of calcium-dependent protease (CDP II) in *Allomyces arbuscula*," Journal of Cell Science 116:1095-1105, The Company of Biologists, United Kingdom (2003).

Powers, C.J., et al., "Signal peptide-Dependent Inhibition of MHC Class I Heavy Chain Translation by Rhesus Cytomegalovirus," PLOS Pathogens 4(10):e1000150, Public Library of Science, United States.

Powers, C., et al., "The US2-11 region of RhCMV is both necessary and sufficient to counteract CD8+ T-cell immunity during re-infection of rhesus macaques," 34th Annual International Herpesvirus Workshop, Jul. 25, 2009, Ithaca, New York.

Smith, M.S., et al., "Roles of Phosphatidylinositol 3-Kinase and NF-B in Human Cytomegalovirus-Mediated Monocyte Diapedesis and Adhesion: Strategy for Viral Persistence," Journal of Virology 81(14):7683-7694, American Society for Microbiology, United States (2007).

Bentz, G.L., et al., "Human Cytomegalovirus (HCMV) Infection of endothelial Cells Promotes Naïve Monocyte Extravasation and transfer of Productive Virus to Enhance Hematogenous Dissemination of HCMV," Journal of Virology 80(23):11539-15555, American Society for Microbiology, United States (2006).

Gerna, G., et al., "Dendritic-cell infection by human cytomegalovirus is restricted to strains carrying functional UL131-128 genes and mediates efficient viral antigen presentation to CD8+ T cells," Journal of General Virology 86:275-284, Microbiology Society, United Kingdom (2005).

(56) References Cited

OTHER PUBLICATIONS

Bego, M., et al., "Characterization of an Antisense Transcript Spanning the Ul81-82 Locus of Human Cytomegalovirus," Journal of Virology, 79(17)11022-11034, American Society for Microbiology, United States (Sep. 2005).

Khan, N., et al., "Identification of Cytomegalovirus-Specific Cytotoxic T Lymphocytes In Vitro Is Greatly Enhanced by the Use of Recombinant Virus Lacking the Us2 to Us11 Region or Modified Vaccinia Virus Ankara Expressing Individual Viral Genes," Journal of Virology, 79(5):2869-2879, American Society for Microbiology, United States (Mar. 2005).

Nicholson, I.P., et al., "Properties of Virion Transactivator Proteins Encoded by Primate Cytomegaloviruses," Journal of Virology, 6:65, BioMed Central, England (2009).

Noriega, V., et al., "Diverse Immune Evasion Strategies by Human Cytomegalovirus," Immunologic Research, 54(1-3):140-151, Humana Press, United States (Dec. 2012).

Supplementary European Search Report for EP Application No. EP 16749813, Munich, Germany, dated Aug. 29, 2018.

Noreiga, V., et al., "Human Cytomegalovirus US28 Facilitates Cell-to-cell Viral dissemination," Viruses 6(3):1202-1218, Nature, United States (2013).

Kenneson, A and Cannon, M.J., "Review and Meta-analysis of the Epidemiology of Congenital Cytomegalovirus (CMV) Infection," Reviews in Medical Virology 17(4): 253-276, Wiley, England (Jul.-Aug. 2007).

Bowman, J.J., et al., "Rhesus and Human Cytomegalovirus Glycoprotein L are Required for Infection and Cell-to-Cell Spread of Virus but Cannot Complement Each Other," Journal of Virology, 85(5): 2089-2099, American Society for Microbiology, United States (Mar. 2011).

Corpet, F, "Multiple Sequence Alignment With Hierarchical Clustering," Nucleic Acids Research 16(22):10881-10890, Oxford University Press, England (Nov. 1988).

Dhuruvasan, K., et al., "Roles of Host and Viral MicroRNAs in Human Cytomegalovirus Biology," Virus Research, 157(2):180-192, Elsevier Science, Netherlands (May 2011).

Hancock, J.M and Armstrong, J.S., "SIMPLE34: an Improved and Enhanced Implementation for Vax and Sun Computers of the Simple Algorithm for Analysis of Clustered Repetitive Motifs in Nucleotide Sequences," Computer Applications in the Biosciences,10(1):67-70, Oxford University Press, England (Feb. 1994).

Hobom, U., et al., "Fast Screening Procedures for Random Transposon Libraries of Cloned Herpesvirus Genomes: Mutational Analysis of Human Cytomegalovirus Envelope Glycoprotein Genes," Journal of Virology, 74(17):7720-7729, American Society for Microbiology (Sep. 2000).

Matthews, T.J., et al., "Prospects for Development of a Vaccine against HTLV-III-related Disorders," AIDS Research and Human Retroviruses, 3(1):197-206, Mary Ann Liebert, United States (1987).

O'Connor, C.M., et al., "Host microRNA Regulation of Human Cytomegalovirus Immediate Early Protein Translation Promotes Viral Latency," Journal of Virology, 88(10):5524-5532, American Society for Microbiology, United States (May 2014).

Snyder, C.M., et al., "Cross-presentation of a Spread-defective MCMV is Sufficient to Prime the Majority of Virus-specific CD8+T Cells," PLoS One, 5(3):e9681, Public Library of Science, United States (Mar. 2010).

Mann, J. et al., "HIV-1 vaccine immunogen design strategies," Virology Journal 12(3): 1-11, BioMed Central, United Kingdom (2015).

Wu, H., et al., "Universal, MHC-E restricted CD8 T cell responses participate in cytomegalovirus vaccine vector-induced protection against SIV," <retrieved from https://youtube.com/watch?v=0vv9o115ZDQ>.

Dolan, A., et al., "Genetic Content of Wild-Type Human Cytomegalovirus," Journal of General Virology, 85(Pt 5):1301-1312, Microbiology Society, England (May 2004).

Geisler, A., et al., "MicroRNA-Regulated Viral Vectors for Gene Therapy," World Journal of Experimental Medicine, 6(2):37-54, Baishideng Publishing Group, United States (May 2016).

Guo, X.Z., et al., "Rapid Cloning, Expression, and Functional Characterization of Paired $\alpha\beta$ and $\gamma\delta$ T-Cell Receptor Chains from Single-Cell Analysis," Molecular Therapy: Methods & Clinical Development, 3:15054, Cell Press, United States (Jan. 2016).

Hahn, G., et al., "The Human Cytomegalovirus Ribonucleotide Reductase Homolog Ul45 Is Dispensable for Growth in Endothelial Cells, as Determined by a Bac-Cloned Clinical Isolate of Human Cytomegalovirus With Preserved Wild-Type Characteristics," Journal of Virology, 76(18):9551-9555, American Society for Microbiology, United States (Sep. 2002).

O'Connor, C.M and Shenk, T., "Human Cytomegalovirus pUL78 G Protein-Coupled Receptor Homologue Is Required for Timely Cell Entry in Epithelial Cells but Not Fibroblasts," Journal of Virology, 86(21):11425-11433, American Society for Microbiology, United States (Nov. 2012).

Retrieved from the Internet: (URL: http://www.microma.org/microma/getTargets.do?matureName=hsa-miR-142-3p&organism=9606), last accessed Oct. 6, 2015.

Terhune, S., et al., "Human Cytomegalovirus Ul38 Protein Blocks Apoptosis," Journal of Virology, 81(7):3109-3123, American Society for Microbiology, United States (Apr. 2007).

Wagner, S., et al., "The 7-transmembrane Protein Homologue Ul78 of the Human Cytomegalovirus Forms Oligomers and Traffics Between the Plasma Membrane and Different Intracellular Compartments," Archives of Virology, 157(5):935-949, Springer-Verlag, Austria (May 2012).

Office action dated Sep. 5, 2018, in U.S. Appl. No. 15/549,814, §371(c) filed Aug. 9, 2017, inventor Frueh, K., et al., 12 pages.

Office action dated Mar. 17, 2020, in U.S. Appl. No. 15/549,814, §371(c) filed Aug. 9, 2017, inventor Frueh, K., et al., 12 pages.

RH67 deleted; strain 68-1 RhCMV/gag (UL128/UL130 deleted) vaccine:

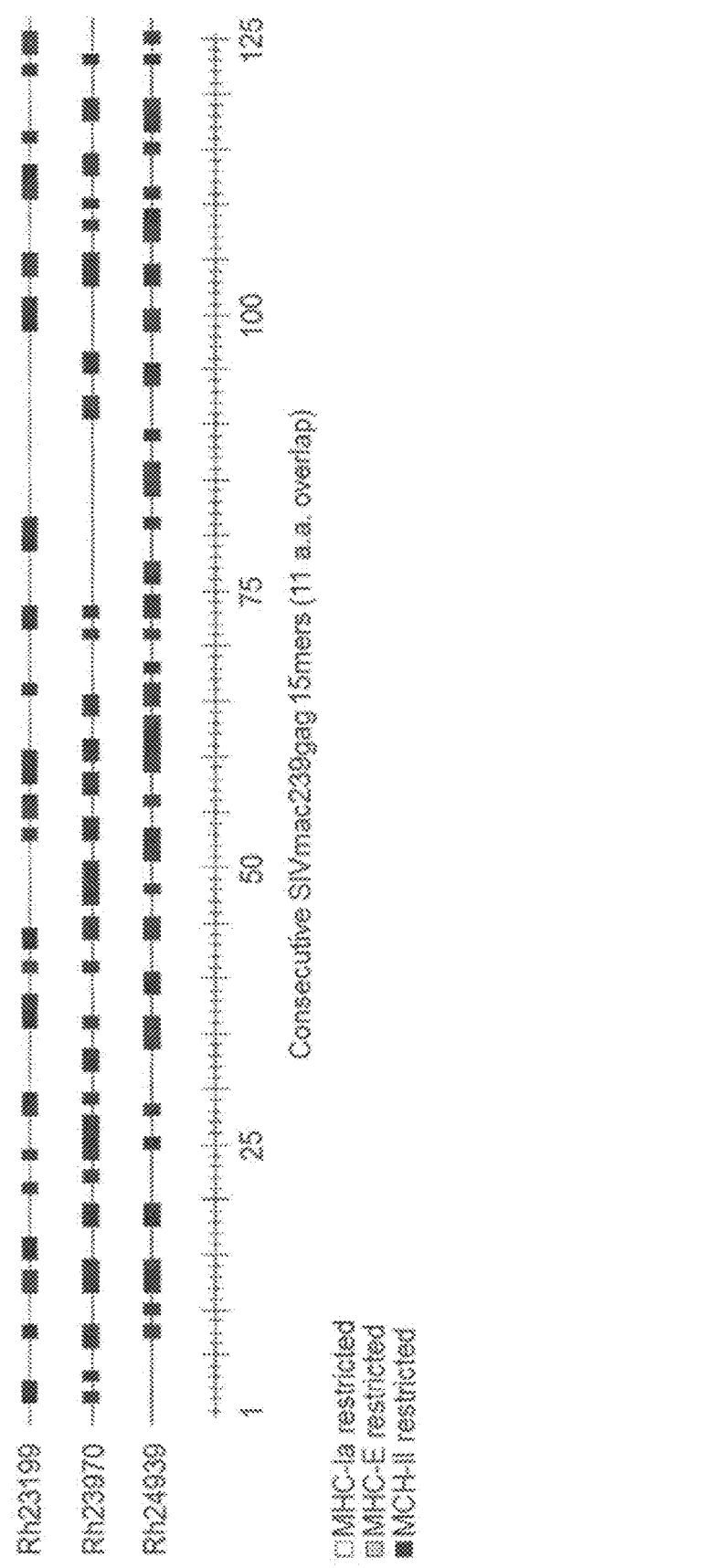

| Mamu Class I Alleles | Rhesus macaques | | | |
|---|---|---|---|---|
| | 21826 | 22034 | 22436 | 22607 |
| A1*001:01 | X | | | X |
| A1*002:01 | X | X | X | X |
| A1*012:01 | | | X | |
| A1*023:01 | | X | | |
| A2*05:01; A2*05:11; A2*05:28; A2*05:32:01; A2*05:32:02; A2*05:45 | | | X | |
| A2*05:04:01; A2*05:04:03; A2*05:10; A2*05:14 | | | | X |
| A3*13:02 | X | X | X | X |
| A4*14:03:01; A2*14:09 | | X | | |
| B*001:01:01 | | X | | X |
| B*007:02 | | | | X |
| B*012:01 | X | | | X |
| B*017:01 | X | | | |
| B*021:01 | | X | | |
| B*022:01 | X | | | |
| B*028:01 | | X | | |
| B*029:01 | X | | | |
| B*030:01 | X | | | |
| B*030:05 | | X | | X |
| B*031:01 | X | | | |
| B*041:01 | | | X | |
| B*046:01:02 | | X | | |
| B*048:01 | | | X | |
| B*055:01 | | | X | |
| B*057:01 | X | | | X |
| B*058:02 | | | X | |
| B*060:02 | | | | |
| B*061:01 | X | | | |
| B*064:01 | | | X | |
| B*068:03 | | X | | |
| B*072:01; B*072:02; Mm-B*nov121 | | X | | X |
| B*074:01 | X | | | X |
| B*082:02 | | | | X |
| Mm-B*nov037 | X | | | |
| Mm-B*nov113 | | X | | |
| E*02:01:02 | | | | |
| E*02:10; E*02:11 | X | | | X |
| E*02:04 | X | X | X | X |
| E*02:09 | X | | | |
| E*02:12:01; E*02:12:02 | | X | | |
| E*02:20 | X | | | X |

▓ Transfectant generated

| Macaque | A1*001:01 | A1*002:01 | Gag$_{69-83}$ (18) | Gag$_{129-143}$ (33) | Gag$_{197-211}$ (55) |
|---|---|---|---|---|---|
| Rh22607 | + | + | + | + | − |
| Rh21826 | + | + | − | + | + |
| Rh25565 | + | − | + | + | + |
| Rh25545 | + | − | − | − | − |
| Rh22034 | − | + | + | − | − |
| Rh28819 | − | + | − | − | − |
| Rh28808 | − | + | − | + | − |
| Rh22436 | − | + | − | − | + |
| Rh24194 | − | + | − | − | + |
| Rh27517 | − | − | + | + | − |
| Rh22063 | − | − | + | − | − |
| Rh27473 | − | − | + | − | − |
| Rh27715 | − | − | + | − | − |
| Rh29483 | − | − | + | − | − |
| Rh25222 | − | − | − | + | + |
| Rh29208 | − | − | − | + | + |
| Rh29212 | − | − | − | + | − |
| Rh22624 | − | − | − | + | − |
| Rh29482 | − | − | − | − | + |
| Rh21756 | − | − | − | − | − |

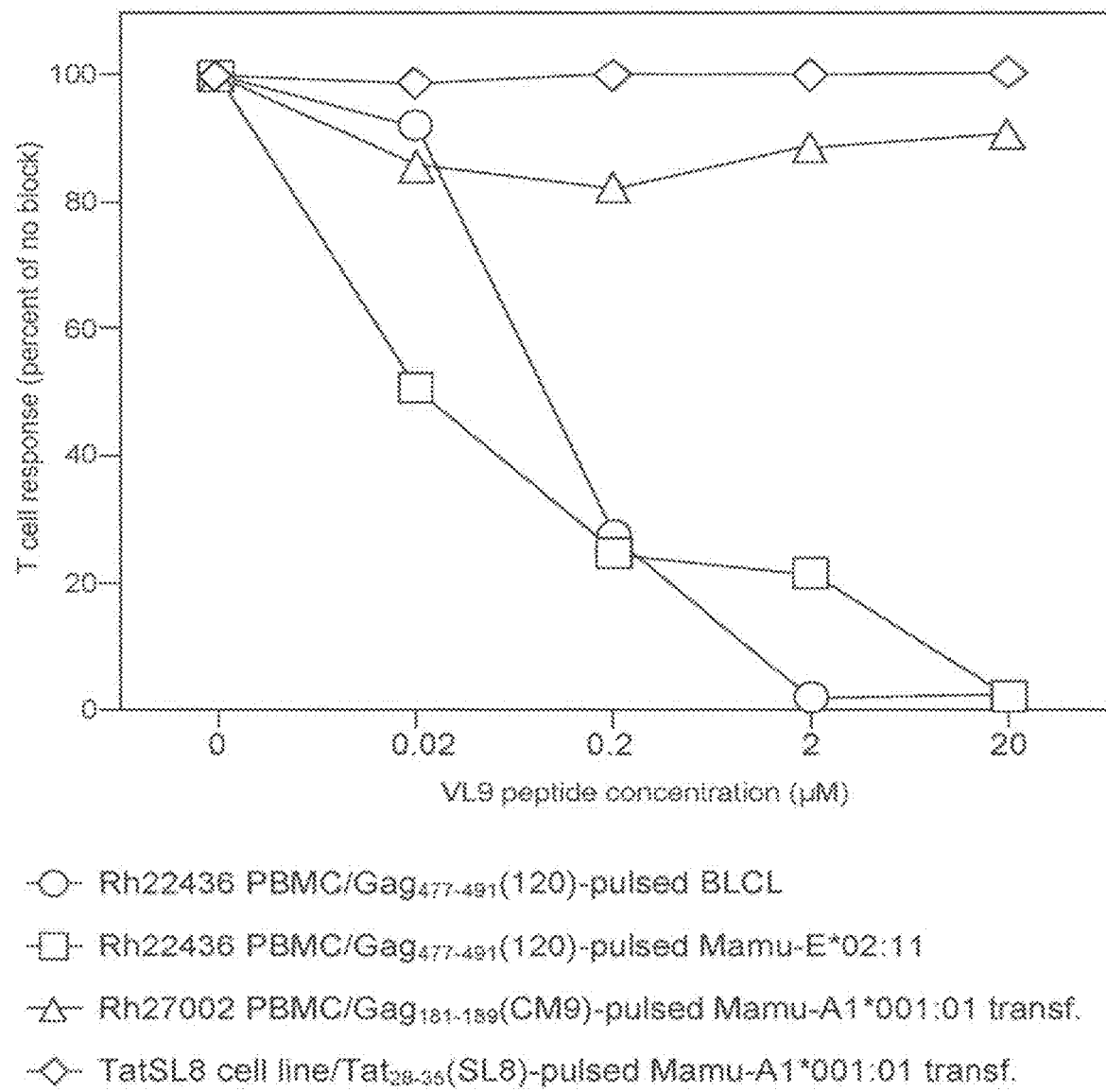

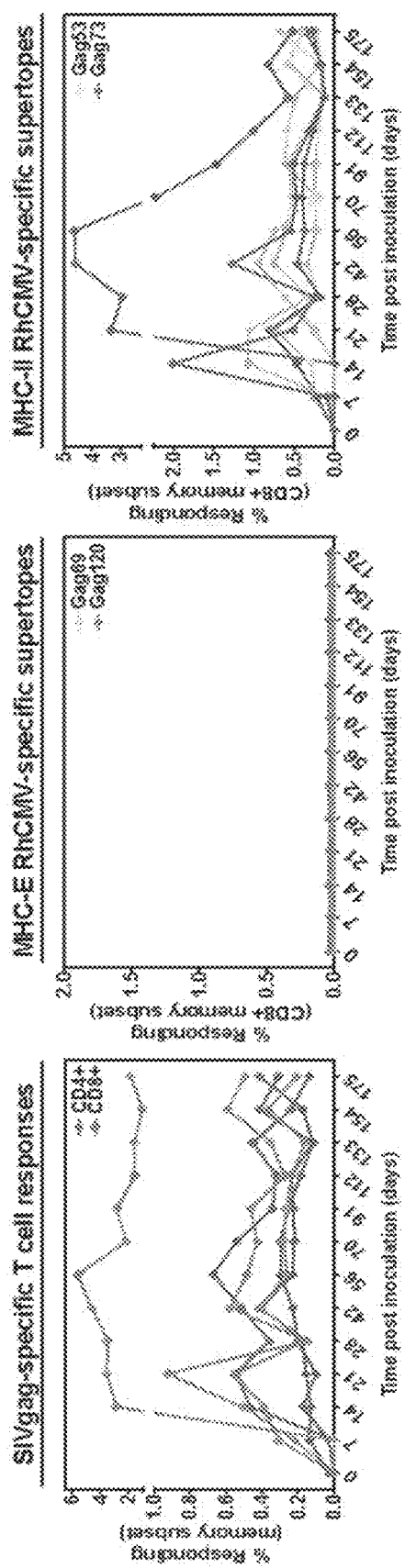

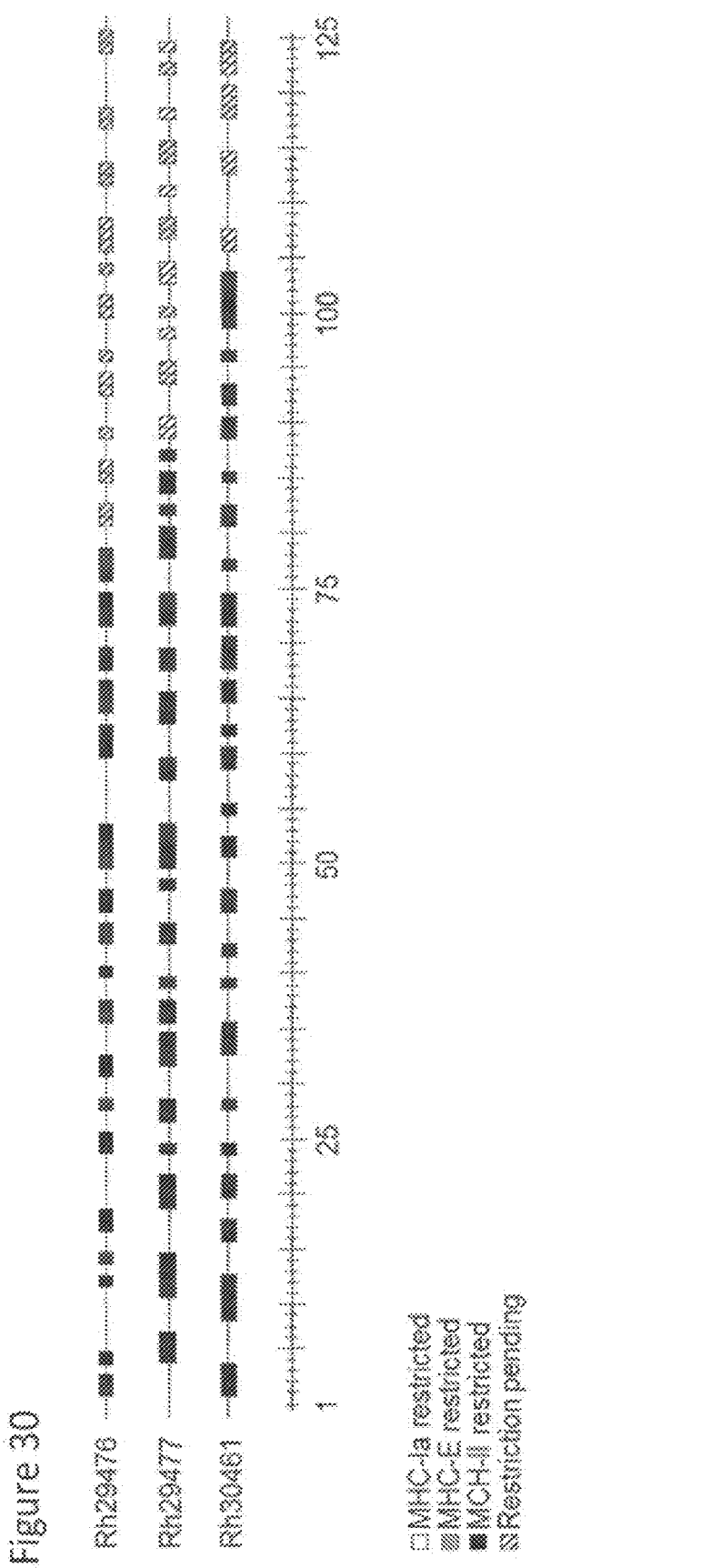

METHODS AND COMPOSITIONS USEFUL IN GENERATING NON CANONICAL CD8+ T CELL RESPONSES

CROSS REFERENCE TO RELATED APPLICATIONS

The present application claims the priority benefit of U.S. Provisional Application No. 62/114,203, filed Feb. 10, 2015; U.S. Provisional Application No. 62/196,520, filed Jul. 24, 2015; and U.S. Provisional Application No. 62/220,703, filed Sep. 18, 2015, each of which are hereby incorporated by reference in their entirety.

ACKNOWLEDGEMENT OF GOVERNMENT SUPPORT

This invention was created with the support of the United States government under the terms of grant number P01 AI094417, awarded by the National Institutes of Health. The United States government has certain rights in this invention.

FIELD

Generally, the held is the use of CMV vectors in immunization. More specifically, the field is the generation of CD8$^+$ immune responses characterized by non-canonical MHC restriction. Still more specifically, the field is the generation of T cells, including CD8$^+$ with receptors that are restricted by MHC-E.

BACKGROUND

Rhesus Cytomegalovirus (RhCMV) vaccine vectors expressing Simian Immunodeficiency Virus (SIV) proteins (RhCMV/SIV) provide protection from pathogenic SIV (Hansen, S. G. et al., *Nat Med* 15, 293 (2009); Hansen, S. G. et al., *Nature* 473, 523 (2011); both of which are incorporated by reference herein). This protection is fundamentally distinct from other T cell vaccines in its extreme efficacy and nearly instantaneous onset, with ~50% of vaccinnees manifesting complete control of viral replication following a profoundly blunted and contracted acute phase of viremia. Although RhCMV-protected macaques exhibited periodic low-level "blips" of viremia, CD4$^+$ memory T cell depletion was not observed, SIV-specific antibody responses did not develop, and subsequently, over time, viral nucleic acid became barely quantifiable while replication competent virus disappeared from the tissues of protected animals. These events did not occur in spontaneous SIV elite controllers and DNA prime/Ad5 boost vaccinated controllers (Hansen, S. G. et al., *Nature* 502, 100 (2013); incorporated by reference herein). Given the central role of RhCMV-induced CD8$^+$ T cells in mediating this protective effect in RhCMV/SIV-vaccinated macaques, defining the functional properties of these T cells is critical to understanding their mechanistic contribution to RhCMV/SIV vector-induced control of SIV replication. Understanding these properties can in turn lead to new uses for cytomegalovirus (CMV) vaccine vectors expressing heterologous antigens.

SUMMARY

Disclosed herein is a method of generating an immune response to at least one heterologous antigen in a subject. The method involves administering to the subject an effective amount of a CMV vector. The CMV vector comprises a first nucleic acid that encodes the at least one heterologous antigen, a second nucleic acid sequence that encodes at least one active UL40 protein, or a homolog or ortholog thereof, and a third nucleic acid sequence that encodes at least one US28 protein, or a homolog or ortholog thereof. The CMV vector does not express an active UL128 protein, or an ortholog thereof, and does not express an active UL130 protein, or an ortholog thereof, and at least 10% of the CD8$^+$ T cells generated by the vector are restricted by MHC-E or a homolog thereof. In some embodiments, the third nucleic acid sequence encodes two through five active US28 proteins, or homologs or orthologs thereof. The heterologous antigen can be any antigen, including a pathogen-specific antigen derived from, for example, human immunodeficiency virus (HIV), simian immunodeficiency virus (SIV), herpes simplex virus, hepatitis B or C virus, papillomavirus, *Plasmodium* parasites, and *Mycobacterium tuberculosis*. In still further examples, the heterologous antigen can be a tumor antigen including, for example, a tumor antigen related to acute myelogenous leukemia, chronic myelogenous leukemia, myelodysplastic syndrome, acute lymphoblastic leukemia, chronic lymphoblastic leukemia, non-Hodgkin's lymphoma, multiple myeloma, malignant melanoma, breast cancer, lung cancer, ovarian cancer, prostate cancer, pancreatic cancer, colon cancer, renal cell carcinoma (RCC), and germ cell tumors. In still further examples, the heterologous antigen can be a tissue-specific antigen or a host self-antigen including, for example, an antigen derived from the variable region of a T cell receptor (TCR), an antigen derived from the variable region of a B cell receptor, a sperm antigen, or an egg antigen. In still further examples, the vector does not encode (1) an active UL40 protein (or an ortholog thereof) and/or an active US28 protein (or an ortholog thereof), (2) an active UL128 protein (or an ortholog thereof), and (3) on active UL130 protein (or an ortholog thereof), giving rise to MHC-II "supertope" restricted CD8$^+$ T cells but not HLA-E restricted CD8$^+$ T cells.

Also disclosed herein is a human or animal cytomegalovirus vector that includes a first nucleic acid sequence that encodes (1) at least one heterologous protein antigen, (2) a second nucleic acid sequence that encodes at least one active UL40 protein, or a homolog or ortholog thereof, and (3) a third nucleic acid sequence that encodes at least one active US28 protein, or a homolog or ortholog thereof. The vector does not express active UL128 and UL130 proteins, or orthologs thereof. In some embodiments, the third nucleic add sequence encodes two through five active US28 proteins, or homologs or orthologs thereof.

Also disclosed is a human or animal cytomegalovirus vector that (1) does not express an active UL128 protein (or an ortholog thereof), (2) does not express an active UL130 protein (or an ortholog thereof), and (3) does not express an active UL40 protein (or an ortholog thereof) and/or an active US28 protein (or an ortholog thereof).

Also disclosed herein is a method of generating CD8$^+$ T cells that recognize MHC-E-peptide complexes. This method involves administering to a first subject a CMV vector that encodes (1) at least one heterologous antigen, (2) at least one active UL40 protein (or an ortholog or homolog thereof), and (3) at least one active US28 gene (or an ortholog or homolog thereof), in an amount effective to generate a set of CD8$^+$ T cells that recognize MHC-E/peptide complexes. The CMV vector does not encode active UL128 and UL130 proteins, or orthologs thereof. In some embodiments, the CMV vector encodes two through five active US28 proteins or orthologs or homologs thereof. The heterologous antigen can be any antigen, including a pathogen-specific antigen, a tumor antigen, a self antigen, or a tissue-specific antigen. In some embodiments, the self-antigen is an antigen derived from the variable region of a T or B cell receptor. In some embodiments, this method may further comprise identifying a first CD8$^+$ T cell receptor from the set of CD8$^+$ T cells, wherein the first CD8$^+$ TCR recognizes a MHC-E/heterologous antigen derived peptide complex. In some embodiments, the first CD8$^+$ T cell receptor is identified by DNA or RNA sequencing. In some embodiments, this method may further comprise transfecting one or more T cells isolated from the first subject or a second subject with an expression vector, wherein the expression vector comprises a nucleic acid sequence encoding a second CD8$^+$ T cell receptor and a promoter operably linked to the nucleic acid sequence encoding the second CD8$^+$ T cell receptor, wherein the second CD8$^+$ T cell receptor comprises CDR3α and CDR3β of the first CD8$^+$ T cell receptor, thereby generating one or more transfected CD8$^+$ T cells that recognize a MHC-E/heterologous antigen-derived peptide complex. In some embodiments, this method may further comprise administering the transfected CD8$^+$ T cells to the first or second subject to treat a disease, such as cancer, a pathogenic infection, or an autoimmune disease or disorder. In some embodiments, this method may further comprise administering the transfected CD8$^+$ T cells to the first or second subject to induce an autoimmune response to a self-antigen or a tissue specific antigen.

Also disclosed is a transfected CD8$^+$ T cell that recognizes MHC-E-peptide complexes prepared by a process comprising the steps of: (1) administering to a first subject a CMV vector in an amount effective to generate a set of CD8$^+$ T cells that recognize MHC-E/peptide complexes, wherein the CMV vector comprises a first nucleic acid sequence encoding at least one heterologous antigen, a second nucleic acid sequence encoding at least one active UL40 protein, or an ortholog or homolog thereof, and a third nucleic acid sequence encoding at least one active US28 protein, or an ortholog or homolog thereof, and wherein the CMV vector does not express active UL128 and UL130 proteins, or orthologs thereof; (2) identifying a first CD8$^+$ T cell receptor from the set of CD8$^+$ T cells, wherein the first CD8$^+$ T cell receptor recognizes a MHC-E/heterologous antigen-derived peptide complex; (3) isolating one or more CD8$^+$ T cells from the first subject or a second subject; and (4) transfecting the one or more CD8$^+$ T cells isolated from the first or second subject with an expression vector, wherein the expression vector comprises a nucleic acid sequence encoding a second CD8$^+$ T cell receptor and a promoter operably linked to the nucleic acid sequence encoding the second T cell receptor, wherein the second CD8$^+$ T cell receptor comprises CDR3α and CDR3β of the first CD8$^+$ T cell receptor, thereby creating a transfected T cell that recognizes MHC-E-peptide complexes. The heterologous antigen can be any antigen, including a pathogen-specific antigen or a tumor antigen. In some embodiments, the third nucleic acid sequence of the CMV vector encodes two through five active US28 proteins, or orthologs or homologs thereof. Also disclosed herein are methods of treating a disease, such as cancer, a pathogenic infection, or an autoimmune disease or disorder, the method comprising administering the transfected CD8$^+$ T cell that recognizes MHC-E-peptide complexes to the first or second subject.

BRIEF DESCRIPTION OF THE SEVERAL VIEWS OF THE DRAWINGS

Some of the graphs and plots included herein may be better understood using color, which is not available in a patent application publication. Applicants consider all originally disclosed images and graphs (whether in color or not) part of the original disclosure and reserve the right to present color graphs and plots of the herein described figures in later proceedings.

FIG. 6 is a table illustrating the CD8$^+$ T cell responses to SIVmac239 Gag epitope-mapped using flow cytometric ICS to detect recognition of 125 consecutive 15 mer Gag peptides (with an 11 amino acid overlap) in macaques vaccinated with strain 68-1 RhCMV/gag factors (n=3) lacking Rh67. Peptides resulting in above background CD8$^+$ T cell responses were subjected to MHC-I (mAb W6/32), MHC-E (Rh67 VL9), and MHC-II (mAb G46-6) blockade and classified as MHC-I blocked (boxes with white fill), MHC-E blocked (boxes with grey fill), and MHC-II blocked (boxes with black fill). Note that all peptides are restricted by MHC-II demonstrating the need for Rh67 to elicit HLA-E specific CD8$^+$ T cell responses.

FIG. 8B is a table showing PBMC from the 4 indicated RM (#s 21826, 22436, 22034, and 22607; Mamu-I alleles shown in FIG. 7B) were incubated with autologous B lymphoblastoid cells (BLCL), MHC-I-null 0.221 or K562 cells, or the indicated single Mamu-I transfectants pulsed with the indicated SIVgag peptides and were then analyzed for CD8+ T cell responses by flow cytometric ICS (see FIG. 1). Beginning in the second column, combinations that resulted in CD8+ T cell responses above background (no peptide) are indicated by + signs (grey boxes); combinations that did not result in CD8+ T cell responses above background are indicated by signs (open boxes). In the first column, Mamu-I alleles that are expressed in each RM are indicated in grey boxes; non-expressed alleles are shown in open boxes.

FIG. 11 collectively shows MHC restriction of strain 68-1 RhCMV/SIVgag-elicited CD8+ T cells.

FIG. 12 collectively shows that MHC-E restriction is limited to CD8+ T cell responses elicited by ΔRh157.5/.4 RhCMV vectors.

FIG. 15 collectively shows the validation of transfected cell lines expressing single MHC-I molecules corresponding to MHC-I molecules expressed by 4 strain 68-1 RhCMV/SIVgag-vaccinated macaques.

FIG. 15A is a table showing the results where four strain 68-1 RhCMV/SIVgag-vaccinated macaques were Mamu-A, -B, and -E genotyped by Roche/454 pyrosequencing. Grey shading indicates alleles selected for MHC-I transfectant generation. Where multiple alleles are listed, a transfectant expressing the bolded allomorph was produced.

FIGS. 16A and 16B collectively show a comprehensive analysis of the MHC-Ia and MHC-Ib specificity of RhCMV/SIVgag induced CD8+ T cell response in 4 macaques.

FIG. 16A is a set of plots showing representative flow cytometric ICS profiles of MHC restriction analysis of the $SIVgag_{433-447}(109)$ response using PBMC from Rh22034. The TNF-α vs. IFN-γ flow profiles shown were gated on CD3+, CD8+ lymphocytes, with the fraction of cells in each quadrant indicated in the figure.

FIG. 16B is a table showing PBMC from the 4 indicated macaques (MHC-typing shown in FIG. 15A) that were incubated with autologous B-lymphoblastoid cells (BLCL), MHC-I-negative 0.221 or K562 cells, or single MHC-I transfectants pulsed (and washed) with the indicated SIVgag peptides, and were then analysed for CD8+ T cell responses by flow cytometric ICS. Beginning in the second column, combinations that resulted in CD8+ T cell responses above background (no peptide) are indicated by + signs (grey boxes); combinations that did not result in CD8+ T cell responses above background are indicated by − signs (open boxes). In the first column, MHC-I alleles expressed in each RM are indicated in grey boxes; non-expressed alleles are shown in open boxes (expression of Mamu-F*01:01 unknown).

FIG. 17 is a table showing that classical MHC-Ia allomorphs capable of presenting SIVgag peptides to strain 68-1 RhCMV/SIVgag-elicited CD8+ T cells are not the restricting MHC alleles for these T cell responses. A cohort of 20 strain 68-1 RhCMV/SIVgag vector-vaccinated macaques were MHC-typed for the presence of Mamu-A1*001:01 and -A1*002:01 and tested for CD8+ T cell responses specific for $SIVgag_{69-83}(18)$, $SIVgag_{129-143}(33)$, and $SIVgag_{197-211}$ (50). Note that the detection of CD8+ T cells specific for these three epitopes in strain 68-1 RhCMV/gag vector-vaccinated macaques is independent of the presence of Mamu-A1*001:01 or -A1*002:01 in the vaccinated animal.

FIG. 18A is a set of plots showing PBMCs from strain 68-1 RhCMV/SIVgag vector-vaccinated macaques [Rh21826: $SIVgag_{89-103}(23)$, $SIVgag_{129-143}(33)$, $SIVgag_{257-271}(65)$, $SIVgag_{473-487}(119)$; Rh22034: $SIVgag_{61-75}(16)$, $SIVgag_{69-83}(18)$, $SIVgag_{271-287}(69)$, $SIVgag_{385-399}(97)$, $SIVgag_{477-491}(120)$; Rh22436: $SIVgag_{197-211}(30)$, $SIVgag_{197-211}(50)$] were evaluated for peptide specific CD8+ T cell recognition using flow cytometric ICS to detect IFN-γ and/or TNF-α production (response frequencies of CD8+ T cells shown in each quadrant) following incubation with the indicated Gag 15-mer peptides pulsed (and washed) on the indicated MHC-E transfectants and control antigen presenting cells (see FIG. 11). Note that all 12 MHC-E-restricted 15 mer peptide epitopes can be effectively presented to strain 68-1 RhCMV/SIVgag vector-elicited CD8+ T cells on both Mamu-E allomorphs and on HLA-E.

FIG. 18B is an amino acid alignment of the α1 and α2 regions of human and rhesus macaque MHC-E molecules expressed by transfectants represented in FIG. 18A, with the key B and F pocket residues indicated with grey shading. All of the B and F pocket residues interacting with bound peptide are conserved between HLA-E*01:03, Mamu-E*02:04, and Mamu-E*02:11, while substitutions exist in these residues in Mamu-E*02:20, the most disparate of the MHC-E molecules studied here. Despite harboring substitutions in both B and F pocket residues compared to the other allomorphs, Mamu-E*02:20 is able to bind and present the identical peptides.

FIG. 20B is a plot where the indicated antigen presenting cells were pre-incubated with increasing concentrations of VL9 prior to pulse with the SIVgag$_{477-491}$(120) SIVgag 15-mer or optimal Mamu-A1*001:01-restricted Gag-CM9 or Tat-SL8 peptides. These antigen-presenting cells were then incubated with the indicated effectors for flow cytometric ICS analysis, as described for FIG. 20A. Rh22436 is a 68-1 RhCMV/SIVgag-vaccinated RM, while Rh27002 is SIV-infected. Note that increasing concentrations of VL9 peptide progressively block the ability of MHC-E-expressing antigen-presenting cells to activate SIVgag$_{477-491}$(120)-specific CD8+ T cells from a strain 68-1 RhCMV/gag vector vaccinated macaque, but have no effect on conventionally MHC-Ia-restricted CD8+ T cells specific for Gag-CM9 or Tat-SL8.

FIG. 22A is a set of plots showing a representative analysis of the dose response to SIVgag$_{476-484}$ in Rh22607.

FIG. 22B is a set of plots showing the dose response (mean±SEM response frequencies) for CD8+ T cells responding to SIVgag$_{258-267}$, SIVgag$_{276-284}$, SIVgag$_{482-490}$ with response frequencies normalized to the response observed with the transfectant pulsed with 10 μM peptide dose.

FIG. 24A shows representative flow cytometric response profiles (IFN-γ vs. TNF-α on gated CD3+, CD8+ T cells) of MHC-I-dependent, SIVgag epitope-specific CD8+ T cells elicited by the strain 68-1 (Rh157.4/.5-deleted) RhCMV/gag vectors, with and without blocking with the pan anti-MHC-I-blocking mAh W6-32 or the MHC-E-blocking VL9 peptide.

FIG. 24B shows representative flow cytometric response profiles (IFN-γ vs. TNF-α on gated CD3+, CD8+ T cells) of MHC-I-dependent, SIVgag epitope-specific CD8+ T cells elicited by the strain 68-1.2 (Rh157.4/.5-intact) RhCMV/gag vectors, with and without blocking with the pan anti-MHC-I-blocking mAb W6-32 or the MHC-E-blocking VL9 peptide (see FIG. 20). Note that the VL9 peptide only blocks all MHC-I-dependent responses elicited by the strain 68-1 RhCMV vector.

FIG. 3C). However, all but one of the 125 consecutive SIVgag 15 mers are recognised by MHC-Ia-restricted CD8+ T cells in at least one macaque, and all but 13 SIVgag 15 mers are targeted in 2 or more macaques. In contrast, the MHC-E-restricted CD8+ T cells elicited in 42 macaques by the strain 68-1 RhCMV/gag vector failed to recognize 16 of 125 SIVgag 15 mers. Thus, while the MHC-E-restricted CD8+ T cell responses elicited by strain 68-1 RhCMV vectors are remarkably broad for a functionally monomorphic restricting element, they are not as broad as responses supported by an entire population of polymorphic MHC-Ia molecules, perhaps accounting for the evolutionary dominance of the MHC-Ia-restricted antigen presentation system.

FIG. 29 is a set of three plots. The left panel shows the percentage of CD8+ T cells in PBMC from a rhesus macaque inoculated with a Rh214 to Rh220-deleted 68-1RhCMV expressing SIVgag showing IFN-γ and/or TNF-α production following incubation with overlapping peptides corresponding to SIVgag at the indicated time points. The gene region Rh214 to Rh220 encodes five genes with homology to human cytomegalovirus (HCMV) US28: Rh214, Rh215, Rh216, Rh218, Rh220 (D. Malouli et al., *J Virol* 86, 8959 (2012); incorporated by reference herein). The center panel shows that CD8+ T cells in PBMC from the same animal do not respond to the Mamu-E-restricted peptides $Gag_{273-287}$ (Gag69) or $Gag_{477-491}$ (Gag120). The right panel shows the percentage of CD8+ T cells in PBMC from the same animal responding to MHC-II restricted peptides (Gag53 and Gag73). The MHC-II peptides correspond to so-called supertopes, i.e. these peptides are presented by many different MHC-II alleles and hence elicit responses in most animals.

FIG. 30 is a table illustrating the CD8+ T cell responses to SIVmac239 Gag epitope-mapped using flow cytometric ICS to detect recognition of 125 consecutive 15 mer Gag peptides (with an 11 amino add overlap) in macaques vaccinated with strain 68-1 RhCMV/gag vectors (n=3) lacking Rh214-220. Peptides resulting in above background CD8+ T cell responses were subjected to MHC-I (mAb W6/32), MHC-E (Rh67 VL9), and MHC-II (mAb G46-6) blockade and classified as MHC-I blocked (boxes with white fill), MHC-E blocked (boxes with grey fill), MHC-II blocked (boxes with black fill), or indeterminate (boxes with hatch fill). Note that all peptides are restricted by MHC-II demonstrating the need for Rh214-220 to elicit HLA-E specific CD8+ T cell responses.

DETAILED DESCRIPTION

Figure 1A:
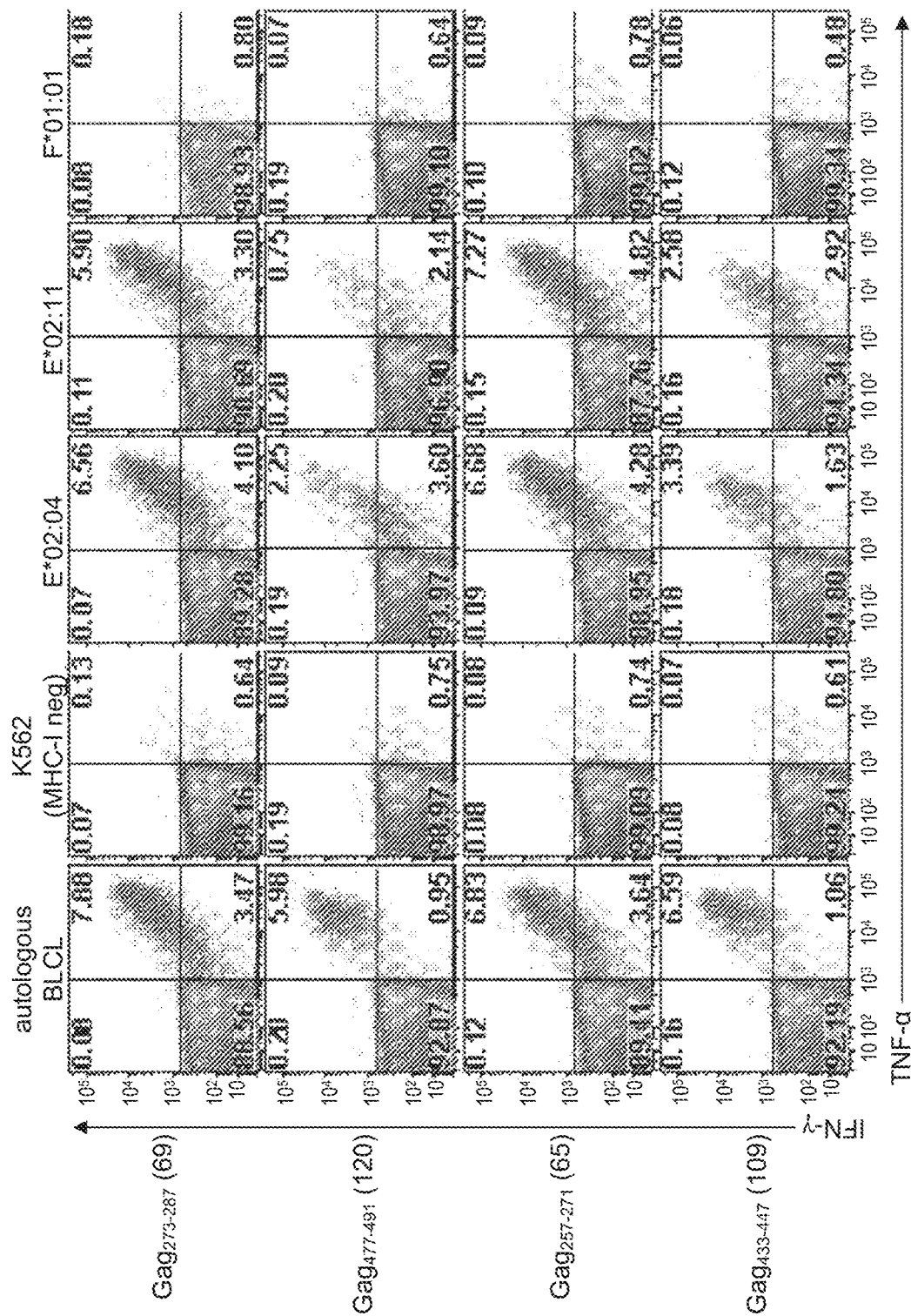
FIG. 1A is a set of flow cytometry plots of peripheral blood mononuclear cells (PBMCs) from a strain 68-1 RhCMV/gag-vaccinated macaque (either Rh22034 or Rh21826). As discussed in Example 1, RhCMV strain 68-1 does not express gene products from the Rh13, Rh60, Rh157.5 and 157.4 (HCMV RL11, UL36, UL128 and UL130, respectively) open reading frames. PBMCs were evaluated for peptide-specific CD8$^+$ T cell recognition using flow cytometric intracellular cytokine staining (ICS) to detect IFN-γ and/or TNF-α production (response frequencies of CD8$^+$ T cells shown in each quadrant) following incubation with the indicated antigen presenting cells that were pulsed with the peptide shown. The parental, MHC-I negative K562 cells were used as negative controls and also transfected to express the MHC-I molecule indicated, while autologous B-lymphoblastoid cell lines (BLCL) were used as the positive control.

The present invention provides novel recombinant CMV vectors including, but not limited to, recombinant CMV vectors comprising nucleic acids encoding at least one heterologous protein antigen, at least one active UL40 protein, and at least one active US28 protein, but that do not express active UL128 and UL130 proteins. The present invention also provides recombinant CMV vectors including, but not limited to, recombinant CMV vectors comprising nucleic acids encoding at least one heterologous antigen, but that do not express (1) an active UL40 protein and/or an active US28 protein, (2) an active UL128 protein, and (3) an active UL130 protein. Methods of using the novel recombinant CMV vectors, such as methods of generating an immune response to at least one heterologous antigen in a subject, methods of generating CD8+ T cells that recognize MHC-E-peptide complexes, and methods of treating disease, are further provided.

I. Definitions

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference; published by VCR Publishers, Inc., 1995 (ISBN 1-56081-569-8).

All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise, it is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." In addition, the materials, methods, and examples are illustrative only and not intended to be limiting. In order to facilitate review of the various embodiments of the disclosure, the following explanations of specific terms are provided:

Antigen: As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

Administration: To provide or give a subject an agent, such as a composition comprising an effective amount of an HCMV vector comprising an exogenous antigen by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes.

Cancer: A disease or condition in which abnormal cells divide without control and are able to invade other tissues. Cancer cells may spread to other body parts through the blood and lymphatic systems. Cancer is a term for many diseases. There are more than 100 different types of cancer in humans. Most cancers are named after the organ in which they originate. For instance, a cancer that begins in the colon may be called a colon cancer. However, the characteristics of a cancer, especially with regard to the sensitivity of the cancer to therapeutic compounds, are not limited to the organ in which the cancer originates. A cancer cell is any cell derived from any cancer, whether in vitro or in vivo.

Cancer also includes malignant tumors characterized by abnormal or uncontrolled cell growth. Other features often associated with cancer include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc.

"Metastatic disease" or "metastasis" refers to cancer cells that have left the original tumor site and migrate to other parts of the body for example via the bloodstream or lymph system. The "pathology" of cancer includes all phenomena that compromise the wellbeing of the subject. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

Effective amount: As used herein, the term "effective amount" refers to an amount of an agent, such as a CMV vector comprising a heterologous antigen or a transfected CD8+ T cell that recognizes a MHC-E/heterologous antigen-derived peptide complex, that is sufficient to generate a desired response, such as reduce or eliminate a sign or symptom of a condition or disease or induce an immune response to an antigen. In some examples, an "effective amount" is one that treats (including prophylaxis) one or more symptoms and/or underlying causes of any of a disorder or disease. An effective amount can be a therapeutically effective amount, including an amount that prevents one or more signs or symptoms of a particular disease or condition from developing, such as one or more signs or symptoms associated with infectious disease, cancer, or autoimmune disease.

Mutation: A mutation is any difference in a nucleic acid or polypeptide sequence from a normal, consensus or "wild type" sequence. A mutant is any protein or nucleic acid sequence comprising a mutation. In addition a cell or an organism with a mutation may also be referred to as a mutant.

Some types of coding sequence mutations include point mutations (differences in individual nucleotides or amino acids); silent mutations (differences in nucleotides that do not result in an amino acid changes); deletions (differences in which one or more nucleotides or amino acids are missing, up to and including a deletion of the entire coding sequence of a gene); frameshift mutations (differences in which deletion of a number of nucleotides indivisible by 3 results in an alteration of the amino acid sequence. A mutation that results in a difference in an amino acid may also be called an amino acid substitution mutation. Amino acid substitution mutations may be described by the amino acid change relative to wild type at a particular position in the amino acid sequence.

As used herein, an "inactivating mutation" is any mutation in a viral gene which finally leads to a reduced function or to a complete loss of function of the viral protein.

Nucleotide sequences or nucleic acid sequences: The terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic adds. The nucleic add can be single-stranded, or partially or completely double stranded (duplex). Duplex nucleic acids can be homoduplex or heteroduplex.

Recombinant: A recombinant nucleic acid or polypeptide is one that has a sequence that is not naturally occurring or has a sequence that is made by an artificial combination of two or more, otherwise separated segments of sequence, for example a CMV vector comprising a heterologous antigen and/or made replication deficient by the mutation of one or more genes. This artificial combination is often accomplished by chemical synthesis or, more commonly, by the artificial manipulation of isolated segments of nucleic acids, e.g., by genetic engineering techniques. A recombinant polypeptide can also refer to a polypeptide that has been made using recombinant nucleic acids, including recombinant nucleic acids transferred to a host organism that is not the natural source of the polypeptide (for example, nucleic acids encoding polypeptides that form a CMV vector comprising a heterologous antigen).

Replication-deficient: As used herein, a replication deficient CMV is a virus that once in a host cell, cannot undergo viral replication, or is significantly limited in its ability to replicate its genome and thus produce virions. In other examples, replication-deficient viruses are dissemination-deficient, i.e. they are capable of replicating their genomes, but unable to infect another cell either because virus particles are not released from the infected cell or because non-infectious viral particles are released. In other examples, replication-deficient viruses are spread deficient, i.e. infectious virus is not secreted from the infected host are therefore the virus is unable to spread from host to host. In some embodiments, a replication-deficient CMV is a CMV comprising a mutation that results in a lack of expression of one or more genes essential for viral replication ("essential genes") or required for optimal replication ("augmenting genes"). CMV essential and augmenting genes have been described in the art (in particular US 2013/0136768, which is incorporated by reference herein) and are disclosed herein.

Pharmaceutically acceptable carriers: The pharmaceutically acceptable carriers of use are conventional. Remington's Pharmaceutical Sciences, by E. W. Martin, Mack Publishing Co., Easton, Pa., 19th Edition, 1995, describes compositions and formulations suitable for pharmaceutical delivery of the compositions disclosed herein. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: As used herein, the term "polynucleotide" refers to a polymer of ribonucleic add (RNA) or deoxyribonucleic acid (DNA). A polynucleotide is made up of four bases; adenine, cytosine, guanine, and thymine/uracil (uracil is used in RNA). A coding sequence from a nucleic acid is indicative of the sequence of the protein encoded by the nucleic acid.

Polypeptide: The terms "protein", "peptide", "polypeptide", and "amino acid sequence" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage identity or similarity (which takes into account conservative amino acid substitutions); the higher the percentage, the more similar the sequences are. Polypeptides or protein domains thereof that have a significant amount of sequence identity and also function the same or similarly to one another (for example, proteins that serve the same functions in different species or mutant forms of a protein that do not change the function of the protein or the magnitude thereof) can be called "homologs."

Methods of alignment of sequences for comparison are well known in the art. Various programs and alignment algorithms are described in: Smith & Waterman, *Adv Appl Math* 2, 482 (1981); Needleman & Wunsch, *J Mol Biol* 48, 443 (1970); Pearson & Lipman, *Proc Natl Acad Sci USA* 85, 2444 (1988); Higgins & Sharp, *Gene* 73, 237-244 (1988); Higgins & Sharp, *CABIOS* 5, 151-153 (1989); Corpet et al., *Nuc Acids Res* 16, 10881-10890 (1988); Huang et al, *Computer App Biosci* 8, 155-165 (1992); and Pearson et al, *Meth Mol Bio* 24, 307-331 (1994). In addition, Altschul et al., *J Mol Biol* 215, 403-410 (1990), presents a detailed consideration of sequence alignment methods and homology calculations.

The NCBI Basic Local Alignment Search Tool (BLAST) (Altschul et al. (1990), supra) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr database, swissprot database, and patented sequences database. Queries searched with the blastn program are filtered with DUST (Hancock & Armstrong, *Comput Appl Biosci* 10, 67-70 (1994).) Other programs use SEG. In addition, a manual alignment can be performed. Proteins with even greater similarity will show increasing percentage identities when assessed by this method, such as at least about 75%, 80%, 85%, 90%, 95%, 98%, or 99% sequence identity to a protein.

When aligning short peptides (fewer than around 30 amino acids), the alignment is be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least about 60%, 70%, 75%, 80%, 85%, 90%, 95%, 98%, or 99% sequence identity to a protein. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least about 50%, 60%, 70%, 80%, 90%, 95%, 98%, or 99% sequence identity to a nucleic add that encodes a protein.

Subject: As used herein, the term "subject" refers to a living multi-cellular vertebrate organisms, a category that includes both human and non-human mammals.

Treatment: As used herein, the term "treatment" refers to an intervention that ameliorates a sign or symptom of a disease or pathological condition. As used herein, the terms "treatment", "treat" and "treating," with reference to a disease, pathological condition or symptom, also refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A prophylactic treatment is a treatment administered to a subject who does not exhibit signs of a disease or exhibits only early signs, for the purpose of decreasing the risk of developing pathology. A therapeutic treatment is a treatment administered to a subject after signs and symptoms of the disease have developed.

II. Recombinant CMV Vectors and Methods of Using the Same

Disclosed herein are human or animal cytomegalovirus (CMV) vectors capable of repeatedly infecting an organism. The CMV vectors comprise a nucleic acid sequence that encodes a heterologous protein antigen and lack expression of active UL128 and UL130 proteins, or orthologs thereof (homologous genes of CMVs that infect other species). The heterologous antigen can be any antigen, including a pathogen-specific antigen derived from, for example, HIV, SIV, herpes simplex virus, hepatitis B or C virus, papillomavirus, *Plasmodium* parasites, and *Mycobacterium tuberculosis*. In still further examples, the heterologous antigen can be a tumor antigen including, for example, a tumor antigen related to acute myelogenous leukemia, chronic myelogenous leukemia, myelodysplastic syndrome, acute lymphoblastic leukemia, chronic lymphoblastic leukemia, non-Hodgkin's lymphoma, multiple myeloma, malignant melanoma, breast cancer, lung cancer, ovarian cancer, prostate cancer, pancreatic cancer, colon cancer, renal cell carcinoma (RCC), and germ cell tumors. In some examples the CMV vectors also lack an active UL40 protein (or an ortholog thereof) and/or an active US28 protein (or an ortholog thereof). In still further examples, the heterologous antigen can be a tissue-specific antigen or a host self-antigen including, for example, an antigen derived from the variable region of a T cell receptor, an antigen derived from the variable region of a B cell receptor, a sperm antigen, or an egg antigen.

In some examples, the vector does not express an active UL128, UL130, US28 or UL40 protein due to the presence of a mutation in the nucleic acid sequence encoding UL128, UL130, or UL40 (or orthologs thereof). The mutation may be any mutation that results in a lack of expression of active UL128, UL130, US28 or UL40 protein. Such mutations can include point mutations, frameshift mutations, deletions of less than all of the sequence that encodes the protein (truncation mutations), or deletions of all of the nucleic acid sequence that encodes the protein, or any other mutations.

In further examples, the vector does not express an active UL128, UL130, US28 or UL40 protein (or an ortholog thereof) due to the presence of a nucleic acid sequence in the vector that comprises an antisense or RNAi sequence (siRNA or miRNA) that inhibits the expression of the UL128, UL130, or UL40 protein (or an ortholog thereof). Mutations and/or antisense and/or RNAi can be used in any combination to generate a CMV vector lacking active UL128, UL130, US28 or UL40 (or an ortholog thereof).

The CMV vector can comprise additional inactivating mutations known in the art to provide different immune responses, such as an inactivating US11 mutation or an inactivating UL82 (pp71) mutation, or any other inactivating mutation. The CMV vector may also comprise at least one inactivating mutations in one or more viral genes encoding viral proteins known in the art to be essential or augmenting for viral dissemination (i.e. spread from cell to cell) in vivo. Such inactivating mutations may result from point mutations, frameshift mutations, truncation mutations, or a deletion of all of the nucleic acid sequence encoding the viral protein. Inactivating mutations include any mutation in a viral gene which finally leads to a reduced function or to a complete loss of function of the viral protein.

Also disclosed herein are methods of generating $CD8^+$ T cell responses to heterologous antigens in a subject. The methods involve administering an effective amount of a CMV vector to the subject. In one embodiment, the CMV vector is characterized by having a nucleic acid sequence that encodes at least one heterologous antigen and a nucleic acid sequence that does not express an active UL128 protein (or an ortholog thereof), does not express an active UL130 protein (or an ortholog thereof), and expresses at least one active UL40 protein and at least one active US28 protein. The at least one active UL40 protein and the at least one active US28 protein can be orthologs or homologs of UL40 and US28. The $CD8^+$ T cell response elicited by this vector is characterized by having at least 10% of the $CD8^+$ T cells directed against epitopes presented by MHC-E. In further examples, at least 20%, at least 30%, at least 40%, at least 50%, at least 60%, at least 75%, at least 90%, at least 95% or at least 95% of the $CD8^+$ T cells are restricted by MHC-E. In some embodiments, the CMV vector expresses two to five active US28 proteins or orthologs or homologs thereof. In some embodiments, the method further comprises identifying a $CD8^+$ T cell receptor from the $CD8^+$ T cells elicited by the CMV vector, wherein the $CD8^+$ T cell receptor recognizes a MHC-E/heterologous antigen-derived peptide complex. In some embodiments, the $CD8^+$ T cell receptor is identified by RNA or DNA sequencing. In another embodiment, the CMV vector is characterized by having a nucleic acid sequence that does not express active UL128, UL130, and UL40 proteins, and this vector can be used to elicit $CD8^+$ T cells recognizing MC-II supertopes either together with HLA-E-restricted $CD8^+$ T cells (elicited by one or more additional vectors containing intact US28 and UL40) or without HLA-E restricted $CD8^+$ T cells (elicited by one or more additional vectors lacking a functional UL40 or US28 protein). In another embodiment, the CMV vector is characterized by having a nucleic acid sequence that does not express active UL128, UL130, and US28 proteins, and this vector can be used to elicit $CD8^+$ T cells recognizing MC-II supertopes either together with HLA-E-restricted $CD8^+$ T cells (elicited by one or more additional vectors containing intact US28 and UL40) or without HLA-E restricted $CD8^+$ T cells (elicited by one or more additional vectors lacking a functional UL40 or US28 proteins). In another embodiment, the CMV vector is characterized by having a nucleic acid sequence that does not express active UL128, UL130, US28, and UL40 proteins, and this vector can be used to elicit $CD8^+$ T cells recognizing MC-II supertopes either together with HLA-E-restricted $CD8^+$ T cells (elicited by one or more additional vectors containing intact US28 and UL40) or without HLA-E restricted $CD8^+$ T cells (elicited by one or more additional vectors lacking a functional UL40 or US28 proteins).

Also disclosed herein is a method of generating $CD8^+$ T cells that recognize MHC-E-peptide complexes. This method involves administering to a first subject (or animal) a CMV vector that encodes at least one heterologous antigen and an active UL40 protein, or a homolog or ortholog thereof, to generate a set of $CD8^+$ T cells that recognize MHC-E/peptide complexes. The CMV vector does not encode active UL128 and UL130 proteins, or orthologs thereof, and the heterologous antigen can be any antigen, including a pathogen-specific antigen, a tumor antigen, a tissue-specific antigen, or a host self-antigen. In some embodiments, the host self-antigen is an antigen derived from the variable region of a T cell receptor or a B cell receptor. This method further comprises: identifying a first $CD8^+$ T cell receptor from the set of $CD8^+$ T cells, wherein the first $CD8^+$ T cell receptor recognizes a MHC-E/heterologous antigen-derived peptide complex; and transfecting the one or more $CD8^+$ T cells with an expression vector, wherein the expression vector comprises a nucleic acid sequence encoding a second $CD8^+$ T cell receptor and a promoter operably linked to the nucleic acid sequence encoding the T cell receptor, wherein the second CD8+ T cell receptor comprises CDR3α and CDR3β of the first CD8+ TCR, thereby creating one or more transfected CD8+ T cells that recognize MHC-E-peptide complexes. The one or more CD8+ T cells for transfection with the expression vector may be isolated from the first subject or a second subject. In some embodiments, this method may further comprise administering the one or more transfected T cells to the first or second subject to treat a disease such as cancer, a pathogenic infection, or an autoimmune, disease or disorder. In some embodiments, this method may further comprise administering the one or more transfected T cells to the first or second subject to induce an autoimmune response to a tissue-specific antigen or a host self-antigen.

Also disclosed is a transfected CD8+ T cell that recognizes MHC-E-peptide complexes prepared by a process comprising the steps of: (1) administering to a first subject a CMV vector in an amount effective to generate a set of CD8+ T cells that recognize MHC-E/peptide complexes, wherein the CMV vector comprises a first nucleic acid sequence encoding at least one heterologous antigen and further comprises a second nucleic acid sequence encoding an active UL40 protein, and wherein the CMV vector does not express active UL128 and UL130 proteins, or orthologs thereof; (2) identifying a first CD8+ T cell receptor from the set of CD8+ T cells, wherein the first CD8+ T cell receptor recognizes a MHC-E/heterologous antigen-derived peptide complex; (3) isolating one or more CD8+ T cells from the first subject or a second subject; and (4) transfecting the one or more CD8+ T cells isolated from the first or second subject with an expression vector, wherein the expression vector comprises a nucleic acid sequence encoding a second CD8+ T cell receptor and a promoter operably linked to the nucleic acid sequence encoding the second T cell receptor, wherein the second CD8+ T cell receptor comprises CDR3α and CDR3β of the first CD8+ T cell receptor, thereby creating a transfected T cell that recognizes MHC-E-peptide complexes. The heterologous antigen can be any antigen, including a pathogen-specific antigen, tissue specific antigen, a host self-antigen, or a tumor antigen. In some embodiments, the first CD8+ T cell receptor is identified by RNA or DNA sequencing. Also disclosed herein are methods of treating a disease, such as cancer, a pathogenic infection, or an autoimmune disease or disorder, the method comprising administering the transfected T cell that recognizes MHC-E-peptide complexes to the first or second subject. Also disclosed herein are methods of inducing an autoimmune response to a host self-antigen or tissue-specific antigen, the method comprising administering the transfected T cell that recognizes MHC-E-peptide complexes to the first or second subject.

In further examples, the methods involve administering an effective amount of a second CMV vector, the second CMV vector comprising a nucleic acid sequence that encodes a second heterologous antigen to the subject. This second vector can be any CMV vector, including a CMV vector with an active UL128 protein (or a homolog or ortholog thereof)) and/or an active UL130 protein (or a homolog or ortholog thereof). The second CMV vector can comprise a second heterologous antigen. The second heterologous antigen can be any heterologous antigen, including a heterologous antigen identical to the heterologous antigen in the first CMV vector. The second CMV vector can be administered at any time relative to the administration of the first CMV vector including before, concurrently with, or after the administration of the first CMV vector. This includes administration of the second vector any number of months, days, hours, minutes or seconds before or after the first vector.

Human or animal CMV vectors, when used as expression vectors, are innately non-pathogenic in the selected subjects such as humans. In some embodiments, the CMV vectors have been modified to render them non pathogenic (incapable of host-to-host spread) in the selected subjects.

A heterologous antigen can be any protein or fragment thereof that is not derived from CMV, including cancer antigens, pathogen specific antigens, model antigens (such as lysozyme, keyhole-limpet hemocyanin (KLH), or ovalbumin), tissue-specific antigens, host self-antigens, or any other antigen.

Pathogen-specific antigens can be derived from any human or animal pathogen. The pathogen may be a viral pathogen, a bacterial pathogen, or a parasite, and the antigen may be a protein derived from the viral pathogen, bacterial pathogen, or parasite. The parasite may be an organism or disease caused by an organism. For example, the parasite may be a protozoan organism, a protozoan organism causing a disease, a helminth organism or worm, a disease caused by a helminth organism, an ectoparasite, or a disease caused by an ectoparasite.

The antigen can be a protein derived from cancer. The cancers include, but are not limited to, acute myelogenous leukemia, chronic myelogenous leukemia, myelodysplastic syndrome, acute lymphoblastic leukemia, chronic lymphoblastic leukemia, non Hodgkin's lymphoma, multiple myeloma, malignant melanoma, breast cancer, lung cancer, ovarian cancer, prostate cancer, pancreatic cancer, colon cancer, renal cell carcinoma (RCC), and germ cell tumors.

The antigen can be a host self-antigen. Host self antigens include, but are not limited to, antigens derived from the variable region of a T cell receptor or from the variable region of a B cell receptor. The antigen can be a tissue-specific antigen. Tissue-specific antigens include, but are not limited to, sperm antigens or egg antigens.

The CMV vectors disclosed herein can be used as an immunogenic, immunological or vaccine composition containing the recombinant CMV virus or vector, and a pharmaceutically acceptable carrier or diluent. An immunological composition containing the recombinant CMV virus or vector (or an expression product thereof) elicits an immunological response—local or systemic. The response can, but need not be, protective. An immunogenic composition containing the recombinant CMV virus or vector (or an expression product thereof) likewise elicits a local or systemic immunological response which can, but need not be, protective. A vaccine composition elicits a local or systemic protective response. Accordingly, the terms "immunological composition" and "immunogenic composition" include a "vaccine composition" (as the two former terms can be protective compositions).

The CMV vectors disclosed herein can be used in methods of inducing an immunological response in a subject comprising administering to the subject an immunogenic, immunological or vaccine composition comprising the recombinant CMV virus or vector and a pharmaceutically acceptable carrier or diluent. For purposes of this specification, the term "subject" includes all animals, including non-human primates and humans, while "animal" includes all vertebrate species, except humans; and "vertebrate" includes all vertebrates, including animals (as "animal" is used herein) and humans. And, of course, a subset of "animal" is "mammal", which for purposes of this specification includes all mammals, except humans.

The CMV vectors disclosed herein can be used in therapeutic compositions containing the recombinant CMV virus or vector and a pharmaceutically acceptable carrier or diluent. The CMV vectors disclosed herein can be prepared by inserting DNA comprising a sequence that encodes the heterologous antigen into an essential or non-essential region of the CMV genome. The method can further comprise deleting one or more regions from the CMV genome. The method can comprise in vivo recombination. Thus, the method can comprise transfecting a cell with CMV DNA in a cell-compatible medium in the presence of donor DNA comprising the heterologous DNA flanked by DNA sequences homologous with portions of the CMV genome, whereby the heterologous DNA is introduced into the genome of the CMV, and optionally then recovering CMV modified by the in vivo recombination. The method can also comprise cleaving CMV DNA to obtain cleaved CMV DNA, ligating the heterologous DNA to the cleaved CMV DNA to obtain hybrid CMV-heterologous DNA, transfecting a cell with the hybrid CMV-heterologous DNA, and optionally then recovering CMV modified by the presence of the heterologous DNA. Since in vivo recombination is comprehended, the method accordingly also provides a plasmid comprising donor DNA not naturally occurring in CMV encoding a polypeptide foreign to CMV, the donor DNA is within a segment of CMV DNA that would otherwise be co-linear with an essential or non-essential region of the CMV genome such that DNA from an essential or nonessential region of CMV is flanking the donor DNA. The heterologous DNA can be inserted into CMV to generate the recombinant CMV in any orientation that yields stable integration of that DNA, and expression thereof, when desired.

The DNA encoding the heterologous antigen in the recombinant CMV vector can also include a promoter. The promoter can be from any source such as a herpes virus, including an endogenous CMV promoter, such as a HCMV, RhCMV, murine CMV (MCMV), or other CMV promoter. The promoter can also be a non-viral promoter such as the EF1α promoter. The promoter can be a truncated transcriptionally active promoter which comprises a region transactivated with a transactivating protein provided by the virus and the minimal promoter region of the full-length promoter from which the truncated transcriptionally active promoter is derived. The promoter can be composed of an association of DNA sequences corresponding to the minimal promoter and upstream regulatory sequences. A minimal promoter is composed of the CAP site plus TATA box (minimum sequences for basic level of transcription; unregulated level of transcription); "upstream regulatory sequences" are composed of the upstream element(s) and enhancer sequencer(s). Further, the term "truncated" indicates that the full-length promoter is not completely present, i.e., that some portion of the full-length promoter has been removed. And, the truncated promoter can be derived from a herpesvirus such as MCMV or HCMV, e.g., HCMV-IE or MCMV-IE. There can be up to a 40% and even up to a 90% reduction in size, from a full-length promoter, based upon base pairs. The promoter can also be a modified non-viral promoter. As to HCMV promoters, reference is made to U.S. Pat. Nos. 5,168,062 and 5,385,839. As to transfecting cells with plasmid DNA for expression therefrom, reference is made to Feigner et al. (1994), *J. Biol. Chem.* 269, 2550-2561. And, as to direct injection of plasmid DNA as a simple and effective method of vaccination against a variety of infectious diseases reference is made to *Science,* 259:1745-49, 1993. It is therefore within the scope of this invention that the vector can be used by the direct injection of vector DNA.

Also disclosed is an expression cassette that can be inserted into a recombinant virus or plasmid comprising the truncated transcriptionally active promoter. The expression cassette can further include a functional truncated polyadenylation signal; for instance an SV40 polyadenylation signal which is truncated, yet functional. Considering that nature provided a larger signal, it is indeed surprising that a truncated polyadenylation signal is functional. A truncated polyadenylation signal addresses the insert size limit problems of recombinant viruses such as CMV. The expression cassette can also include heterologous DNA with respect to the virus or system into which it is inserted; and that DNA can be heterologous DNA as described herein.

As to antigens for use in vaccine or immunological compositions, see also Stedman's Medical Dictionary (24th edition, 1982, e.g., definition of vaccine (for a list of antigens used in vaccine formulations); such antigens or epitopes of interest from those antigens can be used. As to heterologous antigens, one skilled in the art can select a heterologous antigen and the coding DNA therefor from the knowledge of the amino acid and corresponding DNA sequences of the peptide or polypeptide, as well as from the nature of particular amino acids (e.g., size, charge, etc.) and the codon dictionary, without undue experimentation.

One method to determine T epitopes of an antigen involves epitope mapping. Overlapping peptides of the heterologous antigen are generated by oligo-peptide synthesis. The individual peptides are then tested for their ability to bind to an antibody elicited by the native protein or to induce T cell or B cell activation. This approach has been particularly useful in mapping T-cell epitopes since the T cell recognizes short linear peptides complexed with MHC molecules.

An immune response to a heterologous antigen is generated, in general, as follows; T cells recognize proteins only when the protein has been cleaved into smaller peptides and is presented in a complex called the "major histocompatibility complex (MHC)" located on another cell's surface. There are two classes of MHC complexes—class I and class II, and each class is made up of many different alleles. Different species, and individual subjects have different types of MHC complex alleles; they are said to have a different MHC type. One type of MHC class I molecule is called MHC-E (HLA-E in humans, Mamu-E in RM, Qa-1b in mice).

It Is noted that the DNA comprising the sequence encoding the heterologous antigen can itself include a promoter for driving expression in the CMV vector or the DNA can be limited to the coding DNA of the heterologous antigen. This construct can be placed in such an orientation relative to an endogenous CMV promoter that it is operably linked to the promoter and is thereby expressed. Further, multiple copies of DNA encoding the heterologous antigen or use of a strong or early promoter or early and late promoter, or any combination thereof, can be done so as to amplify or increase expression. Thus, the DNA encoding the heterologous antigen can be suitably positioned with respect to a CMV-endogenous promoter, or those promoters can be translocated to be inserted at another location together with the DNA encoding the heterologous antigen. Nucleic acids encoding more than one heterologous antigen can be packaged in the CMV vector.

Further disclosed are pharmaceutical and other compositions containing the disclosed CMV vectors. Such pharmaceutical and other compositions can be formulated so as to be used in any administration procedure known in the art. Such pharmaceutical compositions can be via a parenteral route (intradermal, intramuscular, subcutaneous, intravenous, or others). The administration can also be via a mucosal route, e.g., oral, nasal, genital, etc.

The disclosed pharmaceutical compositions can be prepared in accordance with standard techniques well known to those skilled in the pharmaceutical arts. Such compositions can be administered in dosages and by techniques well known to those skilled in the medical arts taking into consideration such factors as the breed or species, age, sex, weight, and condition of the particular patient, and the route of administration. The compositions can be administered alone, or can be co-administered or sequentially administered with other CMV vectors or with other immunological, antigenic or vaccine or therapeutic compositions. Such other compositions can include purified native antigens or epitopes or antigens or epitopes from the expression by a recombinant CMV or another vector system; and are administered taking into account the aforementioned factors.

Examples of compositions include liquid preparations for orifice, e.g., oral, nasal, anal, genital, e.g., vaginal, etc., administration such as suspensions, syrups or elixirs; and, preparations for parenteral, subcutaneous, intradermal, intramuscular or intravenous administration (e.g., injectable administration) such as sterile suspensions or emulsions. In such compositions the recombinant may be in admixture with a suitable carrier, diluent, or excipient such as sterile water, physiological saline, glucose or the like.

Antigenic, immunological or vaccine compositions typically can contain an adjuvant and an amount of the CMV vector or expression product to elicit the desired response. In human applications, alum (aluminum phosphate or aluminum hydroxide) is a typical adjuvant. Saponin and its purified component Quil A, Freund's complete adjuvant and other adjuvants used in research and veterinary applications have toxicities which limit their potential use in human vaccines. Chemically defined preparations such as muramyl dipeptide, monophosphoryl lipid A, phospholipid conjugates such as those described by Goodman-Snitkoff et al. J. Immunol. 147:410-415 (1991), encapsulation of the protein within a proteoliposome as described by Miller et al., J. Exp. Med. 176:1739-1744 (1992), and encapsulation of the protein in lipid vesicles such as Novasome lipid vesicles (Micro Vescular Systems, Inc., Nashua, N.H.) can also be used.

The composition may be packaged in a single dosage form for immunization by parenteral (i.e., intramuscular, intradermal or subcutaneous) administration or orifice administration, e.g., perlingual (e.g., oral), intragastric, mucosal including intraoral, intraanal, intravaginal, and the like administration. And again, the effective dosage and route of administration are determined by the nature of the composition, by the nature of the expression product, by expression level if recombinant CMV is directly used, and by known factors, such as breed or species, age, sex, weight, condition and nature of host, as well as $LD_{50}$ and other screening procedures which are known and do not require undue experimentation. Dosages of expressed product can range from a few to a few hundred micrograms, e.g., 5 to 500 µg. The CMV vector can be administered in any suitable amount to achieve expression at these dosage levels. In nonlimiting examples: CMV vectors can be administered in an amount of at least $10^2$ pfu; thus, CMV vectors can be administered in at least this amount; or in a range from about $10^2$ pfu to about $10^7$ pfu. Other suitable carriers or diluents can be water or a buffered saline, with or without a preservative. The CMV vector can be lyophilized for resuspension at the time of administration or can be in solution. "About" can mean within 1%, 5%, 10% or 20% of a defined value.

It should be understood that the proteins and the nucleic acids encoding them of the present invention can differ from the exact sequences illustrated and described herein. Thus, the invention contemplates deletions, additions, truncations, and substitutions to the sequences shown, so long as the sequences function in accordance with the methods of the invention. In this regard, substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, and tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the proteins described but possessing minor amino acid substitutions that do not substantially affect the immunogenicity of the protein are, therefore, within the scope of the disclosure.

The nucleotide sequences of the present invention can be codon optimized, for example the codons can be optimized for use in human cells. For example, any viral or bacterial sequence can be so altered. Many viruses, including HIV and other lentiviruses, use a large number of rare codons and, by altering these codons to correspond to codons commonly used in the desired subject enhanced expression of the heterologous antigen can be achieved as described in Andre et al., J. Virol. 72:1497-1503, 1998.

Nucleotide sequences encoding functionally and/or antigenically equivalent variants and derivatives of the CMV vectors and the glycoproteins included therein are contemplated. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

Sequence identity or homology is determined by comparing the sequences when aligned so as to maximize overlap and identity while minimizing sequence gaps, in particular, sequence identity may be determined using any of a number of mathematical algorithms. A nonlimiting example of a mathematical algorithm used for comparison of two sequences is the algorithm of Karlin & Altschul, Proc. Natl.

Acad. Sci. USA 1990; 87: 2264-2268, modified as in Karlin & Altschul, Proc. Natl Acad. Sci. USA 1993; 93: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al. (1990), supra; Gish & States, 1993; Nature Genetics 3: 266-272; Karlin & Altschul, Proc. Natl. Acad. Sci. USA 90: 5873-5877 (1993); all of which are incorporated by reference herein).

The various recombinant nucleotide sequences and antibodies and/or antigens of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the viruses of the present invention can be used in accordance with the present invention. In certain embodiments, the disclosed viruses can be used in vitro (such as using cell-free expression systems) and/or in cultured cells grown in vitro in order to produce the encoded heterologous antigen (e.g., pathogen-specific antigens, HIV antigens, tumor antigens, and antibodies) which may then be used for various applications such as in the production of proteinaceous vaccines. For such applications, any vector that allows expression of the virus in vitro and/or in cultured cells may be used.

For the disclosed heterologous antigens to be expressed, the protein coding sequence of the heterologous antigen should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The disclosure relates to a recombinant viral vector expressing a heterologous protein antigen. In some examples, the antigen is an HIV antigen. Advantageously, the HIV antigens include, but are not limited to, the HIV antigens discussed in U.S. Pub. Nos. 2008/0199493 A1 and 2013/0136768 A1, both of which are incorporated by reference herein. HIV, nucleic acid or immunogenic fragments thereof, may be utilized as an HIV protein antigen. Tor example, the HIV nucleotides discussed in U.S. Pub. Nos. 2008/0199493 A1 and 2013/0136768 A1 can be used. Any antigen recognized by an HIV antibody can be used as an HIV protein antigen. The protein antigen can also be an SIV antigen. For example, the SIV antigens discussed in U.S. Pub. Nos. 2008/0199493 A1 and 2013/0136768 A1 can be used.

The vectors used in accordance with the present invention can contain a suitable gene regulatory region, such as a promoter or enhancer, such that the antigens of the invention can be expressed.

Expressing antigens of the invention in vivo in a subject, for example in order to generate an immune response against an HIV-1 antigen and/or protective immunity against HIV-1, expression vectors that are suitable for expression on that subject, and that are safe for use in vivo, should be chosen. In some examples, it may be desired to express the antibodies and/or antigens in a laboratory animal, such as for pre-clinical testing of the HIV-1 immunogenic compositions and vaccines of the invention. In other examples, one can express the antigens in human subjects, such as in clinical trials and for actual clinical use of the immunogenic, compositions and vaccine of the invention.

The CMV vectors described herein can contain mutations that can prevent host to host spread, thereby rendering the virus unable to infect immunocompromised or other subjects that could face complications as a result of CMV infection. The CMV vectors described herein can also contain mutations that result in the presentation of immunodominant and non-immunodominant epitopes as well as non-canonical MHC restriction. However, mutations in the CMV vectors described herein do not affect the ability of the vector to re-infect a subject that has been previously infected with CMV. Such CMV mutations are described in, for example, US Patent Publications 2013-0136768; 2010-0142823; 2014-0141038; and PCT application publication WO 2014/138209, all of which are incorporated by reference herein.

The disclosed CMV vectors can be administered in vivo, for example where the aim is to produce an immunogenic response, including a $CD8^+$ immune response, including an immune response characterized by a high percentage of the $CD8^+$ T cell response being restricted by MHC Class II and/or MHC-E (or a homolog or ortholog thereof). For example, in some examples it may be desired to use the disclosed CMV vectors in a laboratory animal, such as rhesus macaques for pre clinical testing of immunogenic compositions and vaccines using RhCMV. In other examples, it will be desirable to use the disclosed CMV vectors in human subjects, such as in clinical trials and for actual clinical use of the immunogenic compositions using HCMV.

For such in vivo applications the disclosed CMV vectors are administered as a component of an immunogenic composition further comprising a pharmaceutically acceptable carrier. The immunogenic compositions of the invention are useful to stimulate an immune response against the heterologous antigen, including a pathogen-specific antigen and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the antigens of the invention to a subject, such as a human, such that the antigens are then expressed in the subject to elicit an immune response.

Immunization schedules (or regimens) are well known for animals (including humans) and can be readily determined for the particular subject and immunogenic composition. Hence, the immunogens can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. In a particularly advantageous embodiment of the present invention, the interval is longer, advantageously about 10 weeks, 12 weeks, 14 weeks, 16 weeks, 18 weeks, 20 weeks, 22 weeks, 24 weeks, 26 weeks, 28 weeks, 30 weeks, 32 weeks, 34 weeks, 36 weeks, 38 weeks, 40 weeks, 42 weeks, 44 weeks, 46 weeks, 48 weeks, 50 weeks, 52 weeks, 54 weeks, 56 weeks, 58 weeks, 60 weeks, 62 weeks, 64 weeks, 66 weeks, 68 weeks or 70 weeks. The immunization regimes typically have from 1 to 6 administrations of the immunogenic composition, but may have as few as one or two or four. The methods of inducing an immune response can also include administration of an adjuvant with the immunogens. In some instances, annual, biannual or other long interval (5-10 years) booster immunization can supplement the initial immunisation protocol. The present methods also include a variety of prime-boost regimens. In these methods, one or more priming immunisations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens. CMV vectors can be used repeatedly while expressing different antigens derived from different pathogens.

EXAMPLES

The following examples are illustrative of disclosed methods. In light of this disclosure, those of skill in the art will recognize that variations of these examples and other examples of the disclosed method would be possible without undue experimentation.

Example 1

Induction of MHC-E Restricted CD8$^+$ T Cells by Rhesus Cytomegalovirus Vaccine Vectors Lacking UL128 and UL130 but Containing UL40 and US28 Genes It has been previously demonstrated that RhCMV/SIV vectors drive an alternate SIV-specific CD8$^+$ T cell response that is completely distinct from the canonical responses engendered by conventional vaccine modalities and even from SIV infection itself (Hansen, S. G. et al., *Science* 340, 1237874 (2013), incorporated by reference herein).

While it had been established that the RhCMV/SIV-induced CD8$^+$ T cell response was dominated by the existence of a population of MHC-II restricted CD8$^+$ T cells, the molecule restricting the remaining CD8$^+$ T cells—those which were inhibited by the pan-MHC-I blocking antibody W6/32—remained unknown.

Figure 7A:
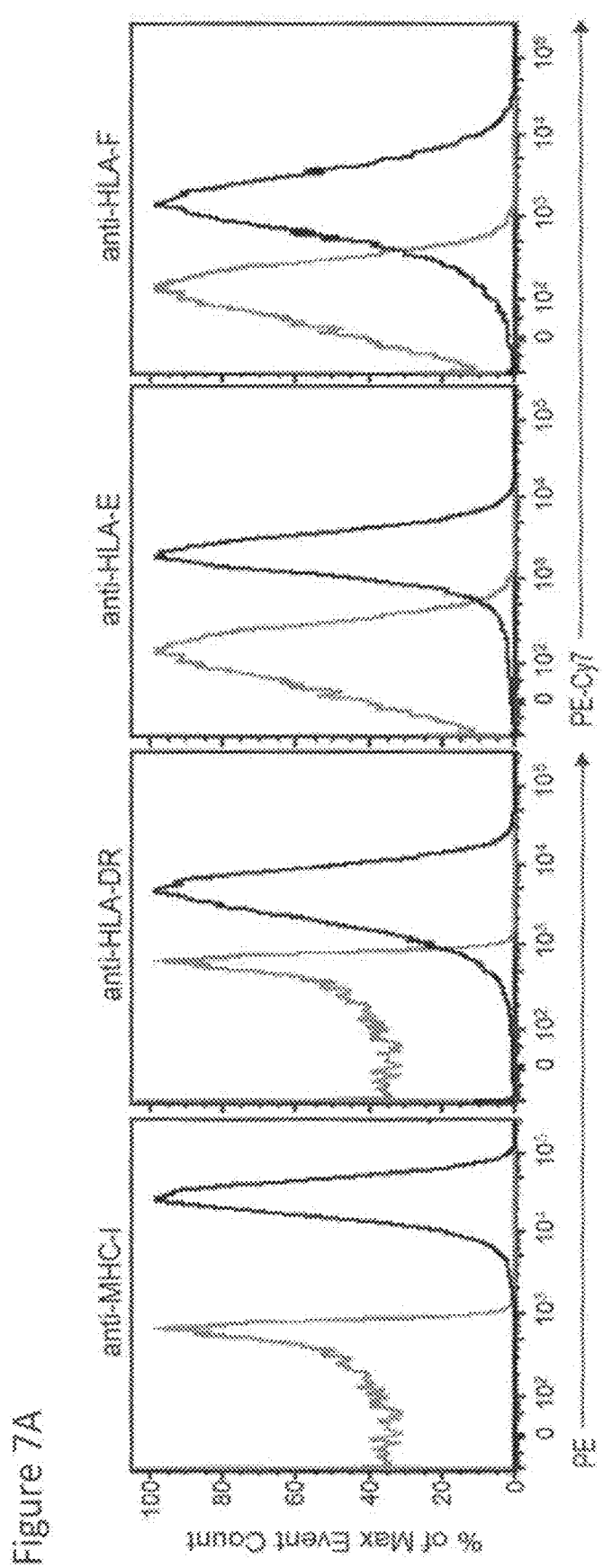
FIG. 7A is a set of plots showing surface staining of MHC-II, MHC-Ia, MHC-E, or MHC-F by cell lines transfected with single Mamu-D molecules.
Figure 7B:
FIG. 7B is a table showing genotyping of the indicated rhesus macaque (RM) individuals. Individuals were Mamu-A, -B, and -E genotyped by Roche/454 pyrosequencing. Grey shading indicates alleles selected for MHC-I transfectant generation. Where multiple alleles are listed, the bolded allele was produced.
Figure 7C:
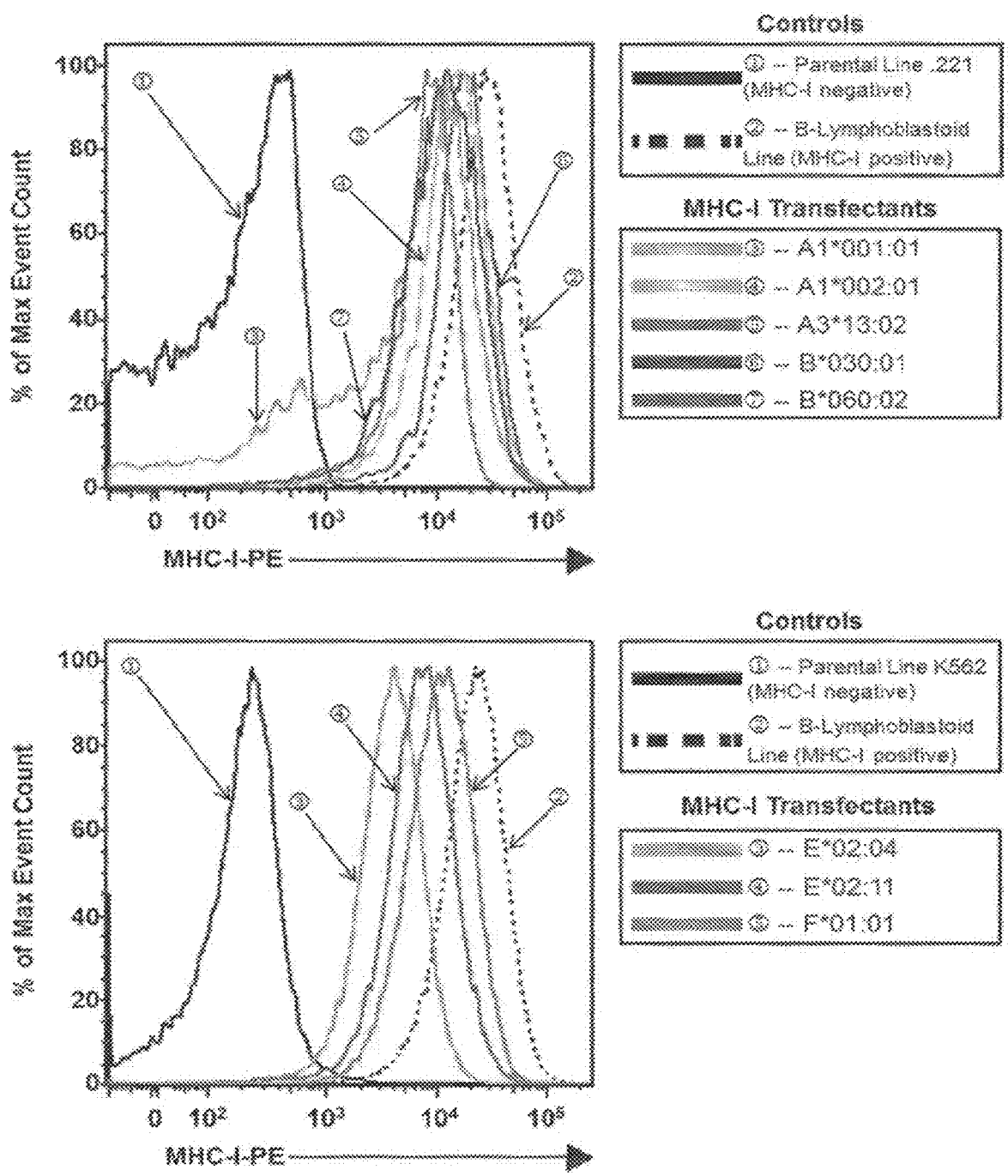
FIG. 7C is a set of two plots wherein one MHC-Ia or MHC-Ib allele was transfected into a parental (MHC-I negative) cell line (0.221 cells or K562, respectively). Cells were stained with a cross-reactive human MHC-I monoclonal antibody (W6/32) for 15 minutes at room temperature to assess MHC-I expression. Cells were washed once with 1× PBS supplemented with 10% fetal bovine serum, fixed with 2% paraformaldehyde, collected on a LSRII flow cytometer, and analyzed with FlowJo. MHC-I-expressing B-lymphoblastoid cells (BLCL) served as a positive control, while the MHC-I negative parental cell lines were used as a negative control.

In particular, administration of 68-1 RhCMV/gag vector elicited MHC-I-restricted CD8$^+$ T cells targeting the SIVmac239 Gag$_{273-287}$ (Gag 15-mer #69) and Gag$_{477-491}$ (Gag 15-mer #120) "supertopes" in every RhCMV/gag vector-vaccinated macaque regardless of MHC-Ia expression. This implied the involvement of a functionally conserved "non-classical" (i.e. non-polymorphic) MHC-Ib molecule. Described herein is the identification of the restricting MHC-I allele of these CD8$^+$ T cells. A panel of MHC-I transfectants expressing either a single "classical" (i.e., polymorphic) MHC-Ia or non-classical MHC-Ib allele was developed from a cohort of four strain 68-1 RhCMV/gag-vaccinated macaques mounting strong RhCMV/gag induced CD8$^+$ T cell responses (FIG. 7). Using a previously described MHC restriction assay (Hansen et al. *Science* (2013), supra), it was established that CD8$^+$ T cells targeting the Gag$_{273-287}$ and Gag$_{477-491}$ supertopes recognize these epitopes in the context of MHC-E (FIG. 1A).

MHC-E (HLA-E in humans, Mamu-E in rhesus macaques, and Qa-1$^b$ in mice) is a highly monomorphic, non-classical MHC-Ib molecule expressed in nearly every nucleated cell in the body, with particularly high expression in immune system cells (N. Lee et al., *Proc Natl Acad Sci USA* 95, 5199 (1998) and S. Coupel et al., *Blood* 109, 2806 (2007), both of which are incorporated by reference herein). In contrast to the over 8,500 HLA class I alleles currently identified (J. Robinson et al., *Nucleic Acids Res* 41, D1222 (2013); incorporated by reference herein) only two HLA-E molecules exist, which vary at one amino acid located outside the peptide-binding groove, and are thus likely functionally identical (R. K. Strong et al., *J Biol Chem* 278, 5082 (2003); incorporated by reference herein). This highly monomorphic nature of MHC-E likely explains how every RhCMV/gag-vaccinated macaque is able to target the same Gag MHC-I supertope independent of the MHC-Ia alleles present in each animal.

MHC-E was also identified as the restricting allele for the remaining MHC-I blocked CD8$^+$ T cells in RhCMV/gag-vaccinated macaques (FIG. 1A). Although the structure of MHC-E is similar to that of classical MHC-Ia molecules, under normal physiological conditions MHC-E repetitively binds and presents only a single 9-mer peptide derived from the leader sequence of MHC-Ia molecules for presentation to NK cells. However, under conditions of cellular stress such as during viral infection, MHC-E binds a completely separate set of highly diverse CD8+ T cell epitopes whose binding motif do not match that of the dominant MHC-Ia leader peptides (Lampen et al., supra and C. C. Oliviera et al., J Exp Med 207, 207 (2010); both of which are incorporated by reference herein). The ability of MHC-E to disengage the leader peptide and subsequently present an alternate peptide repertoire to CD8+ T cells suggests that the alternate MHC-I-restricted CD8+ T cell response is due largely, if not entirely, to presentation by MHC-E.

HLA-E restricted CD8+ T cells have recently been discovered against several human pathogens including CMV (G. Pietra et al., *Proc Natl Acad Sci USA* 100, 10896 (2003); incorporated by reference herein); EBV (Jorgensen P B et al., PLoS One 7, e46120 (2012); incorporated by reference herein); *Salmonella typhi* (R. Salerno-Goncalves, et al., *J Immunol* 173, 5852 (2004); incorporated by reference herein); and *Mycobacterium tuberculosis* (A. S. Heinzel et al., *J Exp Med* 196, 1473 (2002) and S A Joosten et al. PLoS Pathol 6, e1000782 (2010); both of which are incorporated by reference herein). However, no HIV/SIV-specific MHC-E restricted CD8+ T cell response has been reported and no vaccine platform currently exists that induces these non-classically restricted CD8+ T cells against any heterologous antigen.

Figure 1B:
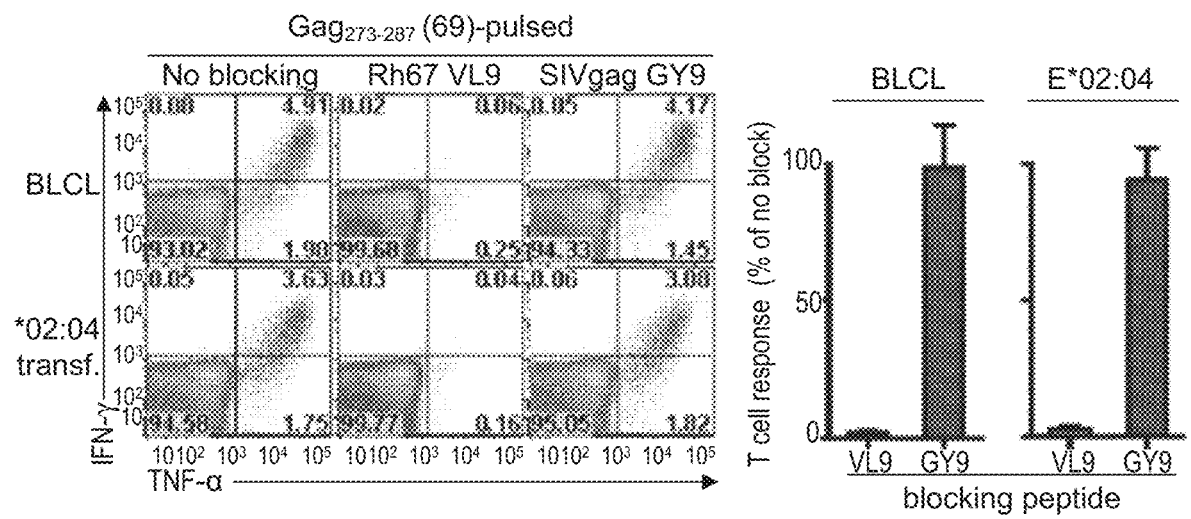
FIG. 1B is a set of flow cytometry plots (left panel) and a bar graph (right panel) of CD8$^+$ T cells in PBMC from a strain 68-1 RhCMV/gag vector-vaccinated macaque (Rh22034 and Rh21826) showing IFN-γ and/or TNF-α production (response frequencies of CD8$^+$ T cells shown in each quadrant) following incubation with antigen presenting cells (autologous BLCL or K562 transfectant expressing only Mamu-E) that were pulsed with Gag$_{273-287}$ (SIVmac239 Gag 15-mer #69). The antigen presenting cells were incubated with the Gag 15-mer indicated along with either no additional peptide (no blocking) or in the presence of the Mamu-E binding peptide Rh67$_{8-16}$ VL9 (Rh67 VL9) or the Mamu-A*002:01 binding peptide Gag$_{71-79}$ GY9 (SIVgag GY9). The right panel is a comparison of peptide blocking conditions on IFN-γ and/or TNF-α production from CD8$^+$ T cells from four strain 68-1 RhCMV/gag vector-vaccinated macaques incubated with autologous BLCL or a Mamu-E transfectant pulsed with Gag$_{273-287}$ (SIVmac239 Gag 15-mer #69). Data are normalized to the response observed with no peptide blocking.
Figure 1C:
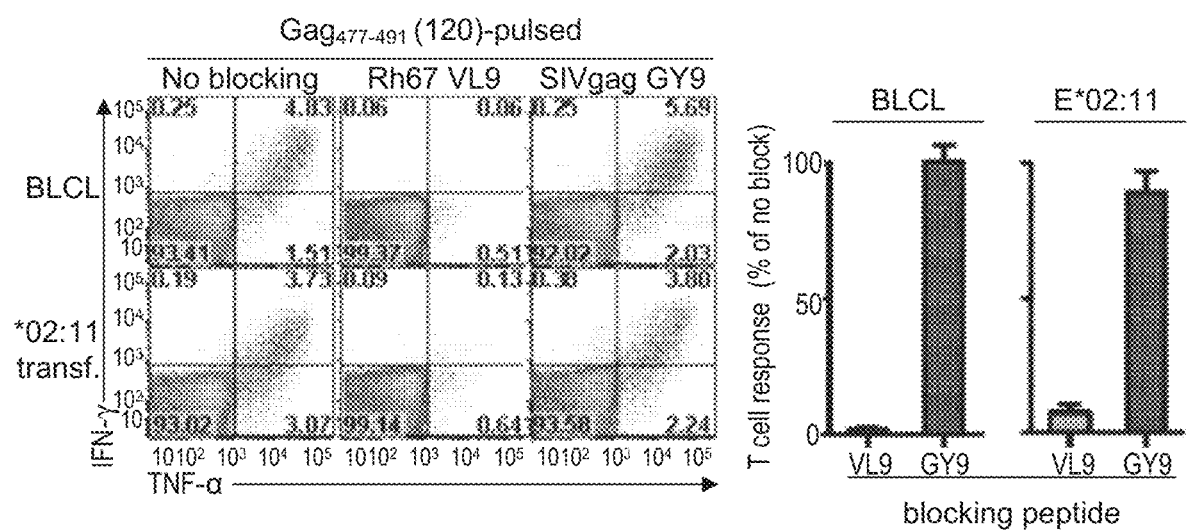
FIG. 1C is a set of flow cytometry plots (left panel) and a bar graph (right panel) of CD8$^+$ T cells in PBMC from a strain 68-1 RhCMV/gag vector-vaccinated macaque (Rh22034 and Rh21826) showing IFN-γ and/or TNF-α production (response frequencies of CD8$^+$ T cells shown in each quadrant) following incubation with antigen presenting cells (autologous BLCL or K562 transfectant expressing only Mamu-E) that were pulsed with Gag$_{477-491}$ (SIVmac239 Gag 15-mer #120). The antigen presenting cells were incubated with the Gag 15-mer indicated along with either no additional peptide (no blocking) or in the presence of the Mamu-E binding peptide Rh67$_{8-16}$ VL9 (Rh67 VL9) or the Mamu-A*002:01 binding peptide Gag$_{75-79}$ GY9 (SIVgag GY9). The right panel is a comparison of peptide blocking conditions on IFN-γ and/or TNF-α production from CD8$^+$ T cells from four strain 68-1 RhCMV/gag vector-vaccinated macaques incubated with autologous BLCL or a Mamu-E transfectant pulsed with Gag$_{477-491}$ (SIVmac239 Gag 15-mer #120). Data are normalized to the response observed with no peptide blocking.

MHC restriction data from animals was confirmed using MHC "blocking" peptides that bind to specific MHC allomorphs with high affinity, thereby outcompeting other peptides for the binding groove of that MHC molecule. To protect its infected host cell from NK-cell mediated lysis, HCMV encodes the glycoprotein UL40 (the RCMV homolog is Rh67), that contains the exact 9-mer peptide (VMAPRTLLL, Rh67$_{8-16}$ VL9) derived from classical MHC-Ia leader sequences. The VLB peptide specifically binds the MHC-E peptide binding groove with extremely high affinity (P. Tomasec et al., *Science* 287, 1031 (2000); incorporated by reference herein). Antigen presenting cells were pre-incubated with either the Rh67-derived VL9 peptide to block binding of the Gag$_{273-287}$ and Gag$_{477-491}$ peptides to MHC-E, or with an irrelevant Mamu-A*002:01 (A*02)-binding Gag$_{71-79}$ GY9 peptide. CD8+ T cell recognition of the Gag$_{273-287}$ and Gag$_{477-491}$ supertopes on both autologous BLCL and transfectants expressly a single MHC-E allele was completely inhibited by the presence of the MHC-E high-affinity binding peptide Rh67$_{8-16}$ VL9, confirming MHC-E as the presenting allele for the MHC-I supertope responses (FIGS. 1B and 1C).

Figure 2A:
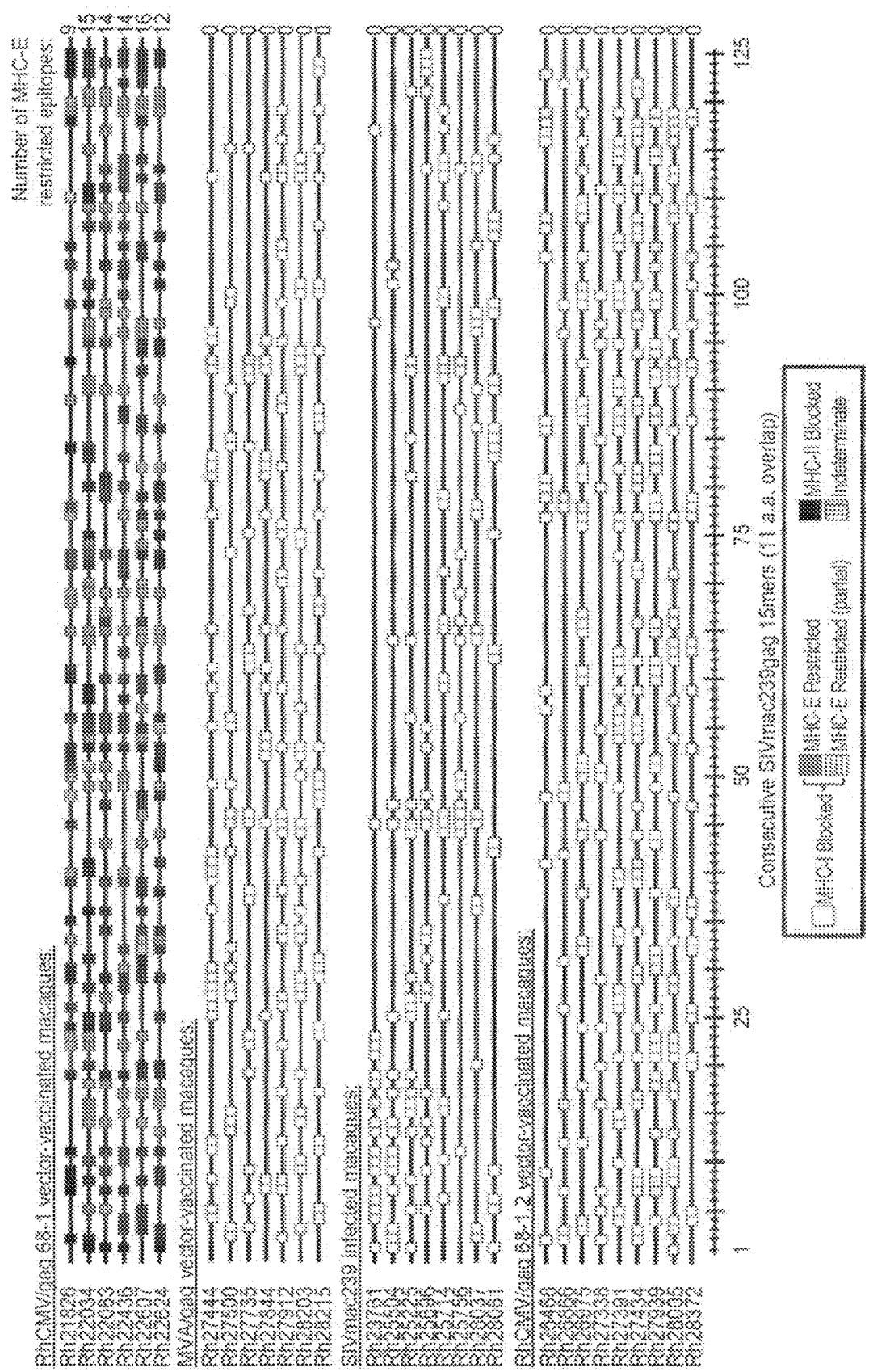
FIG. 2A is a table illustrating the CD8$^+$ T cell responses to SIVmac239 Gag epitope mapped using flow cytometric ICS to detect recognition of 125 consecutive 15 mer Gag peptides (with an 11 amino add overlap) in macaques vaccinated with strain 68-1 RhCMV/gag vectors (n=6), strain 68-1.2 RhCMV/gag vectors (n=9), MVA/gag vectors (n=7), and in SIVmac239 infected macaques (n=8). As discussed in Example 1, expression of Rh60, Rh157.5, and Rh157.4 (HCMV UL36, UL128, and UL130, respectively) is restored in RhCMV strain 68-1.2. Peptides resulting in above background CD8$^+$ T cell responses were subjected to MHC-I (mAb W6/32), MHC-E (Rh67 VL9), and MHC-II (mAb G46-6) blockade and classified as MHC-I blocked (boxes with white fill), fully MHC-E blocked (boxes with grey fill), partially MHC-E blocked (boxes with horizontal hatch fill), MHC-II blocked (boxes with black fill), or indeterminate (boxes with vertical hatch fill). The minimal number of independent MHC-E blocked epitopes potentially contained within these reactive peptides in each macaque is designated at right (see Methods). Note that macaques 22063 and 22624 were vaccinated with BAC-derived RhCMV/gag while macaques 21826, 22034, 22436, and 22607 were vaccinated with non BAC derived RhCMVgag (L).
Figure 8A:
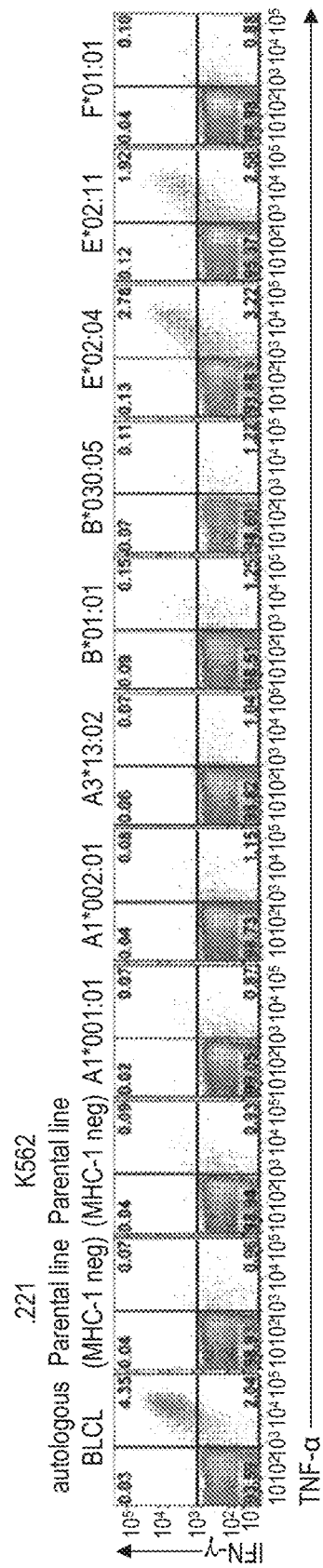
FIG. 8A is a set of plots showing representative flow data of a restriction assay from Rh22607 for Gag 120.
Figure 8B:
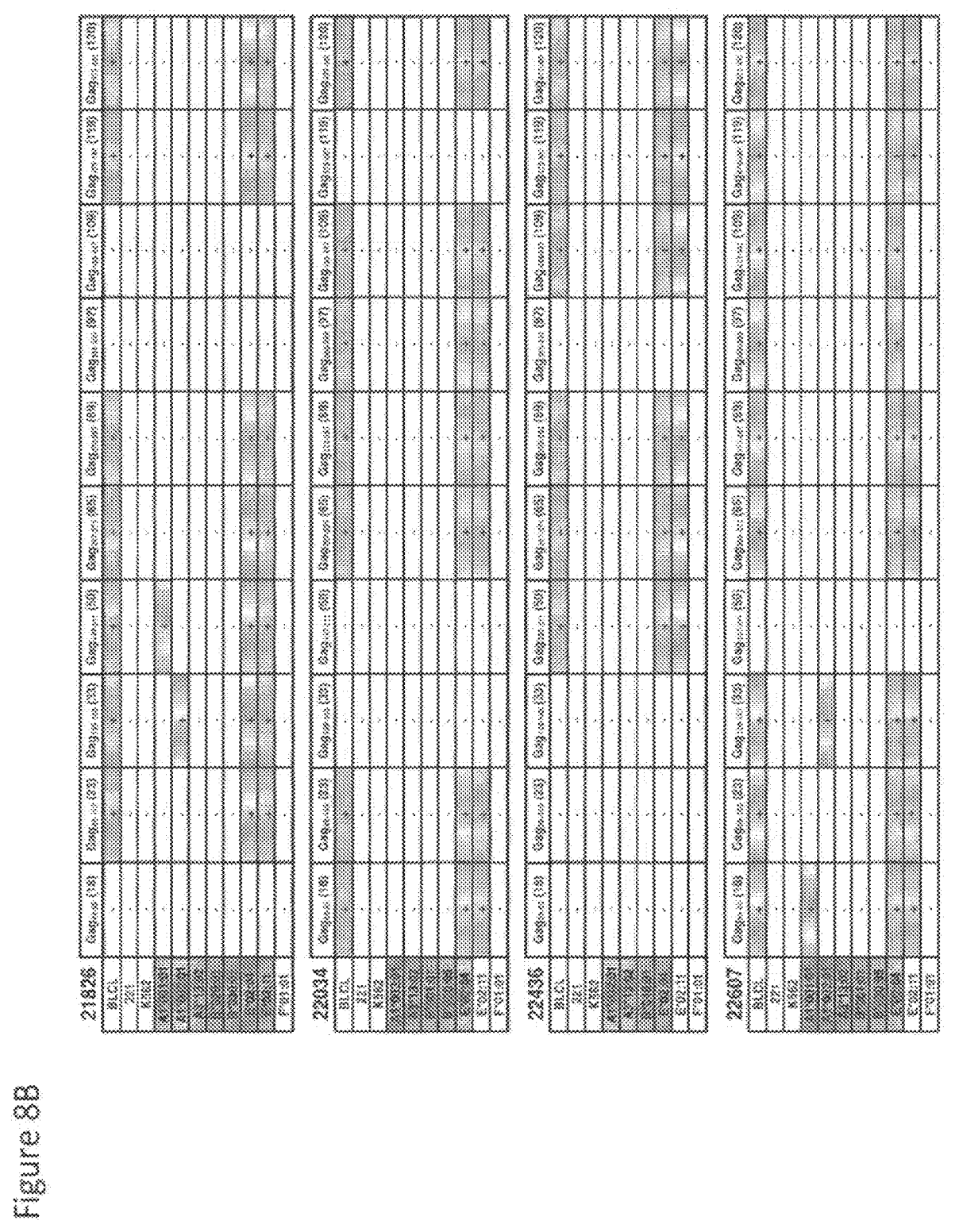
Figure 9:
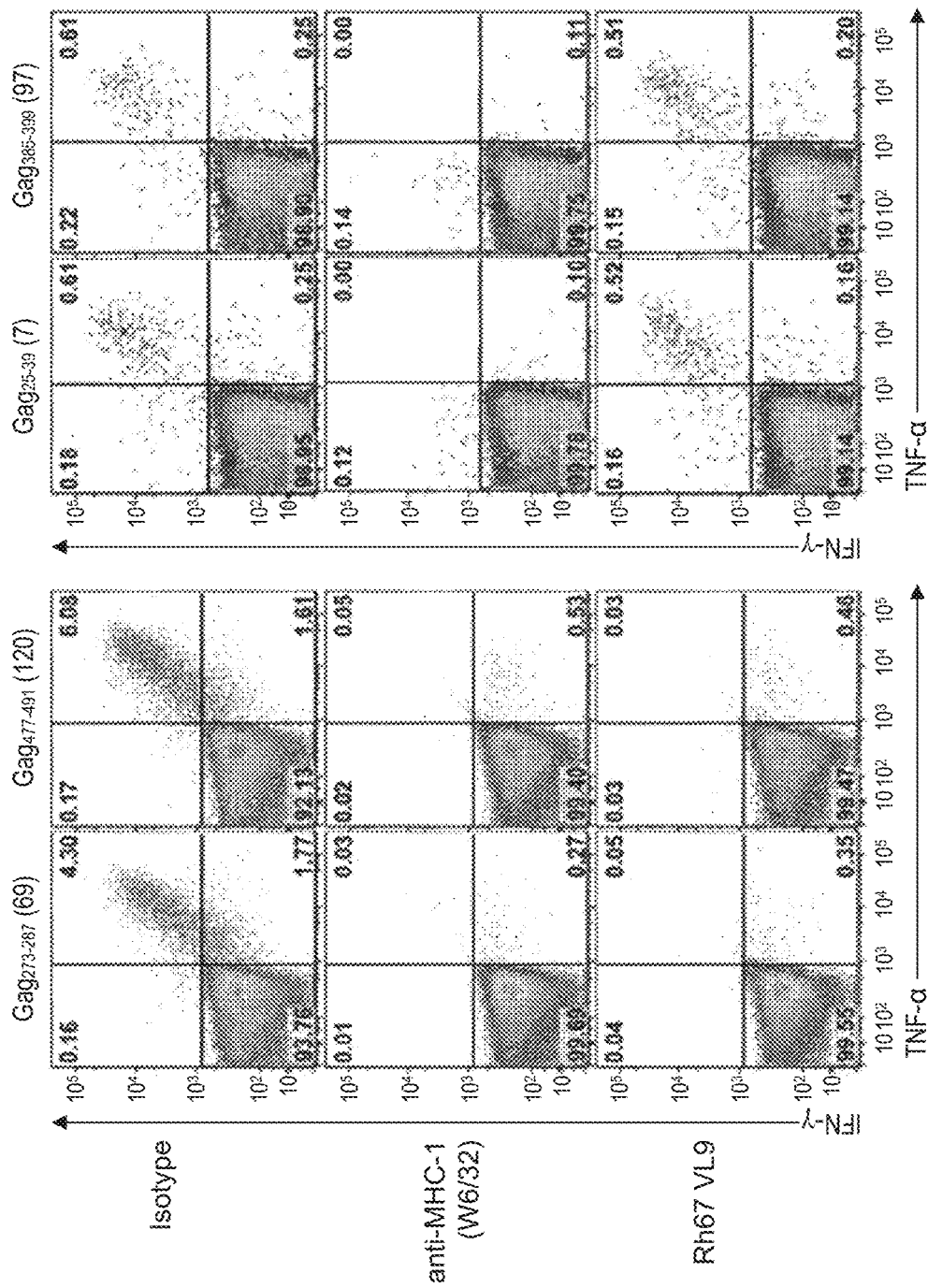
FIG. 9 is a set of flow cytometry plots of MHC-I vs. MHC-E blockade studies. Representative flow cytometry plots of CD8+ T cells in PBMC from (left) a strain 68-1 RhCMV/gag vector vaccinated macaque, or (8) a strain 68-1.2 RhCMV/gag vector-vaccinated macaque showing IFN-γ and/or TNF-α production (response frequencies of CD8+ T cells shown in each quadrant) following incubation with the Gag 15-mer peptide indicated on top and the blocking condition indicated at left.

The contribution of MHC-E to the overall Gag-specific CD8+ T cell response elicited by RhCMV/gag vectors was compared to that of a conventional Modified Vaccinia Ankara (MVA/gag) vector and native SIV infection. Flow cytometric ICS using blocking monoclonal antibodies (mAbs) specific for MHC-I or MHC-II along with the MHC-E blocking Rh67$_{8-16}$ VL9 peptide was used to assess the restriction of each epitope specific response found in a cohort of 25 macaques; 6 vaccinated with strain 68-1 RhCMV/gag, 9 with strain 68-1.2 RhCMV/gag, 7 with MVA/gag, and 8 SIV-infected macaques. MHC-E-blocked CD8+ T cell responses were found only in macaques vaccinated with strain 68-1 RhCMV/gag. Furthermore, every MHC-I-blocked response observed in the macaques vaccinated with strain 68-1 RhCMV/gag was presented by MHC-E (FIGS. 2A, 8, and 9). No MHC-E restricted CD8+ T cells were observed in macaques vaccinated with strain 68-1.2 RhCMV/gag vector.

The lack of MHC-E restricted CD8+ T cells in strain 68-1.2 RhCMV/gag vector vaccinated macaques was surprising given the minimal differences between the two CMV strains. During in vitro culture on fibroblasts prior to being cloned as a bacterial artificial chromosome (BAC). RhCMV 68-1 lost the ability to express gene products from the Rh13, Rh60, Rh157.5, and Rh157.4 (HCMV RL11, UL36, UL128, and UL130, respectively) open reading frames (D. Malouli et al., *J Virol* 86, 8959 (2012) and WO 2014/138209; incorporated by reference herein). Of these, expression is restored for Rh60, Rh157.5, and Rh157.4 in the RhCMV 68-1.2 strain (A. E. Lilja, T. Shenk, *Proc Natl Acad Sci USA* 105, 19950 (2008); incorporated by reference herein), suggesting that the presence of one or a combination of these gene products is sufficient to inhibit priming of CD8+ T cells on MHC-E. Rh60 can be excluded as the gene mediating this inhibitory effect because it is present in the non-BAC derived RhCMV/gag(L) vector (Hansen, S. G. et al., *Science* 328, 102 (2010); incorporated by reference herein) which induces MHC-E restricted CD8+ T cells (FIG. 2A). Thus, the absence of the genes Rh157.5 and Rh157.4 (UL128-130 in HCMV) from CMV is necessary for induction of MHC-E restricted CD8+ T cells.

Figure 2B:
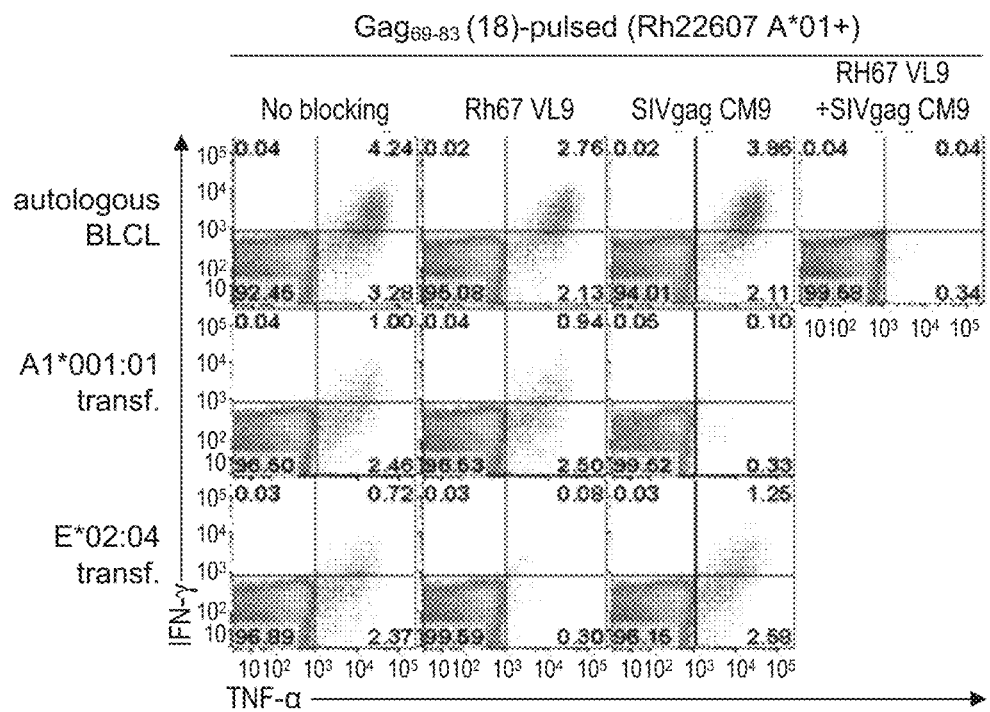
FIG. 2B is a set of flow cytometry plots of CD8$^+$ T cells in PBMC from a MamuA1*001:01+ strain 68-1 RhCMV/gag vector-vaccinated macaque showing IFN-γ and/or TNF-α production (response frequencies of CD8$^+$ T cells shown in each quadrant) following incubation with antigen presenting cells (autologous BLCL or K562 transfectant expressing only MamuA1*001:01 or Mamu-E) that were pulsed with the Gag$_{60-83}$ (Gag #18) peptide alone (no blocking), or in the presence of MHC-E-binding Rh67$_{8-16}$ VL9 or Mamu A*01-binding Gag$_{181-189}$ CM9 peptide.
Figure 2C:
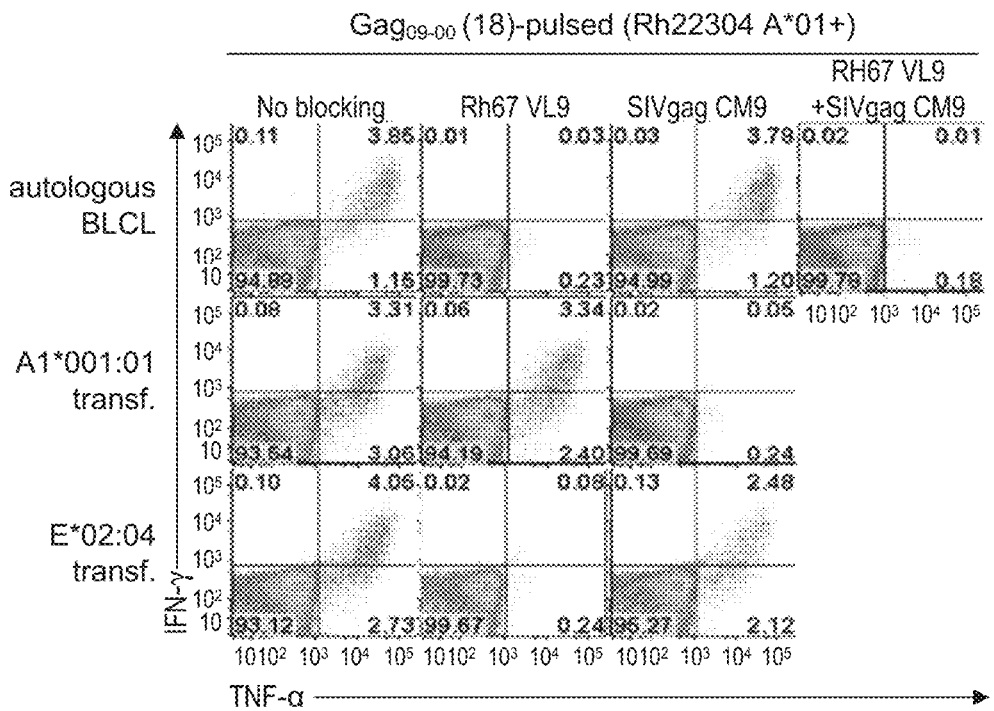
FIG. 2C is a set of flow cytometry plots of CD8$^+$ T cells in PBMC from a MamuA1*001:01-strain 68-1 RhCMV/gag vector-vaccinated macaque incubated with antigen presenting cells as described for FIG. 2B.

Incomplete VL9 blocking for certain responses was observed (see Gag 15-mer #18 in Rh22607 in FIG. 2A). Indeed, while every RhCMV/gag-induced, W6/32-blocked CD8+ T cell response recognized peptide in the context of MHC-E, these incompletely VL9-blocked peptides were recognized in the context of classical MHC-Ia alleles, such as Gag$_{69-83}$ (Gag 15-mer #18) presented by Mamu-A*001:01 (A*01) in Rh22607 (FIG. 8B). To more closely understand this dual presentation, peptide blockade studies were performed. These showed that although the presence of the Mamu-A*01-binding Gag$_{183-189}$ CM9 peptide was sufficient to inhibit presentation of Gag$_{69-83}$ on the Mamu-A*01 transfectant, and the presence of the Rh67-derived VL9 peptide inhibited presentation of Gag$_{69-83}$ on the MHC-E transfectant, both peptides were required to completely block presentation of Gag$_{69-83}$ on autologous BLCL from a Mamu-A*01+ macaque (FIG. 2B). In contrast, presentation of the same Gag$_{69-83}$ epitope was fully blocked by the presence of the Rh67$_{8-16}$ VL9 peptide alone on BLCL from a Mamu-A*01-macaque, underscoring MHC-E as the primary restricting allele for these peptides (FIG. 2C). However, given the ability of MHC-E restricted CD8+ T cells to respond to cognate peptide in the context of either MHC-E or a classical MHC-Ia molecule, the TCR of these cells likely directly recognize the MHC-bound peptide itself or in conjunction with a conserved MHC structural motif. Surprisingly, the presence of an MHC allele capable of binding a specific peptide epitope was not sufficient for the generation of a CD8+ T cell response targeting that epitope (FIG. 8), indicating additional layers of immunological regulation in determining the specific set of epitopes targeted in each RhCMV-vaccinated macaque.

Figure 3A:
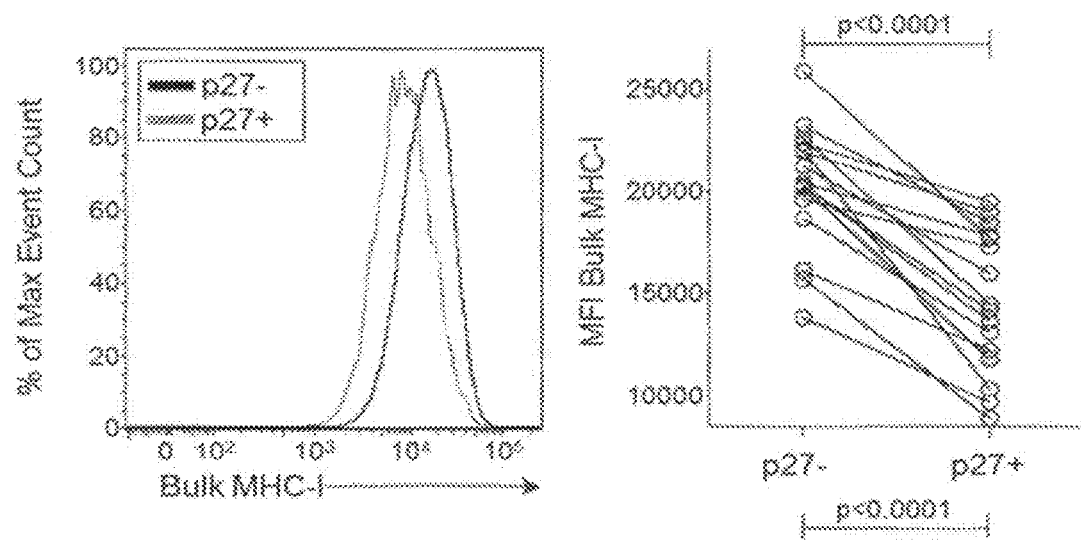
FIG. 3A is a set of two plots showing bulk surface MHC-I (measured by mAb W6/32) on the surface of productively SIV-infected (CD4$^+$ Gag p27$^+$) or uninfected (CD4$^+$ Gagp27) CD4+ T cell targets. Representative flow cytometry plots are shown on the left panel while the right panel depicts the mean fluorescent intensity (MFI) of bulk MHC-I staining in SIV infected versus uninfected CD4$^+$ T cells derived from a total of 16 unrelated rhesus macaques.
Figure 3B:
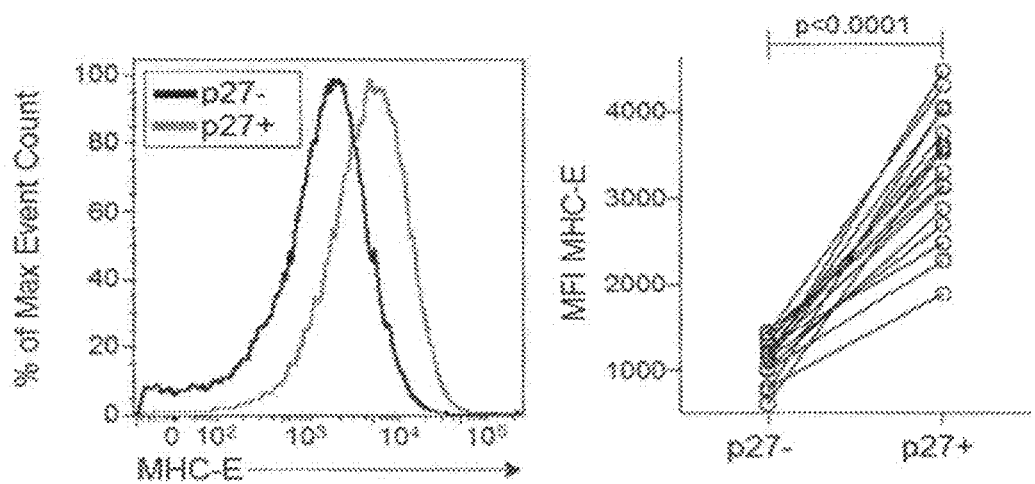
FIG. 3B is a set of two plots showing MHC-E (measured by mAb 4D12) on the surface of productively SIV-infected (CD4$^+$ Gag p27$^+$) or uninfected (CD4$^+$ Gagp27) CD4$^+$ T cell targets. Representative flow cytometry plots are shown on the left panel while the right panel depicts the MFI of MHC-E staining in SIV infected versus uninfected CD4$^+$ T cells derived from a total of 16 unrelated rhesus macaques.

Next, it was established that MHC-E restricted CD8+ T cells participate in the immune response against SIV. HIV and SIV evade CD8+ T cell recognition by Nef-mediated down regulation of the classical MHC class I molecules from the cell surface (O. Schwartz, et al., *Nat Med* 2, 338 (1996); K. L. Collins et al., *Nature* 391, 397 (1998); both of which are incorporated by reference herein). In contrast, Nef is unable to down regulate HLA-E and its surface expression actually increases with HIV infection (J. Natterman et al., Antivir Ther 10, 95, (2005); incorporated by reference herein). First, the fate of Mamu-E on the surface of productively SIV-infected CD4+ T cells was determined. Using the pan-MHC-I mAb W6/32 and the Mamu-E-specific mAb 4D12, it was demonstrated that, like HLA-E during HIV infection, Mamu-E surface expression is significantly increased during SIV infection (FIGS. 3A and 3B). Therefore, MHC-E restricted CD8+ T cells might be particularly effective since they would be impervious to Nef-mediated down-modulation of their restricting MHC-I molecule. MHC-E interacts with both TCRαβ and CD94/NKG2 complexes, which are expressed on the surface of CD8+ T cells (V. M. Braud et al., *Nature* 391, 795 (1998); incorporated by reference herein).

Figure 3C:
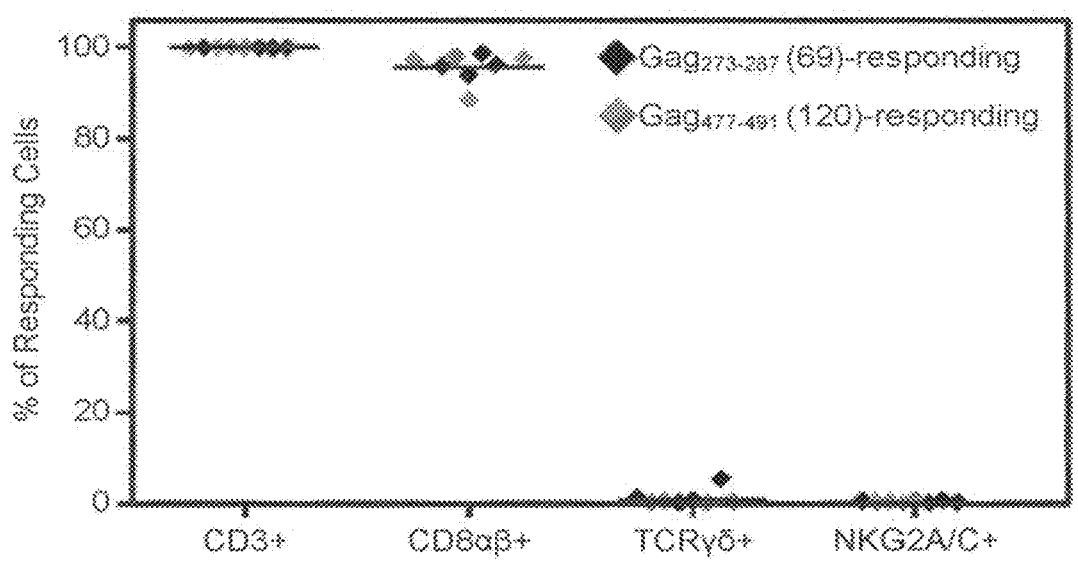
FIG. 3C is a plot showing the phenotype of MHC-E restricted CD8$^+$ T cells responding to Gag$_{273-287}$ (69) or Gag$_{427-491}$ (120) peptide stimulation. Percentages were calculated by examining the number of IFN-γ and/or TNF-α producing cells expressing each marker.
Figure 10A:
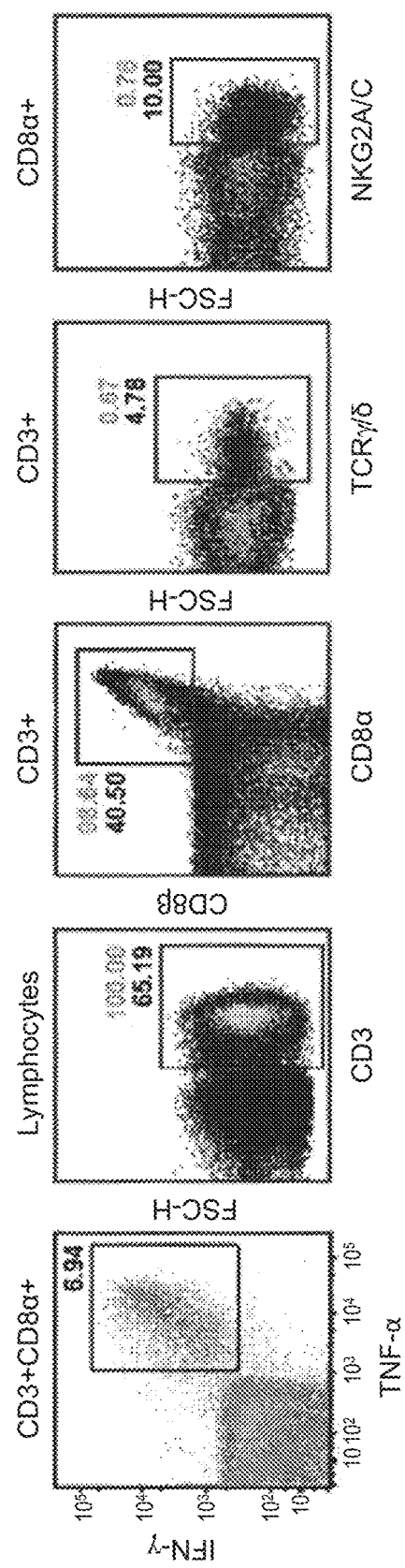
FIG. 10A is a set of flow cytometry plots showing PBMC from strain 68-1 RhCMV/gag vector-vaccinated macaques were stimulated with $Gag_{273-287}$ (SIVmac239 Gag 15-mer #69) and flow cytometric ICS was performed. CD8+ T cells responding to these MHC-E bound Gag peptides were identified via IFN-γ and TNF-α and then compared against the remaining cells in PBMC for expression of the markers indicated. Numbers in black indicate the overall percentage of cells in PBMC that are positive for the marker indicated, while the numbers in gray indicate the percentage of IFN-γ and TNF-α producing cells that are positive.
Figure 10B:
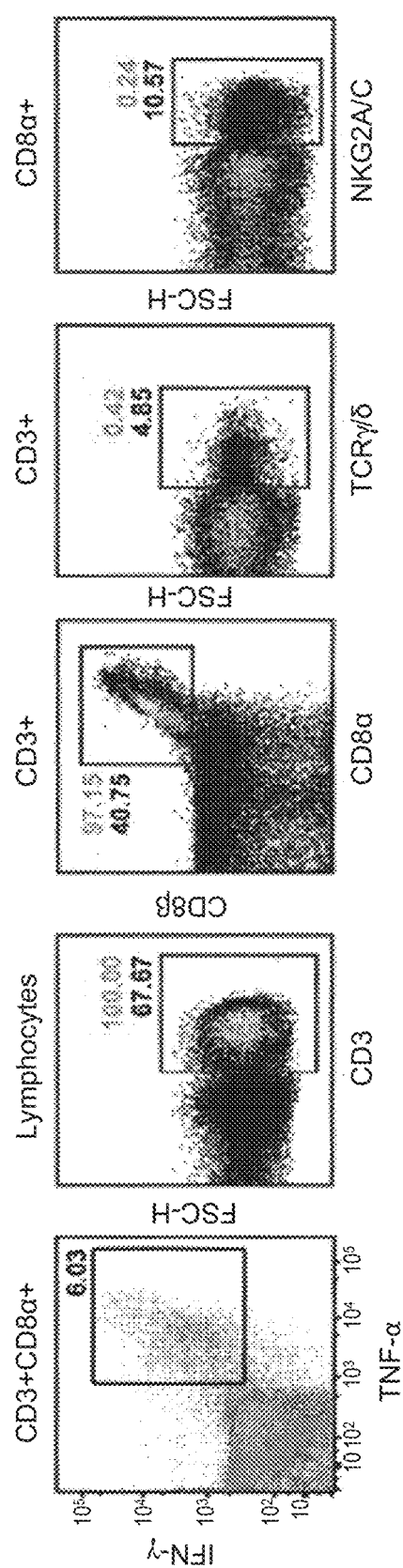
FIG. 10B is a set of flow cytometry plots showing PBMC from strain 68-1 RhCMV/gag vector-vaccinated macaques were stimulated with $Gag_{477-491}$ (SIVmac239 Gag 15-mer #120) and flow cytometric ICS was performed. CD8+ T cells responding to these MHC-E bound Gag peptides were identified via IFN-γ and TNF-α and then compared against the remaining cells in PBMC for expression of the markers indicated. Numbers in black indicate the overall percentage of cells in PBMC that are positive for the marker indicated, while the numbers in gray indicate the percentage of IFN-γ and TNF-α producing cells that are positive.

In particular, high NKG2C expression is driven by CMV infection, and engagement of the NKG2C receptor triggers activation of NK and T cells interacting with MHC-E (S. Lopez-Verges et al., *Proc Natl Acad Sci USA* 108, 14725 (2011) and M. Guma et al., Eur J Immunol 35, 2071 (2005); both of which are incorporated by reference herein). To investigate the possibility that the MHC-E restricted CD8+ T cells in strain 68-1 RhCMV/gag-vaccinated macaques utilize NKG2C receptors to mediate MHC-E induced activation, the surface phenotype of these cells was examined, and little, if any, NKG2A/NKG2C expression (FIGS. 3C and 10) was found. Furthermore, the MHC-E restricted CD8+ T cells exhibited a conventional CD3+, CD8αβ+, TCRγδ+, NKG2A/C phenotype suggesting that these T cells recognized MHC-E-bound peptides via CD8-stabilized TCRαβ interactions.

Figure 4A:
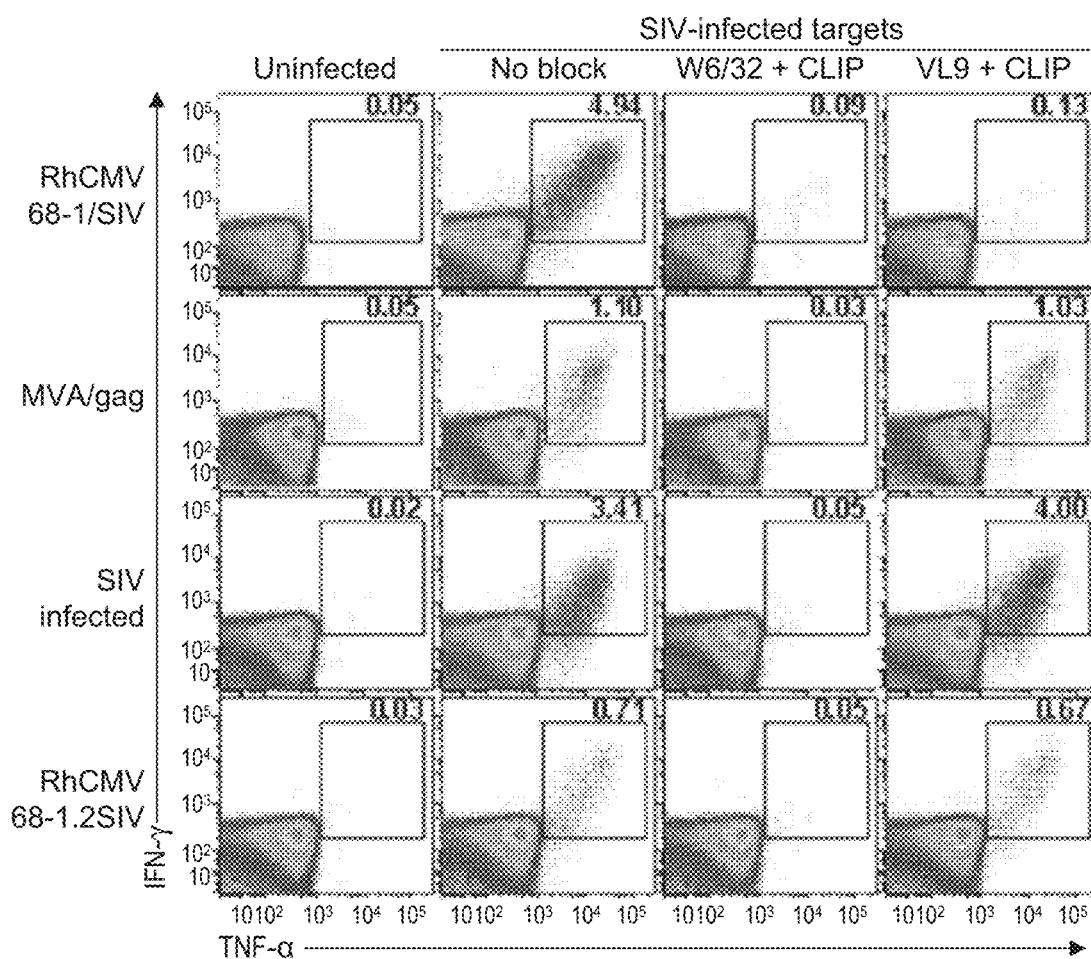
FIG. 4A is a set of representative flow cytometry plots of CD8$^+$ T cells isolated from macaques vaccinated with either strain 68-1 RhCMV/gag, MVA/gag, strain 68-1.2 RhCMV/gag, or infected with SIV, showing IFN-γ and/or INF-α production from CD8$^+$ T cells following incubation with autologous SIVmac239-infected CD4$^+$ T cells alone (no block), or in the presence of the MHC-II binding Class II-associated invariant chain peptide (CLIP) plus the pan-MHC-I blocking mAb W6/32 (W6/32+CLIP), or Rh67$_{8-16}$ VL9 plus CLIP (VL9+CLIP).
Figure 4B:
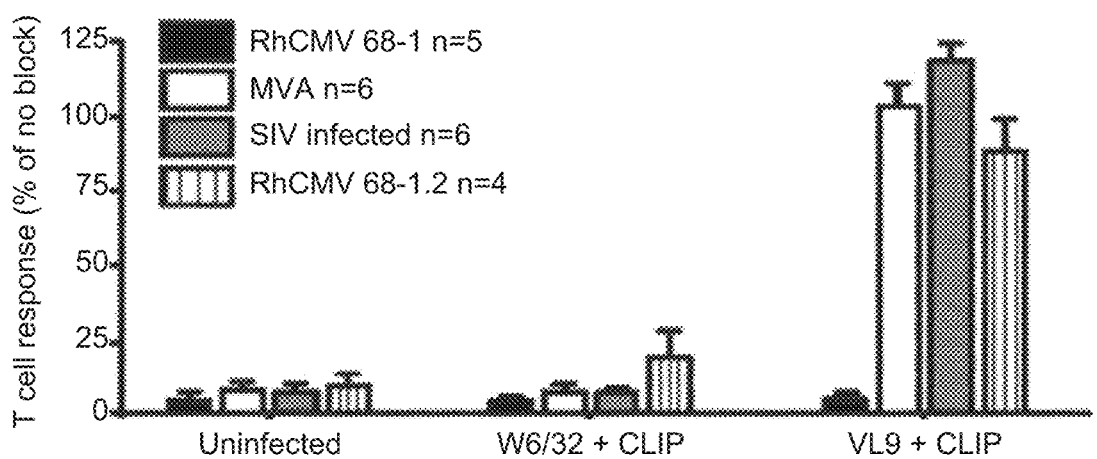
FIG. 4B is a bar graph of a comparison of the normalized response frequencies for the recognition and blocking experiments represented in FIG. 4A for CD8$^+$ T cells from macaques vaccinated with strain 68-1 RhCMV/gag (n=5), MVA/gag (n=6), strain 68-1.2 RhCMV/gag (n=4), or infected with SIV (n=6).

Next, the ability of MHC-E restricted CD8+ T cells present in 68-1 RhCMV/SIV vaccinated macaques to specifically recognize autologous, SIV-infected CD4+ T cells was compared to that of the classically MHC-I restricted CD8+ T cells found in macaques vaccinated with MVA/gag or strain 68-1.2 RhCMV/gag or infected with SIV. CD8+ T cells isolated from all treated macaques robustly recognized autologous SIV-infected CD4+ T cells, and this recognition was completely blocked by the addition of the pan-MHC-I blocking mAb W6/32 and the MHC-II binding CLIP peptide (FIGS. 4A and 4B). In contrast, CD8+ T cell recognition of infected cells was fully restored when the MHC-I blocking mAb W6/32 was replaced by the MHC-E blocking Rh67$_{8-16}$ VL9 peptide in all cases except for CD8+ T cells isolated from strain 68-1 RhCMV/SIV-vaccinated macaques. This suggests that MHC-E restricted CD8+ T cells recognized SIV infected cells.

Figure 4C:
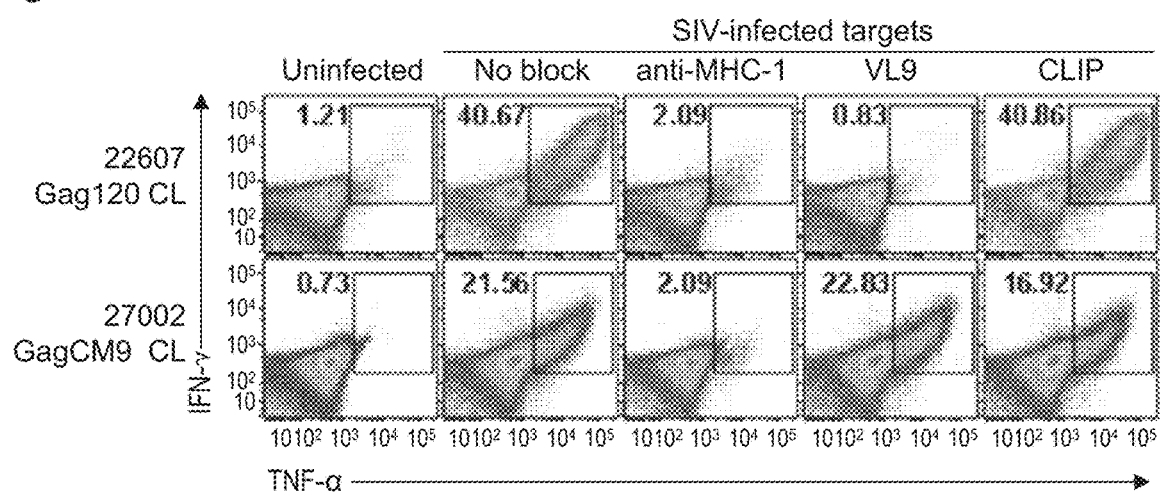
FIG. 4C is a set of how cytometry plots illustrating the recognition of SIV-infected cells by CD8$^+$ T cell lines (CL) specific for either the MHC-E restricted Gag$_{477-481}$ Gag #120 epitope (top row) or the Mamu-A*001:01 restricted Gag$_{181-189}$ CM9 epitope (bottom row). CLs were incubated with uninfected or SIV-infected CD4$^+$ T cells (from Rh22607) in the presence of the blocking conditions indicated.

To more precisely examine if MHC-E bound, SIV derived epitopes were present on the surface of infected cells a Gag$_{477-491}$(Gag #120) supertope specific, MHC-E restricted CD8+ T cell line was generated. This line was tested for the ability to respond to autologous SIV-infected CD4+ T cells. For comparison, a classically MHC-restricted (Mamu-A*001:01 restricted) Gag$_{181-189}$ CM9 CD8+ T cell line was also assessed. Both Gag-specific CD8+ T cell lines specifically recognized SIV-infected cells, and recognition was blocked when targets were pre-incubated with the pan-MHC-I blocking mAb W6/32. In contrast, only the MHC-E restricted CD8+ T cell line was unable to recognize SIV-infected cells when targets were pre-incubated with the MHC-E binding peptide Rh67$_{8-16}$ VL9 (FIG. 4C). Cumulatively, these data indicate that MHC-E restricted CD8+ T cells specifically recognize SIV-derived peptide epitopes on the surface of infected cells.

Strain 68-1 vectors induce CD8+ T cells that recognize peptide antigen in the context of the non-classical MHC-E molecule. Such CD8+ T cells represent a new cellular immune response for vaccine development and may be particularly effective given the unique immunobiology of MHC-E. In contrast to classical HLA molecules that are down regulated from the surface of HIV-infected cells, HLA-E expression is up regulated, and the increase of MHC-E expression occurs within the first 24 hours of infection at the portal of viral entry (J. Natterman et al., *Antivir Ther* 10, 95 (2005) and L. Shang et al., *J Immonol* 193, 277 (2014); both of which are incorporated by reference herein). Only two functionally identical HLA-E alleles are present in the human population (R. K. Strong et al., *J Biol Chem* 278, 5082 (2003); incorporated by reference herein). Therefore, a vaccine platform specifically inducing MHC-E restricted T cells could result in a truly universal CD8+ T cell vaccine with every vaccinated individual mounting identical T cell responses impervious to HIV Nef-mediated immune evasion. Indeed, as disclosed herein, MHC-E-restricted CD8+ T cells are strongly elicited by strain 68-1 RhCMV vectors, which have shown unparalleled protection against SIV in macaques (Hansen et al. (2009), supra; Hansen et al. (2011), supra: Hansen et al. *Nature* (2013), supra). Thus, a HIV vaccine that induces responses against both classical as well as non-classical epitopes might provide the necessary breadth of T cell responses required to effectively block viral replication and subsequently blunt viral transmission.

Figure 5:
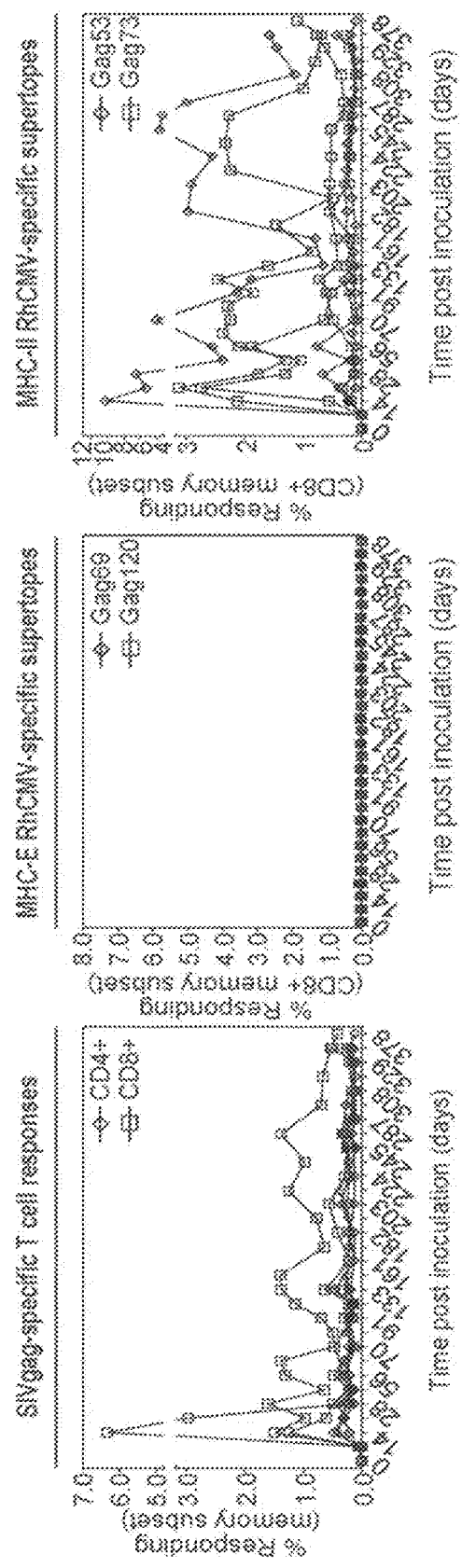
FIG. 5 (left panel) shows the percentage of CD8$^+$ T cells in PBMC from a rhesus macaque inoculated with a Rh67 (UL40)-deleted 68-1 RhCMV expressing SIVgag showing IFN-γ and/or TNF-α production following incubation with overlapping peptides corresponding to SIVgag at the indicated time points. The central panel shows that CD8$^+$ T cells in PBMC from the same animal do not respond to the Mamu-E-restricted peptides Gag$_{273-287}$ (Gag69) or Gag$_{477-491}$ (Gag120). The right panel shows the percentage of CD8$^+$ T cells in PBMC from the same animal responding to MHC-II restricted peptides (Gag53 and Gag73). The MHC-II peptides correspond to so-called supertopes, i.e. these peptides are presented by many different MHC-II alleles and hence elicit responses in most animals.

As mentioned above, HCMV encodes the glycoprotein UL40 (the RCMV homolog is Rh67), that contains the 9-mer peptide (VMAPRTLLL, Rh67$_{8-16}$ VL9) binding the MHC-E peptide binding groove with extremely high affinity (P. Tomasec et al., *Science* 287, 1031 (2000); incorporated by reference herein). Since the in vitro data indicated that VL9 competes for binding with antigen-derived peptides the possibility that deletion of Rh67 (UL40) from the genome of RhCMV 68-1 would further increase the frequency of HLA-E restricted CD8+ T cells in vivo was considered. To examine this possibility, Rh67 (UL40) was deleted from the 68-1 RhCMV/gag vector. The resulting recombinant virus was inoculated into an animal that was naturally infected with RhCMV. At days 0, 7, 14, 21, 28 and 42 post inoculation, PBMC were obtained, and the frequency of CD8+ T cells responding to total SIVgag as well as MHC-E was measured by intracellular cytokine staining using specific peptides. As shown in FIG. 5, SIVgag responses to total SIVgag were detectable beginning at day 14 post inoculation. In addition, CD8+ T cells responded to MHC-II-restricted "supertope" peptides Gag53 and Gag73. Contrary to our expectations however, there was no increase of T cell responses to HLA-E-specific supertopes. In fact, no responses were detected to either HLA-E peptides examined in this experiment (Gag69 and Gag120). This surprising result therefore suggests that vectors lacking UL40 and UL128 and UL130 induce MHC-II restricted CD8+ T cells, including MHC-II restricted supertopes, but not MHC-E-restricted CD8+ T cells. Induction of MHC-E restricted CD8+ T cells thus requires the presence of UL40 and the absence of UL128 and UL130.

To determine whether, in addition to Rh67 (UL40), RhCMV encodes additional genes that are required for the induction of HLA-E and/or MHC-II restricted T cell responses by RhCMV lacking UL128-130, gene regions that are non-essential for growth in vitro were deleted from RhCMV 68-1, and the T cell response upon inoculation of rhesus macaques was monitored. While most deletion mutants did not affect T cell specificities, it was observed that deletion of the gene region Rh214-Rh220 eliminated the ability of RhCMV 68-1 to elicit MHC-E restricted responses, whereas MHC-II restricted CD8⁺ T cell responses were still observed (FIGS. 29 and 30). This result was unexpected since the Rh214-Rh220 region encodes five copies of genes that are homologous to (i.e., homologs of) HCMV US28: Rh214, Rh215, Rh216, Rh218 and Rh220 (also known as RhUS28.4, RhUS28.3, RhUS28.2, RhUS28.1, and RhUS28.5, respectively, M. E. Penfold et al. *J Virol* 77: 10404 (2003) incorporated by reference herein). The previously predicted open reading frames Rh217 and Rh219 are not considered to represent functional genes based on a series of previously described criteria (D. Malouli et al., *J Virol* 86, 8959 (2012) incorporated by reference herein). HCMV US28 encodes a G-protein coupled receptor that binds to CC-chemokines (J. L. Gao and P. M. Murphy *J Biol Chem* 269: 28539 (1993)) and chemokine binding was confirmed for at least one of the five RhCMV homologues (M. E. Penfold et al. J Virol 77: 10404 (2003)). However, a requirement of US28 for the induction of MHC-E restricted T cell responses was unexpected. This surprising result therefore suggests that vectors lacking US28, UL128, and UL130 induce MHC-II restricted CD8⁺ T cells. Including MHC-II restricted supertopes, but not MHC-E-restricted CD8⁺ T cells. Induction of MHC-E restricted CD8⁺ T cells thus requires the presence of US28 and UL40, and the absence of UL128 and UL130.

Materials and Methods:

Rhesus macaques: A total of 46 purpose bred male or female rhesus macaques (RM) (*Macaca mulatta*) of Indian genetic background were used in the experiments reported in this example, including 9 RM vaccinated with strain 68-1 RhCMV/gag, RM vaccinated with strain 68-1.2 RhCMV/gag, 1 RM inoculated with Rh67-deleted 68-1 RhCMV/gag, 7 RM vaccinated with MVA/gag, 19 unvaccinated RM with SIV infection, and 6 unvaccinated RM naturally infected with colony-circulating strains of RhCMV. All RM were used with the approval of the Oregon National Primate Research Center Institutional Animal Care and Use Committee, under the standards of the US National Institutes of Health Guide for the Care and Use of Laboratory Animals. RM used in these experiments were free of cercopithicine herpesvirus 1, D-type simian retrovirus, and simian T-lymphotrophic virus type 1. Selected RM were MHC-I-genotyped by deep sequencing. Briefly, amplicons of Mamu class I sequences were generated via amplification of cDNA by PCR using high-fidelity Phusion™ polymerase (New England Biolabs) and a pair of universal MHC-I-specific primers with the following thermocycling conditions: 98° C. for 3 min, (98° C. for 5 s, 57° C. for 1 s, 72° C. for 20 s) for 23 cycles, and 72° C. for 5 min. Each PCR primer contained a unique 10 bp Multiplex Identifier (MID) tag along with an adaptor sequence for 454 Sequencing™ (5'-GCCTCCCTCGCGCCATCAG-MID-GC-TACGTGGACGACACG-3', 5'-GCCTTGCCAGCCCGCTCAG-MID-TCGCTCTGGTTGTAGTAGC-3'). Resulting amplicons span 190 bp of a highly polymorphic region within exon two. The primary cDNA-PCR products were purified using AMPure XP magnetic beads (Beckman Coulter Genomics). Emulsion PCR and pyrosequencing procedures were carried out with Genome Sequencer FLX instruments (Roche/454 Life Sciences) as per the manufacturer's instructions. Data analysis was performed using a Labkey database in conjunction with Geneious-Pro® bioinformatics software (Biomatters Ltd.) for sequence assembly.

RhCMV/SIV Vectors: The construction, characterization, and administration of strain 68-1-derived RhCMV/SIV have been previously described in detail (Hansen et al. (2009), supra; Hansen et al. (2011), supra; Hansen et al. *Nature* (2013), supra; Hansen et al. *Science* (2013), supra; Hansen et al. (2010), supra). All recombinant viruses used in this study were derived from strain RhCMV 68-1 BAC. Due to tissue culture adaptation, RhCMV 68-1 constructs contain a deletion of ORF 157.5 and most of ORF Rh157.4 encoding homologs of HCMV UL128 and UL130, respectively (Hansen, S. G. et al., *J Virol* 77, 6620 (2003); incorporated by reference herein).

To generate a vector that lacks UL40 expression, ORF Rh67 was deleted from RhCMV 68-1 by BAC recombineering. Briefly, Rh67 was replaced with a FRT-flanked Kanamycin-resistance gene containing PCR fragment by homologous recombination, followed by excision of the KanR-gene using FLP recombinase. Virus was recovered in rhesus fibroblasts and characterized for antigen expression and loss of Rh67(UL40).

To generate a vector with complete UL128-130 expression, the SIVgag expression cassette was inserted into Rh211 of RhCMV 68-1.2, a recombinant virus in which Rh61/Rh60 (UL36), Rh157.4 (UL130), and Rh157.5 (UL128) had been repaired (A. E. Lilja and T. Shenk, *Proc Natl Acad Sci U.S.A.* 105, 19950 (2008); incorporated by reference herein). All of the recombinant viruses were characterized and confirmed by restriction digest and antigen inserts, including their flanking regions, were sequence verified. Expression of SIV antigens was verified by Immunoblot. Additionally, adjacent gene expression was verified by RT-PCR.

Other Vaccines

MVA/gag was constructed by insertion of codon-optimized, full-length SIVmac239 gag gene into the MVA shuttle vector, pLW44, under the control of MH5, an early/late vaccinia promoter, to generate the recombinant plasmid, pJV7. Flanking sequences within pLW44 directed insertion of the recombinant construct into the thymidine kinase locus by homologous recombination. Chicken embryonic fibroblast cells were transfected with pJV7 followed by infection with MVA strain 1974 to generate recombinant virus expressing SIVmac239gag (SIVgag expression confirmed by Immunoblot). Recombinant virus was plaque-purified and amplified in large-scale culture. Viral stocks were purified over a 24-40% sucrose gradient followed by pelleting through a 36% sucrose cushion with the pellet then suspended in 1 mM Tris-Cl, pH 9.0. For MVA/gag vaccination, RM were administered 10⁸ plaque-forming units of this vector via intramuscular injection.

Antigens and Antigen-Presenting Cells: Sequential 15-mer peptides (overlapping by 11 amino acids) comprising the SIVgag protein were obtained from the NIH AIDS Reagent Program. Synthesis of specific 9-14-mer peptides within these proteins was performed by Genscript (Piscataway, N.J.). All peptides are identified by the position of their inclusive amino acids from the n-terminus (e.g., $Gag_{xx-yy}$). Consecutive 15-mers are also designated by their position starting from the n-terminal 15-mer (e.g., $Gag_{1-35}$ is 15 mer #1; $Gag_{5-19}$ is 15 mer #2, etc.). Unless otherwise specified, these peptides were used in T cell assays used at 2 µg/ml. Autologous B-lymphoblastoid cell lines (BLCL) were generated by infecting rhesus PBMC with Herpesvirus papio, as described previously (Hansen et al. *Science* (2013), supra). Mammalian expression vectors for Mamu class I molecules were generated by ligating each allele into pCEP4 KpnI/NotI or HindIII/NotI restriction sites. Plasmids were cloned in DH5α *E. coli* (Life Technologies, Grand Island, N.Y.), sequence confirmed, and electroporated into MHC-I-negative K562, 721.221, or RMA-S (K. S. Anderson et al.,

*J Immunol* 151, 3407 (1993); incorporated by reference herein) cells using Nucleofector II/Kit C (Lonza, Allendale N.J.). Transfectants were maintained on drug selection (Hygromycin B) and routinely confirmed for surface expression of MHC-I by staining with pan-MHC-I antibody clone W6/32. Throughout use in T cell assays, mRNA from MHC-I transfectants was extracted using the AllPrep DNA/RNA Mini Kit (Qiagen), amplified by RT-PCR using primer pairs flanking a highly polymorphic region within exon 2, and sequence confirmed. MHC-I transfectants and BLCL were pulsed with Gag peptide of interest at a final concentration of 10 μM for 90 minutes then washed three times with warm PBS and once with warm R10 to remove unbound peptide before combining with freshly isolated PBMC at an effector:target ratio of 10:1. In order to stabilize Mamu-E surface expression, Mamu-E transfectants were incubated at 27° C. for 3 hours prior to use in assays and maintained at 27° C. throughout peptide incubation until combined with effectors. Autologous SIV-infected target cells were generated by isolation of $CD4^+$ T cells from PBMC with CD4 microbeads and LS columns (Miltenyi Biotec), activation with a combination of IL-2 (vendor). *Staphylococcus enterotoxin* B (vendor), and anti-CD3 (NHP Reagent Resource), anti-CD28, and anti-CD49d mAbs (BD Biosciences), and spinoculation with sucrose purified SIVmac239, followed by 3-4 days of culture. Prior to use in T cell assays, SIV-infected target cells were purified using CD4 microbeads and LS columns (Miltenyi Biotec), as previously described (J. B. Sacha et al., *J Immunol* 178, 2748 (2007); Incorporated by reference herein). Infected cell preparations were >95% $CD4^+$ T cells and >50% SIV-infected following enrichment and were used at an effector:target ratio of 40:1 (PBMC and isolated $CD8^+$ T cells) or 8:1 (T cell line effectors). In these experiments, uninfected, activated $CD4^+$ T cells served as negative control APCs (uninfected targets from $SIV^+$ RM were cultured with tenofovir (NIH AIDS Reagent Program, concentration)). To assess bulk MHC-I and MHC-E, SIV-infected $CD4^+$ T cells were generated as described above without post-infection purification and stained for surface MHC-I (clone W6/32), MHC-E (clone 4D12; anti-mouse IgG1 M1-14D12), CD3, CD4 and intracellular SIV Gag p27 capsid.

T Cell Assays: Mononuclear cell preparations for immunologic assays were obtained from blood with FicollPaque (GE Healthcare). Purified $CD8^+$ T cells (>90% pure) were obtained from PBMC using CD8 microbeads and LS columns (Miltenyi Biotec). Epitope-specific T cell lines were prepared by stimulation of PBMC with irradiated, peptide-pulsed BLCL and subsequent culture in media containing IL-2 (vendor), with re-stimulation performed weekly. SIV-specific $CD8^+$ T cell responses were measured by flow cytometric ICS. Briefly, effector T cells (mononuclear cells, isolated $CD8^+$ T cells, or T cell lines) were incubated with antigen (peptide, peptide-pulsed APCs, or SIV-infected $CD4^+$ T cells) and co-stimulatory monoclonal antibodies (mAbs) to CD28 and CD49d (BD Biosciences) for 1 hour, followed by addition of Brefeldin A (Sigma-Aldrich) for an additional 8 hours. Co-stimulation in the absence of antigen (no peptide, unpulsed APCs, or uninfected targets) served as background control. In restriction assays using MHC-I transfectants as APCs, co-stimulation in the presence of peptide-pulsed MHC-I-negative parental cell lines K562 or 721.221 cells served as additional negative controls. When indicated, mononuclear cells or antigen-presenting cells were pre-incubated for 1 hour with the following blocking reagents: anti-MHC-I mAb (clone W6/32; 10 μg/ml), CLIP peptide (MHC-II-associated invariant chain, amino acids 89-100; 2 μg/ml), MHC-E-binding peptide VL9 (VMAPRTLLL; 20 μM). Mamu-A1*001:01-binding peptide CM9 (CTPYDINQM; 20 μM), or Mamu-A1*002:01-binding peptide GY9 (GSENLKSLY; 20 μM). Stimulated cells were fixed, permeabilized, and stained as previously described (Sacha et al., *The Journal of Immunology*, 178, 2746-2754 (2007); incorporated by reference herein) and flow cytometric analysis was performed on an LSR-II instrument (BD Biosciences). Analysis was done using FlowJo software (Tree Star), gating first on small lymphocytes followed by progressive gating on $CD3^+$, then $CD4^+/CD8a^+$ T cell subsets. Antigen specific response frequencies for resulting $CD4^+/CD8a^+$ populations were determined from intracellular expression of TNF-α and IFN-γ. For epitope deconvolution experiments, strict response criteria were used to prevent false positives. In these studies, a response to a given 15-mer peptide was considered positive if the frequency of events clustered as $CD69^+$, $TNF-\alpha^+$ and $IFN-\gamma^+$ was >0.05%, with background <0.01% in at least 2 independent assays. The classification of individual peptide responses as blocked, shown in FIGS. 2A and 6, was based on >90% inhibition by blockade relative to the isotype control. Define partial blockade. Responses that did not meet these criteria were considered indeterminate. To be considered MHC-E-restricted by blocking, the individual peptide response must have been (1) blocked by both anti-MHC-I clone W6/32 and MHC-E binding peptide VL9, and (2) not blocked by CLIP.

Antibodies

The following conjugated Abs were used in these studies: a) from BD Biosciences, L200 (CD4; AmCyan), SP34-2 (CD3; PacBlu), SK1 (CD8a; TruRed, AmCyan), 25723.11 (IFNg; APC, FITC), 6.7 (TNF; APC), b) from Beckman Coulter, L78 (CD69; PE).

Example 2

Generation of $CD8^+$ T Cells Specific for Peptides of Interest in the Context of MHC-E T cell receptors recognizing antigen-derived peptides of interest in the context of classical, polymorphic MHC-Ia molecules can be used to transfect autologous T cells for immunotherapy of disease, such as cancer or infectious disease. A major obstacle to this approach is the MHC-Ia diversity in the human population that limits the use of a given TCR to MHC-Ia matched patients. By generating TCR recognizing antigen derived peptides of interest (e.g., tumor antigen derived peptides and pathogen-derived peptides) in the context of non-classical, non-polymorphic MHC-E molecules, MHC-matching becomes obsolete, and the resulting TCR can be used in all patients.

$CD8^+$ T cells recognizing MHC-E/peptide complexes are rare in nature, and there is not currently a reliable method to generate such T cells directed against antigens of interest, such as tumor antigens, pathogen-derived antigens, tissue-specific antigens, or host self-antigens. The method described herein is based upon the finding that a rhesus cytomegalovirus (RhCMV) lacking the genes Rh157.5 and Rh157.4 (homologs of HCMV UL128 and UL130) elicits MHC-E-restricted $CD8^+$ T cells in rhesus monkeys at a frequency of about 1 peptide epitope per 30-40 amino acids of protein sequence. By inserting an antigen of interest into UL128 and 130-deleted RhCMV, $CD8^+$ T cells directed against individual peptides presented by MHC-E can be generated. The MHC-E/peptide-recognizing TCRs can be identified by any of a number of methods but generally rely on sequencing the alpha and beta chains either directly by PCR from the cDNA of single cells, clonally expanded single cells, or deep sequencing pools of peptide specific CD8$^+$ T cells. Alternatively the sequence may be derived indirectly by expanding the RNA template by first creating a whole transcriptome library for a single cell, clonally expanded single cell, or pool of peptide specific CD8$^+$ T cells. Peptide specific variable sequences may be generated by rapid amplification of cDNA ends (RACE) or switching mechanism at 5'end of RNA template (SMART) protocols performed on the mRNA. PCR anchored in flanking constant regions or similarly from whole transcriptome libraries of single peptide reactive CD8$^+$ cells can be sequenced directly or deep sequenced for their respective TCR variable regions. Validated combinations of alpha and beta chains derived from the TCR sequence of individual or pools of peptide reactive CD8$^+$ T-cells can further be synthesized or cloned. The resulting TCR constructs can then be transfected into T cells that can in turn be administered to patients as a therapy (e.g., cancer therapy or infectious disease therapy). Methods of cloning and transfecting TCR variable regions are also discussed in Barsov E V et al., PLoS One 6, e23703 (2011), which is incorporated by reference herein.

Example 3

Broadly Targeted CD8$^+$ T Cell Responses Restricted by Major Histocompatibility Complex-E Major histocompatibility complex (MHC)-E is a highly conserved, ubiquitously expressed, non-classical, MHC-Ib molecule with limited polymorphism primarily involved in regulation of NK cell reactivity via interaction with NKG2/CD94 receptors. Here, priming of rhesus macaques with Rh157.5/.4 gene-deleted RhCMV vectors uniquely diverts MHC-E function to presentation of highly diverse peptide epitopes to CD8α/β$^+$ T cells, approximately 4 distinct epitopes per 100 amino acids, in all tested protein antigens. Since MHC-E is up-regulated on cells infected with HIV/SIV and other persistent viruses to evade NK cell activity, MHC-E-restricted CD8$^+$ T cell responses have the potential to exploit pathogen immune evasion adaptations, a capability that might endow these unconventional responses with superior efficacy.

Adaptive cellular immunity against intracellular pathogens is the primary responsibility of CD8$^+$ T cells that recognize short (8-10 mer) pathogen derived peptide epitopes presented by highly polymorphic MHC-Ia molecules on the surface of infected cells (Neefjes J et al., Nat Rev Immunol 11, 823 (2011) and Nikolich-Zugich J et al., Microbes Infect 6, 501 (2004); both of which are incorporated by reference herein). MHC-Ia allomorphs vary considerably in their peptide binding properties, and therefore the particular pathogen derived peptides targeted by pathogen specific CD8$^+$ T cells is largely determined by the peptide binding specificity of the limited number of MHC-Ia allomorphs expressed by the infected individual (Yewdell J W, Immunity 25, 533 (2006); incorporated by reference herein) Consequently, the epitopes recognized by CD8$^+$ T cells responding to the same pathogen are highly diverse across individuals. This recognition heterogeneity is important, as the nature of epitopes targeted by CD8$^+$ T cell responses can have an enormous influence on the ability of the individual to clear or control various intracellular pathogens, in particular agents like HIV with a high intrinsic capacity for mutational immune escape (Nikolich Zugich (2004), supra and Goulder, P. J. and Watkins, D. I. Nat Rev Immunol 8, 610 (2008); incorporated by reference herein). From an evolutionary perspective, this MHC-Ia polymorphism-mediated response diversity allows large populations to survive emerging pathogens because of the high likelihood that at least some members of the population will have MHC-Ia allomorphs that support effective CD8$^+$ T cell responses (Nikolich-Zugich (2004), supra and Prugnolle F et al., Curr Biol 15, 1022 (2005); incorporated by reference herein). On the other hand, this biology inevitably results in certain individuals within a population being highly susceptible to a given pathogen, even when vaccinated, which hampers efforts to develop universally effective vaccines based on CD8$^+$ T cell responses (Goulder and Watkins (2008), supra and Picker, L. J. et al., Ann Rev Med 63, 95 (2012); incorporated by reference herein)

Figure 14:
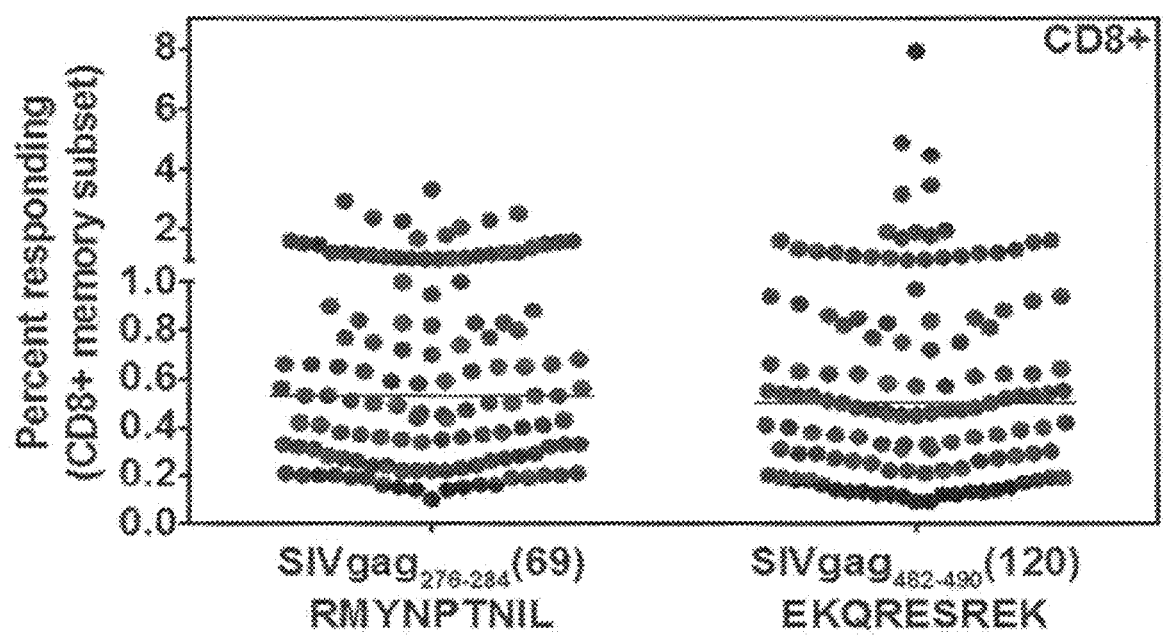
FIG. 14 is a plot showing that the $SIVgag_{276-284}$ and $SIVgag_{482-490}$ epitopes are recognized by CD8+ T cells in all strain 68-1 RhCMV/gag-vaccinated rhesus macaques. The CD8+ T cell response to the indicated SIVgag 9 mer peptides was determined in 120 strain 68-1 RhCMV/gag-vaccinated RM using flow cytometric ICS, using peptide-specific induction of TNF-α and/or IFN-γ within CD3+/CD8+ T cells as the response read-out. All macaques manifested detectable responses to these supertopic epitopes after background subtraction. The response frequencies shown have been memory corrected to reflect the frequency of epitope-responding cells with the CD8+, $CD95^{high}$ memory subset. Horizontal bars indicate median values.

It was recently reported that SIV targeted vaccine vectors based on strain 68-1 (fibroblast adapted) RhCMV strikingly violate the above-described rules of MHC-Ia-restricted CD8$^+$ T cell recognition (Hansen et al. *Science* (2013), supra), and offer a potential solution to MHC-Ia-dependent response diversity in CD8$^+$ T cell-targeted vaccination. In rhesus monkeys, RhCMV/SIV vectors provide profound protection against highly pathogenic SIV challenge, resulting in stringent control and ultimate clearance of infection (Hansen et al. (2011), supra and Hansen et al. *Nature* (2013), supra). These vectors elicit SIV-specific CD8$^+$ T cell responses that are entirely non-overlapping with conventional MHC-Ia-restricted CD8$^+$ T cells, despite responding to 3-fold as many epitopes as conventional vaccines expressing the same SIV protein. Part of this lack of epitope overlap was explained by the finding that many of these epitopes were restricted by MHC-II molecules, rather than MHC-Ia, a rare, but not unprecedented mode of epitope recognition by CD8$^+$ T cells (Hansen et al. *Science* (2013), supra). Strain 68-1 RhCMV/SIVgag vectors also elicited CD8$^+$ T cells that recognized multiple MHC-I-dependent epitopes (e.g., responses entirely blocked by anti-MHC-I antibodies) that were common to most, or even all MHC-disparate macaques, an unprecedented degree of cross recognition for MHC-Ia-restricted CD8+ T cell responses. Indeed, two epitopes in the SIV gag protein (SIVgag$_{276-284}$ and SIVgag$_{482-490}$) were targeted by 42 of 42 strain 68-1 RhCMV/SIVgag vector-immunized monkeys in the previous report (Hansen et al. *Science* (2013), supra), and CD8$^+$ T cell responses to these two 9 mer epitopes have since been documented in 120 of 120 monkeys inoculated with this vector (FIG. 14).

Figure 11A:
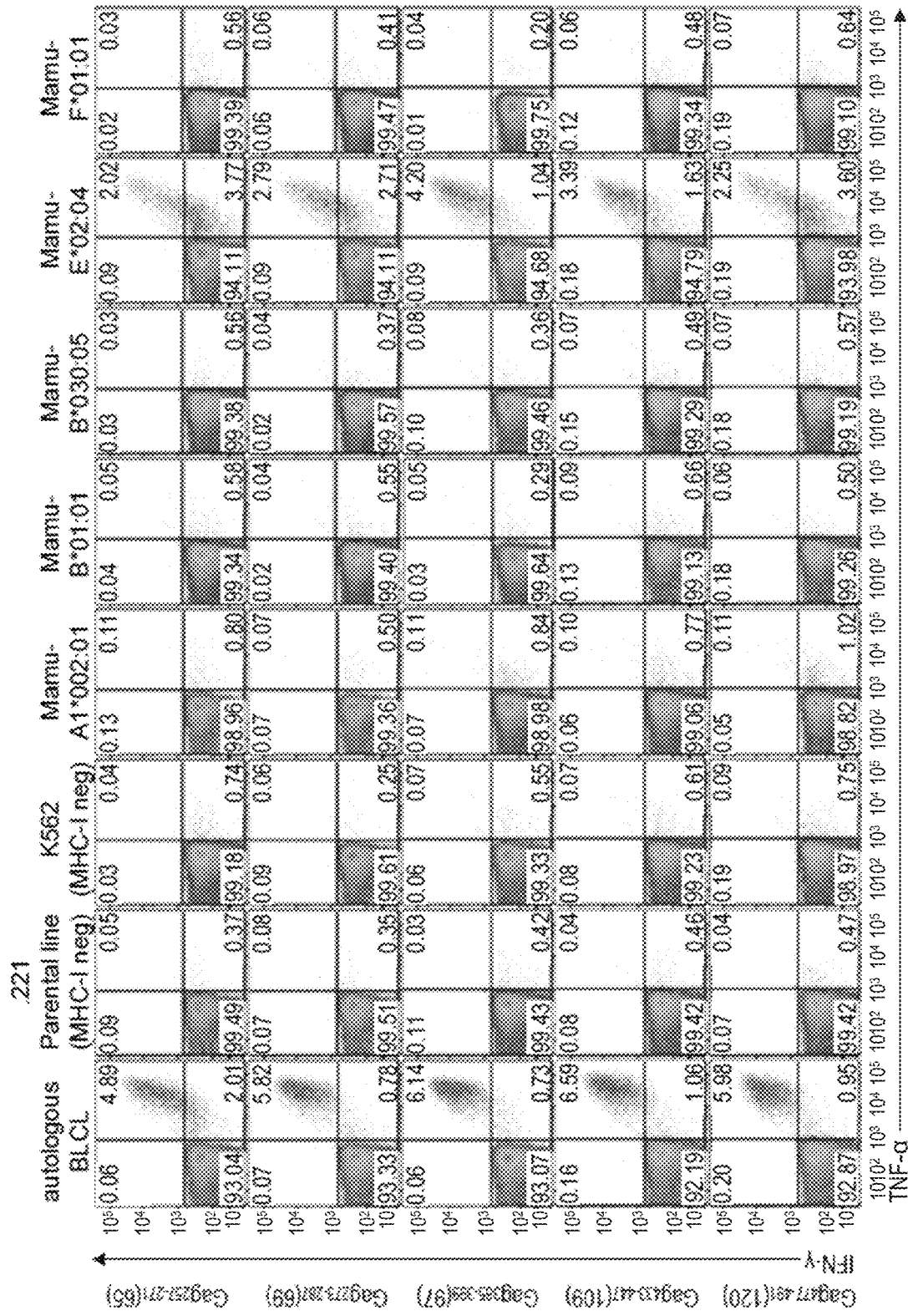
FIG. 11A is a set of plots showing results from flow cytometric intra-cellular cytokine staining (ICS) analysis of PBMC from a representative strain 68-1 RhCMV/SIVgag-vaccinated macaque (Rh22034; of 4 similarly analyzed). PBMC from vaccinated macaques were stimulated with the indicated 15 mer peptide epitopes pulsed onto the surface of the indicated MHC-I transfectants or control cells with CD8+ T cell recognition determined by detection of IFN-γ and/or TNF-α production by flow cytometric ICS assay (response frequencies of gated CD8+ T cells shown in each quadrant). The parental MHC-I-negative 0.221 and K562 cells were used as negative controls, while autologous B-lymphoblastoid cells (BLCL) were used as the positive control. The MHC-I molecules tested included both those expressed by Rh22034.
Figure 11B:
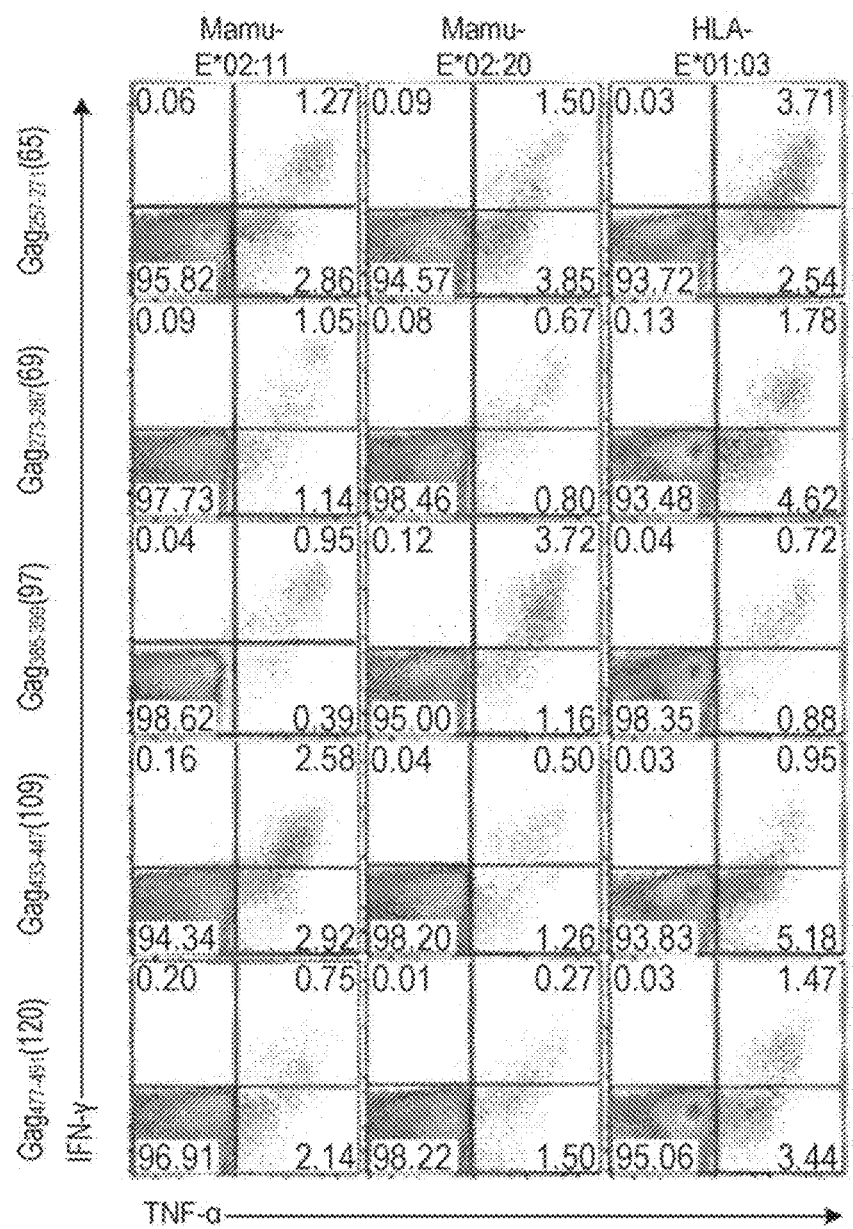
FIG. 11B is a set of plots showing results from flow cytometric ICS analysis of additional macaque and human MHC-E molecules not expressed by Rh22034 similar to that of FIG. 11A.
Figure 15B:
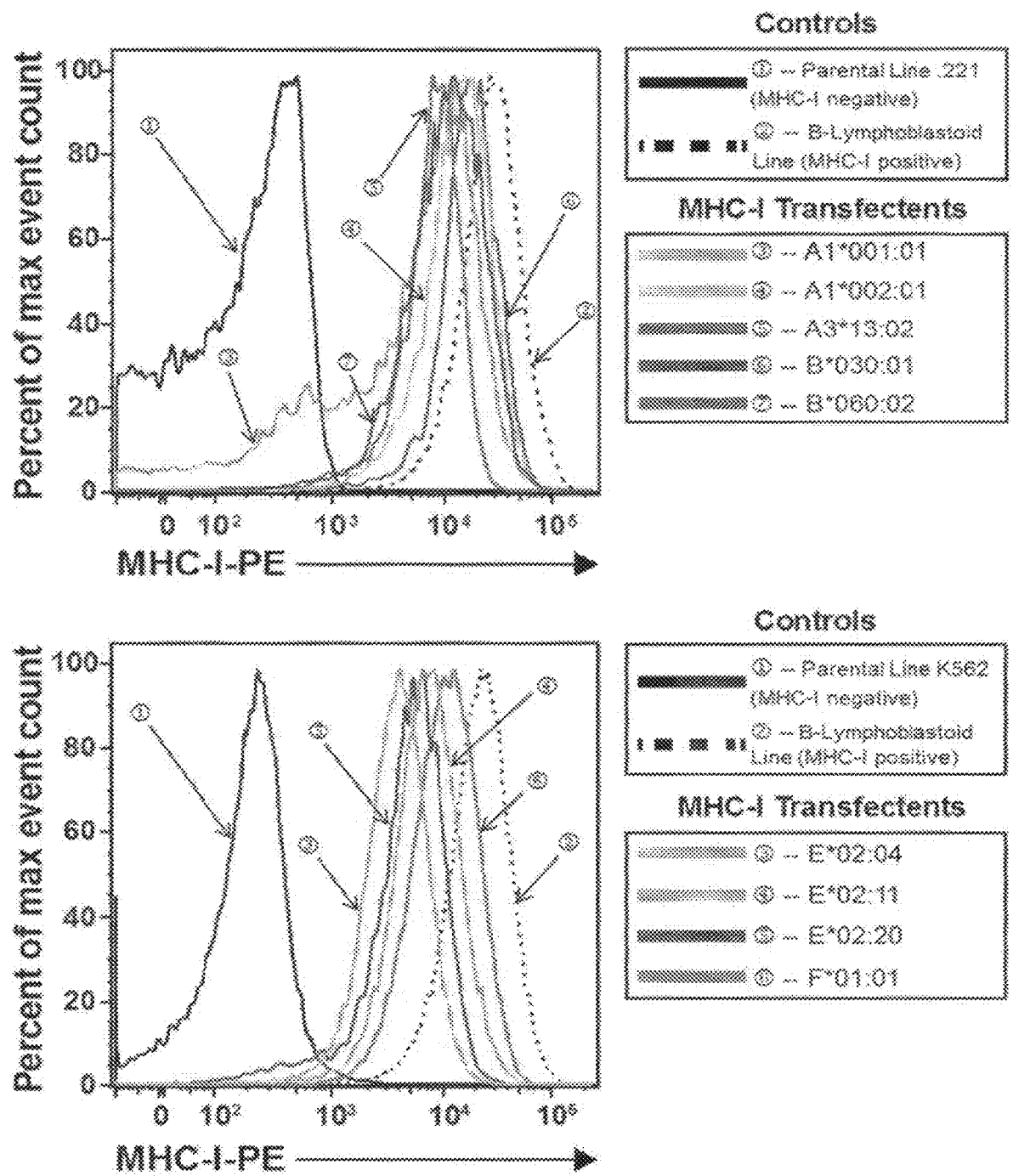
FIG. 15B is a set of two plots showing expression of single MHC-I molecules. MHC-Ia or MHC-Ib alleles were transfected into a parental (MHC-I negative) cell line (0.221 cells or K562 cells) and stained with pan-MHC-I monoclonal antibody (W6/32). MHC-I-expressing B-lymphoblastoid cells (BLCL) served as a positive control, while the MHC-I-negative parental cell lines were used as negative controls.
Figure 16A:
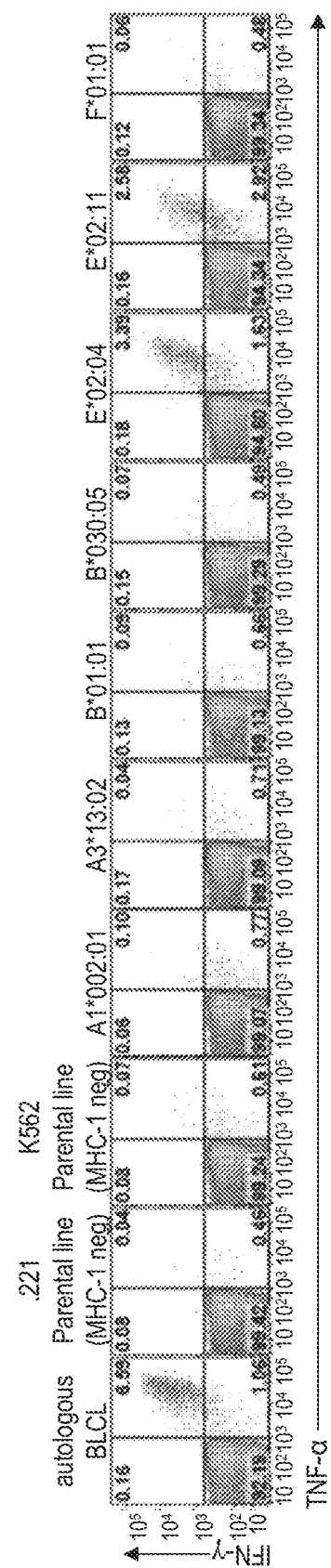
Figure 16B:
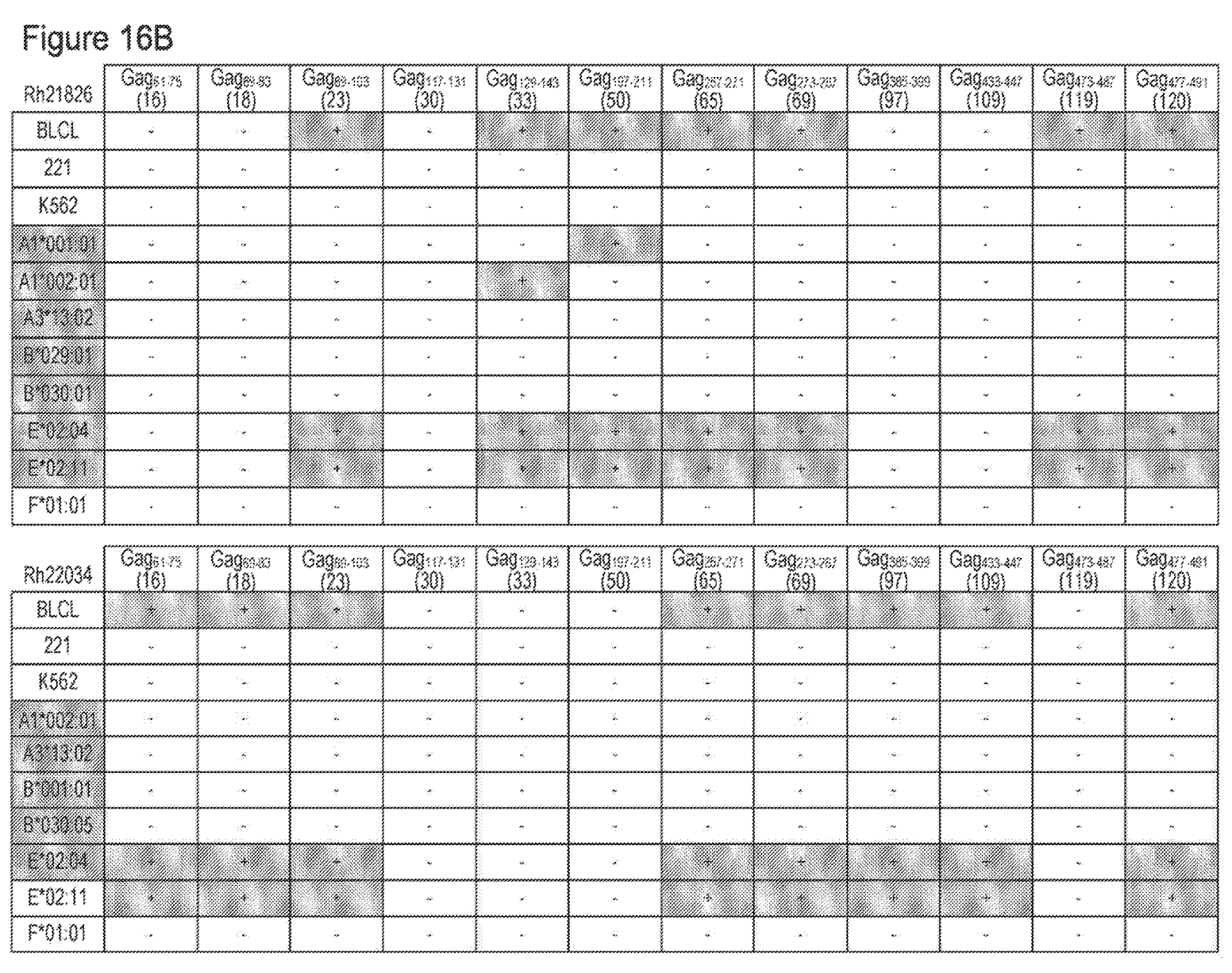
Figure 16B:
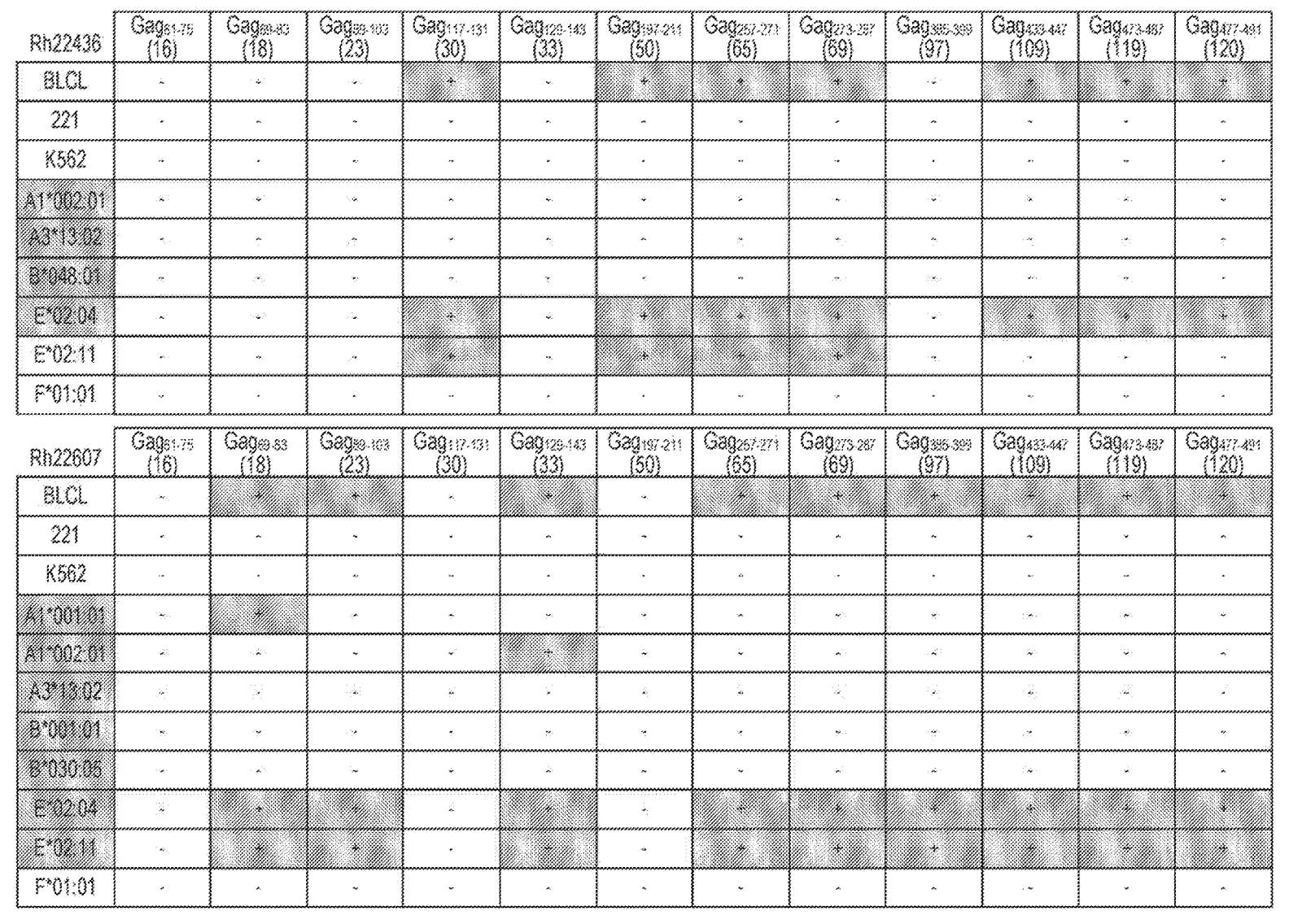

To understand the basis of this unusually universal MHC-I-dependent recognition, 4 strain 68-1 RhCMV/SIVgag vector-vaccinated monkeys were selected for detailed MHC-I restriction analysis. These macaques displayed robust, unconventional MHC-I-dependent CD8$^+$ T cell responses to SIVgag, including responses to the SIVgag$_{276-284}$ and SIVgag$_{482-490}$ supertopes, as well as 10 other commonly recognized responses. The expressed MHC-I genes, both classical MHC-Ia and non-classical MHC-Ib (Wiseman, R. W. et al., Nat Med 15, 1322 (2009); incorporated by reference herein), were sequenced in each monkey, and a panel of MHC-I transfectants singly expressing these MHC-I molecules was constructed individually (FIG. 15). These single MHC-I molecule transfectants were then used in a flow cytometric intra-cellular cytokine staining (ICS) assay to present the epitopic 15 mer peptides to the strain 68-1 RhCMV/SIVgag vector-induced CD8$^+$ T cells from these monkeys (using parental MHC-I-negative and autologous B lymphoblastoid cell lines as negative and positive controls, respectively) (FIGS. 11A, 11B; and 16). Remarkably, classical MHC-Ia allomorphs were able to present only 3 of the 12 epitopic peptides to these T cells (Mamu-A1*001:01: SIVgag$_{69-83}$(18) and SIVgag$_{197-211}$(50); Mamu-A1*002:01: SIVgag$_{129-143}$(33)), and expression of these allomorphs in monkeys did not track with these epitope specific CD8$^+$ T cell responses (e.g., many monkeys lacking these allomorphs were still able to recognize these 3 peptides; FIG. 17). However, all 12 epitopic peptides stimulated CD8$^+$ T cells from all monkeys when presented by non-classical MHC-E molecules, and indeed, all peptides were presented by transfectants expressing 3 different rhesus monkey MHC-E allomorphs (Mamu-E02:04, -E02:11, and -E02:20), independent of whether the responses originated in monkeys that expressed these alleles, as well as by a transfectant expressing a human version of this molecule (HLA-E*01: 03) (FIGS. 11A, 11B, 16 and 18).

Figure 11C:
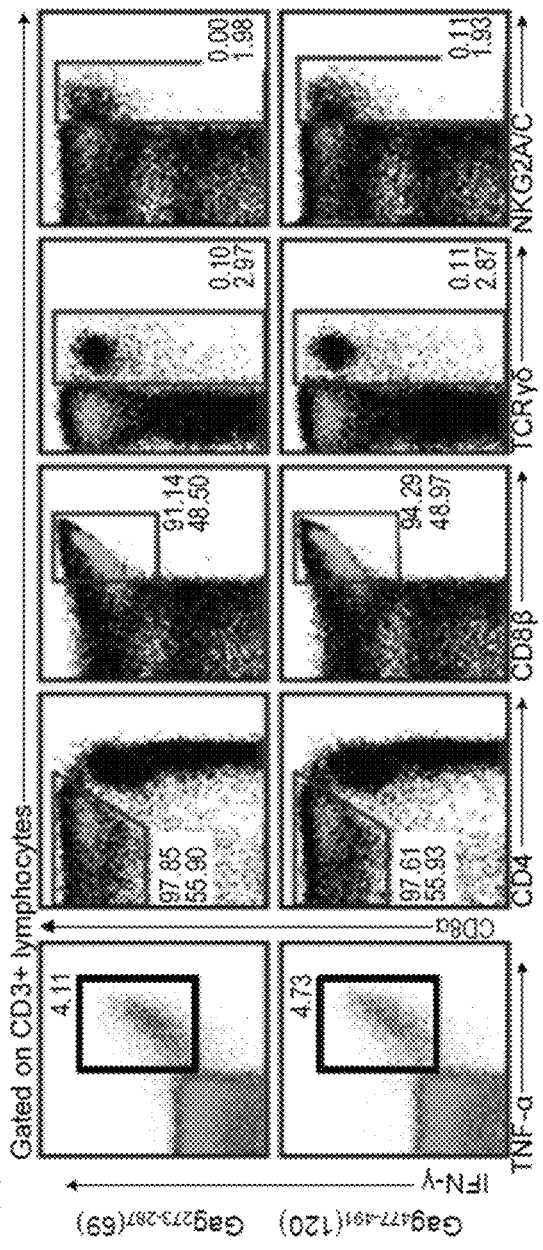
FIG. 11C is a set of plots showing phenotypic analysis of PBMC from RM treated with the same strain 68-1 RhCMV/SIVgag vector-vaccinated macaque as shown above (representative of 4 similarly analyzed) were stimulated with autologous BLCL pulsed with either $SIVgag_{273-287}$(69) or $SIVgag_{477-491}$(120), and responding CD3+ lymphocytes (IFN-γ and TNF-α-producing; gate shown in left plot) were phenotyped by flow cytometric ICS assay with responding cells and non-responding cells within the designated gates indicated in grey and black, respectively, in each plot (and their relative % within the rectangular regions shown in each plot indicated in the same colors).
Figure 11D:
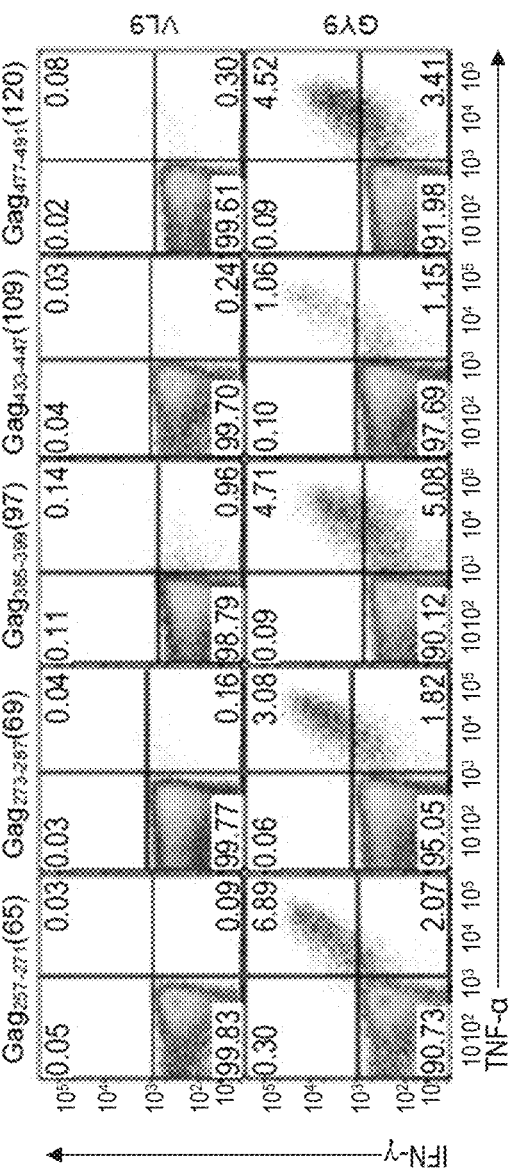
FIG. 11D is a set of plots of the results where single MHC-E transfectants were pre-incubated with canonical MHC-E-binding peptide VMAPRTLLL (VL9) or a control non-MHC-E binding peptide (SIVgag GY9) prior to pulsing with the indicated SIVgag 15 mer peptide epitope. Flow cytometric ICS assays were conducted as described above using PBMC from strain 68-1 RhCMV/SIVgag-vaccinated macaques, and the following MHC-E transfectants; Mamu-E*02:04 for $SIVgag_{273-287}$(69), $SIVgag_{388-399}$(97), and $SIVgag_{433-447}$(109) and Mamu-E*02:11 for $SIVgag_{257-273}$(65) and $SIVgag_{477-491}$(120).
Figure 19:
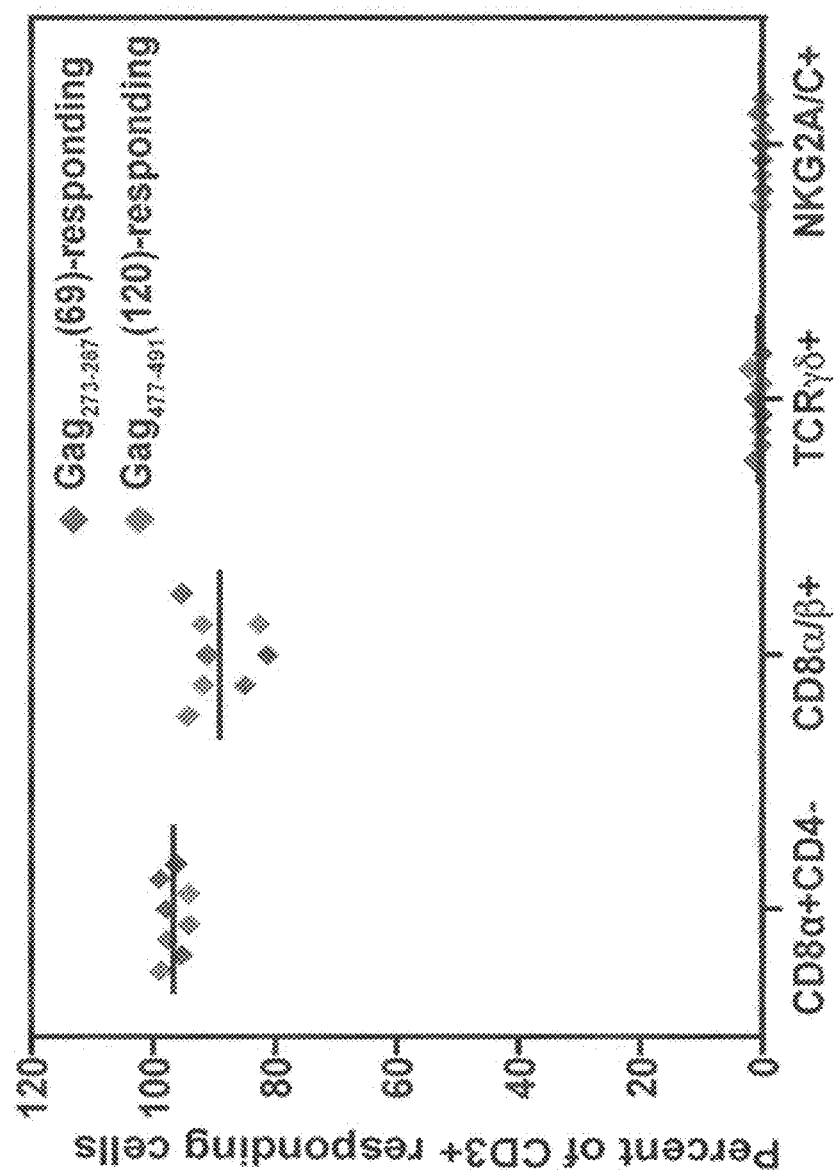
FIG. 19 is a plot showing that strain 68-1 RhCMV/SIVgag-elicited, supertope-specific CD8+ T cells exhibit a conventional CD8αβ* T cell phenotype. The figure summarizes the phenotypic analysis of MHC-E-restricted CD8+ T cells responding to SIVgag$_{273-287}$(69) or SIVgag$_{477-491}$ (120) peptide stimulation in four 68-1 RhCMV/SIVgag vaccinated macaques (Rh21826, Rh22034, Rh22436, Rh22607). The figure shows the percentages of peptide-responding CD3+ T cells (IFN-γ* and TNF-α*) that express the designated phenotypes (see flow cytometric profiles in FIG. 11C).
Figure 20A:
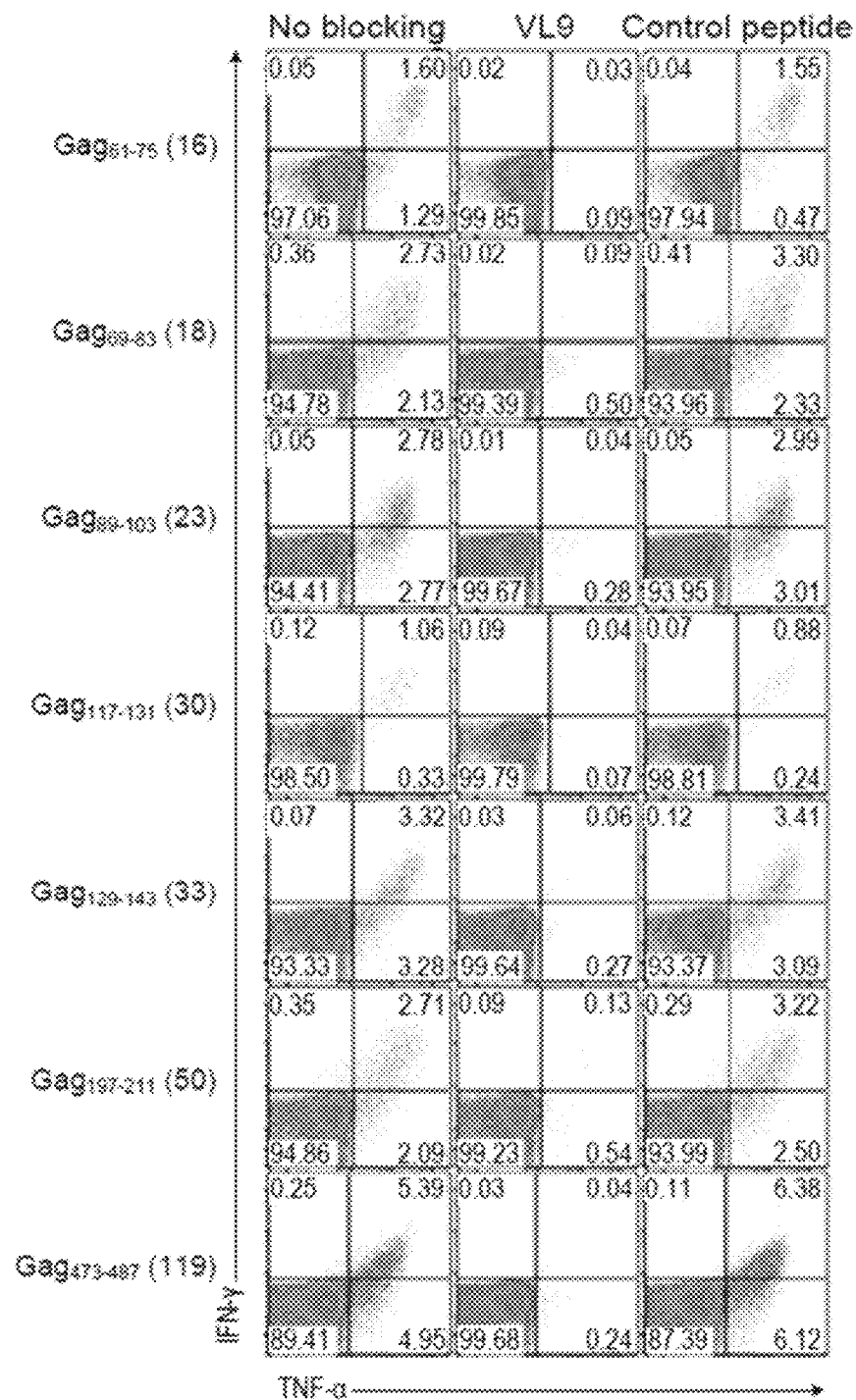
FIG. 20A is a set of plots of single MHC-E transfectants pre-incubated with canonical MHC-E-binding peptide VMAPRTLLL (VL9) or control peptide prior to pulsing with the indicated SIVgag 15-mer peptide epitope. Flow cytometric ICS was conducted as described for FIG. 11 using PBMC from strain 68-1 RhCMV/SIVgag-vaccinated macaques: Rh21826 for SIVgag$_{89-103}$(23), SIVgag$_{129-143}$ (33), SIVgag$_{197-211}$(50), and SIVgag$_{473-487}$(119) responses; Rh22034 for SIVgag$_{61-75}$(16) and SIVgag$_{69-83}$(18) responses; Rh22436 for the SIVgag$_{117-131}$(30) response. The following MHC-E transfectants were utilized: Mamu-E*02:04 for the SIVgag$_{69-83}$(18) and SIVgag$_{89-103}$(23) responses; Mamu-E*02:11 for the SIVgag$_{61-75}$(16), SIVgag$_{117-131}$(30), SIVgag$_{129-143}$(33), SIVgag$_{197-211}$(50), and SIVgag$_{473-487}$ (119) responses. The following control peptides were utilized at a final concentration of 20 μM: Mamu-A1*002:01-binding peptide SIVgag$_{71-79}$(GY9) for SIVgag$_{89-103}$(23), SIVgag$_{117-131}$(30), and SIVgag$_{129-143}$(33) responses, and the Mamu-A1*001:01-binding peptide SIVgag$_{181-189}$(CM9) for the SIVgag$_{69-83}$(18), SIVgag$_{197-211}$(50), and SIVgag$_{473-487}$(119) responses. These data, along with the data in FIG. 11D, indicate that the VL9 peptide efficiently blocks CD8+ T cell recognition of 12 diverse MHC-E-presented 15 mer peptide epitopes.
Figure 21:
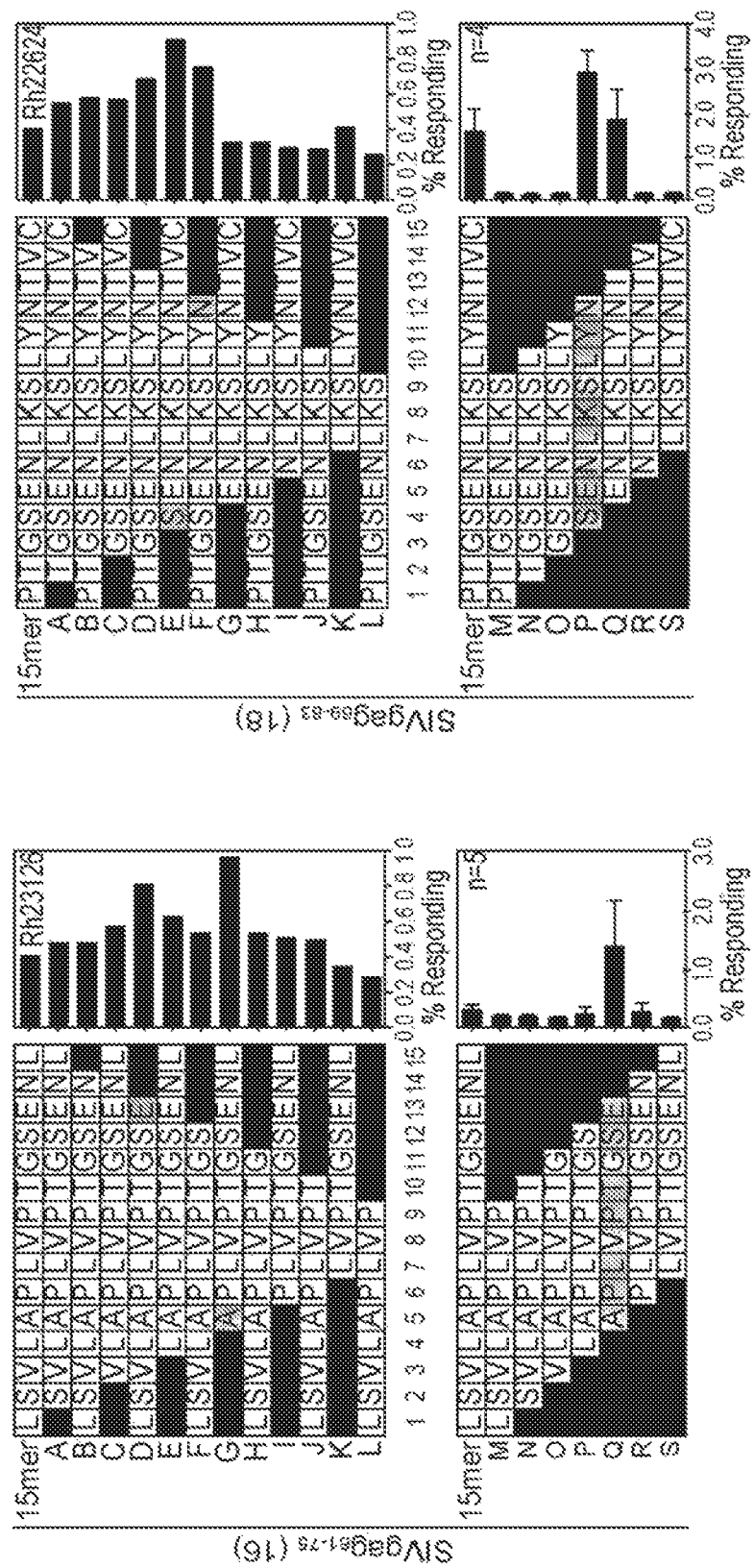
FIG. 21 shows formal truncation analysis for 8 additional MHC-E-restricted 15 peptide epitopes using peptide-specific CD8+ T cell expression of TNF-α and/or IFN-γ by flow cytometric ICS as response readout. CD8+ T cell responses to amino terminal and carboxy terminal truncations of the parent 15 mer were initially determined to define optimal peptide length and the amino- and carboxy termini of the core epitope (top panel, with grey shading indicating the terminal amino acids of the most stimulatory amino- and carboxy-terminal-truncated peptides). The optimal 9 mer implied by this truncation approach was then confirmed by analysis of the 7 consecutive 9 mers that make up each 15 mer (bottom panel). The 9 mers shaded in grey in each of the bottom panels represent the optimal epitope for each parent 15 mer.
Figure 21:
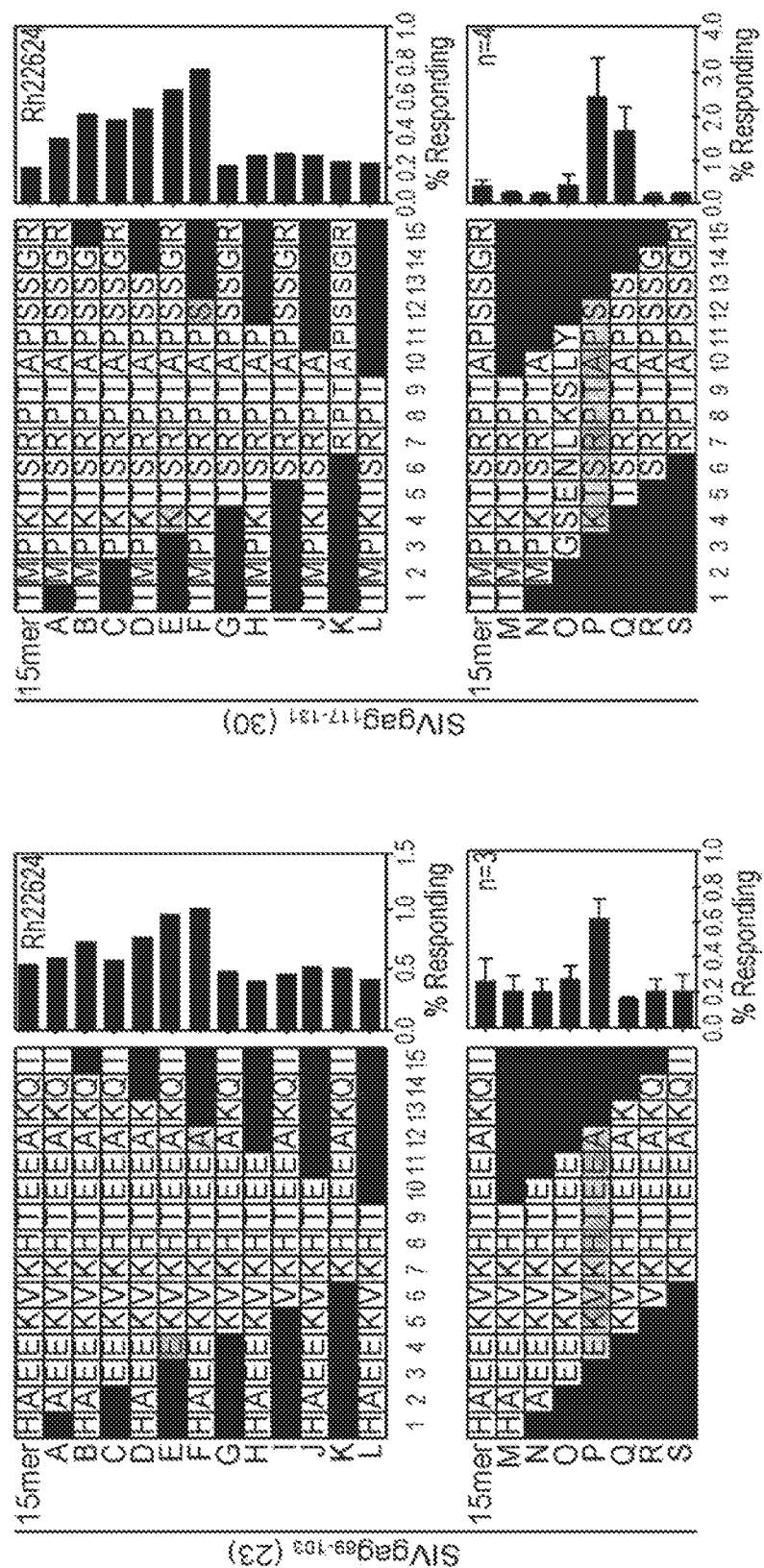
Figure 21:
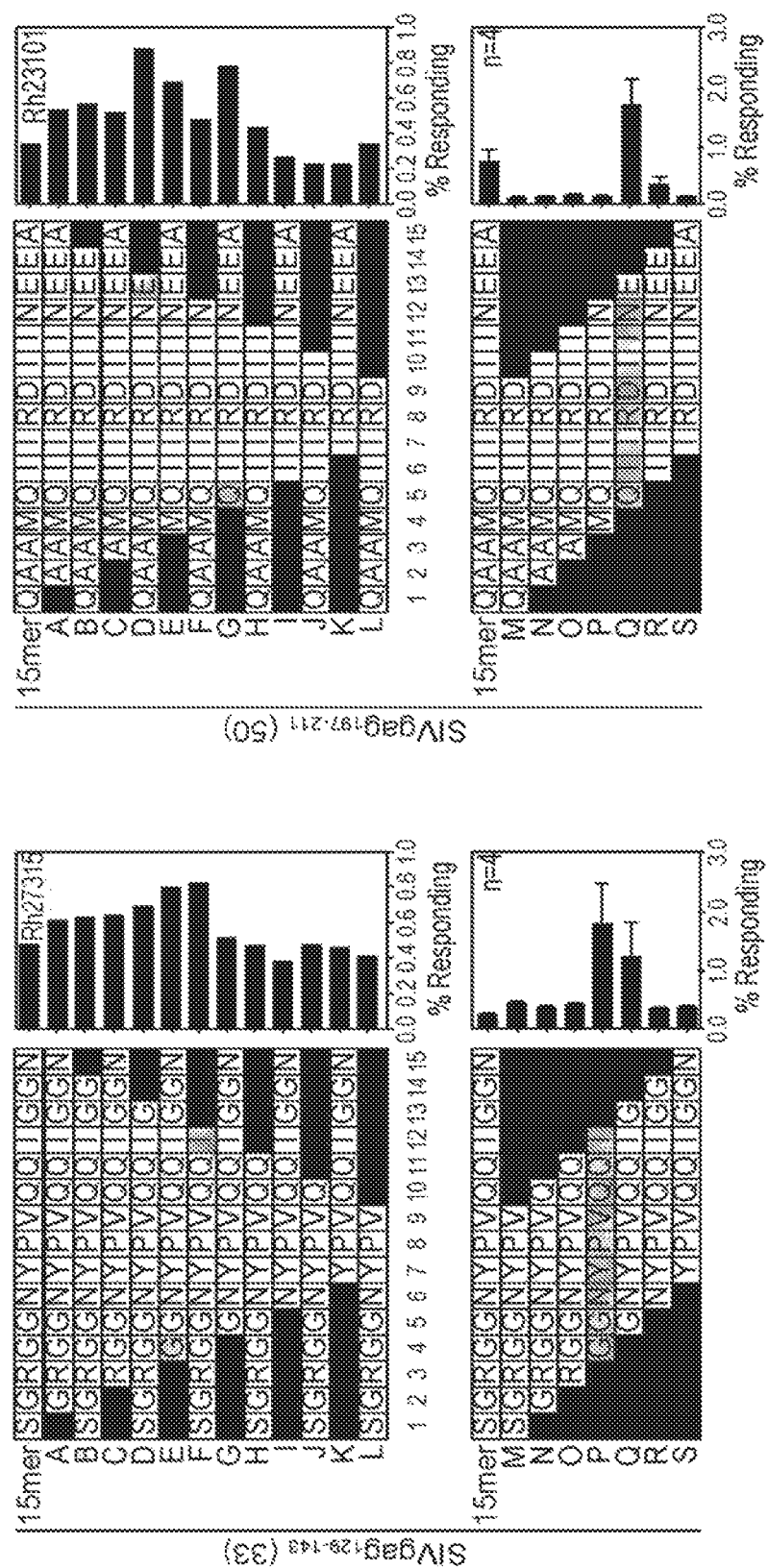
Figure 21:
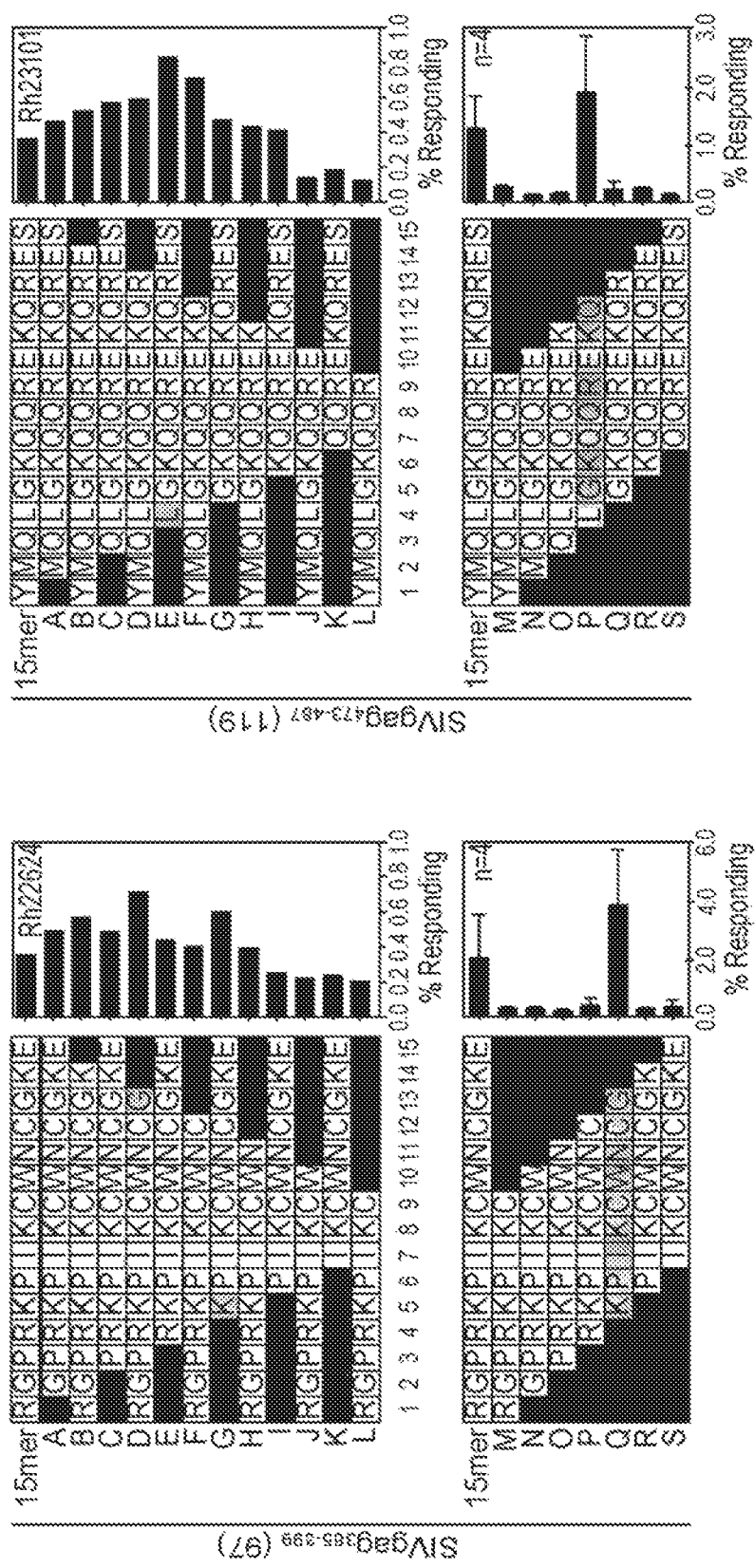

MHC-E is known to avidly bind canonical VMAPRTL (LVI)L peptides and other closely related 9 mer peptides that are derived from positions 3-11 of MHC-Ia leader sequences for presentation to NKG2A (and to a lesser extent, NKG2C) molecules on NK cells (Lee, N. et al., J Immunol 160, 4951 (1998); Braud, V. M. et al., Nature 391, 795 (1998); Sullivan. L. C. et al., Tissue Antigens 72, 415 (2008); and van Hall, T. et al., Microbes Infect 12, 910 (2010); all of which are incorporated by reference herein). This highly conserved interaction delivers a predominately inhibitory signal to NK cells when cells express normal levels of MHC-Ia. However, upon interference with MHC-Ia biosynthesis by viral infection or neoplastic transformation, this inhibitory signal is reduced, facilitating NK cell activation in response to virally-infected or neoplastic cells (Lodoen, M. B. and Lanier, L. L. Nat Rev Microbiol 3, 59 (2005) and Wieten L et al., Tissue Antigens 84, 523 (2014); both of which are incorporated by reference herein). Although a subset of CD8$^+$ T cells can also express NKG2A and/or NKG2C (Arlettaz L et al., Eur J Immunol 34, 3456 (2004); incorporated by reference herein), phenotypic analysis of MHC-E-dependent, strain 68-1 RhCMV/SIVgag vector-elicited CD8$^+$ T cells revealed the vast majority of responding cells were CD8α/β$^+$, TCR γ/δ$^+$ T cells that lack both NKG2A and NKG2C expression (FIGS. 11C and 19). Moreover, pre-incubation of MHC-E transfectants or PBMC with a canonical MHC-E-binding VMAPRTLLL (VL9) peptide prior to specific peptide loading specifically blocked CD8$^+$ T cell recognition of all 12 peptides (FIGS. 11D and 20), suggesting that the T cell recognition of these peptides is not mediated by NKG2A/C binding to peptide-loaded MHC-E, but rather reflects MHC-E-restricted epitope presentation to antigen-specific T cells, indeed, each of the parent 15 mers studied could be truncated to an optimal 9 mer peptide that was common among different strain 68-1 RhCMV/SIVgag vector-vaccinated monkeys with responses to the parent 15 mer (FIG. 21) (Hansen et al. Science (2013), supra). These optimal 9 mers could trigger CD8$^+$ T cells from these monkeys when pulsed on Mamu-E transfectants at doses less than 1 nM (FIG. 22), functional avidities that are comparable to T cell recognition of classically MHC-Ia-restricted epitopes (O'Connor D H et al., Nat Med 8, 493 (2002); incorporated by reference herein). Taken together, these data strongly suggest the unconventional, MHC-I-dependent CD8$^+$ T cells elicited by strain 68-1 RhCMV/SIVgag vectors are SIVgag-specific CD8$^+$ T cells that are primarily restricted by MHC-E, although in some cases can also recognize their specific peptide on conventional MHC-Ia allomorphs.

Figure 12A:
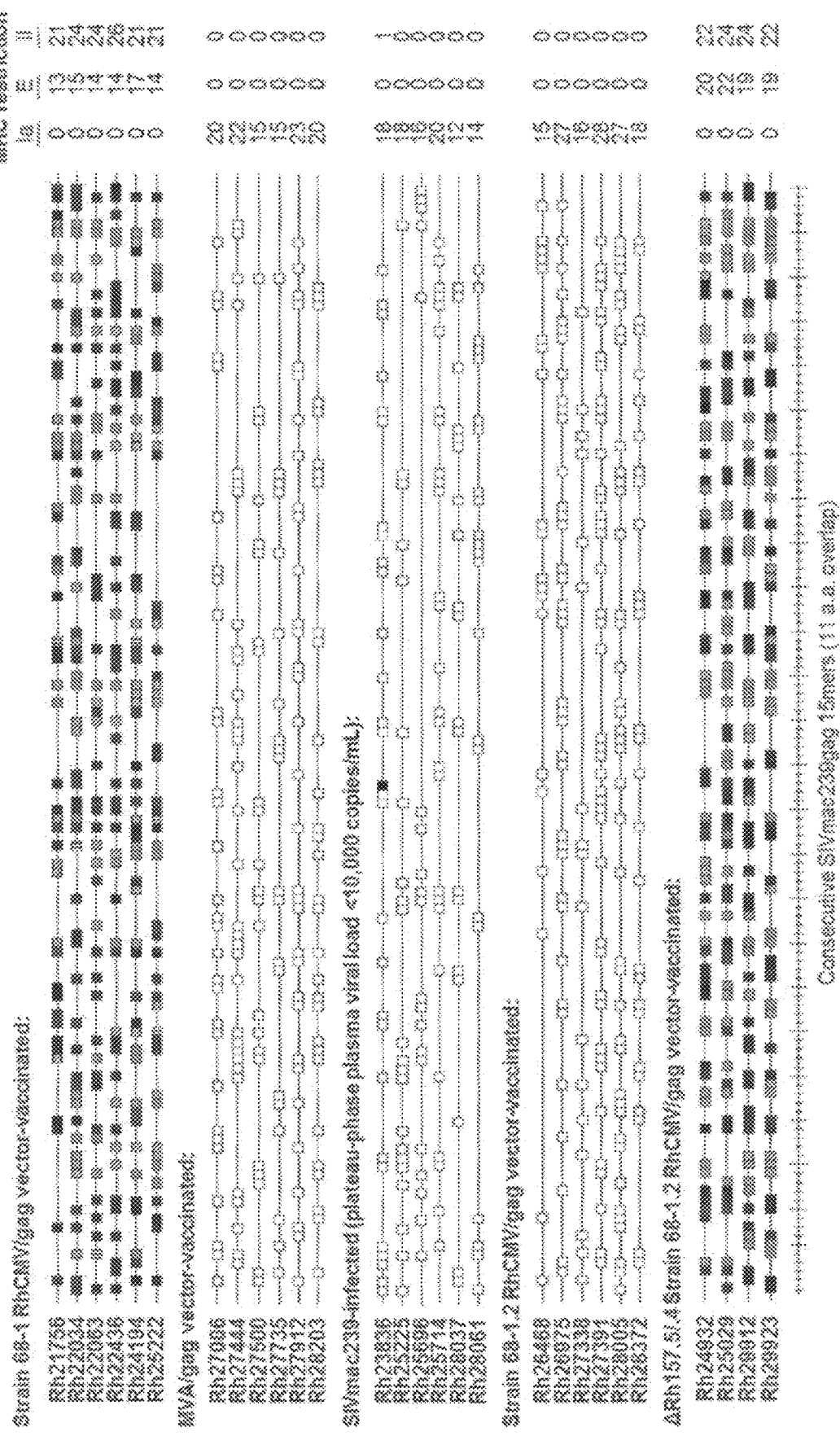
FIG. 12A is a table showing that CD8+ T cell responses to SIVgag were epitope-mapped using flow cytometric ICS to detect recognition of 125 consecutive 15 mer gag peptides (with an 11 amino acid overlap) in macaques vaccinated with the indicated SIVgag expressing viral vectors or infected with SIVmac239 itself (n=6 per group shown). Peptides resulting in above background CD8+ T cell responses are indicated by a box, with the fill of the box designating MHC restriction as determined by blocking with the anti-pan-MHC-I mAb W6-32, the MHC-E blocking peptide VL9 and the MHC-II blocking peptide CLIP, MHC-Ia-, MHC-E-, and MHC-II-restriction was based on >90% response blocking by W6-32 alone (boxes with white fill), W6-32 and VL9 alone (boxes with grey fill), and CLIP alone (boxes with black fill), respectively, with responses not meeting these criteria labeled indeterminate (boxes with vertical hatch fill). The minimal number of independent epitopes in these MHC restriction categories is shown at right for each macaque.
Figure 23:
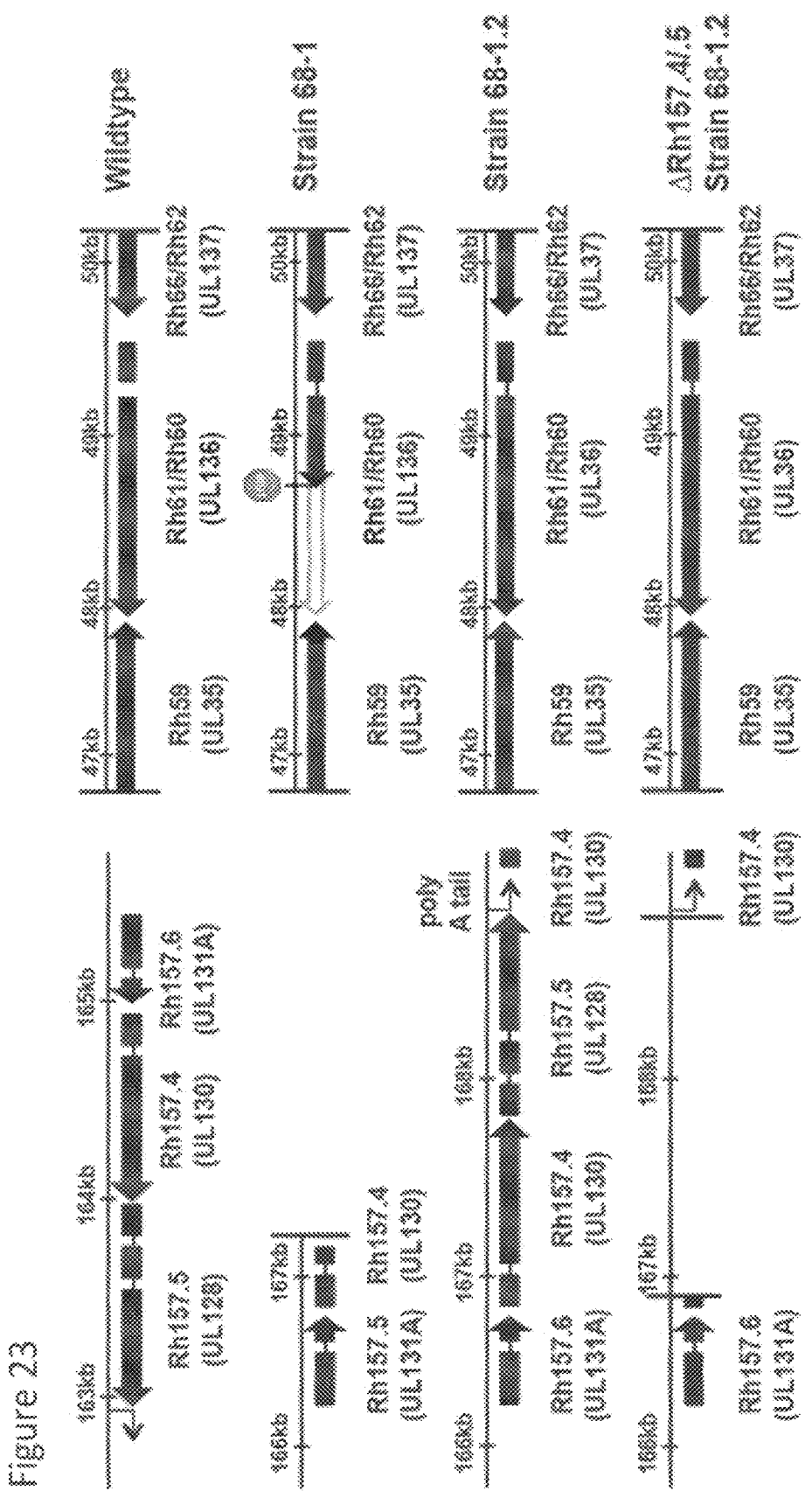
FIG. 23 is a chart of genomic differences between RhCMV vector strains 68-1, 68-1.2 and ΔRh157.4/.5 68-1.2. In low passage isolates of RhCMV, the Rh157.5 (UL128), Rh157.4 (UL130) and Rh157.6 (UL131A) genes are encoded on the $2^{nd}$ strand in reverse orientation. During serial passage in tissue culture, RhCMV 68-1 acquired distinctive fibroblast adaptations. The Rh157.5 (UL128) ORF and most of exon 2 of the Rh157.4 (UL130) ORF were deleted and the adjacent genomic region inverted, resulting in loss of the pentameric receptor complex that mediates viral entry into non-fibroblasts. Fibroblast adaptation of strain 68-1 RhCMV also resulted in insertion of an additional thymidine in the Rh61/Rh60 (UL36) gene, resulting in a frame shift mutation and a premature stop codon. In RhCMV 68-1.2, a functional pentameric complex was restored by insertion of Rh157.5 (UL128) and exon 2 of Rh157.4 (UL130) from RhCMV strain 180.92 into RhCMV 68.1 right after the first exon of Rh157.4 (UL130), and the Rh61/Rh60 (UL36) mutation was reverted to wild type configuration. To ensure that the unconventional MHC restriction of CD8+ T cells elicited by strain 68-1 RhCMV vectors was attributable to the Rh157.5/.4 (UL128/UL130) deletion (and consequent lack of a functional pentameric complex), Rh157.5 (UL128) and Rh157.4 (UL130) were specifically re-deleted from strain 68-1.2 by homologous recombination starting 50 bp upstream of the Rh 157.6 (UL131A) stop codon up to the Rh157.5 (UL128) stop codon, leaving the Rh61/Rh60 (UL36) repair intact. Therefore, phenotypic features shared between this ΔRh157.5/.4 (ΔUL128/UL130) strain 68-1.2 RhCMV vector and the original strain 68-1 vectors that differ from the repaired strain 68-1.2 RhCMV vector would be directly attributable to Rh157.5/.4 (UL128/UL130) deletion.
Figure 24A:
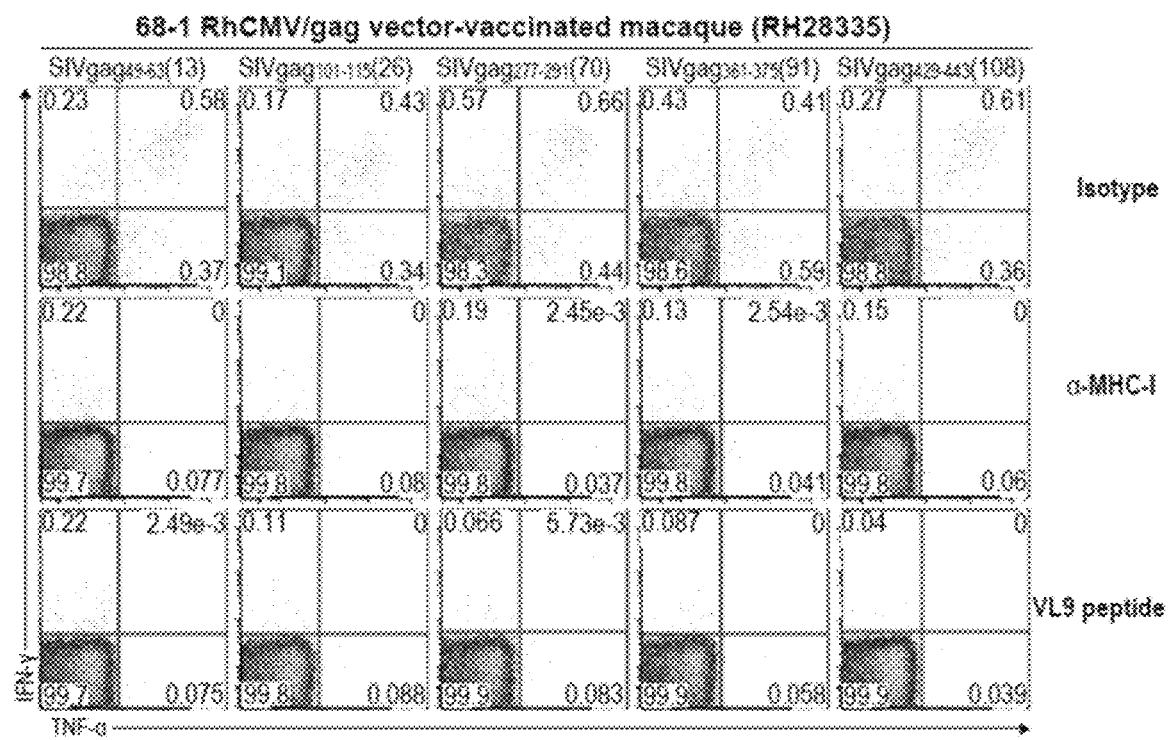
FIGS. 24A and 24b collectively shows differential utilization of MHC-E vs. MHC-Ia by CD8+ T cells elicited by strain 68-1 vs. strain 68-1.2 RhCMV/gag vectors.
Figure 24B:
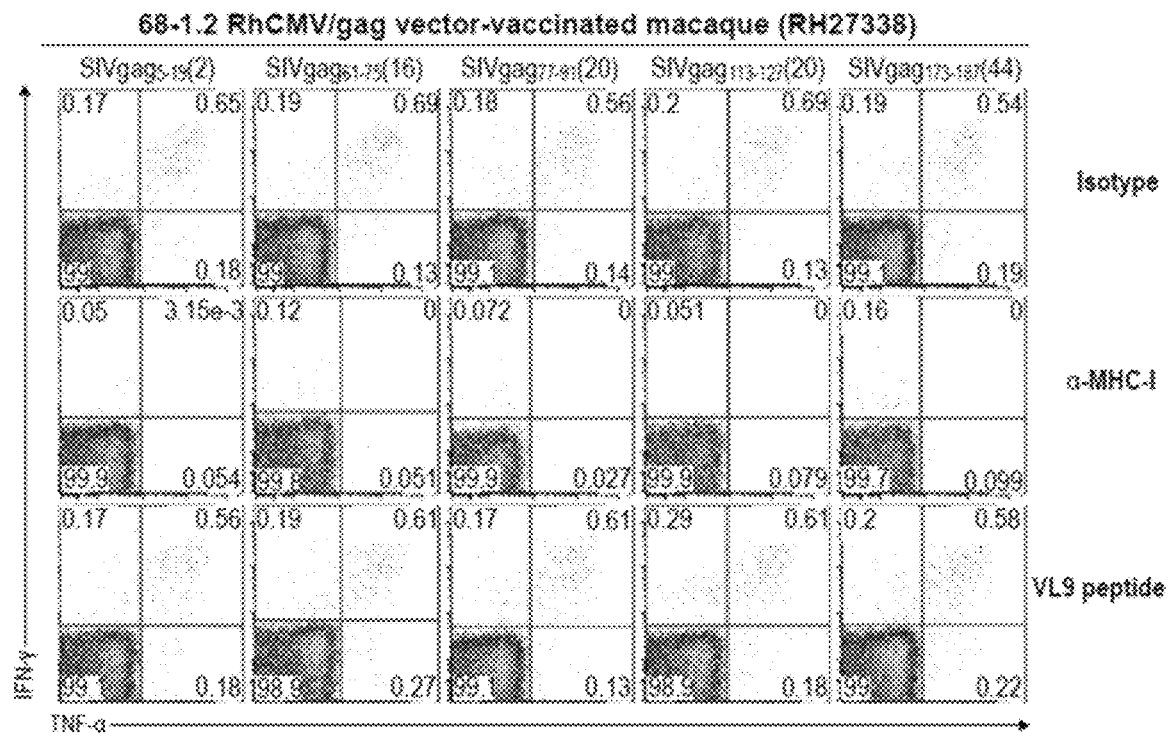
Figure 25:
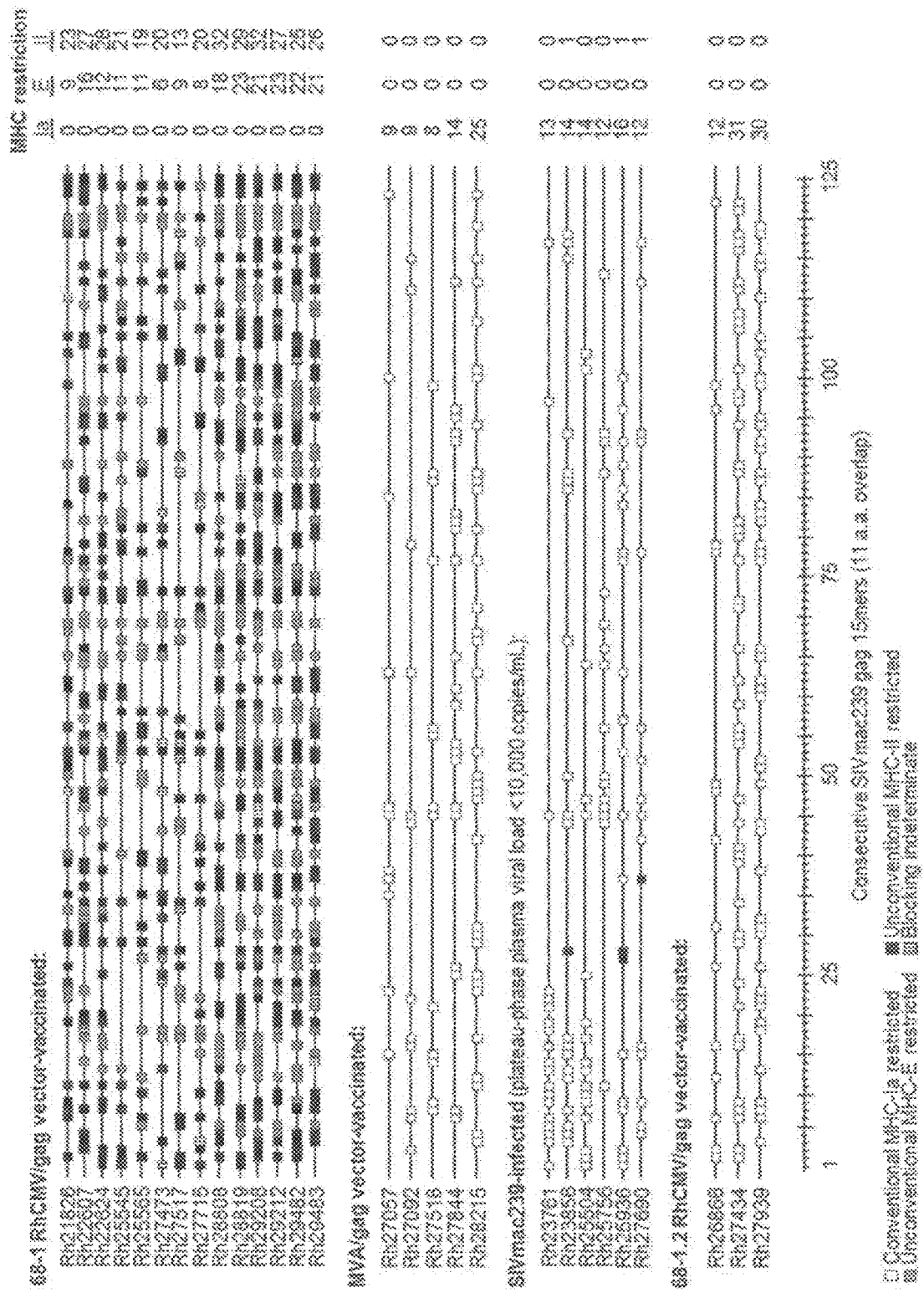
FIG. 25 is a restriction analysis of epitope-specific CD8+ T cell responses elicited by RhCMV/gag vectors (strains 68.1 and 68-1.2). MVA/gag vector, and by controlled SIV infection. As described for FIG. 12A, CD8+ T cell responses to SIVgag were epitope-mapped using flow cytometric ICS to detect recognition of 125 consecutive 15 mer gag peptides (with an 11 amino acid overlap) in additional macaques (over the 6 animals from each group shown in FIG. 12A) vaccinated with the indicated SIVgag expressing viral vectors or infected with SIVmac239 itself (SIVmac239 controller macaques). Peptides resulting in above background CD8+ T cell responses are indicated by a box, with the fill of the box designating MHC restriction, as determined by blocking with the anti-pan-MHC-I mAb W6-32, the MHC-E blocking peptide VL9 and the MHC-II blocking peptide CLIP. MHC-Ia-, MHC-E-, and MHC-II-restriction was based on >90% response blocking by W6-32 alone (boxes with white fill), W6-32 and VL9 alone (boxes with grey fill), and CLIP alone (boxes with black fill), respectively, with responses not meeting these criteria labeled indeterminate (boxes with vertical hatch fill). The minimal number of independent epitopes in these MHC restriction categories is shown at right for each macaque. Note that all evaluable epitopes recognized by CD8+ T cells from strain 68-1 RhCMV/gag vector-vaccinated macaques were unconventionally restricted, either by MHC-II or MHC-E. In contrast, all responses elicited by the strain 68-1.2 RhCMV/gag and MVA/gag vectors were conventionally MHC-Ia-restricted. The vast majority of SIVgag epitope-specific CD8+ T cell responses identified in SIV controller macaques were also MHC-Ia-restricted, but 4 of 12 of these animals manifested one epitope-specific response that was unequivocally MHC-II-restricted (4 responses out of 179 total responses=2.2%), indicating the MHC-II-restricted CD8+ T cells can be identified as a minor component of conventional immune responses to infection.

MHC-E-restricted CD8$^+$ T cell responses have been previously identified in HCMV, Hepatitis C virus, *Mycobacterium tuberculosis*, and *Salmonella enterico* infections, typically involving epitopes that are structurally related to the canonical MHC-Ia leader sequence peptides, but foreign to the host (Sullivan (2008), supra; van Hall (2010), supra; Pietra G et al., J Biomed Biotechnol 2010, 907092 (2010); and Caccamo N et al., Eur J Immunol 45, 1069 (2015); all of which are incorporated by reference herein). To determine the extent to which MHC-E restricts responses to SIVgag in different settings, blocking with high affinity MHC-E-binding peptide VL9 (in conjunction with blocking with anti-MHC-II CLIP peptide and anti-MHC I mAb W6/32) was used to restriction-classify all SIVgag epitope-specific CD8$^+$ T cell responses in monkeys vaccinated with strain 68-1 RhCMV/SIVgag vectors (Rh157.5/.4 gene-deleted), strain 68-1.2 RhCMV/SIVgag vectors (Rh157.5/.4-intact), ΔRh157.5/.4 strain 68-1.2 RhCMV/SIVgag vectors (in which the Rh157.5/.4 genes were specifically re-deleted; FIG. 23), and Modified Vaccinia Ankara (MVA)/SIVgag vectors, as well as monkeys infected with SIV itself (FIGS. 12, 24 and 25). This analysis revealed that essentially all SIVgag epitope-specific responses in strain 68-1 RhCMV/SIVgag vector- and ΔRh157.5/.4 strain 68-1.2 RhCMV/SIVgag vector-vaccinated monkeys were either >90% blocked by the CLIP peptide or by both the anti-MHC-I mAh W6/32 and the VL9 peptide, demonstrating that the unconventional T cell responses elicited by Rh157.5/.4-deficient RhCMV are effectively entirely of either MHC-II- or MHC-E-restricted CD8$^+$ T cells.

Figure 12B:
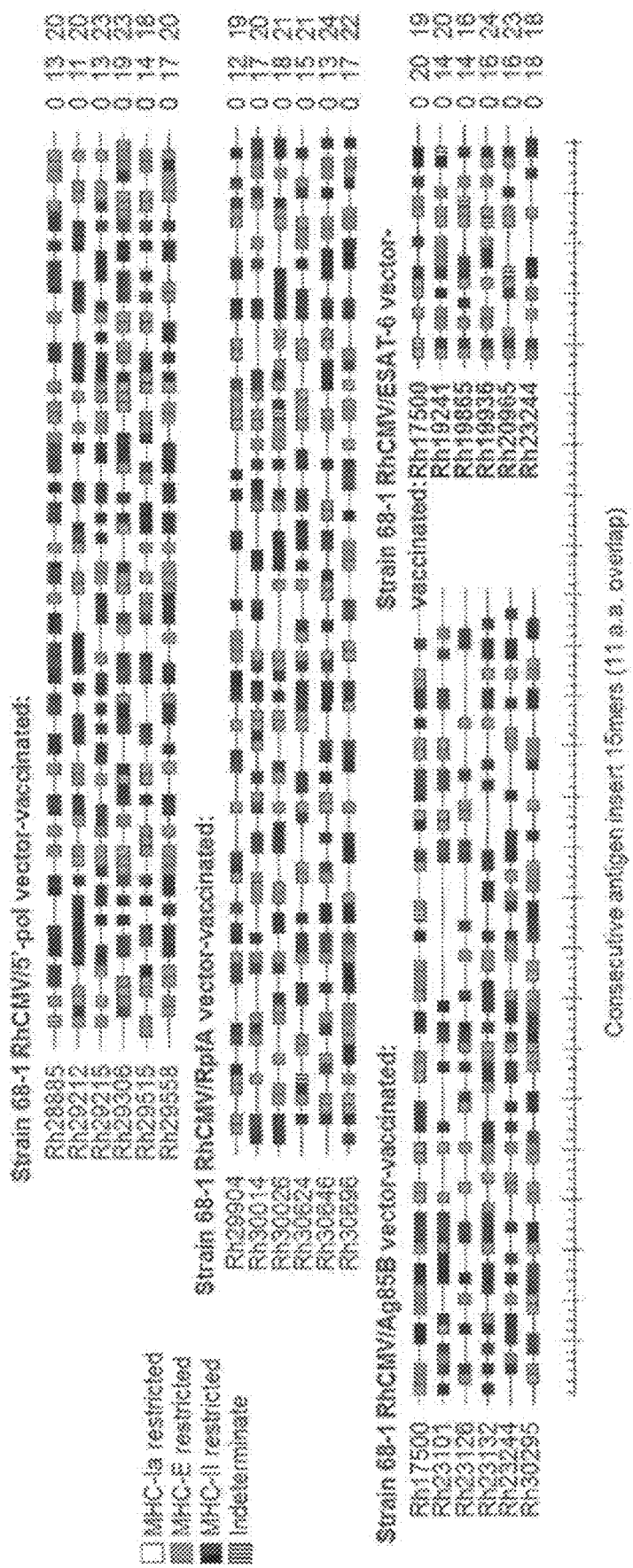
FIG. 12B is a table showing CD8+ T cell responses to SIVpol and the *M. tuberculosis* proteins Ag85B, ESAT-6, and RpfA epitope-mapped as described above in macaques vaccinated with strain 68-1 RhCMV vectors expressing these proteins.
Figure 26:
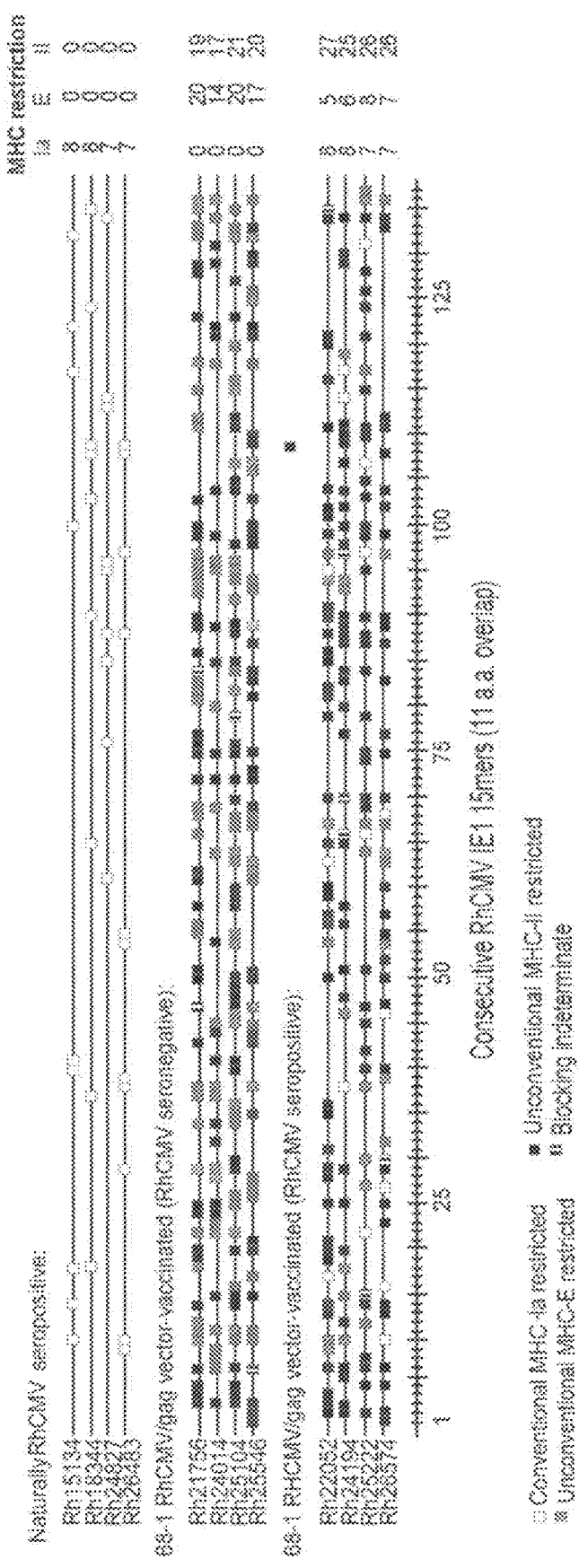
FIG. 26 is a chart showing epitope mapping of CD8+ T cell responses to the RhCMV Immediate Early-1 (IE1) protein in natural (wild type) RhCMV infection and both primary and secondary infection with the strain 68-1 RhCMV/gag vector. CD8+ T cell responses to RhCMV IE1 were epitope-mapped using flow cytometric ICS to detect recognition of 137 consecutive 15 mer IE1 peptides (with an 11 amino acid overlap) in 1) macaques that were naturally infected with wildtype (colony circulating) RhCMV (top panel), 2) RhCMV naïve macaques inoculated with the strain 68-1 RhCMV/gag vector (middle panel), and 3) naturally wild type RhCMV-infected macaques that were superinfected with the strain 68-1 RhCMV/gag vector (bottom panel). Peptides resulting in above background CD8+ T cell responses are indicated by a box, with the fill of the box designating MHC restriction as determined by blocking with the anti-pan-MHC-I mAb W6-32, the MHC E blocking peptide VL9 and the MHC-II blocking peptide CLIP, MHC-Ia-, MHC-E-, and MHC-II-restriction was based on >90% response blocking by W6-32 alone (boxes with white fill), W6-32 and VL9 alone (boxes with grey fill), and CLIP alone (boxes with black fill), respectively, with responses not meeting these criteria labeled indeterminate (boxes with vertical hatch fill). The minimal number of independent epitopes in these MHC restriction categories is shown at right for each macaque. Note that the IE1 epitope-specific responses in the naturally infected macaques are entirely MHC Ia-restricted, whereas in the macaques solely infected with the strain 68-1 RhCMV/gag vector, these responses are broader and entirely unconventionally restricted (an ~1:1 ratio of MHC-II- and MHC-E-restricted epitopes). The naturally RhCMV-infected macaques that were superinfected with the strain 68-1 RhCMV/gag vectors show the expected admixture of IE1-epitope specific CD8+ T cells that were conventionally (MHC-Ia) and unconventionally (MHC-II and MHC-E) restricted.

In contrast, all SIVgag-specific CD8$^+$ T cell responses in the MVA/SIVgag vector-vaccinated and the strain 68-1.2 (Rh157.5/.4 expressing) RhCMV/SIVgag vector vaccinated macaques were blocked by mAb W6/32, but not the VL9 peptide, indicating classical MHC-Ia restriction. This was also the case for 98% of CD8$^+$ T cell responses in SIV-infected macaques, with the exception of 4 MHC-II-restricted CD8$^+$ T cell responses. The ability of Rh157.5/.4-deficient RhCMV vectors to elicit MHC-E- and MHC-II-restricted CD8$^+$ T cells is not limited to SIVgag-specific responses. Similar mixtures of MHC-E- and MHC-II-restricted, antigen-specific CD8$^+$ T cell responses were observed with strain 68-1 (Rh157.5/.4-deficient) RhCMV vectors encoding SIVpol97-441, *M. tuberculosis* proteins (Ag85B, ESAT6 and RpfA), as well as intrinsic RhCMV proteins such as the Immediate Early-1 (IE1) protein (FIGS. 12B and 26).

Figure 12C:
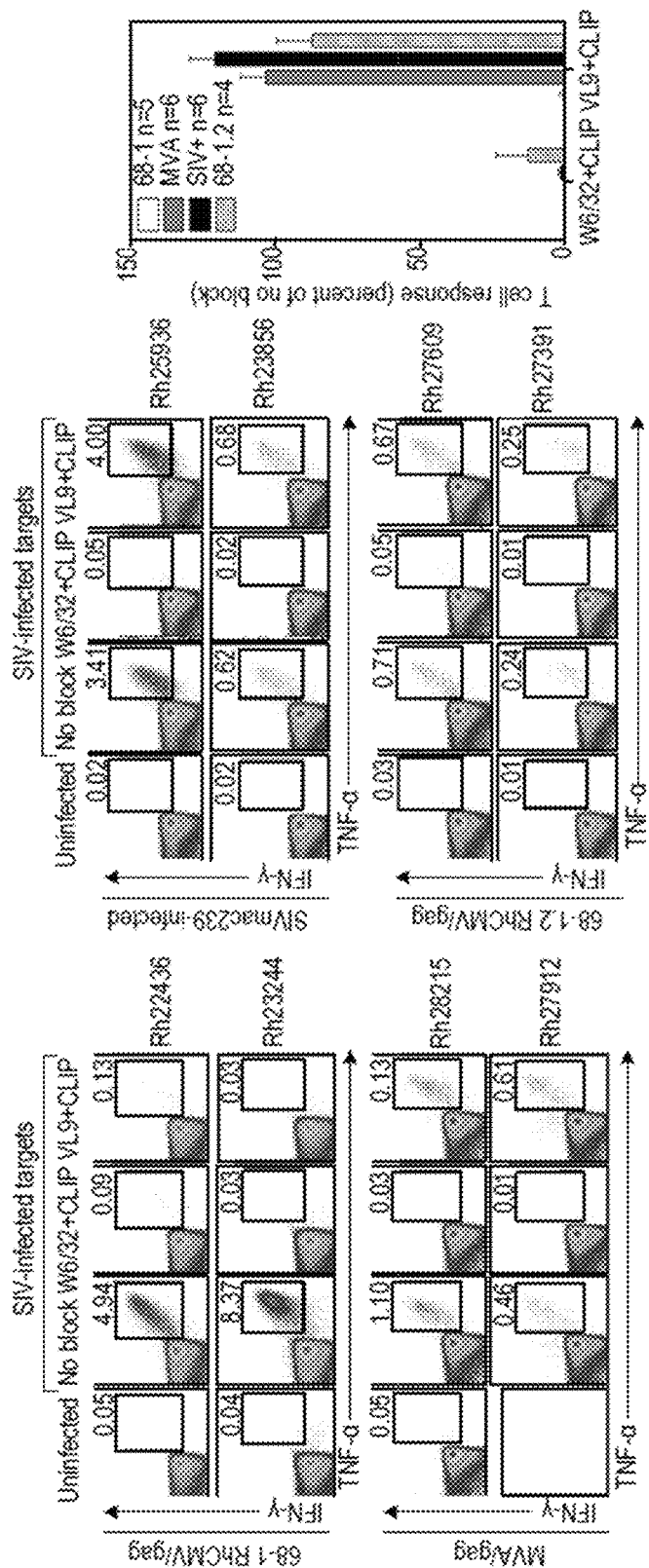
FIG. 12C is a set of plots (right), another set of plots (middle), and a bar graph (right) showing that analysis of SIV-infected CD4+ cell recognition by CD8+ cells isolated from macaques vaccinated with strain 68-1 RhCMV/gag, MVA/gag, strain 68-1.2 RhCMV/gag vectors, or infected with SIV. The flow profiles at left show IFN-γ and TNF-α production following CD8+ T cell incubation with autologous SIVmac239-infected CD4+ T cells alone (no block), or in the presence of the pan-MHC-I-blocking mAh W6/32 plus the MHC-II-binding CLIP peptide (anti-MHC-I+CLIP), or MHC-E-binding peptide VL9 plus CLIP (VL9+CLIP). All plots are gated on live, CD3+, CD8+ cells. The bar graph at right shows the results from all studied macaques.

It has been previously reported that CD8$^+$ T cells elicited by strain 68-1 RhCMV/SIV vectors recognize autologous SIV-infected CD4$^+$ T cells, and that this recognition is partially blocked by the anti-MHC-I mAb W6/32 and by the MHC-II-blocking CLIP peptide (Hansen et al. *Science* (2013), supra). To determine the contribution of MHC-E restriction to the MHC-I component of this recognition, it was asked whether the high affinity MHC-E-binding VL9 peptide could substitute for mAb W6/32 in blocking these responses. This experiment demonstrated that the combination of the MHC-II-blocking CLIP peptide and either mAb W6/32 or the VL9 peptide blocks these responses completely, whereas SIV-infected autologous cell recognition by SIVgag-specific CD8$^+$ T cells elicited by MVA/SIVgag vector- or strain 68-1.2 RhCMV/gag vector-vaccination or SIV infection was insensitive to the CLIP+VL9 peptide combination (FIG. 12C). Taken together, these data confirm that strain 68-1 RhCMV vectors uniquely elicit CD8$^+$ T cell responses that are either MHC-II or MHC-E-restricted, and that this unusual immunobiology is a specific consequence of deletion of the RhCMV Rh157.5/.4 genes, which are orthologs of the HCMV UL128/UL130 genes and encode 2 components of the pentameric receptor complex involved in CMV infection of non-fibroblasts (Lilja A E and Shenk T, Proc Natl Acad Sci U.S.A. 105, 19950 (2008); incorporated by reference herein). Moreover, these data confirm that at least some of the epitopes recognized by these MHC-E-restricted CD8+ T cells are naturally processed and presented by cells infected by SIV, a heterologous (non-CMV) pathogen.

Figure 13A:
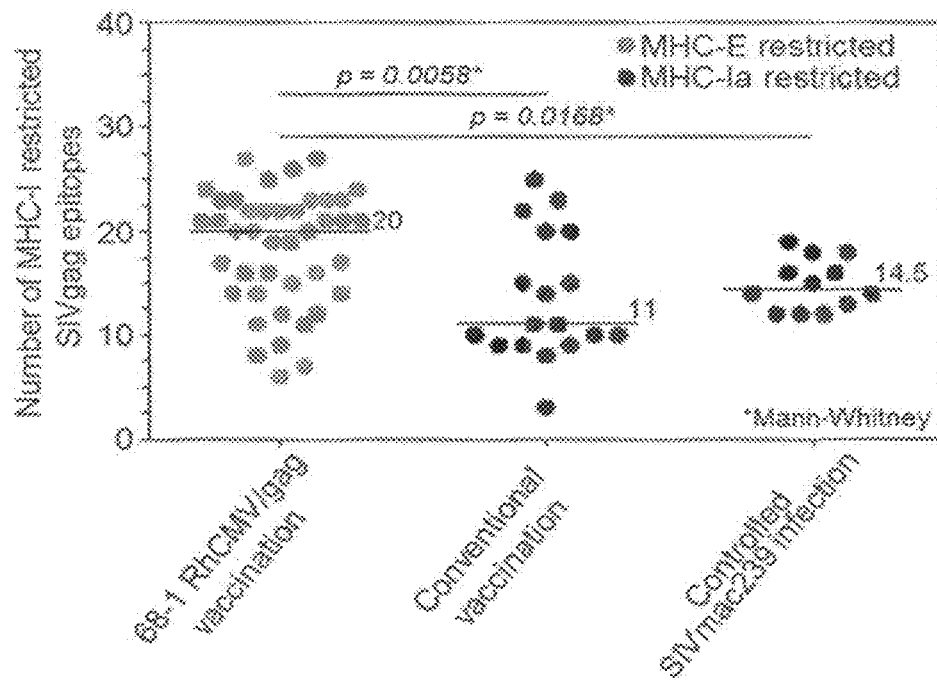
FIG. 13A is a plot showing a comparison of the total number of distinct MHC E- (grey) vs. MHC-Ia (black)-restricted SIVgag epitopes recognized by circulating CD8+ T cells in individual macaques vaccinated with strain 68-1 RhCMV/gag vs. conventional viral vectors, the latter including MVA/gag (n=11), Ad5/gag (n=3) and electroporated DNA/gag+IL-12 (n=4), or in macaques with controlled SIVmac239 infection (plasma viral load <10,000 copies/ml; n=12). The horizontal bars indicate median values.
Figure 13B:
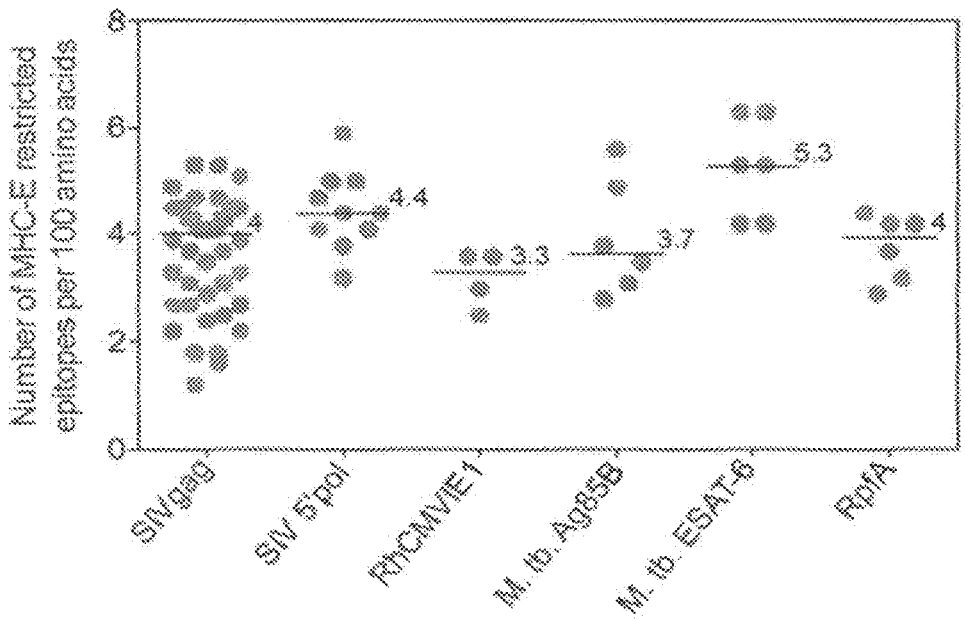
FIG. 13B is a plot showing a comparison of the density (epitope number per 100 amino acids of protein length) of MHC E-restricted epitopes recognized by circulating CD8+ T cells in individual macaques vaccinated with strain 68-1 RhCMV vectors expressing each of the indicated antigens (note: RhCMV IE1 responses were evaluated in CMV naïve macaques administered 68-1 RhCMV/gag). The horizontal bars indicate median values for each group.
Figure 13C:
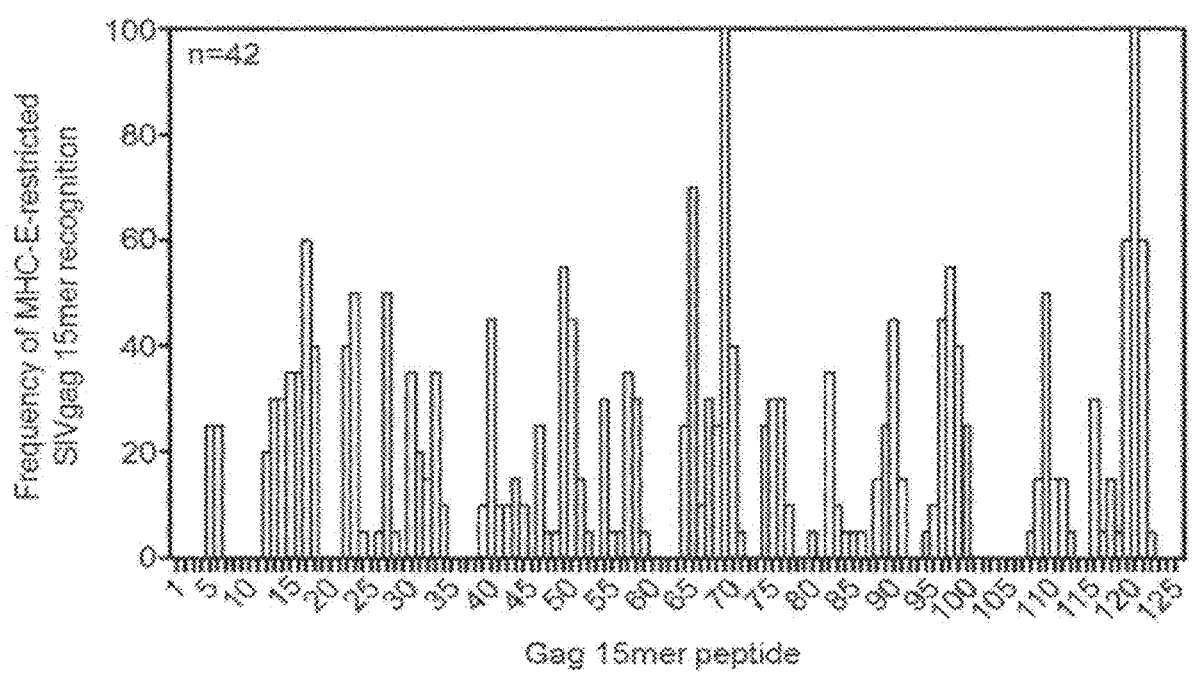
FIG. 13C is a bar graph of an analysis of the breadth of MHC-E-restricted SIVgag epitope-specific CD8+ T cell responses across 125 overlapping (11 amino acid overlap), consecutive SIVgag 15 mer peptides in 42 strain 68-1 RhCMV/gag vector vaccinated macaques. Note that 109/125 15 mers (87%) were recognized by MHC-E-restricted CD8+ T cells in at least 1 macaque.
Figure 13D:
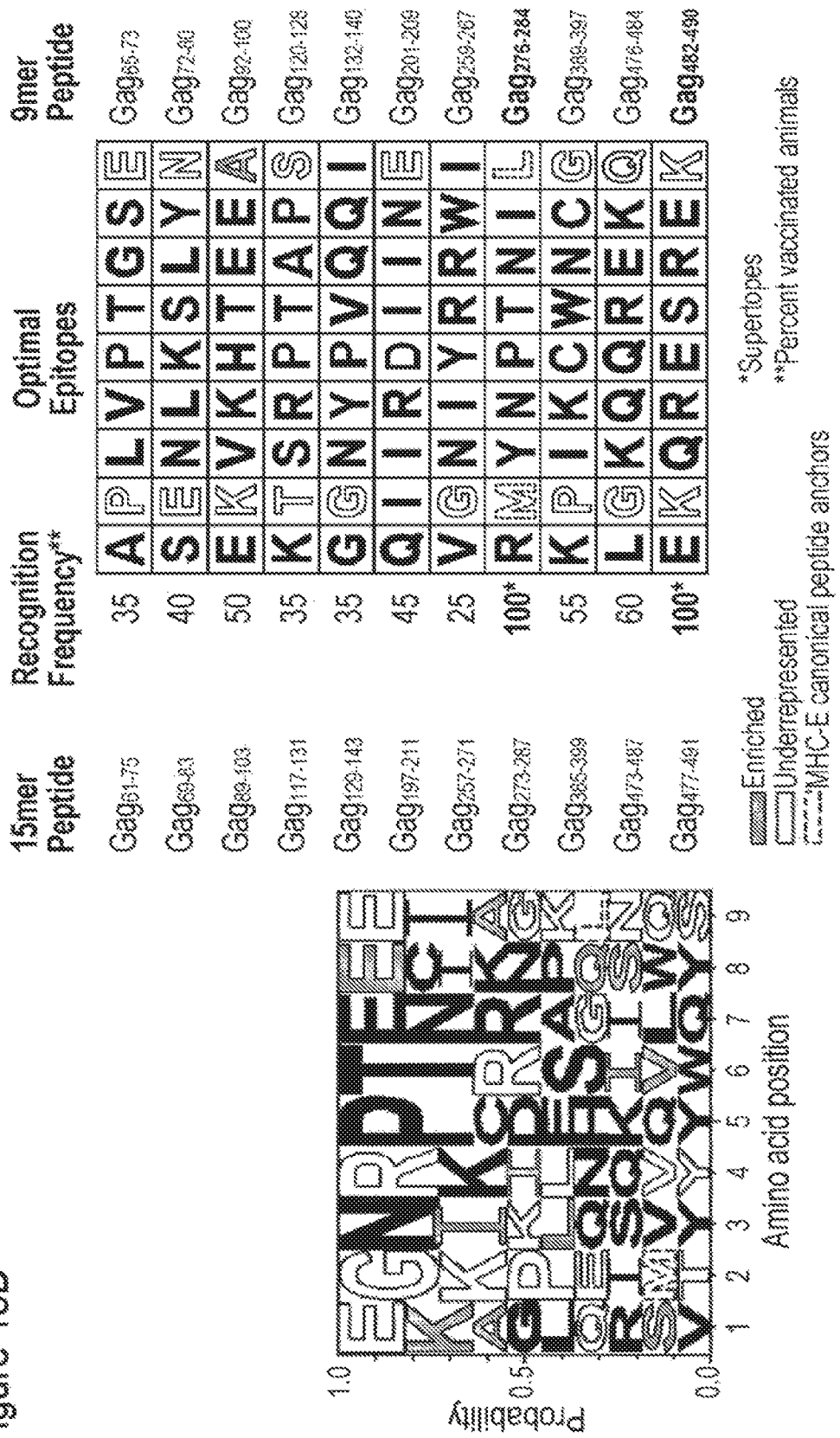
FIG. 13D (left) is a sequence LOGO indicating the frequency of each amino acid in a given position (relative to their background frequency in SIVmac239 Gag; see methods) by the height of the letter, based on 11 optimal, MHC-E-restricted SIVgag 9 mer peptide epitopes recognized by CD8+ T cells in strain 68-1 RhCMV vector-vaccinated macaques. The sequence LOGO is colored according to enrichment (letters with grey fill or hatched letters) or underrepresentation (letters with white fill) among 551 peptides eluted from HLA-E in a TAP-deficient setting by Lampen M H et al., *Mol Immunol* 53, 126-131 (2013); incorporated by reference herein. Amino acids enriched in the $2^{nd}$ and C-terminal anchor positions among the 551 Lampen et al. peptides were rare among our 11 optimal SIVgag peptides (right), while those that were significantly underrepresented were enriched. The percentage of strain 68-1 RhCMV/gag-vaccinated macaques that responded to each optimal peptide is noted as the "Recognition Frequency".
Figure 18A:
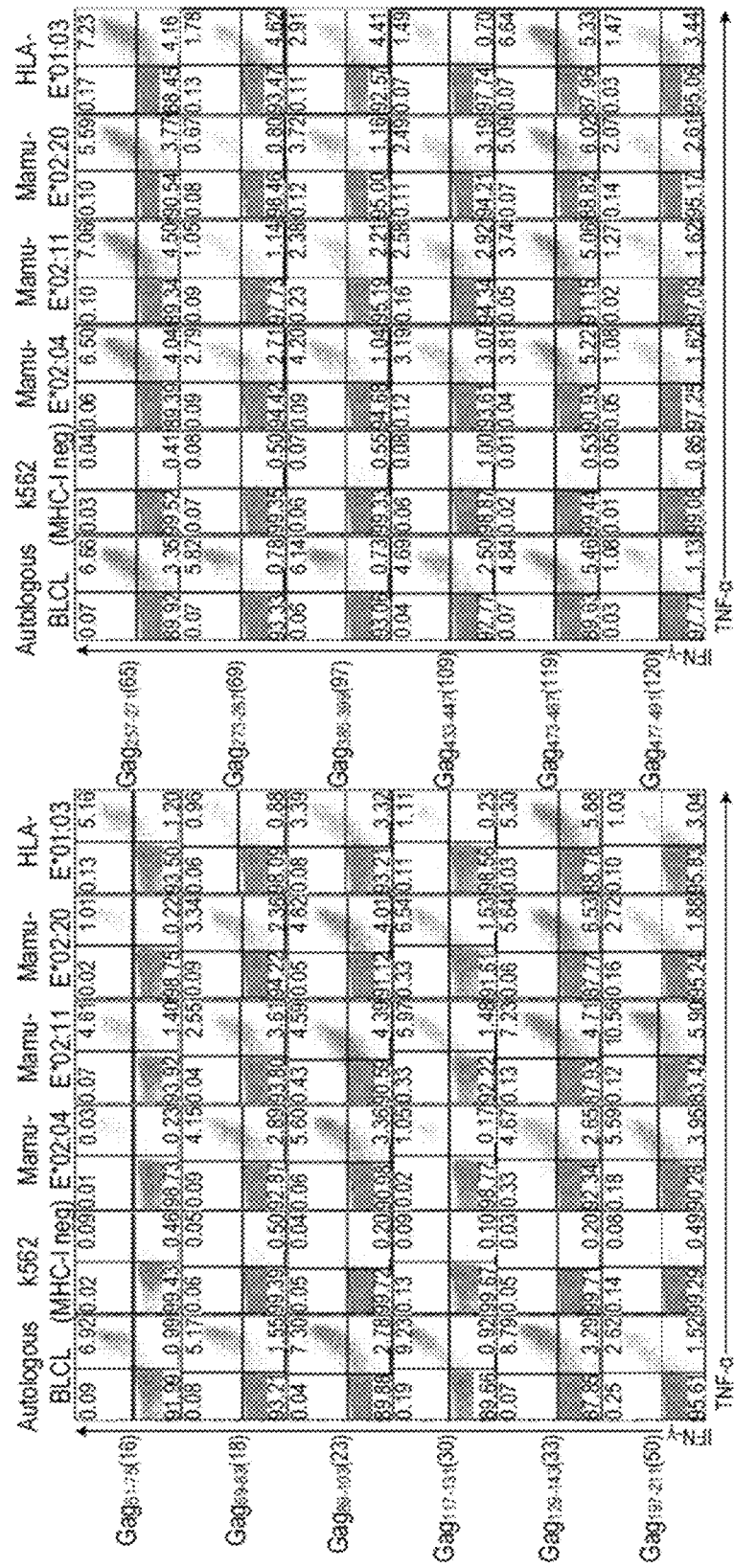
FIGS. 18A and 18B collectively show that strain 68-1 RhCMV/SIVgag-elicited CD8+ T cells recognize peptide in the context of both rhesus macaque and human MHC-E molecules.
Figure 18B:
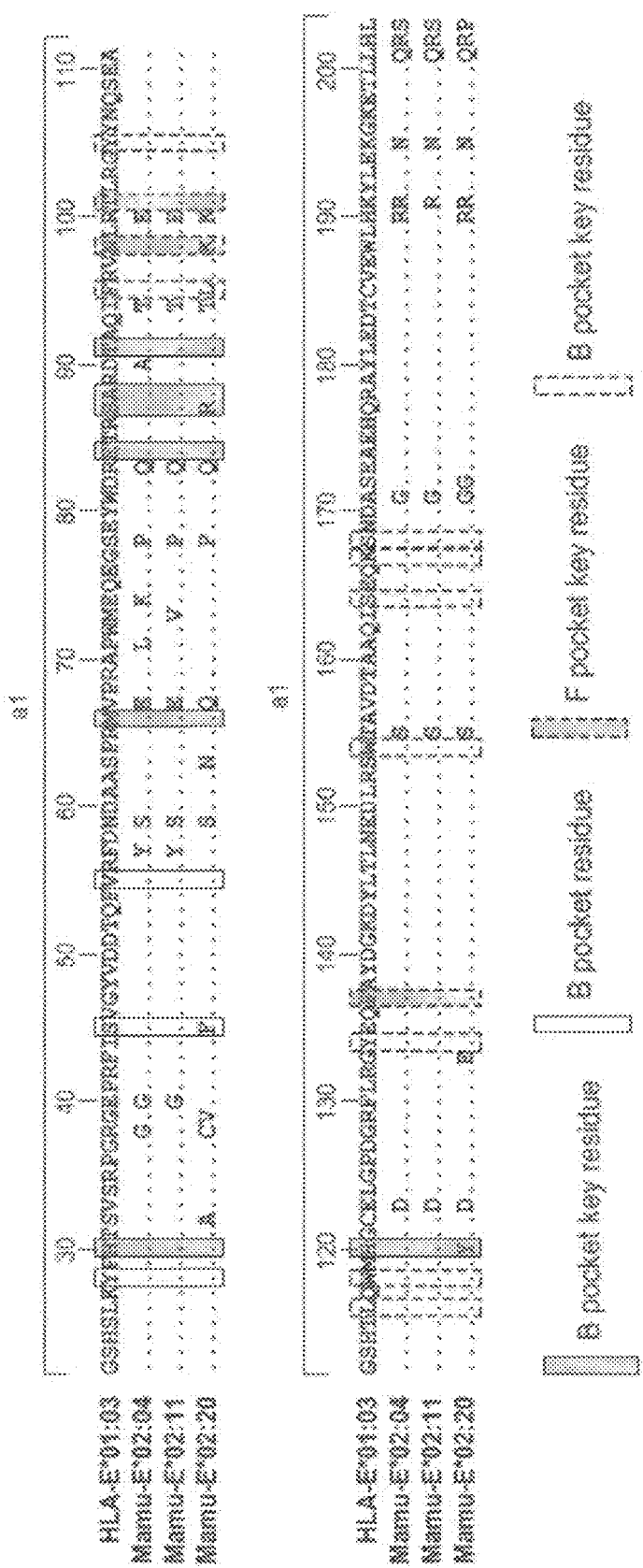
Figure 22A:
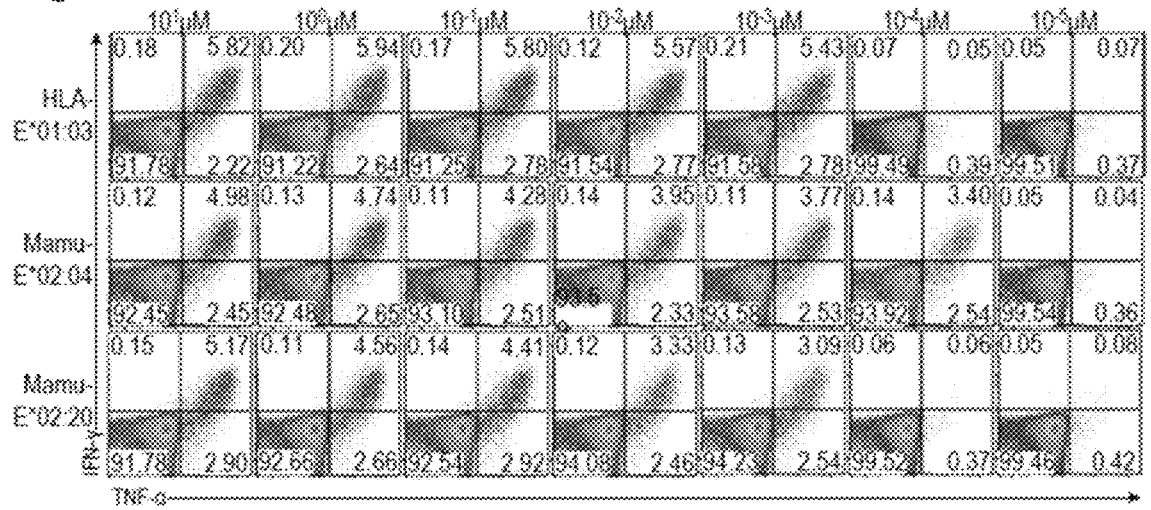
FIGS. 22A and 22B collectively show dose response of MHC-E restricted CD8+ T cells to optimal 9 mers pulsed on human and rhesus macaques MHC-E transfectants. Mamu-E*02:04, Mamu-E*02:20 and HLA-E*01:03 transfectants were pulsed with the indicated concentration of the optimal SIVgag 9 mer peptide epitopes SIVgag$_{476-484}$, SIVgag$_{259-267}$, or SIVgag$_{276-284}$, or SIVgag$_{482-490}$ (see FIG. 21), washed, and combined with PBMC from 3-4 68-1 RhCMV/SIVgag-vaccinated macaques for flow cytometric ICS determination of the frequency of responding CD8+ T cells (IFN-γ+ and/or TNF-α+).
Figure 22B:
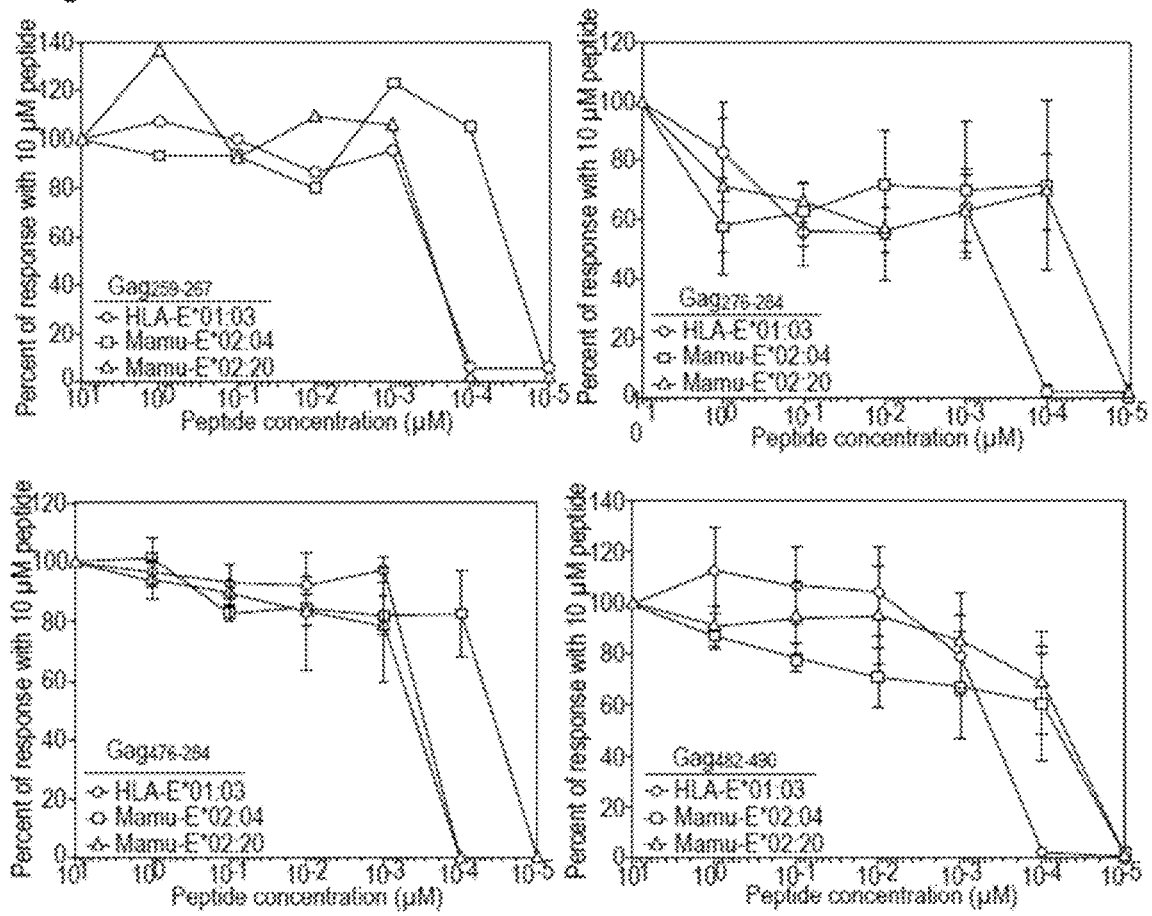

Among 42 strain 68-1 RhCMV/SIVgag vector-vaccinated monkeys, a median of 20 distinct CD8+ T cell-recognized, MHC-E-restricted, SIVgag 15 mer epitopes per animal were identified, a breadth that exceeds the median 11 and 14.5 distinct MHC-Ia-restricted SIVgag-specific epitopes identified within SIVgag-specific CD8+ T cell responses elicited by conventional vaccines or SIV infection, respectively (FIG. 13A). The density of MHC-E-restricted epitopes (~4 independent MHC-E-restricted epitopes per 100 amino acids of protein length) is similar among all strain 68-1 RhCMV vector-elicited CD8+ T cell responses, regardless of nature of the antigen analyzed (FIG. 13B). Notably, among the same 42 strain 68-1 RhCMV/SIVgag vector-vaccinated macaques, 109 of the 125 overlapping SIVgag 15 mer peptides (87%) were recognized by MHC-E-restricted CD8+ T cells in at least one macaque (FIG. 13C). Although MHC-E has previously been shown to bind a broader array of peptides than the canonical leader sequence peptides (van Hall (2010), supra and Lampen et al., supra), the extent of epitope diversity and breadth observed is highly surprising, especially given the limited polymorphism of MHC-E and the observation that the presentation of all MHC-E-restricted epitopes tested to date is independent of this limited sequence polymorphism as well as the sequence difference between Mamu-E and HLA-E (FIGS. 11B, 18 and 22). These data suggest that MHC-E-mediated epitope presentation (e.g., MHC-E peptide binding) is even more diverse than previously believed. In keeping with this, sequence analysis of 11 optimal MHC-E-restricted SIVgag 9 mer epitopes showed only one epitope (the $Gag_{273-287}$ supertope) with a canonical (M at position 2: L at position 9) MHC-E-binding motif, whereas the other 10 optimal epitopes not only lacked this motif, but manifested no statistically significant overlap with previously characterized sets of MHC-E bound peptides (Lampen et al., supra) (FIG. 13D). Indeed, the other $SIVgag_{482-490}$ supertope manifested what could be considered an anti-MHC-E peptide binding motif with lysines at both positions 2 and 9 (FIG. 13D). The molecular mechanisms for loading and binding of epitopic peptides to MHC-E are discussed in Hansen, S. G. et al., "Broadly targeted CD8+ T cell responses restricted by major histocompatibility complex E", Science, published electronically on Jan. 21, 2016, which is incorporated by reference herein.

Both HCMV and RhCMV encode proteins with a strategically embedded canonical VL9 peptide within the UL40 and Rh67 genes, respectively (Prod'homme, V. et al., J Immunol 188, 2794 (2012) and Richards, R. et al., J Virol 85, 8766 (2011); both of which are incorporated by reference herein). The VL9 peptide of UL40 was shown to be loaded onto nascent MHC-E chains by a TAP-independent mechanism, and therefore functions to stabilize and up-regulate MHC-E expression in HCMV-infected cells in the face of virus-mediated TAP inhibition and profound MHC-Ia down regulation mediated by the HCMV US2-11 gene products (Lodoen & Lanier (2005), supra and Prod'homme (2012), supra). A similar function is likely for RhCMV Rh67 (Richards (2011), supra). MHC-E up-regulation is therefore thought to be a key viral strategy for evading the NK cell response to infected cells that lack MHC-Ia expression. However, this evasion strategy would have the consequence of enhancing MHC-E expression in virally infected cells, increasing the opportunity for loading and presentation of novel peptides to MHC-E-restricted T cells. In this regard, the canonical MHC-E binding VL9 peptide might act as a chaperone that facilitates stable high expression of MHC-E and delivery to an endosomal compartment that would facilitate peptide exchange, analogous to the invariant chain-associated CLIP peptide and MHC-II. Consistent with such a peptide exchange mechanism, MHC-E peptide loading has been directly demonstrated in the *M. tuberculosis* phagolysosome (Grotzke J E et al., PloS Pathog 5, e1000374 (2009); incorporated by reference herein).

Figure 27A:
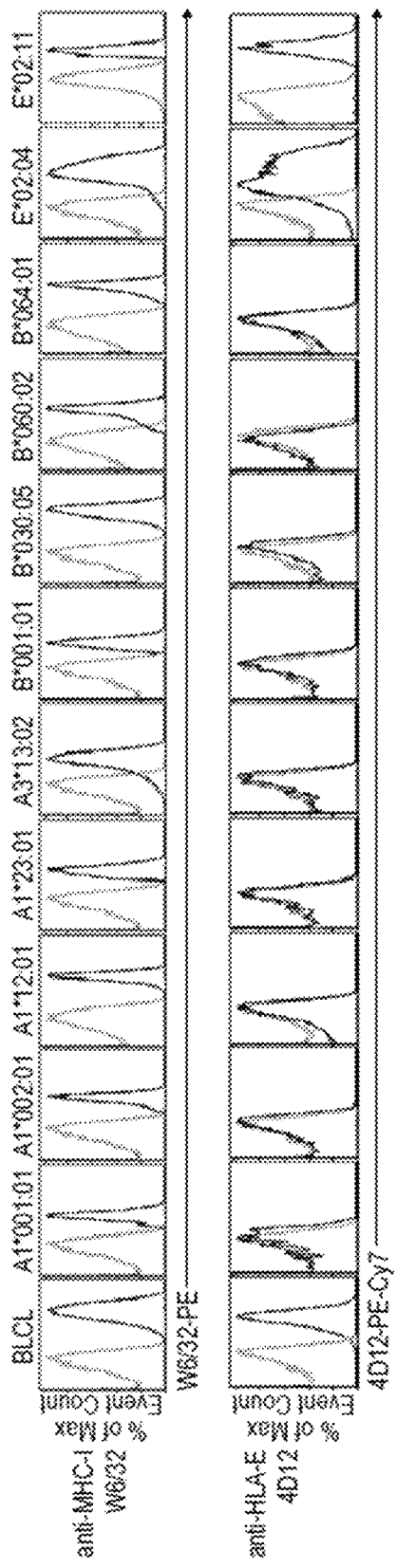
FIG. 27A is a validation of the specificity of MHC-E-specific mAb 4D12 in rhesus macaques. Histograms showing surface staining of single MHC-Ia or MHC-Ib transfectants by the pan-MHC-I mAb W6/32 (top row) versus the MHC-E-specific mAb 4D12 (bottom row). Note that all Mamu-Ia and Mamu-E allomorphs were transfected into the murine cell line RMA-S, which expresses human β2-microglubulin. Macaque BLCL were used as a positive control, whereas the parent RMA-S cell line was used as a negative control (light gray histogram). Note the restriction of 4D12 reactivity to the Mamu-E transfectants.
Figure 27C:
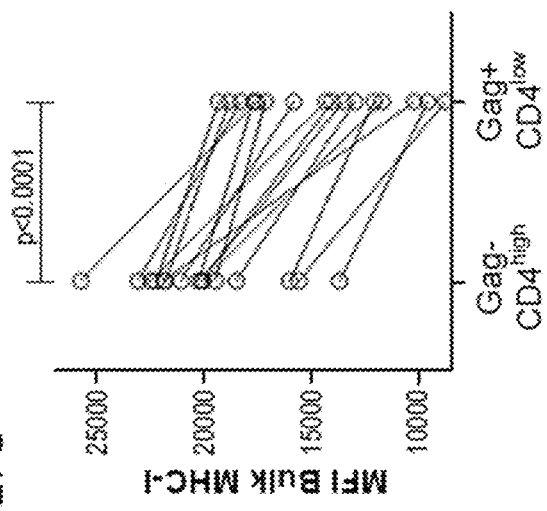
FIG. 27C shows the surface expression of total MHC-I, as determined by staining with mAb 4D12, on productively SIV-infected and uninfected CD4+ T cells in the same cultures, with SIV-infected cells recognized by intracellular expression of Gag Ag and CD4 down-regulation (Gag+/CD4$^{low}$), and uninfected cells recognized by lack of Gag reactivity and high levels of surface CD4 expression (Gag+/CD4$^{high}$). The left panels show representative flow cytometric histograms. The right panels depict the MFI of total MHC-I or specific MHC-E staining in SIV infected versus uninfected CD4+ T cells derived from a total of 16 unrelated macaques. P values were determined by the paired Student's T test.
Figure 27B:
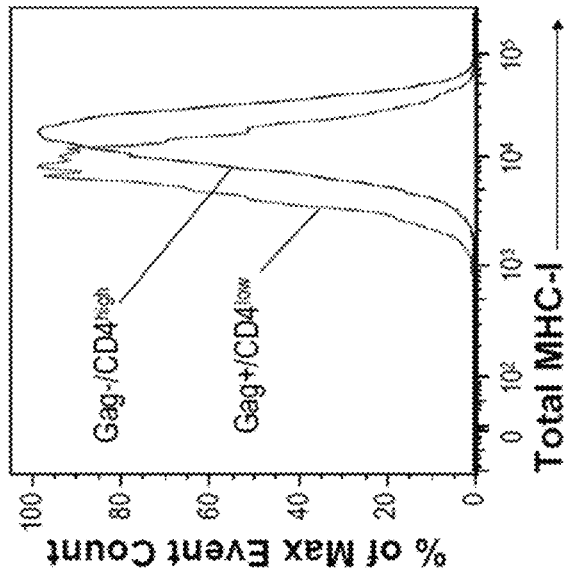
FIG. 27B shows the surface expression of total MHC-I as determined by staining with mAb W6/32).
Figure 28:
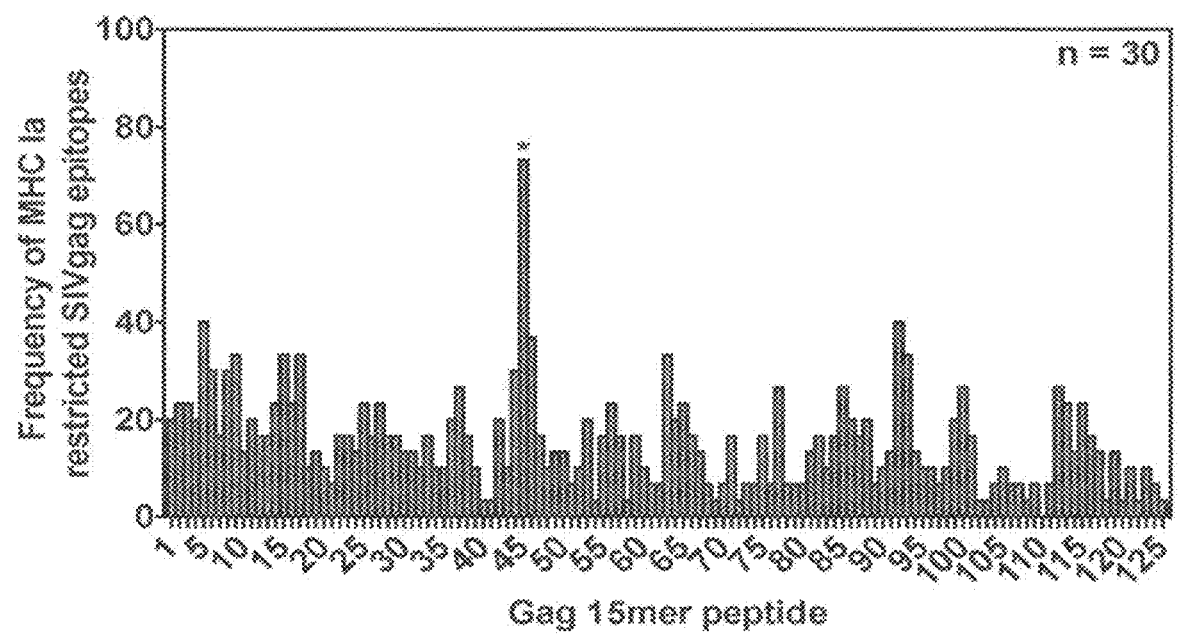
FIG. 28 is a population-level analysis of MHC-Ia-restricted CD8+ T cell responses to SIVgag. Analysis of the breadth of conventionally MHC-Ia restricted SIVgag epitope-specific CD8+ T cell responses across 125 overlapping (11 amino acid), consecutive SIVgag 15 mer peptides in 30 macaques vaccinated with conventional SIVgag-expression vaccines (11 MVA/gag, 3 Ad5/gag, 4 DNA/gag+IL-12) or infected with SIVmac239 (with plateau-phase viral loads <10,000 copies/ml; n=12). The asterisk (*) indicates the Gag-45 15 mer peptide which includes the Mamu-A1*001:01-restricted immunodominant SIVgag$_{181-189}$(CM9) epitope. Selection of monkeys for this cohort was largely unbiased with respect to MHC-Ia allomorphs, except for preferential selection of Mamu-A1*001:01 (expressed by 19 of the 30 macaques), accounting for the high frequency of monkeys responding to the Gag45 15 mer. Except for the Gag45 peptide, with its artificially increased response frequency, the frequency of monkeys with MHC-I-restricted CD8+ T cells reactive to any of the other Gag 15 mers is relatively low (only two 15 mers with 40% recognition and none >40%), compared to the MHC-E-restricted CD8+ T cell responses elicited by the strain 68-1 RhCMV/gag vector (19 epitopes with ≥40% recognition frequency; including 2 universal supertopes.

CMV is not the only intracellular pathogen to up-regulate MHC-E expression. Hepatitis C also encodes an MHC-E-binding peptide which up-regulates MHC-E expression (Natterman J et al., Am J Pathol 166, 443 (2005); incorporated by reference herein), and both HIV and SIV up-regulate MHC-E by an uncharacterized mechanism in concert with MHC-Ia down-regulation (Natterman J et al., Antivir Ther 10, 95 (2005); incorporated by reference herein) (FIG. 27). This common adaptation suggests that, for these and likely other intracellular pathogens, the evolutionary pressure to up-regulate MHC-E to counter NK cell responses outweighs the potential risk of increased susceptibility to MHC-E restricted CD8+ T cells, perhaps because MHC-E-restricted CD8+ T cells are poorly primed during infection by these agents. The reason MHC-E restricted CD8+ T cell responses are such a minor component of the modern mammalian immune system is unclear, especially given the finding in this report that such responses can be quite diverse and broad (although, arguably, less diverse and broad on a population level than polymorphic MHC-Ia; FIG. 28). However, Rh157.5/.4 gene deleted RhCMV vectors are able to bypass the intrinsic constraint of MHC-E-restricted CD8+ T cell priming. Although the mechanism by which this bypass is accomplished remains to be elucidated, the ability of these vectors to strongly elicit broad, diverse and MHC-Ia haplotype-independent CD8+ T cell responses offers the opportunity to develop MHC-E-restricted, CD8+ T cell-targeted vaccines that exploit MHC-E up-regulation, an intrinsic vulnerability in the immune-evasion strategies of many highly adapted persistent pathogens. Moreover, because of limited MHC-E polymorphism, an MHC-E-restricted CD8+ T cell response targeted vaccine would elicit largely similar responses in ail or most vaccinees, potentially providing for efficacy in all individuals regardless of MHC genotype. Evolution may have disfavored MHC-E as a primary restricting molecule for CD8+ T cells in modern mammals in lieu of the polymorphic MHC-Ia system, but if HCMV vectors are able to recapitulate in humans the biology of Rh157.5/.4 gene-deleted RhCMV vectors in macaques (or if alternative, non-CMV-based strategies to elicit broadly targeted MHC-E-restricted CD8+ T cell responses can be developed), vaccinologists may be able to resurrect this dormant MHC-E-based adaptive immune system to attack pathogens with novel immune responses that they are not adapted to effectively evade.

Materials and Methods:

Vaccines: The construction, characterization, and administration of 1) the strain 68-1 RhCMV vectors expressing SIV Gag and 5'-Pol, 2) the strain 68-1.2 RhCMV vector expressing SIV Gag, 3) the MVA and Adenovirus 5 (Ad5) vectors expressing SIV Gag, and 4) the SIV Gag-encoding DNA+IL-12 vaccine have been previously reported (Hansen et al. Science (2013), supra; Hansen et al. (2011), supra;

Hansen et al. Nature (2013), supra; and Hansen et al. (2009), supra). A strain RhCMV 68-1 expressing a fusion protein of the *M. tuberculosis* gene products RpfA, RpfC and RpfD driven by an MCMV IE promoter and inserted into the 5' region of Rh211 was provided by Aeras (Rockville, Md., USA). A Rh157.5 (UL128)-Rh157.4 (UL130) double deletion mutant based on strain 68-1.2 RhCMV/gag was also constructed by homologous recombination. To accomplish this, recombination primers flanking the target region (forward mutagenesis primer 5'-AAAACTATAAT-CAACAACTCTATACCTTTGTTTTGCTGATGCTA TTGCGT-3' and reverse mutagenesis primer 5'-ATTTTTC-GATAAAAAAATCACAGCAAACATACTG GTTTTA-CACACTTTAT-3') were designed. Since the Rh157.6 (UL131A) and Rh157.4 (UL130) open reading frames (ORFs) overlap in RhCMV, the deletion was constructed in a fashion that retained the end of the Rh157.6 (UL131A) ORF plus additional 50 bp to ensure expression of the encoded protein. Mini plasmid R6K-kan-F5 was used to amplify a kanamycin resistance cassette flanked by alternative (F5) FRT sites using the forward primer binding site (5'-GAAAAGTGCCACCTGCAGAT-3') and reverse primer binding site (5'-CAGGAACACTTAACGGCTGA-3'), which were added to the 3' end of the mutagenesis primers. E/T homologous recombination in *E. coli* strain SW105 (Warming S et al., Nucleic Acids Res 33, e36 (2005); incorporated by reference herein) was performed as published elsewhere (Muyrers J P et al., Nucleic Acids Res 27, 1555 (1999); incorporated by reference herein). Successful deletion of the targeted ORFs was confirmed by performing polymerase chain reactions on viral DNA and cDNA of infected cells with primers specific for the deleted and neighboring genes. Expression of the SIVmac239gag transgene was confirmed by immunoblot analysis of primary rhesus fibroblasts infected with the ΔRh157.5 (UL128)-Rh157.4 (UL130) 68-1.2 RhCMV/gag vector. See FIG. 23 for depiction of genomic differences between strain 68-1, 68-1.2, and ΔRh157.5/Rh157.4 (ΔUL128/UL130) RhCMV vectors.

Rhesus Macaques: A total of 207 purpose-bred male or female rhesus macaques (*Macaca mulatta*) of Indian genetic background were used in the experiments reported in this example, 88 of which were also studied in a previous report (Hansen et al. Science (2013), supra). These macaques included 159 macaques vaccinated with strain 68-1 RhCMV vectors expressing SIVgag, SIV5'-pol, TB-ESAT-6/Ag85B or TB-RpfA/RpfC/RpfD inserts (62 previously reported); 9 macaques vaccinated with strain 68-1.2 RhCMV/gag vectors (6 previously reported); 4 macaques vaccinated with ΔRh157.5/.4 deleted strain 68-1.2 RhCMV/gag vectors (none previously reported); 11, 3, and 4 macaques vaccinated with SIVgag-expressing MVA/gag, Ad5/gag, and DNA/gag+IL-12 vaccines, respectively (3, all, and all previously reported, respectively); 13 unvaccinated macaques with controlled SIVmac239 infection (plateau phase plasma viral loads <10,000 copies/ml; 6 previously reported); and 4 unvaccinated macaques naturally infected with ONPRC colony-circulating strains of RhCMV (all previously reported). All macaques were used with the approval of the Oregon National Primate Research Center Institutional Animal Care and Use Committee, under the standards of the US National Institutes of Health Guide for the Care and Use of Laboratory Animals. Macaques used in these experiments were free of cercopithicine herpesvirus 1, D-type simian retrovirus, and simian T-lymphotrophic Virus type 1. Selected macaques were MHC-I genotyped by deep sequencing, as described (Wiseman (2009), supra). Briefly, amplicons of Mamu class I sequences were generated via amplification of cDNA by PCR using high-fidelity Phusion™ polymerase (New England Biolabs) and a pair of universal MHC-I-specific primers with the following thermocycling conditions; 98° C. for 3 minutes, (98° C. for 5 seconds, 57° C. for 1 second, 72° C. for 20 seconds) for 23 cycles, and 72° C. for 5 minutes. Each PCR primer contained a unique 10 bp Multiplex Identifier (MID) tag along with an adaptor sequence for 454 Sequencing™ (5'-GCCTCCCTCGCGCCATCAG-MID-GC-TACGTGGACGACACG-3'; 5'-GCCTTGCCAGCCCGCTCAG-MID-TCGCTCTGGTTGTAGTAGC-3'). Resulting amplicons span 190 bp of a highly polymorphic region within exon two. The primary cDNA PCR products were purified using AMPure XP magnetic beads (Beckman Coulter Genomics). Emulsion PCR and pyrosequencing procedures were carried out with Genome Sequencer FLX instruments (Roche/454 Life Sciences) as per the manufacturer's instructions. Data analysis was performed using a Labkey database in conjunction with Geneious-Pro® bioinformatics software (Biomatters Ltd.) for sequence assembly.

Antigens and Antigen-Presenting Cells: The synthesis of sequential 15-mer peptides (overlapping by 11 amino acids) comprising the SIVgag and pol, RhCMV IE1, and TB Ag85B, ESAT-6, and RpfA proteins, as well as specific 9-14 mer peptides within these proteins, was performed by Intavis AG, based on the SIVmac239 Gag and Pol sequence (Genbank Accession #M33262), the strain 68-1 RhCMV IE-1 sequence (Genbank Accession #AY186194), or Erdman strain *M. tuberculosis* Ag85B, ESAT-6, and RpfA sequences (Genbank Accession #s BAL65871.1; BAL68013.1; and BAL64766.1, respectively). All peptides are identified by the position of their inclusive amino acids from the N-terminus (e.g., $Gag_{xx-yy}$). Consecutive 15 mers are also designated by their position starting from the N-terminal 15 mer (e.g., Gag1-15 (1) is 15 mer #1; Gag5-19 (2) is 15 mer #2, etc.). Unless otherwise specified, these peptides were used in T cell assays at 2 µg/ml. Autologous B-lymphoblastoid cell lines (BLCL) were generated by infecting rhesus macaque PBMC with Herpesvirus papio, as previously described (Hansen et al. Science (2013), supra). Mammalian expression vectors for Mamu class I molecules were generated by ligating each allele into pCEP4 KpnI/NotI or HindIII/NotI restriction (Ulbrecht M et al., J Immunol 164, 5019 (2000); incorporated by reference herein) sites. Plasmids were cloned in DH5α *E. coli* (Life Technologies), sequence confirmed, and electroporated into MHC-I-negative K562, 721.221, or RMAS cells (Anderson K S et al., J Immunol 151, 3407 (1993); incorporated by reference herein) using Nucleofector II/Kit C (Lonza). Transfectants were maintained on drug selection (Hygromycin B) and routinely confirmed for surface expression of MHC-I by staining with pan-MHC-I antibody clone W6/32. Throughout use in T cell assays, mRNA from MHC-I transfectants was extracted using the AllPrep DNA/RNA Mini Kit (Qiagen), amplified by RT-PCR using primer pairs flanking a highly polymorphic region within exon 2, and sequence confirmed. MHC-I transfectants and BLCL were pulsed with peptides of interest at a final concentration of 10 µM for 90 minutes then washed three times with warm PBS and once with warm RPMI 1640 media with 10% fetal calf serum to remove unbound peptide before combining with freshly isolated PBMC at an effector:target ratio of 10:1. In order to stabilize Mamu-E surface expression, Mamu-E transfectants were incubated at 27° C. for >3 hours prior to use in assays and maintained at 27° C. throughout peptide incubation until combined with effectors. Autologous SIV-infected target cells were generated by isolation of CD4+ T cells from PBMC with CD4 microbeads and LS columns (Miltenyi Biotec), activation with a combination of IL-2 (NIH AIDS Reagent Program), *Staphylococcus enterotoxin* B (Toxin Technologies Inc.), and anti-CD3 (NHP Reagent Resource), anti-CD28, and anti-CD49d mAbs (BD Biosciences), and spinoculation with sucrose-purified SIVmac239, followed by 3-4 days of culture. Prior to use in T cell assays, SIV infected target cells were purified using CD4 microbeads and LS columns (Miltenyi Biotec), as previously described (Sacha J B et al, J Immunol 178, 2746 (2007); incorporated by reference herein). Infected cell preparations were >95% CD4+ T cells and >50% SIV-infected following enrichment and were used at an effector:target ratio of 40:1 (PBMC and Isolated CD8+ T cells) or 8:1 (T cell line effectors). In these experiments, uninfected, activated CD4+ T cells served as negative control APCs (uninfected targets from SIV+ macaques were cultured with 400 μM tenofovir (NIH AIDS Reagent Program)). To assess total MHC-I and MHC-E expression, SIV-infected CD4+ T cells were generated as described above without post-infection purification and stained for surface MHC-I (clone W6/32), MHC-E (clone 4D12; anti-mouse IgG1 clone M1-14D12), CD3, and CD4, followed by intracellular SIV Gag.

T Cell Assays: SIV-, RhCMV-, and TB-specific CD8+ T cell responses were measured in mononuclear cell preparations from blood by flow cytometric ICS, as previously described (Hansen et al. *Science* (2013), supra). Briefly, mononuclear cells or isolated CD8+ T cells were incubated with antigen (peptides, peptide-pulsed BLCL or MHC-Ia or MHC-E transfectants, or SIV-infected autologous CD4+ T cells) and the co-stimulatory molecules CD28 and CD49d (BD Biosciences) for 1 hour, followed by addition of Brefeldin A (Sigma-Aldrich) for an additional 8 hours. Co-stimulation without antigen served as the primary background control. The MHC association (MHC-Ia, MHC-E, MHC-II) of a response was determined by pre-incubating isolated mononuclear cells, antigen-presenting cells or SIV-infected CD4+ cells for 1 hour at room temperature (prior to adding peptides or combining effector and target cells and incubating per the standard ICS assay) in the presence of the following blockers: 1) the pan anti-MHC-I mAb W6/32 (10 mg/ml), 2) the MHC-II-blocking CLIP peptide (MHC-II-associated invariant chain, amino acids 89-100; 20 μM), and 3) the MHC-E blocking VL9 peptide (VMAPRTLLL; 20 μM), alone or in combination. In some experiments, the Mamu-A1*001:01-binding peptide CM9 (CTPYDINQM; 20 μM), or the Mamu-A1*002:01-binding peptide GY9 (GSENLKSLY; 20 μM) were used as blocking controls. Stimulated cells were fixed, permeabilized and stained as previously described (Hansen et al. *Science* (2013), supra), and flow cytometric analysis was performed on an LSR-II instrument (BD Biosciences). Analysis was done using FlowJo software (Tree Star). In all analyses, gating on the light scatter signature of small lymphocytes was followed by progressive gating on the CD3+ population and then the CD4+/CD8+ T cell subset. Antigen-specific response frequencies for CD8+ T cell populations were routinely determined from intracellular expression of CD69 and either or both TNF-α and IFN-γ. For epitope deconvolution experiments, strict response criteria were used to prevent false positives. In these studies, a response to a given 15 mer peptide was considered positive if the frequency of events clustered as CD69+, TNP-α+ and IFN-γ+ was >0.05%, with background <0.01% in at least 2 independent assays. The classification of an individual peptide response as blocked was based on >90% inhibition by blockade relative to the isotype control. Responses that did not meet these criteria were considered indeterminate. To be considered MHC-E-restricted by blocking, the individual peptide response must have been blocked by both anti-MHC-I clone W6/32 and MHC-E-binding peptide VL9, and not blocked by the CLIP peptide. Minimal independent epitope numbers were estimated from the positive responses identified by testing of consecutive 15 mer peptides by the following criteria: single positive peptide of same restriction type=1 independent epitope; 2 adjacent positive peptides of same restriction type=1 independent epitope; 3 adjacent positive peptides of same restriction type=2 independent epitopes; 4 adjacent positive peptides of same restriction type=2 independent epitopes; and 5 adjacent positive peptides of same restriction type=3 independent epitopes.

Antibodies: The following conjugated antibodies were used in these studies: a) from BD Biosciences, L200 (CD4; AmCyan), SP34-2 (CD3; PacBlu), SK1 (CD8a; TruRed, AmCyan), 25723.11 (IFN-γ; APC, FITC), 6.7 (TNF; APC), MAb11 (TNF; Alexa700), b) from Beckman Coulter, L78 (CD69; PE), 2ST8.5H7 (CD8β; PE), Z199 (NKG2A/C or CD159a/c; PE), c) from Biolegend, W6/32 (pan-MHC-I; PE), OKT-4 (CD4; PE-Cy7), B1 (TCRγ/δ; Alexa647), d) from Miltenyi Biotec, M-T466 (CD4; APC), e) from eBiosciences, M1-14D12 (mouse IgG1; PE-Cy7). The following unconjugated antibodies were used in these studies: a) from Advanced BioScience laboratories, 4324 (SIV Gag p27), b) from LSBio, 4D12 (HLA-E), c) W6/32 (pan-MHC-I). LIVE/DEAD Fixable Yellow Dead Cell Stain (LIFE Technologies) was used to assess cell viability.

Epitope Sequence Analysis: Sequence LOGOs were created using the Los Alamos HIV database tool Analyze Align (http://www.hiv.lanl.gov/content/sequence/ANALYZEALIGN/analyze_align.html), which was based on WebLogo3 (Crooks, 2004 #150). Statistical enrichment or underrepresentation of amino acids in each position in the 11 optimal MHC-E 9-mer epitopes recognized in the macaques, and for the 551 HLA-E eluted peptides from TAP-deficient cells published in Lampen et al., supra were calculated using the Composition Profiler Tool (http://cprofiler.org/cgi-bin/profiler.cgi) (Vacic V et al., BMC Bioinform 8, 211 (2007); incorporated by reference herein). The amino acid composition of each position in the 11 optimal peptides was compared to the amino acid frequencies found in SIVmac239 Gag (GenBank accession #M33262), the insert strain used for the vaccine. To compare the per position composition of the 11 optimal peptides to previously published peptides eluted from HLA-E in a TAP-deficient setting, the full set of 551 eluted peptides previously published in Lampen et al. was used. The peptides in Lampen et al. varied in length, between 8 and 13 amino acids; 9 was the most common length. They had used a motif searching algorithm to explore amino acid enrichment and under representation among 315 9 mers in their eluted set (FIG. 2 in Lampen et al.) as position 2 and the C-terminal position was of most interest, regardless of length, a slightly different approach was taken to exploring their published data, and characterized an aligned version of all of their 551 eluted peptides. Gaps were added to maintain the alignment as needed after position 8, to enable a $2^{nd}$ position and aligned C-terminus evaluation including all peptides. Their data was compared for each alignment position to the amino acid frequencies found in natural proteins based on SwissProt 51 (Bairoch A et al., Nucleic Acids Res 33, D154 (2005); incorporated by reference herein).

The sequence LOGO shown in FIG. 13D indicates the frequency of each amino acid in a given position (relative to their background frequency in SIVmac239 Gag) by the height of the letter, based on 11 optimal, MHC-E-restricted SIVgag 9 mer peptide epitopes recognized by CD8+ T cells in strain 68-1 RhCMV vector-vaccinated macaques. The sequence LOGO in FIG. 13D is colored according to enrichment (boxes with grey fill or hatched boxes) or underrepresentation (boxes with white fill) among 551 peptides eluted from HLA-E in a TAP-deficient setting by Lampen et al. As shown in the right panel of FIG. 13D, amino acids enriched in the $2^{nd}$ and C-terminal anchor positions among the 551 Lampen et al. peptides were rare among our 11 optimal SIVgag peptides, while those that were significantly underrepresented were enriched.

It is understood that the examples and embodiments described herein are for illustrative purposes only and that various modifications or changes in light thereof will be suggested to person skilled in the art and are to be included within the spirit and purview of this application.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

The invention claimed is:

1. A method of generating $CD8^+$ T cells that recognize MHC-E-peptide complexes, the method comprising:

(1) administering to a first subject a recombinant cytomegalovirus (CMV) in an amount effective to generate a first set of $CD8^+$ T cells that recognize MHC-E/peptide complexes, wherein the recombinant CMV vector comprises (a) a first nucleic acid sequence encoding at least one heterologous antigen; (b) a second nucleic acid sequence encoding at least one active UL40 protein, or an ortholog or homolog thereof; and (c) a third nucleic acid sequence encoding at least one active US28 protein, or an ortholog or homolog thereof; wherein the CMV vector does not express an active UL128 protein, or an ortholog thereof, and does not express an active UL130 protein, or an ortholog thereof;

(2) identifying a first $CD8^+$ T cell receptor (TCR) from the first set of $CD8^+$ T cells, wherein the first $CD8^+$ TCR recognizes a MHC-E/heterologous antigen-derived peptide complex;

(3) isolating a second set of $CD8^+$ T cells from the first subject or from a second subject; and (4) transfecting the second set of $CD8^+$ T cells with an expression vector, wherein the expression vector comprises a nucleic acid sequence encoding a second $CD8^+$ TCR and a promoter operably linked to the nucleic acid sequence encoding the second $CD8^+$ TCR, wherein the second $CD8^+$ TCR comprises CDR3α and CDR3β of the first $CD8^+$ TCR, thereby generating one or more transfected $CD8^+$ T cells that recognize a MHC-E/heterologous antigen-derived peptide complex.

2. A transfected CD8+ T cell generated by the method of claim 1 which recognizes a MHC-E/heterologous antigen-derived peptide complex.

3. The CD8+ T cell of claim 2, wherein the at least one heterologous antigen of the recombinant CMV vector comprises a pathogen-specific antigen.

4. The CD8+ T cell of claim 3, wherein the pathogen-specific antigen is derived from a pathogen selected from the group consisting of: human immunodeficiency virus, simian immunodeficiency virus, herpes simplex virus, hepatitis B virus, hepatitis C virus, papillomavirus, *Plasmodium* parasites, and *Mycobacterium tuberculosis*.

5. A method of treating a pathogenic infection, the method comprising administering the CD8+ T cell of claim 3 to a subject.

6. A method of treating a pathogenic infection, the method comprising administering the $CD8^+$ T cell of claim 4 to a subject.

7. The method of claim 6, wherein the pathogen-specific antigen is derived from a human immunodeficiency virus.

8. The $CD8^+$ T cell of claim 2, wherein the at least one heterologous antigen of the CMV vector comprises a tumor antigen.

9. The $CD8^+$ T cell of claim 8, wherein the tumor antigen is related to a cancer selected from the group consisting of: acute myelogenous leukemia, chronic myelogenous leukemia, myelodysplastic syndrome, acute lymphoblastic leukemia, chronic lymphoblastic leukemia, non-Hodgkin's lymphoma, multiple myeloma, malignant melanoma, breast cancer, lung cancer, ovarian cancer, prostate cancer, pancreatic cancer, colon cancer, renal cell carcinoma (RCC), and germ cell tumors.

10. A method of treating cancer, the method comprising administering the CD8+ T cell of claim 8 to a subject.

11. The method of claim 1, wherein the at least one heterologous antigen is derived from a pathogen selected from the group consisting of: human immunodeficiency virus, simian immunodeficiency virus, herpes simplex virus, hepatitis B virus, hepatitis C virus, papillomavirus, *Plasmodium* parasites, and *Mycobacterium tuberculosis*.

12. The method of claim 11, wherein the at least one heterologous antigen is derived from human immunodeficiency virus.

13. The method of claim 1, wherein the at least one heterologous antigen is derived from a tumor antigen.

14. The method of claim 1, wherein the CMV vector does not express an active UL128 or UL130 protein, or orthologs thereof, due to the presence of one or more mutations in the nucleic acid sequence encoding UL128 or UL130, or orthologs thereof.

15. The method of claim 14, wherein the one or more mutations in the nucleic acid sequence encoding UL128 or UL130, or orthologs thereof, are selected from the group consisting of: point mutations, frameshift mutations, truncation mutations, and deletion of all of the nucleic acid sequence encoding the protein.

16. The method of claim 1, wherein the CMV vector further comprises at least one inactivating mutation in one or more viral genes encoding viral proteins that are essential, non-essential, or augmenting for growth in vivo.

17. The method of claim 16, wherein the at least one inactivating mutation is selected from the group consisting of: point mutation, frameshift mutation, truncation mutation, and deletion of all of the nucleic acid sequence encoding the viral protein.

18. The method of claim 16, wherein the at least one inactivating mutation is in UL82 (pp71).

19. The method of claim 16, wherein the at least one inactivating mutation is in US11.

20. The method of claim 1, wherein the first subject is a human or nonhuman primate.

* * * * *

SEQUENCE LISTING

```
<160> NUMBER OF SEQ ID NOS: 161

<210> SEQ ID NO 1
<211> LENGTH: 50
<212> TYPE: DNA
<213> ORGANISM: Artificial Sequence
<220> FEATURE:
<223> OTHER INFORMATION: 5' forward mutagenesis primer

<400> SEQUENCE: 1
aaaactataa tcaacaactc tataccttttg ttttgctgat gctattgcgt          50

<210> SEQ ID NO 2
<211> LENGTH: 50
<212> TYPE: DNA
<213> ORGANISM: Artificial Sequence
<220> FEATURE:
<223> OTHER INFORMATION: 5' reverse mutagenesis primer

<400> SEQUENCE: 2
atttttcgat aaaaaaatca cagcaaacat actggtttta cacactttat          50

<210> SEQ ID NO 3
<211> LENGTH: 20
<212> TYPE: DNA
<213> ORGANISM: Artificial Sequence
<220> FEATURE:
<223> OTHER INFORMATION: forward primer binding

<400> SEQUENCE: 3
gaaaagtgcc acctgcagat                                           20

<210> SEQ ID NO 4
<211> LENGTH: 20
<212> TYPE: DNA
<213> ORGANISM: Artificial Sequence
<220> FEATURE:
<223> OTHER INFORMATION: reverse primer binding site

<400> SEQUENCE: 4
caggaacact taacggctga                                           20

<210> SEQ ID NO 5
<211> LENGTH: 46
<212> TYPE: DNA
<213> ORGANISM: Artificial Sequence
<220> FEATURE:
<223> OTHER INFORMATION: 454 sequencing
<220> FEATURE:
<221> NAME/KEY: misc_feature
<222> LOCATION: (20)..(29)
```

<223> OTHER INFORMATION: n is a, c, g, or t

<400> SEQUENCE: 5
gcctccctcg cgccatcagn nnnnnnnnng ctacgtggac gacacg       46

<210> SEQ ID NO 6
<211> LENGTH: 48
<212> TYPE: DNA
<213> ORGANISM: Artificial Sequence
<220> FEATURE:
<223> OTHER INFORMATION: 454 sequencing
<220> FEATURE:
<221> NAME/KEY: misc_feature
<222> LOCATION: (20)..(29)
<223> OTHER INFORMATION: n is a, c, g, or t

<400> SEQUENCE: 6
gccttgccag cccgctcagn nnnnnnnnnt cgctctggtt gtagtagc     48

<210> SEQ ID NO 7
<211> LENGTH: 9
<212> TYPE: PRT
<213> ORGANISM: Artificial Sequence
<220> FEATURE:
<223> OTHER INFORMATION: MHC-E blocking VL9 peptide

<400> SEQUENCE: 7

Val Met Ala Pro Arg Thr Leu Leu Leu
1               5

<210> SEQ ID NO 8
<211> LENGTH: 9
<212> TYPE: PRT
<213> ORGANISM: Artificial Sequence
<220> FEATURE:
<223> OTHER INFORMATION: Mamu-A1* 001:01- binding peptide CM9

<400> SEQUENCE: 8

Cys Thr Pro Tyr Asp Ile Asn Gln Met
1               5

<210> SEQ ID NO 9
<211> LENGTH: 9
<212> TYPE: PRT
<213> ORGANISM: Artificial Sequence
<220> FEATURE:
<223> OTHER INFORMATION: Mamu-A1*002:01-binding peptide GY9

<400> SEQUENCE: 9

Gly Ser Glu Asn Leu Lys Ser Leu Tyr
1               5

<210> SEQ ID NO 10
<211> LENGTH: 9
<212> TYPE: PRT
<213> ORGANISM: Artificial Sequence
<220> FEATURE:
<223> OTHER INFORMATION: GAG65-73

<400> SEQUENCE: 10

Ala Pro Leu Val Pro Thr Gly Ser Glu
1               5

<210> SEQ ID NO 11
<211> LENGTH: 9
<212> TYPE: PRT
<213> ORGANISM: Artificial Sequence

<220> FEATURE:
<223> OTHER INFORMATION: GAG72-80

<400> SEQUENCE: 11

Ser Glu Asn Leu Lys Ser Leu Tyr Asn
1               5

<210> SEQ ID NO 12
<211> LENGTH: 9
<212> TYPE: PRT
<213> ORGANISM: Artificial Sequence
<220> FEATURE:
<223> OTHER INFORMATION: GAG92-100

<400> SEQUENCE: 12

Glu Lys Val Lys His Thr Glu Glu Ala
1               5

<210> SEQ ID NO 13
<211> LENGTH: 9
<212> TYPE: PRT
<213> ORGANISM: Artificial Sequence
<220> FEATURE:
<223> OTHER INFORMATION: GAG120-128

<400> SEQUENCE: 13

Lys Thr Ser Arg Pro Thr Ala Pro Ser
1               5

<210> SEQ ID NO 14
<211> LENGTH: 9
<212> TYPE: PRT
<213> ORGANISM: Artificial Sequence
<220> FEATURE:
<223> OTHER INFORMATION: GAG132-140

<400> SEQUENCE: 14

Gly Gly Asn Tyr Pro Val Gln Gln Ile
1               5

<210> SEQ ID NO 15
<211> LENGTH: 9
<212> TYPE: PRT
<213> ORGANISM: Artificial Sequence
<220> FEATURE:
<223> OTHER INFORMATION: GAG201-209

<400> SEQUENCE: 15

Gln Ile Ile Arg Asp Ile Ile Asn Glu
1               5

<210> SEQ ID NO 16
<211> LENGTH: 9
<212> TYPE: PRT
<213> ORGANISM: Artificial Sequence
<220> FEATURE:
<223> OTHER INFORMATION: GAG259-267

<400> SEQUENCE: 16

Val Gly Asn Ile Tyr Arg Arg Trp Ile
1               5

<210> SEQ ID NO 17
<211> LENGTH: 9
<212> TYPE: PRT
<213> ORGANISM: artificial sequence
<220> FEATURE:

-continued

<223> OTHER INFORMATION: GAG276-284

<400> SEQUENCE: 17

Arg Met Tyr Asn Pro Thr Asn Ile Leu
1               5

<210> SEQ ID NO 18
<211> LENGTH: 9
<212> TYPE: PRT
<213> ORGANISM: artificial sequence
<220> FEATURE:
<223> OTHER INFORMATION: GAG389-397

<400> SEQUENCE: 18

Lys Pro Ile Lys Cys Trp Asn Cys Gly
1               5

<210> SEQ ID NO 19
<211> LENGTH: 9
<212> TYPE: PRT
<213> ORGANISM: artificial sequence
<220> FEATURE:
<223> OTHER INFORMATION: GAG476-484

<400> SEQUENCE: 19

Leu Gly Lys Gln Gln Arg Glu Lys Gln
1               5

<210> SEQ ID NO 20
<211> LENGTH: 9
<212> TYPE: PRT
<213> ORGANISM: artificial sequence
<220> FEATURE:
<223> OTHER INFORMATION: GAG482-490

<400> SEQUENCE: 20

Glu Lys Gln Arg Glu Ser Arg Glu Lys
1               5

<210> SEQ ID NO 21
<211> LENGTH: 182
<212> TYPE: PRT
<213> ORGANISM: artificial sequence
<220> FEATURE:
<223> OTHER INFORMATION: HLA-E*01:03

<400> SEQUENCE: 21

Gly Ser His Ser Leu Lys Tyr Phe His Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Asn Asp Ala Ala Ser Pro Arg Met Val Pro Arg
        35                  40                  45

Ala Pro Trp Met Glu Gln Glu Gly Ser Glu Tyr Trp Asp Arg Glu Thr
    50                  55                  60

Arg Ser Ala Arg Asp Thr Ala Gln Ile Phe Arg Val Asn Leu Arg Thr
65                  70                  75                  80

Leu Arg Gly Tyr Tyr Asn Gln Ser Glu Ala Gly Ser His Thr Leu Gln
                85                  90                  95

Trp Met His Gly Cys Glu Leu Gly Pro Asp Gly Arg Phe Leu Arg Gly
            100                 105                 110

Tyr Glu Gln Phe Ala Tyr Asp Gly Lys Asp Tyr Leu Thr Leu Asn Glu
        115                 120                 125

```
Asp Leu Arg Ser Trp Thr Ala Val Asp Thr Ala Ala Gln Ile Ser Glu
        130                 135                 140

Gln Lys Ser Asn Asp Ala Ser Glu Ala Glu His Gln Arg Ala Tyr Leu
145                 150                 155                 160

Glu Asp Thr Cys Val Glu Trp Leu His Lys Tyr Leu Glu Lys Gly Lys
                165                 170                 175

Glu Thr Leu Leu His Leu
        180
```

<210> SEQ ID NO 22
<211> LENGTH: 182
<212> TYPE: PRT
<213> ORGANISM: artificial sequence
<220> FEATURE:
<223> OTHER INFORMATION: Mamu-E*02:04

<400> SEQUENCE: 22

```
Gly Ser His Ser Leu Lys Tyr Phe His Thr Ser Val Ser Arg Pro Gly
1               5                   10                  15

Gly Gly Gly Pro Arg Phe Ile Ser Val Gly Tyr Val Asp Asp Thr Gln
            20                  25                  30

Phe Val Arg Tyr Asp Ser Asp Ala Ala Ser Pro Arg Met Glu Pro Arg
        35                  40                  45

Ala Leu Trp Met Lys Gln Glu Gly Pro Glu Tyr Trp Asp Gln Glu Thr
    50                  55                  60

Arg Ser Ala Arg Ala Thr Ala Gln Thr Phe Arg Val Asn Leu Glu Thr
65                  70                  75                  80

Leu Arg Gly Tyr Tyr Asn Gln Ser Glu Ala Gly Ser His Thr Leu Gln
                85                  90                  95

Trp Met His Gly Asp Glu Leu Gly Pro Asp Gly Arg Phe Leu Arg Gly
            100                 105                 110

Tyr Glu Gln Phe Ala Tyr Asp Gly Lys Asp Tyr Leu Thr Leu Asn Glu
        115                 120                 125

Asp Leu Arg Ser Trp Ser Ala Val Asp Thr Ala Ala Gln Ile Ser Glu
    130                 135                 140

Gln Lys Ser Asn Asp Gly Ser Glu Ala Glu His Gln Arg Ala Tyr Leu
145                 150                 155                 160

Glu Asp Thr Cys Val Glu Trp Leu Arg Arg Tyr Leu Glu Asn Gly Lys
                165                 170                 175

Glu Thr Leu Gln Arg Ser
        180
```

<210> SEQ ID NO 23
<211> LENGTH: 182
<212> TYPE: PRT
<213> ORGANISM: artificial sequence
<220> FEATURE:
<223> OTHER INFORMATION: Mamu-E*02:11

<400> SEQUENCE: 23

```
Gly Ser His Ser Leu Lys Tyr Phe His Thr Ser Val Ser Arg Pro Gly
1               5                   10                  15

Arg Gly Gly Pro Arg Phe Ile Ser Val Gly Tyr Val Asp Asp Thr Gln
            20                  25                  30

Phe Val Arg Tyr Asp Ser Asp Ala Ala Ser Pro Arg Met Glu Pro Arg
        35                  40                  45

Ala Pro Trp Val Glu Gln Glu Gly Pro Glu Tyr Trp Asp Gln Glu Thr
```

-continued

```
                 50                  55                  60
Arg Ser Ala Arg Asp Thr Ala Gln Thr Phe Arg Val Asn Leu Glu Thr
 65                  70                  75                  80

Leu Arg Gly Tyr Tyr Asn Gln Ser Glu Ala Gly Ser His Thr Leu Gln
                 85                  90                  95

Trp Met His Gly Cys Asp Leu Gly Pro Asp Gly Arg Phe Leu Arg Gly
                100                 105                 110

Tyr Glu Gln Phe Ala Tyr Asp Gly Lys Asp Tyr Leu Thr Leu Asn Glu
                115                 120                 125

Asp Leu Arg Ser Trp Ser Ala Val Asp Thr Ala Ala Gln Ile Ser Glu
                130                 135                 140

Gln Lys Ser Asn Asp Gly Ser Glu Ala Glu His Gln Arg Ala Tyr Leu
145                 150                 155                 160

Glu Asp Thr Cys Val Glu Trp Leu His Arg Tyr Leu Glu Asn Gly Lys
                    165                 170                 175

Glu Thr Leu Gln Arg Ser
                180
```

<210> SEQ ID NO 24
<211> LENGTH: 182
<212> TYPE: PRT
<213> ORGANISM: artificial sequence
<220> FEATURE:
<223> OTHER INFORMATION: Mamu-E*02:20

<400> SEQUENCE: 24

```
Gly Ser His Ser Leu Lys Tyr Phe His Thr Ala Val Ser Arg Pro Gly
 1               5                  10                  15

Cys Val Glu Pro Arg Phe Ile Phe Val Gly Tyr Val Asp Asp Thr Gln
                20                  25                  30

Phe Val Arg Phe Asp Ser Asp Ala Ala Asn Pro Arg Met Gln Pro Arg
                35                  40                  45

Ala Pro Trp Met Glu Gln Glu Gly Pro Glu Tyr Trp Asp Gln Glu Thr
 50                  55                  60

Arg Arg Ala Arg Asp Thr Ala Gln Thr Leu Arg Val Lys Leu Lys Thr
 65                  70                  75                  80

Leu Arg Gly Tyr Tyr Asn Gln Ser Glu Ala Gly Ser His Thr Leu Gln
                 85                  90                  95

Trp Met Tyr Gly Cys Asp Leu Gly Pro Asp Gly Arg Phe Leu Arg Glu
                100                 105                 110

Tyr Glu Gln Phe Ala Tyr Asp Gly Lys Asp Tyr Leu Thr Leu Asn Glu
                115                 120                 125

Asp Leu Arg Ser Trp Ser Ala Val Asp Thr Ala Ala Gln Ile Ser Glu
                130                 135                 140

Gln Lys Ser Asn Asp Gly Gly Glu Ala Glu His Gln Arg Ala Tyr Leu
145                 150                 155                 160

Glu Asp Thr Cys Val Glu Trp Leu Arg Arg Tyr Leu Glu Asn Gly Lys
                    165                 170                 175

Glu Thr Leu Gln Arg Pro
                180
```

<210> SEQ ID NO 25
<211> LENGTH: 15
<212> TYPE: PRT
<213> ORGANISM: artificial sequence
<220> FEATURE:
<223> OTHER INFORMATION: SIVgag61-75(16)

```
<400> SEQUENCE: 25

Leu Ser Val Leu Ala Pro Leu Val Pro Thr Gly Ser Glu Asn Leu
1               5                   10                  15

<210> SEQ ID NO 26
<211> LENGTH: 14
<212> TYPE: PRT
<213> ORGANISM: artificial sequence
<220> FEATURE:
<223> OTHER INFORMATION: SIVgag61-75(sub)

<400> SEQUENCE: 26

Ser Val Leu Ala Pro Leu Val Pro Thr Gly Ser Glu Asn Leu
1               5                   10

<210> SEQ ID NO 27
<211> LENGTH: 14
<212> TYPE: PRT
<213> ORGANISM: artificial sequence
<220> FEATURE:
<223> OTHER INFORMATION: SIVgag61-75(sub)

<400> SEQUENCE: 27

Leu Ser Val Leu Ala Pro Leu Val Pro Thr Gly Ser Glu Asn
1               5                   10

<210> SEQ ID NO 28
<211> LENGTH: 13
<212> TYPE: PRT
<213> ORGANISM: artificial sequence
<220> FEATURE:
<223> OTHER INFORMATION: SIVgag61-75(sub)

<400> SEQUENCE: 28

Val Leu Ala Pro Leu Val Pro Thr Gly Ser Glu Asn Leu
1               5                   10

<210> SEQ ID NO 29
<211> LENGTH: 13
<212> TYPE: PRT
<213> ORGANISM: artificial sequence
<220> FEATURE:
<223> OTHER INFORMATION: SIVgag61-75(sub)

<400> SEQUENCE: 29

Leu Ser Val Leu Ala Pro Leu Val Pro Thr Gly Ser Glu
1               5                   10

<210> SEQ ID NO 30
<211> LENGTH: 12
<212> TYPE: PRT
<213> ORGANISM: artificial sequence
<220> FEATURE:
<223> OTHER INFORMATION: SIVgag61-75(sub)

<400> SEQUENCE: 30

Leu Ala Pro Leu Val Pro Thr Gly Ser Glu Asn Leu
1               5                   10

<210> SEQ ID NO 31
<211> LENGTH: 12
<212> TYPE: PRT
<213> ORGANISM: artificial sequence
<220> FEATURE:
<223> OTHER INFORMATION: SIVgag61-75(sub)
```

```
<400> SEQUENCE: 31

Leu Ser Val Leu Ala Pro Leu Val Pro Thr Gly Ser
1               5                   10

<210> SEQ ID NO 32
<211> LENGTH: 11
<212> TYPE: PRT
<213> ORGANISM: artificial sequence
<220> FEATURE:
<223> OTHER INFORMATION: SIVgag61-75(sub)

<400> SEQUENCE: 32

Ala Pro Leu Val Pro Thr Gly Ser Glu Asn Leu
1               5                   10

<210> SEQ ID NO 33
<211> LENGTH: 11
<212> TYPE: PRT
<213> ORGANISM: artificial sequence
<220> FEATURE:
<223> OTHER INFORMATION: SIVgag61-75(sub)

<400> SEQUENCE: 33

Leu Ser Val Leu Ala Pro Leu Val Pro Thr Gly
1               5                   10

<210> SEQ ID NO 34
<211> LENGTH: 10
<212> TYPE: PRT
<213> ORGANISM: artificial sequence
<220> FEATURE:
<223> OTHER INFORMATION: SIVgag61-75(sub)

<400> SEQUENCE: 34

Pro Leu Val Pro Thr Gly Ser Glu Asn Leu
1               5                   10

<210> SEQ ID NO 35
<211> LENGTH: 10
<212> TYPE: PRT
<213> ORGANISM: artificial sequence
<220> FEATURE:
<223> OTHER INFORMATION: SIVgag61-75(sub)

<400> SEQUENCE: 35

Leu Ser Val Leu Ala Pro Leu Val Pro Thr
1               5                   10

<210> SEQ ID NO 36
<211> LENGTH: 9
<212> TYPE: PRT
<213> ORGANISM: artificial sequence
<220> FEATURE:
<223> OTHER INFORMATION: SIVgag61-75(sub)

<400> SEQUENCE: 36

Leu Val Pro Thr Gly Ser Glu Asn Leu
1               5

<210> SEQ ID NO 37
<211> LENGTH: 9
<212> TYPE: PRT
<213> ORGANISM: artificial sequence
<220> FEATURE:
<223> OTHER INFORMATION: SIVgag61-75(sub)

<400> SEQUENCE: 37
```

Leu Ser Val Leu Ala Pro Leu Val Pro
1               5

<210> SEQ ID NO 38
<211> LENGTH: 15
<212> TYPE: PRT
<213> ORGANISM: artificial sequence
<220> FEATURE:
<223> OTHER INFORMATION: SIVgag69-83(sub)

<400> SEQUENCE: 38

Pro Thr Gly Ser Glu Asn Leu Lys Ser Leu Tyr Asn Thr Val Cys
1               5                   10                  15

<210> SEQ ID NO 39
<211> LENGTH: 14
<212> TYPE: PRT
<213> ORGANISM: artificial sequence
<220> FEATURE:
<223> OTHER INFORMATION: SIVgag69-83(sub)

<400> SEQUENCE: 39

Thr Gly Ser Glu Asn Leu Lys Ser Leu Tyr Asn Thr Val Cys
1               5                   10

<210> SEQ ID NO 40
<211> LENGTH: 14
<212> TYPE: PRT
<213> ORGANISM: artificial sequence
<220> FEATURE:
<223> OTHER INFORMATION: SIVgag69-83(sub)

<400> SEQUENCE: 40

Pro Thr Gly Ser Glu Asn Leu Lys Ser Leu Tyr Asn Thr Val
1               5                   10

<210> SEQ ID NO 41
<211> LENGTH: 13
<212> TYPE: PRT
<213> ORGANISM: artificial sequence
<220> FEATURE:
<223> OTHER INFORMATION: SIVgag69-83(sub)

<400> SEQUENCE: 41

Gly Ser Glu Asn Leu Lys Ser Leu Tyr Asn Thr Val Cys
1               5                   10

<210> SEQ ID NO 42
<211> LENGTH: 13
<212> TYPE: PRT
<213> ORGANISM: artificial sequence
<220> FEATURE:
<223> OTHER INFORMATION: SIVgag69-83(sub)

<400> SEQUENCE: 42

Pro Thr Gly Ser Glu Asn Leu Lys Ser Leu Tyr Asn Thr
1               5                   10

<210> SEQ ID NO 43
<211> LENGTH: 12
<212> TYPE: PRT
<213> ORGANISM: artificial sequence
<220> FEATURE:
<223> OTHER INFORMATION: SIVgag69-83(sub)

<400> SEQUENCE: 43

```
Ser Glu Asn Leu Lys Ser Leu Tyr Asn Thr Val Cys
1               5                   10
```

<210> SEQ ID NO 44
<211> LENGTH: 12
<212> TYPE: PRT
<213> ORGANISM: artificial sequence
<220> FEATURE:
<223> OTHER INFORMATION: SIVgag69-83(sub)

<400> SEQUENCE: 44

```
Pro Thr Gly Ser Glu Asn Leu Lys Ser Leu Tyr Asn
1               5                   10
```

<210> SEQ ID NO 45
<211> LENGTH: 11
<212> TYPE: PRT
<213> ORGANISM: artificial sequence
<220> FEATURE:
<223> OTHER INFORMATION: SIVgag69-83(sub)

<400> SEQUENCE: 45

```
Glu Asn Leu Lys Ser Leu Tyr Asn Thr Val Cys
1               5                   10
```

<210> SEQ ID NO 46
<211> LENGTH: 11
<212> TYPE: PRT
<213> ORGANISM: artificial sequence
<220> FEATURE:
<223> OTHER INFORMATION: SIVgag69-83(sub)

<400> SEQUENCE: 46

```
Pro Thr Gly Ser Glu Asn Leu Lys Ser Leu Tyr
1               5                   10
```

<210> SEQ ID NO 47
<211> LENGTH: 10
<212> TYPE: PRT
<213> ORGANISM: artificial sequence
<220> FEATURE:
<223> OTHER INFORMATION: SIVgag69-83(sub)

<400> SEQUENCE: 47

```
Asn Leu Lys Ser Leu Tyr Asn Thr Val Cys
1               5                   10
```

<210> SEQ ID NO 48
<211> LENGTH: 10
<212> TYPE: PRT
<213> ORGANISM: artificial sequence
<220> FEATURE:
<223> OTHER INFORMATION: SIVgag69-83(sub)

<400> SEQUENCE: 48

```
Pro Thr Gly Ser Glu Asn Leu Lys Ser Leu
1               5                   10
```

<210> SEQ ID NO 49
<211> LENGTH: 9
<212> TYPE: PRT
<213> ORGANISM: artificial sequence
<220> FEATURE:
<223> OTHER INFORMATION: SIVgag69-83(sub)

<400> SEQUENCE: 49

```
Leu Lys Ser Leu Tyr Asn Thr Val Cys
```

```
1               5
```

<210> SEQ ID NO 50
<211> LENGTH: 9
<212> TYPE: PRT
<213> ORGANISM: artificial sequence
<220> FEATURE:
<223> OTHER INFORMATION: SIVgag69-83(sub)

<400> SEQUENCE: 50

```
Pro Thr Gly Ser Glu Asn Leu Lys Ser
1               5
```

<210> SEQ ID NO 51
<211> LENGTH: 9
<212> TYPE: PRT
<213> ORGANISM: artificial sequence
<220> FEATURE:
<223> OTHER INFORMATION: SIVgag61-75(sub)

<400> SEQUENCE: 51

```
Ser Val Leu Ala Pro Leu Val Pro Thr
1               5
```

<210> SEQ ID NO 52
<211> LENGTH: 9
<212> TYPE: PRT
<213> ORGANISM: artificial sequence
<220> FEATURE:
<223> OTHER INFORMATION: SIVgag61-75(sub)

<400> SEQUENCE: 52

```
Val Leu Ala Pro Leu Val Pro Thr Gly
1               5
```

<210> SEQ ID NO 53
<211> LENGTH: 9
<212> TYPE: PRT
<213> ORGANISM: artificial sequence
<220> FEATURE:
<223> OTHER INFORMATION: SIVgag61-75(sub)

<400> SEQUENCE: 53

```
Leu Ala Pro Leu Val Pro Thr Gly Ser
1               5
```

<210> SEQ ID NO 54
<211> LENGTH: 9
<212> TYPE: PRT
<213> ORGANISM: artificial sequence
<220> FEATURE:
<223> OTHER INFORMATION: SIVgag61-75(sub)

<400> SEQUENCE: 54

```
Ala Pro Leu Val Pro Thr Gly Ser Glu
1               5
```

<210> SEQ ID NO 55
<211> LENGTH: 9
<212> TYPE: PRT
<213> ORGANISM: artificial sequence
<220> FEATURE:
<223> OTHER INFORMATION: SIVgag61-75(sub)

<400> SEQUENCE: 55

```
Pro Leu Val Pro Thr Gly Ser Glu Asn
1               5
```

```
<210> SEQ ID NO 56
<211> LENGTH: 9
<212> TYPE: PRT
<213> ORGANISM: artificial sequence
<220> FEATURE:
<223> OTHER INFORMATION: SIVgag69-83(sub)

<400> SEQUENCE: 56

Thr Gly Ser Glu Asn Leu Lys Ser Leu
1               5

<210> SEQ ID NO 57
<211> LENGTH: 9
<212> TYPE: PRT
<213> ORGANISM: artificial sequence
<220> FEATURE:
<223> OTHER INFORMATION: SIVgag69-83(sub)

<400> SEQUENCE: 57

Glu Asn Leu Lys Ser Leu Tyr Asn Thr
1               5

<210> SEQ ID NO 58
<211> LENGTH: 9
<212> TYPE: PRT
<213> ORGANISM: artificial sequence
<220> FEATURE:
<223> OTHER INFORMATION: SIVgag69-83(sub)

<400> SEQUENCE: 58

Asn Leu Lys Ser Leu Tyr Asn Thr Val
1               5

<210> SEQ ID NO 59
<211> LENGTH: 15
<212> TYPE: PRT
<213> ORGANISM: artificial sequence
<220> FEATURE:
<223> OTHER INFORMATION: SIVgag89-103(sub)

<400> SEQUENCE: 59

His Ala Glu Glu Lys Val Lys His Thr Glu Glu Ala Lys Gln Ile
1               5                   10                  15

<210> SEQ ID NO 60
<211> LENGTH: 14
<212> TYPE: PRT
<213> ORGANISM: artificial sequence
<220> FEATURE:
<223> OTHER INFORMATION: SIVgag89-103(sub)

<400> SEQUENCE: 60

Ala Glu Glu Lys Val Lys His Thr Glu Glu Ala Lys Gln Ile
1               5                   10

<210> SEQ ID NO 61
<211> LENGTH: 14
<212> TYPE: PRT
<213> ORGANISM: artificial sequence
<220> FEATURE:
<223> OTHER INFORMATION: SIVgag89-103(sub)

<400> SEQUENCE: 61

His Ala Glu Glu Lys Val Lys His Thr Glu Glu Ala Lys Gln
1               5                   10
```

<210> SEQ ID NO 62
<211> LENGTH: 13
<212> TYPE: PRT
<213> ORGANISM: artificial sequence
<220> FEATURE:
<223> OTHER INFORMATION: SIVgag89-103(sub)

<400> SEQUENCE: 62

Glu Glu Lys Val Lys His Thr Glu Glu Ala Lys Gln Ile
1               5                   10

<210> SEQ ID NO 63
<211> LENGTH: 13
<212> TYPE: PRT
<213> ORGANISM: artificial sequence
<220> FEATURE:
<223> OTHER INFORMATION: SIVgag89-103(sub)

<400> SEQUENCE: 63

His Ala Glu Glu Lys Val Lys His Thr Glu Glu Ala Lys
1               5                   10

<210> SEQ ID NO 64
<211> LENGTH: 12
<212> TYPE: PRT
<213> ORGANISM: artificial sequence
<220> FEATURE:
<223> OTHER INFORMATION: SIVgag89-103(sub)

<400> SEQUENCE: 64

Glu Lys Val Lys His Thr Glu Glu Ala Lys Gln Ile
1               5                   10

<210> SEQ ID NO 65
<211> LENGTH: 12
<212> TYPE: PRT
<213> ORGANISM: artificial sequence
<220> FEATURE:
<223> OTHER INFORMATION: SIVgag89-103(sub)

<400> SEQUENCE: 65

His Ala Glu Glu Lys Val Lys His Thr Glu Glu Ala
1               5                   10

<210> SEQ ID NO 66
<211> LENGTH: 11
<212> TYPE: PRT
<213> ORGANISM: artificial sequence
<220> FEATURE:
<223> OTHER INFORMATION: SIVgag89-103(sub)

<400> SEQUENCE: 66

Lys Val Lys His Thr Glu Glu Ala Lys Gln Ile
1               5                   10

<210> SEQ ID NO 67
<211> LENGTH: 11
<212> TYPE: PRT
<213> ORGANISM: artificial sequence
<220> FEATURE:
<223> OTHER INFORMATION: SIVgag89-103(sub)

<400> SEQUENCE: 67

His Ala Glu Glu Lys Val Lys His Thr Glu Glu
1               5                   10

```
<210> SEQ ID NO 68
<211> LENGTH: 10
<212> TYPE: PRT
<213> ORGANISM: artificial sequence
<220> FEATURE:
<223> OTHER INFORMATION: SIVgag89-103(sub)

<400> SEQUENCE: 68

Val Lys His Thr Glu Glu Ala Lys Gln Ile
1               5                   10

<210> SEQ ID NO 69
<211> LENGTH: 10
<212> TYPE: PRT
<213> ORGANISM: artificial sequence
<220> FEATURE:
<223> OTHER INFORMATION: SIVgag89-103(sub)

<400> SEQUENCE: 69

His Ala Glu Glu Lys Val Lys His Thr Glu
1               5                   10

<210> SEQ ID NO 70
<211> LENGTH: 9
<212> TYPE: PRT
<213> ORGANISM: artificial sequence
<220> FEATURE:
<223> OTHER INFORMATION: SIVgag89-103(sub)

<400> SEQUENCE: 70

Lys His Thr Glu Glu Ala Lys Gln Ile
1               5

<210> SEQ ID NO 71
<211> LENGTH: 9
<212> TYPE: PRT
<213> ORGANISM: artificial sequence
<220> FEATURE:
<223> OTHER INFORMATION: SIVgag89-103(sub)

<400> SEQUENCE: 71

His Ala Glu Glu Lys Val Lys His Thr
1               5

<210> SEQ ID NO 72
<211> LENGTH: 15
<212> TYPE: PRT
<213> ORGANISM: artificial sequence
<220> FEATURE:
<223> OTHER INFORMATION: SIVgag117-131(sub)

<400> SEQUENCE: 72

Thr Met Pro Lys Thr Ser Arg Pro Thr Ala Pro Ser Ser Gly Arg
1               5                   10                  15

<210> SEQ ID NO 73
<211> LENGTH: 14
<212> TYPE: PRT
<213> ORGANISM: artificial sequence
<220> FEATURE:
<223> OTHER INFORMATION: SIVgag117-131(sub)

<400> SEQUENCE: 73

Met Pro Lys Thr Ser Arg Pro Thr Ala Pro Ser Ser Gly Arg
1               5                   10

<210> SEQ ID NO 74
```

```
<211> LENGTH: 14
<212> TYPE: PRT
<213> ORGANISM: artificial sequence
<220> FEATURE:
<223> OTHER INFORMATION: SIVgag117-131(sub)

<400> SEQUENCE: 74

Thr Met Pro Lys Thr Ser Arg Pro Thr Ala Pro Ser Ser Gly
1               5                   10

<210> SEQ ID NO 75
<211> LENGTH: 13
<212> TYPE: PRT
<213> ORGANISM: artificial sequence
<220> FEATURE:
<223> OTHER INFORMATION: SIVgag117-131(sub)

<400> SEQUENCE: 75

Pro Lys Thr Ser Arg Pro Thr Ala Pro Ser Ser Gly Arg
1               5                   10

<210> SEQ ID NO 76
<211> LENGTH: 13
<212> TYPE: PRT
<213> ORGANISM: artificial sequence
<220> FEATURE:
<223> OTHER INFORMATION: SIVgag117-131(sub)

<400> SEQUENCE: 76

Thr Met Pro Lys Thr Ser Arg Pro Thr Ala Pro Ser Ser
1               5                   10

<210> SEQ ID NO 77
<211> LENGTH: 12
<212> TYPE: PRT
<213> ORGANISM: artificial sequence
<220> FEATURE:
<223> OTHER INFORMATION: SIVgag117-131(sub)

<400> SEQUENCE: 77

Lys Thr Ser Arg Pro Thr Ala Pro Ser Ser Gly Arg
1               5                   10

<210> SEQ ID NO 78
<211> LENGTH: 12
<212> TYPE: PRT
<213> ORGANISM: artificial sequence
<220> FEATURE:
<223> OTHER INFORMATION: SIVgag117-131(sub)

<400> SEQUENCE: 78

Thr Met Pro Lys Thr Ser Arg Pro Thr Ala Pro Ser
1               5                   10

<210> SEQ ID NO 79
<211> LENGTH: 11
<212> TYPE: PRT
<213> ORGANISM: artificial sequence
<220> FEATURE:
<223> OTHER INFORMATION: SIVgag117-131(sub)

<400> SEQUENCE: 79

Thr Ser Arg Pro Thr Ala Pro Ser Ser Gly Arg
1               5                   10

<210> SEQ ID NO 80
<211> LENGTH: 11
```

```
<212> TYPE: PRT
<213> ORGANISM: artificial sequence
<220> FEATURE:
<223> OTHER INFORMATION: SIVgag117-131(sub)

<400> SEQUENCE: 80

Thr Met Pro Lys Thr Ser Arg Pro Thr Ala Pro
1               5                   10

<210> SEQ ID NO 81
<211> LENGTH: 10
<212> TYPE: PRT
<213> ORGANISM: artificial sequence
<220> FEATURE:
<223> OTHER INFORMATION: SIVgag117-131(sub)

<400> SEQUENCE: 81

Ser Arg Pro Thr Ala Pro Ser Ser Gly Arg
1               5                   10

<210> SEQ ID NO 82
<211> LENGTH: 10
<212> TYPE: PRT
<213> ORGANISM: artificial sequence
<220> FEATURE:
<223> OTHER INFORMATION: SIVgag117-131(sub)

<400> SEQUENCE: 82

Thr Met Pro Lys Thr Ser Arg Pro Thr Ala
1               5                   10

<210> SEQ ID NO 83
<211> LENGTH: 9
<212> TYPE: PRT
<213> ORGANISM: artificial sequence
<220> FEATURE:
<223> OTHER INFORMATION: SIVgag117-131(sub)

<400> SEQUENCE: 83

Arg Pro Thr Ala Pro Ser Ser Gly Arg
1               5

<210> SEQ ID NO 84
<211> LENGTH: 9
<212> TYPE: PRT
<213> ORGANISM: artificial sequence
<220> FEATURE:
<223> OTHER INFORMATION: SIVgag117-131(sub)

<400> SEQUENCE: 84

Thr Met Pro Lys Thr Ser Arg Pro Thr
1               5

<210> SEQ ID NO 85
<211> LENGTH: 9
<212> TYPE: PRT
<213> ORGANISM: artificial sequence
<220> FEATURE:
<223> OTHER INFORMATION: SIVgag89-103(sub)

<400> SEQUENCE: 85

Ala Glu Glu Lys Val Lys His Thr Glu
1               5

<210> SEQ ID NO 86
<211> LENGTH: 9
<212> TYPE: PRT
```

```
<213> ORGANISM: artificial sequence
<220> FEATURE:
<223> OTHER INFORMATION: SIVgag89-103(sub)

<400> SEQUENCE: 86

Glu Glu Lys Val Lys His Thr Glu Glu
1               5

<210> SEQ ID NO 87
<211> LENGTH: 9
<212> TYPE: PRT
<213> ORGANISM: artificial sequence
<220> FEATURE:
<223> OTHER INFORMATION: SIVgag89-103(sub)

<400> SEQUENCE: 87

Lys Val Lys His Thr Glu Glu Ala Lys
1               5

<210> SEQ ID NO 88
<211> LENGTH: 9
<212> TYPE: PRT
<213> ORGANISM: artificial sequence
<220> FEATURE:
<223> OTHER INFORMATION: SIVgag89-103(sub)

<400> SEQUENCE: 88

Val Lys His Thr Glu Glu Ala Lys Gln
1               5

<210> SEQ ID NO 89
<211> LENGTH: 9
<212> TYPE: PRT
<213> ORGANISM: artificial sequence
<220> FEATURE:
<223> OTHER INFORMATION: SIVgag117-131(sub)

<400> SEQUENCE: 89

Met Pro Lys Thr Ser Arg Pro Thr Ala
1               5

<210> SEQ ID NO 90
<211> LENGTH: 9
<212> TYPE: PRT
<213> ORGANISM: artificial sequence
<220> FEATURE:
<223> OTHER INFORMATION: SIVgag117-131(sub)

<400> SEQUENCE: 90

Thr Ser Arg Pro Thr Ala Pro Ser Ser
1               5

<210> SEQ ID NO 91
<211> LENGTH: 9
<212> TYPE: PRT
<213> ORGANISM: artificial sequence
<220> FEATURE:
<223> OTHER INFORMATION: SIVgag117-131(sub)

<400> SEQUENCE: 91

Ser Arg Pro Thr Ala Pro Ser Ser Gly
1               5

<210> SEQ ID NO 92
<211> LENGTH: 15
<212> TYPE: PRT
<213> ORGANISM: artificial sequence
```

<220> FEATURE:
<223> OTHER INFORMATION: SIVgag129-143(sub)

<400> SEQUENCE: 92

Ser Gly Arg Gly Gly Asn Tyr Pro Val Gln Gln Ile Gly Gly Asn
1               5                   10                  15

<210> SEQ ID NO 93
<211> LENGTH: 14
<212> TYPE: PRT
<213> ORGANISM: artificial sequence
<220> FEATURE:
<223> OTHER INFORMATION: SIVgag129-143(sub)

<400> SEQUENCE: 93

Gly Arg Gly Gly Asn Tyr Pro Val Gln Gln Ile Gly Gly Asn
1               5                   10

<210> SEQ ID NO 94
<211> LENGTH: 13
<212> TYPE: PRT
<213> ORGANISM: artificial sequence
<220> FEATURE:
<223> OTHER INFORMATION: SIVgag129-143(sub)

<400> SEQUENCE: 94

Ser Arg Gly Gly Asn Tyr Pro Val Gln Gln Ile Gly Gly
1               5                   10

<210> SEQ ID NO 95
<211> LENGTH: 13
<212> TYPE: PRT
<213> ORGANISM: artificial sequence
<220> FEATURE:
<223> OTHER INFORMATION: SIVgag129-143(sub)

<400> SEQUENCE: 95

Arg Gly Gly Asn Tyr Pro Val Gln Gln Ile Gly Gly Asn
1               5                   10

<210> SEQ ID NO 96
<211> LENGTH: 13
<212> TYPE: PRT
<213> ORGANISM: artificial sequence
<220> FEATURE:
<223> OTHER INFORMATION: SIVgag129-143(sub)

<400> SEQUENCE: 96

Ser Gly Arg Gly Gly Asn Tyr Pro Val Gln Gln Ile Gly
1               5                   10

<210> SEQ ID NO 97
<211> LENGTH: 12
<212> TYPE: PRT
<213> ORGANISM: artificial sequence
<220> FEATURE:
<223> OTHER INFORMATION: SIVgag129-143(sub)

<400> SEQUENCE: 97

Gly Gly Asn Tyr Pro Val Gln Gln Ile Gly Gly Asn
1               5                   10

<210> SEQ ID NO 98
<211> LENGTH: 12
<212> TYPE: PRT
<213> ORGANISM: artificial sequence
<220> FEATURE:

<223> OTHER INFORMATION: SIVgag129-143(sub)

<400> SEQUENCE: 98

Ser Gly Arg Gly Gly Asn Tyr Pro Val Gln Gln Ile
1               5                   10

<210> SEQ ID NO 99
<211> LENGTH: 11
<212> TYPE: PRT
<213> ORGANISM: artificial sequence
<220> FEATURE:
<223> OTHER INFORMATION: SIVgag129-143(sub)

<400> SEQUENCE: 99

Gly Asn Tyr Pro Val Gln Gln Ile Gly Gly Asn
1               5                   10

<210> SEQ ID NO 100
<211> LENGTH: 11
<212> TYPE: PRT
<213> ORGANISM: artificial sequence
<220> FEATURE:
<223> OTHER INFORMATION: SIVgag129-143(sub)

<400> SEQUENCE: 100

Ser Gly Arg Gly Gly Asn Tyr Pro Val Gln Gln
1               5                   10

<210> SEQ ID NO 101
<211> LENGTH: 10
<212> TYPE: PRT
<213> ORGANISM: artificial sequence
<220> FEATURE:
<223> OTHER INFORMATION: SIVgag129-143(sub)

<400> SEQUENCE: 101

Asn Tyr Pro Val Gln Gln Ile Gly Gly Asn
1               5                   10

<210> SEQ ID NO 102
<211> LENGTH: 10
<212> TYPE: PRT
<213> ORGANISM: artificial sequence
<220> FEATURE:
<223> OTHER INFORMATION: SIVgag129-143(sub)

<400> SEQUENCE: 102

Ser Gly Arg Gly Gly Asn Tyr Pro Val Gln
1               5                   10

<210> SEQ ID NO 103
<211> LENGTH: 9
<212> TYPE: PRT
<213> ORGANISM: artificial sequence
<220> FEATURE:
<223> OTHER INFORMATION: SIVgag129-143(sub)

<400> SEQUENCE: 103

Tyr Pro Val Gln Gln Ile Gly Gly Asn
1               5

<210> SEQ ID NO 104
<211> LENGTH: 9
<212> TYPE: PRT
<213> ORGANISM: artificial sequence
<220> FEATURE:
<223> OTHER INFORMATION: SIVgag129-143(sub)

<400> SEQUENCE: 104

Ser Gly Arg Gly Gly Asn Tyr Pro Val
1               5

<210> SEQ ID NO 105
<211> LENGTH: 15
<212> TYPE: PRT
<213> ORGANISM: artificial sequence
<220> FEATURE:
<223> OTHER INFORMATION: SIVgag197-211(sub)

<400> SEQUENCE: 105

Gln Ala Ala Met Gln Ile Ile Arg Asp Ile Ile Asn Glu Glu Ala
1               5                   10                  15

<210> SEQ ID NO 106
<211> LENGTH: 14
<212> TYPE: PRT
<213> ORGANISM: artificial sequence
<220> FEATURE:
<223> OTHER INFORMATION: SIVgag197-211(sub)

<400> SEQUENCE: 106

Ala Ala Met Gln Ile Ile Arg Asp Ile Ile Asn Glu Glu Ala
1               5                   10

<210> SEQ ID NO 107
<211> LENGTH: 14
<212> TYPE: PRT
<213> ORGANISM: artificial sequence
<220> FEATURE:
<223> OTHER INFORMATION: SIVgag197-211(sub)

<400> SEQUENCE: 107

Gln Ala Ala Met Gln Ile Ile Arg Asp Ile Ile Asn Glu Glu
1               5                   10

<210> SEQ ID NO 108
<211> LENGTH: 13
<212> TYPE: PRT
<213> ORGANISM: artificial sequence
<220> FEATURE:
<223> OTHER INFORMATION: SIVgag197-211(sub)

<400> SEQUENCE: 108

Ala Met Gln Ile Ile Arg Asp Ile Ile Asn Glu Glu Ala
1               5                   10

<210> SEQ ID NO 109
<211> LENGTH: 13
<212> TYPE: PRT
<213> ORGANISM: artificial sequence
<220> FEATURE:
<223> OTHER INFORMATION: SIVgag197-211(sub)

<400> SEQUENCE: 109

Gln Ala Ala Met Gln Ile Ile Arg Asp Ile Ile Asn Glu
1               5                   10

<210> SEQ ID NO 110
<211> LENGTH: 12
<212> TYPE: PRT
<213> ORGANISM: artificial sequence
<220> FEATURE:
<223> OTHER INFORMATION: SIVgag197-211(sub)

<400> SEQUENCE: 110

Met Gln Ile Ile Arg Asp Ile Ile Asn Glu Glu Ala
1               5                   10

<210> SEQ ID NO 111
<211> LENGTH: 12
<212> TYPE: PRT
<213> ORGANISM: artificial sequence
<220> FEATURE:
<223> OTHER INFORMATION: SIVgag197-211(sub)

<400> SEQUENCE: 111

Gln Ala Ala Met Gln Ile Ile Arg Asp Ile Ile Asn
1               5                   10

<210> SEQ ID NO 112
<211> LENGTH: 11
<212> TYPE: PRT
<213> ORGANISM: artificial sequence
<220> FEATURE:
<223> OTHER INFORMATION: SIVgag197-211(sub)

<400> SEQUENCE: 112

Gln Ile Ile Arg Asp Ile Ile Asn Glu Glu Ala
1               5                   10

<210> SEQ ID NO 113
<211> LENGTH: 11
<212> TYPE: PRT
<213> ORGANISM: artificial sequence
<220> FEATURE:
<223> OTHER INFORMATION: SIVgag197-211(sub)

<400> SEQUENCE: 113

Gln Ala Ala Met Gln Ile Ile Arg Asp Ile Ile
1               5                   10

<210> SEQ ID NO 114
<211> LENGTH: 10
<212> TYPE: PRT
<213> ORGANISM: artificial sequence
<220> FEATURE:
<223> OTHER INFORMATION: SIVgag197-211(sub)

<400> SEQUENCE: 114

Ile Ile Arg Asp Ile Ile Asn Glu Glu Ala
1               5                   10

<210> SEQ ID NO 115
<211> LENGTH: 10
<212> TYPE: PRT
<213> ORGANISM: artificial sequence
<220> FEATURE:
<223> OTHER INFORMATION: SIVgag197-211(sub)

<400> SEQUENCE: 115

Gln Ala Ala Met Gln Ile Ile Arg Asp Ile
1               5                   10

<210> SEQ ID NO 116
<211> LENGTH: 9
<212> TYPE: PRT
<213> ORGANISM: artificial sequence
<220> FEATURE:
<223> OTHER INFORMATION: SIVgag197-211(sub)

<400> SEQUENCE: 116

```
Ile Arg Asp Ile Ile Asn Glu Glu Ala
1               5

<210> SEQ ID NO 117
<211> LENGTH: 9
<212> TYPE: PRT
<213> ORGANISM: artificial sequence
<220> FEATURE:
<223> OTHER INFORMATION: SIVgag197-211(sub)

<400> SEQUENCE: 117

Gln Ala Ala Met Gln Ile Ile Arg Asp
1               5

<210> SEQ ID NO 118
<211> LENGTH: 9
<212> TYPE: PRT
<213> ORGANISM: artificial sequence
<220> FEATURE:
<223> OTHER INFORMATION: SIVgag129-143(sub)

<400> SEQUENCE: 118

Gly Arg Gly Gly Asn Tyr Pro Val Gln
1               5

<210> SEQ ID NO 119
<211> LENGTH: 9
<212> TYPE: PRT
<213> ORGANISM: artificial sequence
<220> FEATURE:
<223> OTHER INFORMATION: SIVgag129-143(sub)

<400> SEQUENCE: 119

Arg Gly Gly Asn Tyr Pro Val Gln Gln
1               5

<210> SEQ ID NO 120
<211> LENGTH: 9
<212> TYPE: PRT
<213> ORGANISM: artificial sequence
<220> FEATURE:
<223> OTHER INFORMATION: SIVgag129-143(sub)

<400> SEQUENCE: 120

Gly Asn Tyr Pro Val Gln Gln Ile Gly
1               5

<210> SEQ ID NO 121
<211> LENGTH: 9
<212> TYPE: PRT
<213> ORGANISM: artificial sequence
<220> FEATURE:
<223> OTHER INFORMATION: SIVgag129-143(sub)

<400> SEQUENCE: 121

Asn Tyr Pro Val Gln Gln Ile Gly Gly
1               5

<210> SEQ ID NO 122
<211> LENGTH: 9
<212> TYPE: PRT
<213> ORGANISM: artificial sequence
<220> FEATURE:
<223> OTHER INFORMATION: SIVgag197-211(sub)

<400> SEQUENCE: 122
```

Ala Ala Met Gln Ile Ile Arg Asp Ile
1               5

<210> SEQ ID NO 123
<211> LENGTH: 9
<212> TYPE: PRT
<213> ORGANISM: artificial sequence
<220> FEATURE:
<223> OTHER INFORMATION: SIVgag197-211(sub)

<400> SEQUENCE: 123

Ala Met Gln Ile Ile Arg Asp Ile Ile
1               5

<210> SEQ ID NO 124
<211> LENGTH: 9
<212> TYPE: PRT
<213> ORGANISM: artificial sequence
<220> FEATURE:
<223> OTHER INFORMATION: SIVgag197-211(sub)

<400> SEQUENCE: 124

Met Gln Ile Ile Arg Asp Ile Ile Asn
1               5

<210> SEQ ID NO 125
<211> LENGTH: 9
<212> TYPE: PRT
<213> ORGANISM: artificial sequence
<220> FEATURE:
<223> OTHER INFORMATION: SIVgag197-211(sub)

<400> SEQUENCE: 125

Ile Ile Arg Asp Ile Ile Asn Glu Glu
1               5

<210> SEQ ID NO 126
<211> LENGTH: 15
<212> TYPE: PRT
<213> ORGANISM: artificial sequence
<220> FEATURE:
<223> OTHER INFORMATION: SIVgag385-399(sub)

<400> SEQUENCE: 126

Arg Gly Pro Arg Lys Pro Ile Lys Cys Trp Asn Cys Gly Lys Glu
1               5                   10                  15

<210> SEQ ID NO 127
<211> LENGTH: 14
<212> TYPE: PRT
<213> ORGANISM: artificial sequence
<220> FEATURE:
<223> OTHER INFORMATION: SIVgag385-399(sub)

<400> SEQUENCE: 127

Gly Pro Arg Lys Pro Ile Lys Cys Trp Asn Cys Gly Lys Glu
1               5                   10

<210> SEQ ID NO 128
<211> LENGTH: 14
<212> TYPE: PRT
<213> ORGANISM: artificial sequence
<220> FEATURE:
<223> OTHER INFORMATION: SIVgag385-399(sub)

<400> SEQUENCE: 128

Arg Gly Pro Arg Lys Pro Ile Lys Cys Trp Asn Cys Gly Lys

<210> SEQ ID NO 129
<211> LENGTH: 13
<212> TYPE: PRT
<213> ORGANISM: artificial sequence
<220> FEATURE:
<223> OTHER INFORMATION: SIVgag385-399(sub)

<400> SEQUENCE: 129

Pro Arg Lys Pro Ile Lys Cys Trp Asn Cys Gly Lys Glu
1               5                   10

<210> SEQ ID NO 130
<211> LENGTH: 13
<212> TYPE: PRT
<213> ORGANISM: artificial sequence
<220> FEATURE:
<223> OTHER INFORMATION: SIVgag385-399(sub)

<400> SEQUENCE: 130

Arg Gly Pro Arg Lys Pro Ile Lys Cys Trp Asn Cys Gly
1               5                   10

<210> SEQ ID NO 131
<211> LENGTH: 12
<212> TYPE: PRT
<213> ORGANISM: artificial sequence
<220> FEATURE:
<223> OTHER INFORMATION: SIVgag385-399(sub)

<400> SEQUENCE: 131

Arg Lys Pro Ile Lys Cys Trp Asn Cys Gly Lys Glu
1               5                   10

<210> SEQ ID NO 132
<211> LENGTH: 12
<212> TYPE: PRT
<213> ORGANISM: artificial sequence
<220> FEATURE:
<223> OTHER INFORMATION: SIVgag385-399(sub)

<400> SEQUENCE: 132

Arg Gly Pro Arg Lys Pro Ile Lys Cys Trp Asn Cys
1               5                   10

<210> SEQ ID NO 133
<211> LENGTH: 11
<212> TYPE: PRT
<213> ORGANISM: artificial sequence
<220> FEATURE:
<223> OTHER INFORMATION: SIVgag385-399(sub)

<400> SEQUENCE: 133

Lys Pro Ile Lys Cys Trp Asn Cys Gly Lys Glu
1               5                   10

<210> SEQ ID NO 134
<211> LENGTH: 11
<212> TYPE: PRT
<213> ORGANISM: artificial sequence
<220> FEATURE:
<223> OTHER INFORMATION: SIVgag385-399(sub)

<400> SEQUENCE: 134

Arg Gly Pro Arg Lys Pro Ile Lys Cys Trp Asn
1               5                   10

<210> SEQ ID NO 135
<211> LENGTH: 10
<212> TYPE: PRT
<213> ORGANISM: artificial sequence
<220> FEATURE:
<223> OTHER INFORMATION: SIVgag385-399(sub)

<400> SEQUENCE: 135

Pro Ile Lys Cys Trp Asn Cys Gly Lys Glu
1               5                   10

<210> SEQ ID NO 136
<211> LENGTH: 10
<212> TYPE: PRT
<213> ORGANISM: artificial sequence
<220> FEATURE:
<223> OTHER INFORMATION: SIVgag385-399(sub)

<400> SEQUENCE: 136

Arg Gly Pro Arg Lys Pro Ile Lys Cys Trp
1               5                   10

<210> SEQ ID NO 137
<211> LENGTH: 9
<212> TYPE: PRT
<213> ORGANISM: artificial sequence
<220> FEATURE:
<223> OTHER INFORMATION: SIVgag385-399(sub)

<400> SEQUENCE: 137

Ile Lys Cys Trp Asn Cys Gly Lys Glu
1               5

<210> SEQ ID NO 138
<211> LENGTH: 9
<212> TYPE: PRT
<213> ORGANISM: artificial sequence
<220> FEATURE:
<223> OTHER INFORMATION: SIVgag385-399(sub)

<400> SEQUENCE: 138

Arg Gly Pro Arg Lys Pro Ile Lys Cys
1               5

<210> SEQ ID NO 139
<211> LENGTH: 15
<212> TYPE: PRT
<213> ORGANISM: artificial sequence
<220> FEATURE:
<223> OTHER INFORMATION: SIVgag473-487(sub)

<400> SEQUENCE: 139

Tyr Met Gln Leu Gly Lys Gln Gln Arg Glu Lys Gln Arg Glu Ser
1               5                   10                  15

<210> SEQ ID NO 140
<211> LENGTH: 14
<212> TYPE: PRT
<213> ORGANISM: artificial sequence
<220> FEATURE:
<223> OTHER INFORMATION: SIVgag473-487(sub)

<400> SEQUENCE: 140

Met Gln Leu Gly Lys Gln Gln Arg Glu Lys Gln Arg Glu Ser
1               5                   10

<210> SEQ ID NO 141
<211> LENGTH: 14
<212> TYPE: PRT
<213> ORGANISM: artificial sequence
<220> FEATURE:
<223> OTHER INFORMATION: SIVgag473-487(sub)

<400> SEQUENCE: 141

Tyr Met Gln Leu Gly Lys Gln Gln Arg Glu Lys Gln Arg Glu
1               5                   10

<210> SEQ ID NO 142
<211> LENGTH: 13
<212> TYPE: PRT
<213> ORGANISM: artificial sequence
<220> FEATURE:
<223> OTHER INFORMATION: SIVgag473-487(sub)

<400> SEQUENCE: 142

Gln Leu Gly Lys Gln Gln Arg Glu Lys Gln Arg Glu Ser
1               5                   10

<210> SEQ ID NO 143
<211> LENGTH: 13
<212> TYPE: PRT
<213> ORGANISM: artificial sequence
<220> FEATURE:
<223> OTHER INFORMATION: SIVgag473-487(sub)

<400> SEQUENCE: 143

Tyr Met Gln Leu Gly Lys Gln Gln Arg Glu Lys Gln Arg
1               5                   10

<210> SEQ ID NO 144
<211> LENGTH: 12
<212> TYPE: PRT
<213> ORGANISM: artificial sequence
<220> FEATURE:
<223> OTHER INFORMATION: SIVgag473-487(sub)

<400> SEQUENCE: 144

Leu Gly Lys Gln Gln Arg Glu Lys Gln Arg Glu Ser
1               5                   10

<210> SEQ ID NO 145
<211> LENGTH: 12
<212> TYPE: PRT
<213> ORGANISM: artificial sequence
<220> FEATURE:
<223> OTHER INFORMATION: SIVgag473-487(sub)

<400> SEQUENCE: 145

Tyr Met Gln Leu Gly Lys Gln Gln Arg Glu Lys Gln
1               5                   10

<210> SEQ ID NO 146
<211> LENGTH: 11
<212> TYPE: PRT
<213> ORGANISM: artificial sequence
<220> FEATURE:
<223> OTHER INFORMATION: SIVgag473-487(sub)

<400> SEQUENCE: 146

Gly Lys Gln Gln Arg Glu Lys Gln Arg Glu Ser
1               5                   10

```
<210> SEQ ID NO 147
<211> LENGTH: 11
<212> TYPE: PRT
<213> ORGANISM: artificial sequence
<220> FEATURE:
<223> OTHER INFORMATION: SIVgag473-487(sub)

<400> SEQUENCE: 147

Tyr Met Gln Leu Gly Lys Gln Gln Arg Glu Lys
1               5                   10

<210> SEQ ID NO 148
<211> LENGTH: 10
<212> TYPE: PRT
<213> ORGANISM: artificial sequence
<220> FEATURE:
<223> OTHER INFORMATION: SIVgag473-487(sub)

<400> SEQUENCE: 148

Lys Gln Gln Arg Glu Lys Gln Arg Glu Ser
1               5                   10

<210> SEQ ID NO 149
<211> LENGTH: 10
<212> TYPE: PRT
<213> ORGANISM: artificial sequence
<220> FEATURE:
<223> OTHER INFORMATION: SIVgag473-487(sub)

<400> SEQUENCE: 149

Tyr Met Gln Leu Gly Lys Gln Gln Arg Glu
1               5                   10

<210> SEQ ID NO 150
<211> LENGTH: 9
<212> TYPE: PRT
<213> ORGANISM: artificial sequence
<220> FEATURE:
<223> OTHER INFORMATION: SIVgag473-487(sub)

<400> SEQUENCE: 150

Gln Gln Arg Glu Lys Gln Arg Glu Ser
1               5

<210> SEQ ID NO 151
<211> LENGTH: 9
<212> TYPE: PRT
<213> ORGANISM: artificial sequence
<220> FEATURE:
<223> OTHER INFORMATION: SIVgag473-487(sub)

<400> SEQUENCE: 151

Tyr Met Gln Leu Gly Lys Gln Gln Arg
1               5

<210> SEQ ID NO 152
<211> LENGTH: 9
<212> TYPE: PRT
<213> ORGANISM: artificial sequence
<220> FEATURE:
<223> OTHER INFORMATION: SIVgag385-399(sub)

<400> SEQUENCE: 152

Gly Pro Arg Lys Pro Ile Lys Cys Trp
1               5

<210> SEQ ID NO 153
```

```
<211> LENGTH: 9
<212> TYPE: PRT
<213> ORGANISM: artificial sequence
<220> FEATURE:
<223> OTHER INFORMATION: SIVgag385-399(sub)

<400> SEQUENCE: 153

Pro Arg Lys Pro Ile Lys Cys Trp Asn
1               5

<210> SEQ ID NO 154
<211> LENGTH: 9
<212> TYPE: PRT
<213> ORGANISM: artificial sequence
<220> FEATURE:
<223> OTHER INFORMATION: SIVgag385-399(sub)

<400> SEQUENCE: 154

Arg Lys Pro Ile Lys Cys Trp Asn Cys
1               5

<210> SEQ ID NO 155
<211> LENGTH: 9
<212> TYPE: PRT
<213> ORGANISM: artificial sequence
<220> FEATURE:
<223> OTHER INFORMATION: SIVgag385-399(sub)

<400> SEQUENCE: 155

Pro Ile Lys Cys Trp Asn Cys Gly Lys
1               5

<210> SEQ ID NO 156
<211> LENGTH: 9
<212> TYPE: PRT
<213> ORGANISM: artificial sequence
<220> FEATURE:
<223> OTHER INFORMATION: SIVgag473-487(sub)

<400> SEQUENCE: 156

Met Gln Leu Gly Lys Gln Gln Arg Glu
1               5

<210> SEQ ID NO 157
<211> LENGTH: 9
<212> TYPE: PRT
<213> ORGANISM: artificial sequence
<220> FEATURE:
<223> OTHER INFORMATION: SIVgag473-487(sub)

<400> SEQUENCE: 157

Gln Leu Gly Lys Gln Gln Arg Glu Lys
1               5

<210> SEQ ID NO 158
<211> LENGTH: 9
<212> TYPE: PRT
<213> ORGANISM: artificial sequence
<220> FEATURE:
<223> OTHER INFORMATION: SIVgag473-487(sub)

<400> SEQUENCE: 158

Leu Gly Lys Gln Gln Arg Glu Lys Gln
1               5

<210> SEQ ID NO 159
<211> LENGTH: 9
```

-continued

```
<212> TYPE: PRT
<213> ORGANISM: artificial sequence
<220> FEATURE:
<223> OTHER INFORMATION: SIVgag473-487(sub)

<400> SEQUENCE: 159

Gly Lys Gln Gln Arg Glu Lys Gln Arg
1               5

<210> SEQ ID NO 160
<211> LENGTH: 9
<212> TYPE: PRT
<213> ORGANISM: artificial sequence
<220> FEATURE:
<223> OTHER INFORMATION: SIVgag473-487(sub)

<400> SEQUENCE: 160

Lys Gln Gln Arg Glu Lys Gln Arg Glu
1               5

<210> SEQ ID NO 161
<211> LENGTH: 9
<212> TYPE: PRT
<213> ORGANISM: Artificial Sequence
<220> FEATURE:
<223> OTHER INFORMATION: MHC-E binding peptide
<220> FEATURE:
<221> NAME/KEY: MISC_FEATURE
<222> LOCATION: (8)..(8)
<223> OTHER INFORMATION: Xaa is Leu, Val, or Ile

<400> SEQUENCE: 161

Val Met Ala Pro Arg Thr Leu Xaa Leu
1               5
```